(12) United States Patent
Kim et al.

(10) Patent No.: US 9,447,044 B2
(45) Date of Patent: Sep. 20, 2016

(54) THIOARYL DERIVATIVES AS GPR120 AGONISTS

(71) Applicant: LG LIFE SCIENCES LTD., Seoul (KR)

(72) Inventors: Young Kwan Kim, Daejeon (KR); Myoung Yeol Kim, Daejeon (KR); Sang Yun Park, Daejeon (KR); Ok Ku Park, Daejeon (KR); Vasily Artemov, Daejeon (KR); Sang Dae Lee, Daejeon (KR); Hyun Woo Joo, Daejeon (KR); Eun Sil Choi, Daejeon (KR)

(73) Assignee: LG LIFE SCIENCES LTD., Seoul (KR)

( * ) Notice: Subject to any disclaimer, the term of this patent is extended or adjusted under 35 U.S.C. 154(b) by 0 days.

(21) Appl. No.: 14/440,495

(22) PCT Filed: Nov. 5, 2013

(86) PCT No.: PCT/KR2013/009928
§ 371 (c)(1),
(2) Date: May 4, 2015

(87) PCT Pub. No.: WO2014/069963
PCT Pub. Date: May 8, 2014

(65) Prior Publication Data
US 2015/0291527 A1    Oct. 15, 2015

(30) Foreign Application Priority Data
Nov. 5, 2012    (KR) .......................... 10-2012-0124502

(51) Int. Cl.
| | |
|---|---|
| *C07D 213/70* | (2006.01) |
| *A61K 31/44* | (2006.01) |
| *C07D 213/80* | (2006.01) |
| *C07D 241/18* | (2006.01) |

(52) U.S. Cl.
CPC ............ *C07D 213/70* (2013.01); *A61K 31/44* (2013.01); *C07D 213/80* (2013.01); *C07D 241/18* (2013.01)

(58) Field of Classification Search
CPC .. A61K 31/44; C07D 241/18; C07D 213/80; C07D 213/70; A61P 3/10
USPC ............................................................ 546/290
See application file for complete search history.

(56) References Cited

U.S. PATENT DOCUMENTS

| | | | | |
|---|---|---|---|---|
| 5,399,703 A | * | 3/1995 | Yoshimoto ............ | C07D 401/12 546/175 |
| 2003/0229120 A1 | * | 12/2003 | Olsen ................. | A61K 31/4192 514/314 |
| 2005/0054715 A1 | * | 3/2005 | Hayter ................. | C07D 213/78 514/422 |
| 2006/0258722 A1 | * | 11/2006 | Yasuma ................. | C07C 59/64 514/369 |
| 2008/0090840 A1 | * | 4/2008 | Beck ..................... | C07D 261/08 514/255.05 |
| 2008/0167310 A1 | * | 7/2008 | Gossett ................. | C07C 233/63 514/236.8 |
| 2009/0105257 A1 | * | 4/2009 | Corbett ................. | C07C 229/46 514/237.8 |
| 2009/0137561 A1 | * | 5/2009 | Brown .................... | C07C 59/68 514/217.12 |
| 2010/0130559 A1 | | 5/2010 | Hashimoto et al. | |
| 2010/0274022 A1 | | 10/2010 | Tsujimoto et al. | |
| 2011/0065739 A1 | | 3/2011 | Ishikawa et al. | |
| 2011/0082165 A1 | * | 4/2011 | Ellsworth ............ | C07D 207/08 514/275 |
| 2011/0195993 A1 | | 8/2011 | Masson et al. | |
| 2015/0291584 A1 | * | 10/2015 | Lee ...................... | C07D 409/04 514/234.5 |

FOREIGN PATENT DOCUMENTS

| | | |
|---|---|---|
| EP | 0 206 741 A2 | 12/1986 |
| WO | 02/42273 A2 | 5/2002 |
| WO | WO 2008/066131 A1 | 6/2008 |
| WO | WO 2008/103500 A1 | 8/2008 |
| WO | WO 2008/139879 A1 | 11/2008 |
| WO | WO 2009/147990 A1 | 12/2009 |
| WO | WO 2010/048207 A2 | 4/2010 |
| WO | WO 2010/080537 A1 | 7/2010 |
| WO | WO 2010/104195 A1 | 9/2010 |
| WO | WO 2011/159297 A1 | 12/2011 |
| WO | WO2013185766 | * 12/2013 |
| WO | WO2014209034 | * 12/2014 |

OTHER PUBLICATIONS

Negoro; J. Med. Chem. 2012, 55, 1538-1552.*
Chemical Abstracts STN Registry Database Record for RN 54649-51-3, entered on Nov. 16, 1984.*
Chemical Abstracts STN Registry Database Record for RN 1053923-76-4, entered on Sep. 28, 2008.*
Chemical Abstracts STN Registry Database Record for RN 1014441-02-1, entered on Apr. 14, 2008.*
Shimpukade; J. Med. Chem. 2012, 55, 4511-4515.*
Rayasam; Expert Opin. Ther. Targets 2007, 11, 661-671.*

(Continued)

*Primary Examiner* — Andrew D Kosar
*Assistant Examiner* — Daniel Carcanague
(74) *Attorney, Agent, or Firm* — Birch, Stewart, Kolasch & Birch, LLP

(57) ABSTRACT

The present invention relates to thioaryl derivatives of Formula 1 as defined in the specification, a method for preparing the same, a pharmaceutical composition comprising the same and use thereof. The thioaryl derivatives of Formula 1 according to the present invention promote GLP-1 formation in the gastrointestinal tract and improve insulin resistance in macrophages, pancreas cells, etc. due to anti-inflammatory action, and can accordingly be effectively used for preventing or treating diabetes, complications of diabetes, inflammation, obesity, non-alcoholic fatty liver, steatohepatitis or osteoporosis.

10 Claims, No Drawings

(56) References Cited

OTHER PUBLICATIONS

Oh; Cell 2010, 142, 687-698.*
International Search Report issued in PCT/KR2013/009928, mailed on Feb. 24, 2014.
Supplementary European Search Report, dated Apr. 11, 2016, for European Application No. 13 85 2301.
Young et al., "Leukotriene antagonists," XP002756321, Database CAPLUS [Online] Chemical Abstracts Service, US, Accession No. 1987:458842, 1987, 8 pages.
Young, "Structural analysis of sulfide-peptide leukotrienes: application to the design of potent and specific antagonists of leukotriene D4," XP002756322, Database CAPLUS [Online] Chemical Abstracts Service, US, Accession No. 1989:509151, 1989, 1 page.

* cited by examiner

THIOARYL DERIVATIVES AS GPR120 AGONISTS

TECHNICAL FIELD

The present invention relates to novel thioaryl derivatives as GPR120 agonists, a method for preparing the same, a pharmaceutical composition comprising the same and use thereof. Herein a GPR120 agonist means a compound which can be effectively used for preventing or treating diabetes, complications of diabetes, inflammation, obesity, non-alcoholic fatty liver, steatohepatitis or osteoporosis by promoting GLP-1 in the gastrointestinal tract and anti-inflammatory action.

BACKGROUND ART

Diabetes is divided into two types—i.e., insulin-dependent type 1 diabetes and insulin-independent (insulin-resistant) type 2 diabetes which is found in 90% or more of diabetic patients.

In insulin-resistant type 2 diabetic patients, internal insulin does not take effect completely so blood glucose must be controlled in another way, and an oral hypo-glycemic agent is typically used.

Currently, most antidiabetics control blood glucose by a mechanism of action that affects one target organ such as the liver, pancreas or muscle. For example, sul-fonlyureas act directly on the pancreas to cause insulin secretion, and metformins have the mechanism of action of preventing glucolysis in the liver. However, a single drug hardly accomplishes the expected effect in many cases and each drug also has its side effects. For example, sulfonylureas have problems of decreasing the function of the pancreas and incurring hypoglycemia due to excessive secretion of insulin, and metformins cause gastroenteric disorders or renal toxicity. Glitazones also have side effects of weight gain, serious heart failure, etc. Meanwhile, incretin-related drugs such as DPPIV inhibitors or Exenatide, which have recently entered the market, are noted as medicines for solving problems such as increase of glucagon production, gradual decrease of the β-cell function in the pancreas, incurrence of hypoglycemia, weight gain, etc. which cannot be solved by traditional antidiabetics. However, DPPIV inhibitors have a marginal effect, and it is especially reported that Galvus has the side effect of skin toxicity. Furthermore, Exenatide has a disadvantage in that it must be given by means of injection.

As described above, most conventional antidiabetics have various problems and side effects, and it is highly necessary to develop innovative antidiabetics which can be used for the treatment of diabetes effectively and safely.

GPR120 agonists, which are noted for possible treatment of type 2 diabetes, are known to have (1) an antidiabetic effect caused by the actions of increasing incretin hormone in intestinal cells, (2) anti-inflammatory action in macrophages, and (3) an action of improvement on insulin resistance in lipocytes. They are also known as a possible treatment of type 1 diabetes by the action of improvement on proliferation of pancreas cells.

G protein-coupled receptor 120 (GPR120) is expressed copiously in intestines, lungs, adipose tissue, and macrophages which induce inflammation, and is activated by long chain free fatty acid (FFA). GPR120 stimulates the secretion of glucagon-like peptide-1 (GLP-1) by FFA. GLP-1, an incretin hormone, is known to stimulate the secretion of insulin in the pancreas dependently on blood glucose level, and also to have the effect of improvement of insulin resistance, proliferation of β-cells, appetite loss and increase of satiety. Recently, GPR120 is known to relate with improvement of insulin resistance and anti-inflammatory effect, and therefore, it is regarded as a target for developing a drug to effectively improve insulin resistance, type 2 diabetes and obesity involving low-level chronic inflammation. Furthermore, in animal experiments of type 1 diabetes, GPR120 agonists are reported to improve the secretion of insulin by the action of proliferation of β-cells.

Considering the above, researches on GPR120 agonists are actively in progress. In the representative compounds presented as GPR120 agonists, two aryl groups are connected with a center bridge structure, and the characteristic feature is that one of two aryl groups is substituted by carboxylic acid. GPR120 agonist compounds are disclosed in WO2011/159297, WO2010/080537, WO2010/104195, WO2010/048207, WO2009/147990, WO2008/066131, WO2008/103500 and WO2008/139879.

DISCLOSURE OF INVENTION

Technical Problem

The object of the present invention is to provide novel thioaryl derivatives as GPR120 agonists.

Another object of the present invention is to provide a method for preparing the thioaryl derivatives.

Still another object of the present invention is to provide a pharmaceutical composition for the prevention and treatment of diabetes, complications of diabetes, inflammation, obesity, non-alcoholic fatty liver, steatohepatitis or osteoporosis which comprises as active components the thioaryl derivatives, and a method for preparing the composition.

A still further object of the present invention is to provide a method for preventing and treating diabetes, complications of diabetes, inflammation, obesity, non-alcoholic fatty liver, steatohepatitis or osteoporosis which use the thioaryl derivatives as active components.

Solution to Problem

Therefore, the present invention provides thioaryl derivatives of Formula 1, or pharmaceutically acceptable salts or isomers thereof:

[Formula 1]

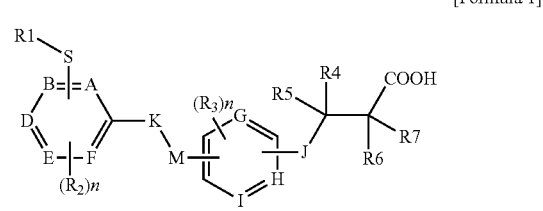

wherein,

A, B, D, E, F, G, H and I represent independently carbon or nitrogen,

R1 represents optionally substituted alkyl, cycloalkyl, heterocycloalkyl, alkylcycloalkyl, aryl, alkylaryl, heteroaryl or alkylheteroaryl, R2 and R3 represent independently hydrogen, halogen, or optionally substituted alkyl, cycloalkyl, heterocycloalkyl, alkoxy, cycloalkoxy, aryloxy, heteroaryloxy, aminoalkyl, aminocycloalkyl, aminoaryl, alkylamine, cycloalkylamine, aminoheteroaryl, thioalkyl, thioaryl or thioheteroaryl, R4, R5, R6 and R7 represent independently hydrogen, fluoro, alkyl or cycloalkyl. Alternatively, R4 and R6 are connected together to form a ring, R5 and R7 are connected together to form a ring, or one of R4 and R5 is connected with J to form a ring.

J does not exist, or represents carbon, nitrogen or oxygen,

K and M represent independently carbon, nitrogen, oxygen or sulfur, and n represents an integer of 0 to 4.

The compounds of Formula 1 according to the present invention can form pharmaceutically acceptable salts, which include acid-addition salts which are formed from inorganic acids such as hydrochloric acid, sulfuric acid, nitric acid, phosphoric acid, hydrobromic acid and hydroiodic acid; organic acids such as tartaric acid, formic acid, citric acid, acetic acid, trichloroacetic acid, trifluoroacetic acid, gluconic acid, benzoic acid, lactic acid, fumaric acid, maleic acid and salicylic acid; or sulfonic acids such as methanesulfonic acid, ethanesulfonic acid, benzenesulfonic acid and p-toluenesulfonic acid, which form non-toxic acid-addition salts including pharmaceutically acceptable anion. For example, the pharmaceutically acceptable carboxylic acid salts include the salts with alkali metal or alkali earth metal such as lithium, sodium, potassium, calcium and magnesium; salts with amino acid such as lysine, arginine and guanidine; organic salts such as dicyclohexylamine, N-methyl-D-glucamine, tris(hydroxymethyl)methylamine, diethanolamine, choline and triethylamine. The compounds of Formula 1 according to the present invention can be converted into their salts by conventional methods.

Furthermore, since the compounds of Formula 1 according to the present invention can have an asymmetric carbon center and asymmetric axis or plane, they can exist as E- or Z-isomer, R- or S-isomer, racemic mixtures or diastereoisomer mixtures and each diastereoisomer, all of which are within the scope of the present invention.

Herein, unless indicated otherwise, the term "the compounds of Formula 1" is used to mean all the compounds of Formula 1, including the pharmaceutically acceptable salts and isomers thereof.

The terms used herein are defined as follows.

Halogen or halo means fluoride (F), chlorine (Cl), bromine (Br) or iodine (I).

Alkyl means straight or branched hydrocarbons which can include single bond, double bond or triple bond and is preferably $C_1$-$C_6$-alkyl. Examples of alkyl include, but are not limited to, methyl, ethyl, n-propyl, i-propyl, n-butyl, i-butyl, tert-butyl, acetylene, vinyl, trifluoromethyl and the like.

Cycloalkyl means partially or fully saturated single or fused ring hydrocarbons and is preferably $C_3$-$C_{10}$-cycloalkyl. Examples of cycloalkyl include, but are not limited to, cyclopropyl, cyclobutyl, cyclopentyl, cyclohexyl, cyclohexenyl and the like.

Aryl means aromatic hydrocarbons and includes, but is not limited to, phenyl, naphthyl and the like.

Heteroaryl means aromatic hydrocarbons which form a single or fused ring including at least one hetero atom selected from N, O and S. Examples of heteroaryl include, but are not limited to, pyridinyl, pyrimidinyl, pyridazinyl, oxadiazolyl, isoxadiazolyl, tetrazolyl, triazolyl, indolyl, isoxazolyl, oxazolyl, thiazolyl, imidazolyl, thiophenyl, benzthiazole, benzimidazole, 1,2,3,4-tetrahydroisoquinolyl, thiazolopyridyl and the like.

Heterocyclyl means partially or fully saturated hydrocarbons which form a single or fused ring including at least one hetero atom selected from N, O and S, and is preferably $C_3$-$C_{10}$-heterocyclyl. Examples of heterocyclyl include, but are not limited to, pyrrolidinyl, piperidinyl, morpholinyl, imidazolinyl, piperazinyl, tetrahydrofuran, tetrahydrothiofuran and the like.

Arylalkyl and heteroarylalkyl mean groups which are formed by the combination of the above-mentioned aryl with alkyl and heteroaryl with alkyl. Examples include, but are not limited to, benzyl, thiophene methyl, pyrimidine methyl and the like.

The above-mentioned amine, alkyl, cycloalkyl, aryl, heteroaryl, heterocyclyl, arylalkyl and heteroarylalkyl may be substituted by at least one group selected from the following groups: alkyl, cycloalkyl, heterocyclyl, aryl, heteroaryl, arylalkyl, heteroarylalkyl, heterocyclylalkyl, oxo, cyano, halo, nitro, —OR, —OC(O)R, —OC(O)OR, SR, —S(O)R, —S(O)$_2$R, —C(O)R, —C(O)OR, —C(S)R, —C(O)NRR, —NR$_2$, —NRCHO, —NRC(O)R, —NRC(O)NRR, —C(S)NRR, —NRC(S)R and —NRC(S)NRR, wherein R is independently selected from hydrogen, alkyl, cycloalkyl, heterocyclyl, aryl, heteroaryl, arylalkyl and heteroarylalkyl, and when two Rs are substituted, they may be connected to form cycloalkyl or heterocyclyl.

Preferable compounds of Formula 1 according to the present invention used as GPR120 agonists are as follows:

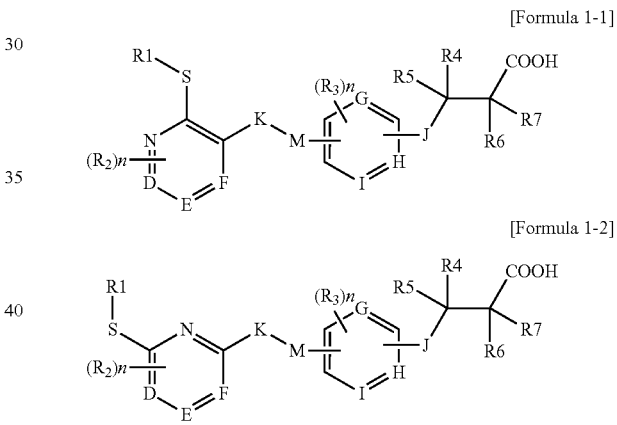

[Formula 1-1]

[Formula 1-2]

wherein,

R1 represents $C_1$-$C_6$-alkyl, $C_3$-$C_{10}$-cycloalkyl, $C_1$-$C_6$-alkyl-$C_3$-$C_{10}$-cycloalkyl, $C_1$-$C_6$-alkyl-$C_3$-$C_{10}$-heterocycloalkyl, aryl, $C_1$-$C_6$-alkylaryl or $C_1$-$C_6$-alkyl-$C_5$-$C_6$-heteroaryl, each of R2 represents independently hydrogen, halogen or optionally substituted $C_1$-$C_6$-alkyl, $C_3$-$C_{10}$-cyclo-$C_1$-$C_6$-alkyl, heterocycloalkyl, $C_1$-$C_6$-alkoxy, $C_3$-$C_{10}$-cycloalkoxy, aryloxy, heteroaryloxy, amino-$C_1$-$C_6$-alkyl, amino-$C_3$-$C_{10}$ C3-C10-cycloalkyl, aminoaryl, di($C_1$-$C_6$-alkyl)amine, $C_3$-$C_{10}$-cycloalkylamine, aminoheteroaryl, thio-$C_1$-$C_6$-alkyl, thioaryl or thioheteroaryl, n represents an integer of 0 to 3, and D, E, F, G, H, I, J, K, M, R3, R4, R5, R6 and R7 are as defined above.

Still other preferable compounds of Formula 1 according to the present invention used as GPR120 agonists are as follows:

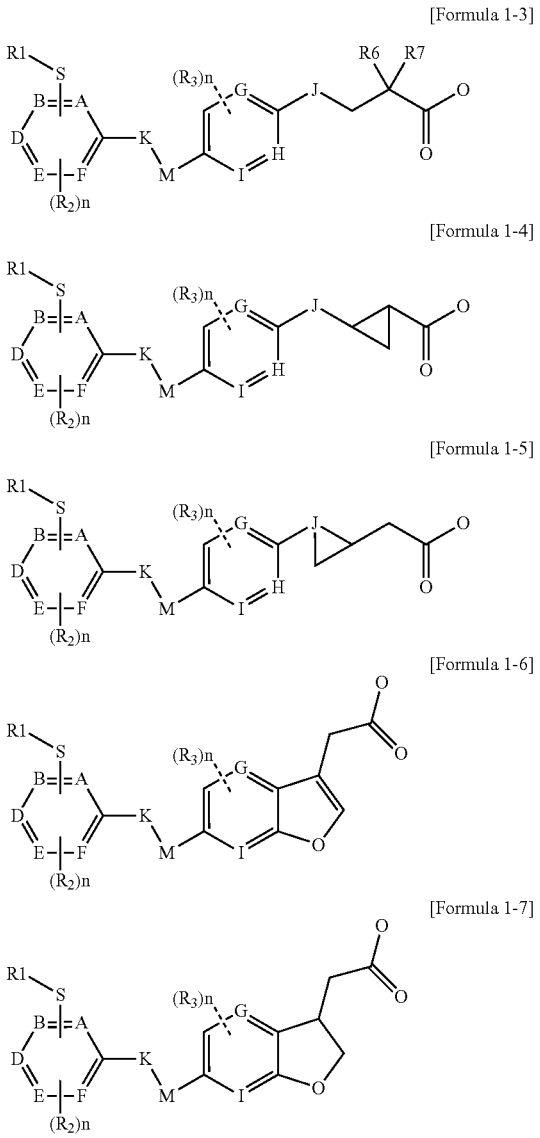

[Formula 1-3]

[Formula 1-4]

[Formula 1-5]

[Formula 1-6]

[Formula 1-7]

wherein, each of R3 represents independently hydrogen, halogen or optionally substituted $C_1$-$C_6$-alkyl, $C_3$-$C_{10}$-cyclo-$C_1$-$C_6$-alkyl, heterocycloalkyl, $C_1$-$C_6$-alkoxy, $C_3$-$C_{10}$-cycloalkoxy, aryloxy, heteroaryloxy, amino-$C_1$-$C_6$-alkyl, amino-$C_3$-$C_{10}$-cycloalkyl, aminoaryl, di($C_1$-$C_6$-alkyl)amine, $C_3$-$C_{10}$-cycloalkylamine, aminoheteroaryl, thio-$C_1$-$C_6$-alkyl, thioaryl or thioheteroaryl, R6 and R7 represent independently hydrogen, fluoro or $C_1$-$C_6$-alkyl, or R6 and R7 are connected together to form $C_3$-$C_6$-cycloalkyl or $C_3$-$C_6$-heterocycle including N, O or S, and n, A, B, D, E, F, G, H, I, J, K, M, R1 and R2 are as described in the definition of the compounds of Formula 1.

Representative compounds of Formula 1 according to the present invention include, but are not limited to, the following compounds:

3-[3,5-difluoro-4-(2-isopropylsulfanyl-pyridin-3-ylmethoxy)-phenyl]-propionic acid;
3-[4-(2-isopropylsulfanyl-pyridin-3-ylmethoxy)-phenyl]-propionic acid;
3-[4-(2-isopropylsulfanyl-5-methyl-pyridin-3-ylmethoxy)-phenyl]-2-methyl-propionic acid;
3-[4-(2-isopropylsulfanyl-pyridin-3-ylmethoxy)-phenyl]-2-methyl-propionic acid;
3-[4-(2-isopropylsulfanyl-5-methyl-pyridin-3-ylmethoxy)-phenyl]-propionic acid;
3-[3-fluoro-4-(2-isopropylsulfanyl-pyridin-3-ylmethoxy)-phenyl]-propionic acid;
3-[2-fluoro-4-(2-isopropylsulfanyl-pyridin-3-ylmethoxy)-phenyl]-propionic acid;
3-[4-(2-cyclopentylsulfanyl-pyridin-3-ylmethoxy)-phenyl]-2-methyl-propionic acid;
3-[3,5-difluoro-4-(2-isopropylsulfanyl-6-methyl-pyridin-3-ylmethoxy)-phenyl]-propionic acid;
3-[4-(2-ethylsulfanyl-pyridin-3-ylmethoxy)-3,5-difluoro-phenyl]-propionic acid;
3-[3,5-difluoro-4-(2-isobutylsulfanyl-pyridin-3-ylmethoxy)-phenyl]-propionic acid;
3-[4-(2-cyclopentylsulfanyl-pyridin-3-ylmethoxy)-3,5-difluoro-phenyl]-propionic acid;
4-[4-(2-isopropylsulfanyl-pyridin-3-ylmethoxy)-phenyl]-butyric acid;
3-[3,5-difluoro-4-(2-propylsulfanyl-pyridin-3-ylmethoxy)-phenyl]-propionic acid;
3-[3,5-difluoro-4-(2-phenylsulfanyl-pyridin-3-ylmethoxy)-phenyl]-propionic acid;
3-[4-(2-t-butylsulfanyl-pyridin-3-ylmethoxy)-3,5-difluoro-phenyl]-propionic acid;
3-[4-(2-cyclopropylmethylsulfanyl-pyridin-3-ylmethoxy)-3,5-difluoro-phenyl]-propionic acid;
3-{3,5-difluoro-4-[2-(2,2,2-trifluoro-ethylsulfanyl)-pyridin-3-ylmethoxy]-phenyl}-propionic acid;
3-[4-(2-sec-butylsulfanyl-pyridin-3-ylmethoxy)-3,5-difluoro-phenyl]-propionic acid;
3-[3,5-difluoro-4-(3-isopropylsulfanyl-pyrazin-2-ylmethoxy)-phenyl]-propionic acid;
4-[4-(2-cyclopentylsulfanyl-pyridin-3-ylmethoxy)-phenyl]-butyric acid;
3-[4-(2-cyclohexylsulfanyl-pyridin-3-ylmethoxy)-3,5-difluoro-phenyl]-propionic acid;
3-[4-(2-cyclobutylsulfanyl-pyridin-3-ylmethoxy)-3,5-difluoro-phenyl]-propionic acid;
3-[3,5-difluoro-4-(2-isopropylsulfanyl-pyrimidin-4-ylmethoxy)-phenyl]-propionic acid;
3-[4-(2-cyclopentylsulfanyl-pyridin-3-ylmethoxy)-phenyl]-2-methyl-propionic acid;
3-[4-(2-butylsulfanyl-pyridin-3-ylmethoxy)-3,5-difluoro-phenyl]-propionic acid;
3-{3,5-difluoro-4-[2-(3,3,3-trifluoro-propylsulfanyl)-pyridin-3-ylmethoxy]-phenyl}-propionic acid;
3-{4-[2-(2,2-dimethyl-propylsulfanyl)-pyridin-3-ylmethoxy]-3,5-difluoro-phenyl}-propionic acid;
3-[4-(6-cyclopentylsulfanyl)-pyridin-2-ylmethoxy]-phenyl]-propionic acid;
3-[4-(6-cyclopentylsulfanyl)-pyridin-2-ylmethoxy]-3,5-difluoro-phenyl]-propionic acid;
3-[4-(6-cyclohexylsulfanyl)-pyridin-2-ylmethoxy]-3,5-difluoro-phenyl]-propionic acid;
3-[4-(6-ethyl-2-isopropylsulfanyl)-pyridin-3-ylmethoxy]-3,5-difluoro-phenyl]-propionic acid;
3-[3,5-difluoro-4-(6-isopropylsulfanyl-pyridin-2-ylmethoxy)-phenyl]-propionic acid;
3-[4-(6-sec-butylsulfanyl-pyridin-2-ylmethoxy)-3,5-difluoro-phenyl]-propionic acid;
2-[4-(6-cyclopentylsulfanyl-pyridin-2-ylmethoxy)-3,5-difluoro-phenyl]-cyclopropane carboxylic acid;

2-[4-(2-cyclobutylsulfanyl-pyridin-3-ylmethoxy)-3,5-difluoro-phenyl]-cyclopropane carboxylic acid;
3-[4-(2-cyclobutylsulfanyl-pyridin-3-ylmethoxy)-3-fluoro-phenyl]-2-methyl-propionic acid;
3-[4-(2-cyclopentylsulfanyl-pyridin-3-ylmethoxy)-3-fluoro-phenyl]-2-methyl-propionic acid;
3-[4-(2-sec-butylsulfanyl-pyridin-3-ylmethoxy)-3-fluoro-phenyl]-2-methyl-propionic acid;
3-[4-(2-cyclopropylmethylsulfanyl-pyridin-3-ylmethoxy)-3-fluoro-phenyl]-2-methyl-propionic acid;
3-[3,5-difluoro-4-(2-isopropylsulfanyl-pyridin-3-ylmethoxy)-phenyl]-2-methyl-propionic acid;
3-[4-(2-sec-butylsulfanyl-pyridin-3-ylmethoxy)-3,5-difluoro-phenyl]-2-methyl-propionic acid;
3-[3,5-difluoro-4-(2-isopropylsulfanyl-6-methoxy-pyridin-3-ylmethoxy)-phenyl]-propionic acid;
3-[4-(6-cyclopentylsulfanyl-pyridin-2-ylmethoxy)-3,5-difluoro-phenyl]-2-methyl-propionic acid;
3-[4-(2-cyclopentylsulfanyl-6-methyl-pyridin-3-ylmethoxy)-3,5-difluoro-phenyl]-propionic acid;
3-[4-(6-cyclobutylsulfanyl-pyridin-2-ylmethoxy)-3,5-difluoro-phenyl]-2-methyl-prop ionic acid;
3-[4-(2-cyclopentylsulfanyl-pyridin-3-ylmethoxy)-3,5-difluoro-phenyl]-2-methyl-propionic acid;
3-[4-(6-sec-butylsulfanyl-pyridin-2-ylmethoxy)-3,5-difluoro-phenyl]-2-methyl-propionic acid;
3-[3,5-difluoro-4-(6-isopropylsulfanyl-pyridin-2-ylmethoxy)-phenyl]-2-methyl-propionic acid;
3-[4-(2-cyclopropylmethylsulfanyl-pyridin-3-ylmethoxy)-3,5-difluoro-phenyl]-2-methyl-propionic acid;
3-[3,5-difluoro-4-(2-propylsulfanyl-pyridin-3-ylmethoxy)-phenyl]-2-methyl-propionic acid;
3-[3-fluoro-4-(6-isopropylsulfanyl-pyridin-2-ylmethoxy)-phenyl]-2-methyl-propionic acid;
3-[4-(6-sec-butylsulfanyl-pyridin-2-ylmethoxy)-3-fluoro-phenyl]-2-methyl-propionic acid;
3-[4-(6-cyclopentylsulfanyl-pyridin-2-ylmethoxy)-3-fluoro-phenyl]-2-methyl-propionic acid;
3-[4-(6-cyclobutylsulfanyl-pyridin-2-ylmethoxy)-3-fluoro-phenyl]-2-methyl-propionic acid;
3-[4-(2-cyclobutylsulfanyl-pyridin-3-ylmethoxy)-3,5-difluoro-phenyl]-2-methyl-prop ionic acid;
3-[4-(2-isopropylsulfanyl-pyridin-3-ylmethoxy)-3-methoxy-phenyl]-propionic acid;
3-[4-(2-cyclopentylsulfanyl-pyridin-3-ylmethoxy)-3-methoxy-phenyl]-propionic acid;
[6-(2-isopropylsulfanyl-pyridin-3-ylmethoxy)-2,3-dihydro-benzofuran-3-yl]-acetic acid;
3-[3-fluoro-4-(2-isopropylsulfanyl-pyridin-3-ylmethoxy)-phenyl]-2-methyl-propionic acid;
3-[4-(2-butylsulfanyl-pyridin-3-ylmethoxy)-3-fluoro-phenyl]-2-methyl-propionic acid;
2-[4-(2-cyclopentylsulfanyl-pyridin-3-ylmethoxy)-3,5-difluoro-phenyl]-cyclopropane carboxylic acid;
2-[4-(2-cyclopropylmethylsulfanyl-pyridin-3-ylmethoxy)-3,5-difluoro-phenyl]-cyclo propane carboxylic acid;
2-[3,5-difluoro-4-(6-isopropylsulfanyl-pyridin-2-ylmethoxy)-phenyl]-cyclopropane carboxylic acid;
2-[3,5-difluoro-4-(2-isopropylsulfanyl-pyridin-3-ylmethoxy)-phenyl]-cyclopropane carboxylic acid;
2-[4-(2-butylsulfanyl-pyridin-3-ylmethoxy)-3,5-difluoro-phenyl]-cyclopropane carboxylic acid;
[6-(6-isopropylsulfanyl-pyridin-2-ylmethoxy)-2,3-dihydro-benzofuran-3-yl]-acetic acid;
[6-(6-cyclopentylsulfanyl-pyridin-2-ylmethoxy)-2,3-dihydro-benzofuran-3-yl]-acetic acid;
3-[4-(2-isopropylsulfanyl-pyridin-3-ylmethoxy)-phenyl]-2,2-dimethyl-propionic acid;
3-[4-(6-isopropylsulfanyl-pyridin-2-ylmethoxy)-phenyl]-2,2-dimethyl-propionic acid;
3-[3,5-difluoro-4-(4-isopropylsulfanyl-2-methyl-pyrimidin-5-ylmethoxy)-phenyl]-propionic acid;
3-[4-(6-isopropylsulfanyl-pyridin-2-ylmethoxy)-3-methoxy-phenyl]-propionic acid;
3-[4-(6-cyclopentylsulfanyl-pyridin-2-ylmethoxy)-3-methoxy-phenyl]-propionic acid;
[6-(2-cyclopentylsulfanyl-pyridin-3-ylmethoxy)-2,3-dihydro-benzofuran-3-yl]-acetic acid;
2-[4-(6-cyclobutylsulfanyl-pyridin-2-ylmethoxy)-3,5-difluoro-phenyl]-cyclopropane carboxylic acid;
3-[4-(2-cyclopentylsulfanyl-6-methoxy-pyridin-3-ylmethoxy)-3,5-difluoro-phenyl]-propionic acid;
3-[3-chloro-4-(2-isopropylsulfanyl-pyridin-3-ylmethoxy)-phenyl]-propionic acid;
3-[3-chloro-4-(2-cyclopentylsulfanyl-pyridin-3-ylmethoxy)-phenyl]-propionic acid;
3-[4-(2-isopropylsulfanyl-pyridin-3-ylmethoxy)-2,3-dimethyl-phenyl]-propionic acid;
3-[4-(2-cyclopentylsulfanyl-pyridin-3-ylmethoxy)-2,3-dimethyl-phenyl]-propionic acid;
[(S)-6-(2-cyclopentylsulfanyl-pyridin-3-ylmethoxy)-2,3-dihydro-benzofuran-3-yl]-acetic acid;
[(R)-6-(2-cyclopentylsulfanyl-pyridin-3-ylmethoxy)-2,3-dihydro-benzofuran-3-yl]-acetic acid;
2-[3-fluoro-4-(2-isopropylsulfanyl-pyridin-3-ylmethoxy)-phenyl]-cyclopropane carboxylic acid;
2-[4-(2-cyclopropylmethylsulfanyl-pyridin-3-ylmethoxy)-3-fluoro-phenyl]-cyclopropane carboxylic acid;
2-[4-(6-cyclopentylsulfanyl-pyridin-2-ylmethoxy)-3-fluoro-phenyl]-cyclopropane carboxylic acid;
2-[4-(6-cyclobutylsulfanyl-pyridin-2-ylmethoxy)-3-fluoro-phenyl]-cyclopropane carboxylic acid;
2-[4-(2-cyclopentylsulfanyl-pyridin-3-ylmethoxy)-3-fluoro-phenyl]-cyclopropane carboxylic acid;
2-[4-(2-cyclobutylsulfanyl-pyridin-3-ylmethoxy)-3-fluoro-phenyl]-cyclopropane carboxylic acid;
2-[2-chloro-4-(2-isopropylsulfanyl-pyridin-3-ylmethoxy)-phenyl]-cyclopropane carboxylic acid;
2-[2-chloro-4-(6-chlorobutylsulfanyl-pyridin-2-ylmethoxy)-phenyl]-cyclopropane carboxylic acid;
3-[3-chloro-4-(2-cyclopropylmethylsulfanyl-pyridin-3-ylmethoxy)-phenyl]-2-methyl-propionic acid;
3-[3-chloro-4-(2-propylsulfanyl-pyridin-3-ylmethoxy)-phenyl]-2-methyl-propionic acid;
3-[3-chloro-4-(6-isopropylsulfanyl-pyridin-2-ylmethoxy)-phenyl]-2-methyl-propionic acid;
3-[3-chloro-4-(6-cyclopentylsulfanyl-pyridin-2-ylmethoxy)-phenyl]-2-methyl-propionic acid;
3-[3-chloro-4-(2-cyclobutylsulfanyl-pyridin-3-ylmethoxy)-phenyl]-2-methyl-propionic acid;
3-[3-chloro-4-(6-cyclobutylsulfanyl-pyridin-2-ylmethoxy)-phenyl]-2-methyl-propionic acid;
2-[3-chloro-4-(2-isopropylsulfanyl-pyridin-3-ylmethoxy)-phenyl]-cyclopropane carboxylic acid;
2-[3-chloro-4-(6-cyclopropylmethylsulfanyl-pyridin-2-ylmethoxy)-phenyl]-cyclopropane carboxylic acid;
2-[3-chloro-4-(6-isopropylsulfanyl-pyridin-2-ylmethoxy)-phenyl]-cyclopropane carboxylic acid;
2-[3-chloro-4-(6-cyclopentylsulfanyl-pyridin-2-ylmethoxy)-phenyl]-cyclopropane carboxylic acid;
2-[3-chloro-4-(2-cyclopentylsulfanyl-pyridin-3-ylmethoxy)-phenyl]-cyclopropane carboxylic acid;

2-[3-chloro-4-(2-cyclobutylsulfanyl-pyridin-3-ylmethoxy)-phenyl]-cyclopropane carboxylic acid;
2-[3-chloro-4-(6-cyclobutylsulfanyl-pyridin-2-ylmethoxy)-phenyl]-cyclopropane carboxylic acid;
2-[2-chloro-4-(6-chloropentylsulfanyl-pyridin-2-yl-methoxy)-phenyl]-cyclopropane carboxylic acid;
2-[4-(2-isopropylsulfanyl-pyridin-3-ylmethoxy)-2,3-dimethyl-phenyl]-cyclopropane carboxylic acid;
2-[4-(2-cyclopropylmethylsulfanyl-pyridin-3-ylmethoxy)-2,3-dimethyl-phenyl]-cyclopropane carboxylic acid;
2-[3-chloro-4-(2-cyclopropylmethylsulfanyl-pyridin-3-yl-methoxy)-phenyl]-cyclopropane carboxylic acid;
2-[3-chloro-4-(2-propylsulfanyl-pyridin-3-ylmethoxy)-phenyl]-cyclopropane carboxylic acid;
2-[3-chloro-4-(2-isopropylsulfanyl-6-methoxy-pyridin-3-ylmethoxy)-phenyl]-cyclopropane carboxylic acid;
2-[4-(6-cyclopentylsulfanyl-pyridin-2-ylmethoxy)-3,5-difluoro-benzyl]-cyclopropane carboxylic acid;
[6-(2-cyclobutylsulfanyl-pyridin-3-ylmethoxy)-5,7-difluoro-2,3-dihydro-benzofuran-3-yl]-acetic acid;
2-[2,3-dimethyl-4-(2-propylsulfanyl-pyridin-3-ylmethoxy)-phenyl]-cyclopropane carboxylic acid;
2-[4-(2-cyclobutylsulfanyl-pyridin-3-ylmethoxy)-2,3-dimethyl-phenyl]-cyclopropane carboxylic acid;
2-[4-(6-isopropylsulfanyl-pyridin-2-ylmethoxy)-2,3-dimethyl-phenyl]-cyclopropane carboxylic acid;
2-[4-(6-cyclobutylsulfanyl-pyridin-2-ylmethoxy)-3,5-difluoro-benzyl]-cyclopropane carboxylic acid;
2-[3,5-difluoro-4-(2-isopropylsulfanyl-pyridin-3-ylmethoxy)-benzyl]-cyclopropane carboxylic acid;
2-[3,5-difluoro-4-(2-propylsulfanyl-pyridin-3-ylmethoxy)-benzyl]-cyclopropane carboxylic acid;
[6-(2-cyclopentylsulfanyl-pyridin-3-ylmethoxy)-7-methyl-benzofuran-3-yl]-acetic acid;
2-[3-fluoro-4-(2-propylsulfanyl-pyridin-3-ylmethoxy)-phenyl]-cyclopropane carboxylic acid (less polar);
{2-[4-(6-cyclopentylsulfanyl-pyridin-2-ylmethoxy)-3-fluoro-phenyl]-cyclopropyl}-acetic acid;
{2-[3-fluoro-4-(2-propylsulfanyl-pyridin-3-ylmethoxy)-phenyl]-cyclopropyl}-acetic acid;
[6-(2-cyclopentylsulfanyl-pyridin-3-ylmethoxy)-5,7-difluoro-benzofuran-3-yl]-acetic acid;
[6-(2-cyclopentylsulfanyl-pyridin-3-ylmethoxy)-5,7-difluoro-2,3-dihydro-benzofuran-3-yl]-acetic acid;
2-[3-chloro-4-(2-cyclobutylsulfanyl-pyridin-3-ylmethoxy)-phenyl]-cyclopropane carboxylic acid (less polar);
2-[3-chloro-4-(2-cyclobutylsulfanyl-pyridin-3-ylmethoxy)-phenyl]-cyclopropane carboxylic acid (more polar);
2-[3-chloro-4-(2-isopropylsulfanyl-pyridin-3-ylmethoxy)-phenyl]-cyclopropane carboxylic acid (more polar);
2-[3-chloro-4-(2-cyclopropylmethylsulfanyl-pyridin-3-yl-methoxy)-phenyl]-cyclopropane carboxylic acid (more polar);
2-[3-chloro-4-(6-cyclopropylmethylsulfanyl-pyridin-2-yl-methoxy)-phenyl]-cyclopropane carboxylic acid (more polar);
2-[4-(2-cyclopropylmethylsulfanyl-pyridin-3-ylmethoxy)-3-fluoro-phenyl]-cyclopropane carboxylic acid (less polar);
2-[4-(2-cyclopentylsulfanyl-pyridin-3-ylmethoxy)-3-fluoro-phenyl]-cyclopropane carboxylic acid (less polar);
2-[3-fluoro-4-(6-isopropylsulfanyl-pyridin-2-ylmethoxy)-phenyl]-cyclopropane carboxylic acid (less polar);
2-[3-chloro-4-(6-cyclobutylsulfanyl-pyridin-2-ylmethoxy)-phenyl]-cyclopropane carboxylic acid (more polar);
2-[4-(2-cyclobutylsulfanyl-pyridin-3-ylmethoxy)-3-fluoro-phenyl]-cyclopropane carboxylic acid (less polar);
2-[4-(6-cyclopentylsulfanyl-pyridin-2-ylmethoxy)-3-fluoro-phenyl]-cyclopropane carboxylic acid (less polar);
2-[4-(6-cyclobutylsulfanyl-pyridin-2-ylmethoxy)-3-fluoro-phenyl]-cyclopropane carboxylic acid (less polar);
2-[4-(2-cyclopropylmethylsulfanyl-pyridin-3-ylmethoxy)-3,5-difluoro-phenyl]-cyclo propane carboxylic acid (less polar);
2-[4-(2-cyclopropylmethylsulfanyl-pyridin-3-ylmethoxy)-3,5-difluoro-phenyl]-cyclo propane carboxylic acid (more polar);
2-[3,5-difluoro-4-(2-isopropylsulfanyl-pyridin-3-yl-methoxy)-phenyl]-cyclopropane carboxylic acid (more polar);
2-[3,5-difluoro-4-(2-propylsulfanyl-pyridin-3-ylmethoxy)-phenyl]-cyclopropane carboxylic acid (more polar);
2-[4-(2-cyclopentylsulfanyl-pyridin-3-ylmethoxy)-3,5-difluoro-phenyl]-cyclopropane carboxylic acid (more polar);
3-[3-chloro-4-(6-isopropylsulfanyl-pyridin-2-ylmethoxy)-phenyl]-propionic acid;
3-[3-chloro-4-(6-cyclopropylmethylsulfanyl-pyridin-2-yl-methoxy)-phenyl]-propionic acid;
3-[3-chloro-4-(6-cyclopentylsulfanyl-pyridin-2-yl-methoxy)-phenyl]-propionic acid;
3-[3-fluoro-4-(2-propylsulfanyl-pyridin-3-ylmethoxy)-phenyl]-propionic acid;
3-[4-(2-cyclobutylsulfanyl-pyridin-3-ylmethoxy)-3-fluoro-phenyl]-propionic acid;
3-[4-(2-cyclopentylsulfanyl-pyridin-3-ylmethoxy)-3-fluoro-phenyl]-propionic acid;
3-[4-(2-cyclopropylmethylsulfanyl-pyridin-3-ylmethoxy)-3-fluoro-phenyl]-propionic acid;
3-[4-(6-cyclobutylsulfanyl-pyridin-2-ylmethoxy)-3-fluoro-phenyl]-propionic acid;
3-[3-fluoro-4-(6-isopropylsulfanyl-pyridin-2-ylmethoxy)-phenyl]-propionic acid;
3-[4-(6-cyclopentylsulfanyl-pyridin-2-ylmethoxy)-3-fluoro-phenyl]-propionic acid;
3-[4-(6-cyclopropylmethylsulfanyl-pyridin-2-ylmethoxy)-3-fluoro-phenyl]-propionic acid;
2-[3,5-difluoro-4-(6-isopropylsulfanyl-pyridin-2-yl-methoxy)-phenyl]-cyclopropane carboxylic acid (more polar);
2-[4-(6-cyclopropylmethylsulfanyl-pyridin-2-ylmethoxy)-3,5-difluoro-phenyl]-cyclo propane carboxylic acid (more polar);
2-[4-(6-cyclopentylsulfanyl-pyridin-2-ylmethoxy)-3,5-difluoro-phenyl]-cyclopropane carboxylic acid (more polar);
2-[4-(6-cyclobutylsulfanyl-pyridin-2-ylmethoxy)-3,5-difluoro-phenyl]-cyclopropane carboxylic acid (more polar);
2-[4-(2-cyclobutylsulfanyl-pyridin-3-ylmethoxy)-3,5-difluoro-phenyl]-cyclopropane carboxylic acid (more polar);
3-[3-chloro-4-(2-cyclopropylmethylsulfanyl-pyridin-3-yl-methoxy)-phenyl]-propionic acid;
3-[3-chloro-4-(2-cyclobutylsulfanyl-pyridin-3-ylmethoxy)-phenyl]-propionic acid;
3-[3-chloro-4-(6-cyclobutylsulfanyl-pyridin-2-ylmethoxy)-phenyl]-propionic acid;
3-[3-chloro-4-(2-isopropylsulfanyl-6-methyl-pyridin-3-yl-methoxy)-phenyl]-propionic acid;
3-[3-chloro-4-(2-cyclopentylsulfanyl-6-methyl-pyridin-3-ylmethoxy)-phenyl]-propionic acid;
2-[3-fluoro-4-(2-isopropylsulfanyl-pyridin-3-ylmethoxy)-phenyl]-cyclopropane carboxylic acid (more polar);
2-[3-fluoro-4-(2-propylsulfanyl-pyridin-3-ylmethoxy)-phenyl]-cyclopropane carboxylic acid (more polar);
2-[4-(2-cyclopentylsulfanyl-pyridin-3-ylmethoxy)-3-fluoro-phenyl]-cyclopropane carboxylic acid (more polar);

2-[4-(2-cyclopropylmethylsulfanyl-pyridin-3-ylmethoxy)-3-fluoro-phenyl]-cyclopropane carboxylic acid (more polar);

2-[3-fluoro-4-(6-isopropylsulfanyl-pyridin-2-ylmethoxy)-phenyl]-cyclopropane carboxylic acid (more polar);

2-[4-(6-cyclobutylsulfanyl-pyridin-2-ylmethoxy)-3-fluoro-phenyl]-cyclopropane carboxylic acid (more polar);

2-[4-(6-cyclopentylsulfanyl-pyridin-2-ylmethoxy)-3-fluoro-phenyl]-cyclopropane carboxylic acid (more polar);

2-[4-(2-cyclobutylsulfanyl-pyridin-3-ylmethoxy)-3-fluoro-phenyl]-cyclopropane carboxylic acid (more polar);

2-[4-(6-cyclopropylmethylsulfanyl-pyridin-2-ylmethoxy)-3-fluoro-phenyl]-cyclopropane carboxylic acid (more polar);

3-{4-[(2-cyclopentylsulfanyl-pyridin-3-ylmethyl)-amino]-phenyl}-propionic acid;

3-{4-[(6-cyclopentylsulfanyl-pyridin-2-ylmethyl)-amino]-phenyl}-propionic acid;

3-[4-[(2-cyclopentylsulfanyl-pyridin-3-ylmethoxy)-2-fluoro-phenyl]-propionic acid;

2-[4-[(2-cyclopentylsulfanyl-pyridin-3-ylmethoxy)-2-fluoro-phenyl]-cyclopropane carboxylic acid;

3-[4-[(2-cyclobutylsulfanyl-pyridin-3-ylmethoxy)-2-fluoro-phenyl]-propionic acid;

3-[4-[(6-cyclobutylsulfanyl-pyridin-2-ylmethoxy)-2-fluoro-phenyl]-propionic acid;

3-[4-[(6-cyclopentylsulfanyl-pyridin-2-ylmethoxy)-2-fluoro-phenyl]-propionic acid;

3-[4-[(2-cyclopropylmethylsulfanyl-pyridin-3-ylmethoxy)-2-fluoro-phenyl]-propionic acid;

3-[4-[(6-cyclopropylmethylsulfanyl-pyridin-2-ylmethoxy)-2-fluoro-phenyl]-propionic acid;

3-[4-[(2-cyclobutylsulfanyl-pyridin-3-ylmethoxy)-phenyl]-propionic acid;

3-[4-[(6-cyclobutylsulfanyl-pyridin-2-ylmethoxy)-phenyl]-propionic acid;

3-[4-[(2-cyclopropylmethylsulfanyl-pyridin-3-ylmethoxy)-phenyl]-propionic acid;

3-[4-[(6-cyclopropylmethylsulfanyl-pyridin-2-ylmethoxy)-phenyl]-propionic acid;

3-[4-[(2-cyclopentylsulfanyl-6-methyl-pyridin-3-ylmethoxy)-phenyl]-propionic acid; and 3-[4-[(2-isopropylsulfanyl-6-methyl-pyridin-3-ylmethoxy)-phenyl]-propionic acid.

The terms and abbreviations used herein have their original meanings unless indicated otherwise.

The present invention also provides a method for preparing the compounds of Formula 1. Hereinafter, the method for preparing the compounds of Formula 1 is explained based on exemplary reactions in order to illustrate the present invention. However, a person skilled in the art could prepare the compounds of Formula 1 by various methods based on the structure of Formula 1, and such methods should be interpreted as being within the scope of the present invention. That is, the compounds of Formula 1 may be prepared by the methods described herein or by combining various methods disclosed in the prior art, which should be interpreted as being within the scope of the present invention. Accordingly, a method for preparing the compounds of Formula 1 is not limited to the following methods.

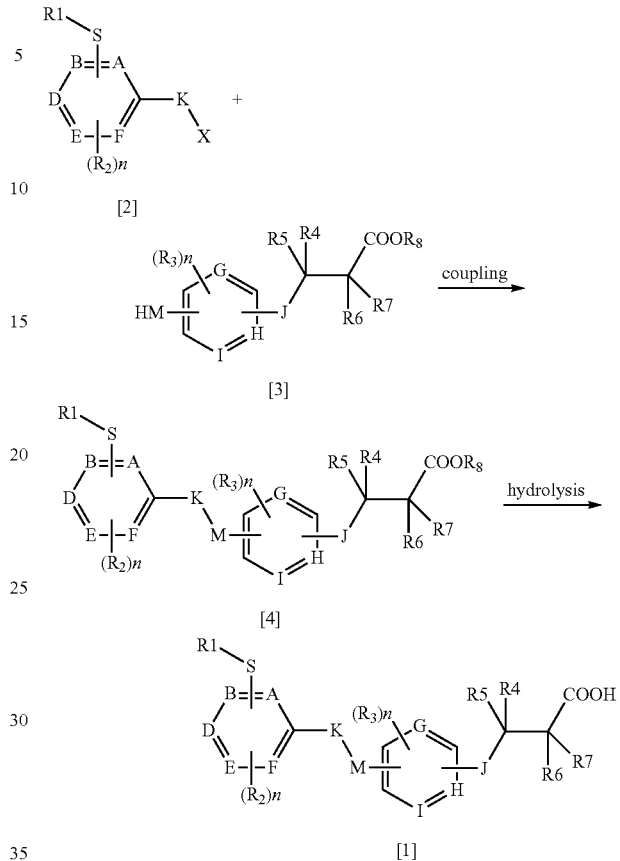

[Reaction scheme 1]

wherein,
X represents OH, SH or halogen,
M represents O, N or S,
R8 represents alkyl or aryl, and
A, B, D, E, F, G, H, I, J, K, M, R1, R2, R3, R4, R6, R7 and n are as described in the definition of the compounds of Formula 1.

Hereinafter, reaction scheme 1 will be explained in detail.

Compound 4 can be obtained by the reaction of Compound 2 in which X is halogen with Compound 3 in the presence of a conventional base. Compound 4 is also obtained by Mitsunobu reaction of Compound 2 in which X is hydroxyl, amine or thiol with Compound 3. Compound 4 is hydrolyzed by using metallic base to obtain Compound 1.

In the above reaction, conventional metallic base and organic base can be used. Exemplary bases include, but are not limited to, metallic base such as sodium hydride (NaH), sodium hydroxide (NaOH), potassium hydroxide (KOH), lithium hydroxide (LiOH), cesium carbonate ($Cs_2CO_3$), sodium carbonate ($Na_2CO_3$) and potassium carbonate ($K_2CO_3$), and organic base such as diisopropylethylamine, triethylamine and 1,8-diazabicyclo[5,4,0]undec-7-ene (DBU).

The above reactions can be carried out in conventional solvents which do not have an adverse effect on the reactions. Preferable solvents include, but are not limited to, dimethylformamide, dimethylacetamide, tetrahydrofuran, acetonitrile, methanol, ethanol, water, 1,2-dichloroethane, dimethylsulfoxide, ethylether, methyl tert-butylether, methylene chloride, chloroform and mixtures thereof.

In the above reactions, unexplained compounds are known compounds or compounds easily obtainable from known compounds by known methods or similar methods.

The compounds of Formula 1 obtained by the above methods can be separated or purified from the reaction products by conventional methods such as recrystallization, ionospheresis, silica gel column chromatography or ion-exchange chromatography.

As described above, the compounds according to the present invention, starting materials or intermediates for the preparation thereof can be prepared by a variety of methods, which should be interpreted as being within the scope of the present invention.

The compounds of Formula 1 according to the present invention have the effect of GPR120 agonists. Accordingly, the present invention provides a pharmaceutical composition as GPR120 agonists comprising the compounds of Formula 1, pharmaceutically acceptable salts or isomers thereof as an active component.

Exemplary diseases which can be prevented or treated by the pharmaceutical composition according to the present invention as GPR120 agonists include, but are not limited to, diabetes, complications of diabetes, inflammation, obesity, non-alcoholic fatty liver, steatohepatitis or osteoporosis. The pharmaceutical composition of the present invention can be used to prevent or treat type 1 or type 2 diabetes. Specifically, the present invention provides a composition for lowering blood glucose level comprising an effective amount of a compound of Formula 1, a pharmaceutically acceptable salt or isomer thereof and a pharmaceutically acceptable carrier.

In addition, the present invention provides a method for preparing the composition for preventing or treating diabetes, complications of diabetes, inflammation, obesity, non-alcoholic fatty liver, steatohepatitis or osteoporosis which comprises the step of mixing the compound of Formula 1, a pharmaceutically acceptable salt or isomer thereof as an active component and a pharmaceutically acceptable carrier.

According to the present invention, the "pharmaceutical composition" or the "composition for lowering blood glucose level" can include other components such as carriers, diluents, excipients, etc., in addition to the active component of the present invention. Accordingly, the pharmaceutical composition can include pharmaceutically acceptable carriers, diluents, excipients or combinations thereof as necessary. The pharmaceutical composition facilitates the administration of compounds into the body. Various methods for administering the compounds include, but are not limited to, oral, injection, aerosol, parenteral and local administration.

Herein, "carriers" mean compounds that facilitate the addition of compounds into the cell or tissue. For example, dimethylsulfoxide (DMSO) is a conventional carrier facilitating the administration of many organic compounds into the living cell or tissue.

Herein, "diluents" mean compounds that not only stabilize a biologically active form but are diluted in solvent dissolving the compounds. Dissolved salts in buffer are used as diluents in this field. A conventionally used buffer is a phosphate buffer saline mimicking salt form in body fluid. Since buffer solution can control the pH of the solution at low concentration, buffer diluents hardly modify the biological activity of compounds.

Herein, "pharmaceutically acceptable" means such property that does not impair the biological activity and physical property of compounds.

The compounds according to the present invention can be formulated as various pharmaceutically administered dosage forms. In the preparation of the pharmaceutical composition of the present invention, an active component—specifically, the compound of Formula 1 or a pharmaceutically acceptable salt or isomer thereof—is mixed with selected pharmaceutically acceptable carriers considering the dosage form to be prepared. For example, the pharmaceutical composition of the present invention can be formulated as injections, oral preparations and the like, as needed.

The compounds of the present invention can be formulated by conventional methods using known pharmaceutical carriers and excipients, and inserted into a unit or multi-unit containers. The formulations may be solution, suspension or emulsion in oil or aqueous solvent and include conventional dispersing agents, suspending agents or sta-bilizing agents. In addition, the compounds may be, for example, dry powder form which is dissolved in sterilized pyrogen-free water before use. The compounds of the present invention can be formulated into suppositories by using a conventional sup-pository base such as cocoa butter or other glycerides. Solid forms for oral administration include capsules, tablets, pills, powders and granules. Capsules and tablets are preferred. Tablets and pills are preferably enteric-coated. Solid forms are manufactured by mixing the compounds of the present invention with at least one carrier selected from inert diluents such as sucrose, lactose or starch, lubricants such as magnesium stearate, disintegrating agents, binders and the like.

The compounds according to the present invention can be administered in combination with other drugs—for example, other antidiabetics, as required.

The dose of the compounds according to the present invention is determined by a physician's prescription considering the patient's body weight, age and disease condition. A typical dose for adults is in the range of about 0.3 to 500 mg per day according to the frequency and intensity of administration. A typical daily dose of intramuscular or intravenous administration for adults is in the range of about 1 to 300 mg per day which can be administered in divided unit dosages. Some patients need a higher daily dose.

The present invention also provides a method for preventing or treating diseases by using an effective amount of the compound of Formula 1 or a pharmaceutically acceptable salt or isomer thereof as an active component of GPR120 agonists. Representative diseases to be treated by GPR120 agonists include, but are not limited to, metabolic disorders such as the above-mentioned diabetes, complications of diabetes, inflammation, obesity, non-alcoholic fatty liver, steatohepatitis, osteoporosis and the like. Herein, the term "treatment" is used to mean deterring, delaying or ameliorating the progress of diseases in a subject exhibiting symptoms of diseases. The term "prevention" is used to mean deterring, delaying or ameliorating the sign of diseases in a subject at risk of exhibiting symptoms of diseases, even if he or she does not exhibit the symptoms.

Advantageous Effects of Invention

The thioaryl derivatives of Formula 1 according to the present invention promote GLP-1 formation in the gastrointestinal tract and improve insulin resistance in macrophages, pancreas cells, etc. due to anti-inflammatory action, and can accordingly be effectively used for preventing or treating diabetes, complications of diabetes, inflammation, obesity, non-alcoholic fatty liver, steatohepatitis or osteoporosis.

MODE FOR THE INVENTION

The present invention is explained in more detail by the following Examples. However, these Examples seek to illustrate the present invention only, and the scope of the present invention is not limited by them.

Hereinafter, M means molar concentration and N means normal concentration. Furthermore, abbreviations used in the following Preparations and Examples are as follows:

$BBr_3$: boron tribromide
$CH_3CN$: acetonitrile
$(CH_3)_3P$: trimethyl phosphine
$Cs_2CO3$: cesium carbonate
DCM, MC: dichloromethane, methylene chloride
Dioxane: dioxane
DMAP: 4-dimethylaminopyridine
DMF: N,N-dimethylformamide
DMSO: dimethylsulfoxide
EtOAc: ethylacetate
EtOH: ethanol
$Et_2O$: diethylether
HCl: hydrochloric acid
Hex: n-hexane
$K_2CO_3$: potassium carbonate
KOH: potassium hydroxide
KHMDS: potassium hexamethyldisilane
LAH: lithium aluminum hydride
LDA: lithium diisopropylamide
LiBH4: lithium borohydride
LiOH: lithium hydroxide
MeI: methyl iodide
MeOH: methanol
$MgSO_4$: magnesium sulfate
$NaBH_4$: sodium borohydride
NaCl: sodium chloride
NaH: sodium hydride
NaOH: sodium hydroxide
$Na_2S_2O_3$ $5H_2O$: sodium thiosulfate pentahydrate
Pd/C: palladium/carbon
$Pd_2(dba)_3$: tris(dibenzylidene acetone)dipalladium(0)
$SOCl_2$: thionyl chloride
TEA: triethylamine
TFA: trifluoroacetic acid
THF: tetrahydrofurane

PREPARATION EXAMPLE 1

3-chloromethyl-2-isopropylsulfanyl-pyridine

Step A: 2-isopropylsulfanyl-nicotinic acid

2-Mercapto-nicotinic acid (5.0 g, 32.22 mmol) was dissolved in DMF (40 mL), and the solution was cooled to 0~5° C. NaH (6.4 g, 161.1 mmol) was added thereto slowly, and the mixture was stirred at 0~5° C. for 30 minutes. 2-Iodopropane (9.65 mL, 96.66 mmol) was added thereto, and the mixture was stirred at room temperature for 2 hours. After the termination of the reaction, the reactant was concentrated under reduced pressure and water was added to dilute the residue. 3N HCl was added to adjust the pH of the aqueous solution to 2~3, and the mixture was extracted with EtOAc. The organic layer was dried with $MgSO_4$ and concentrated under reduced pressure. The reaction product was used in the next step without a separate purification process.

$^1$H-NMR (DMSO-$d_6$) δ 8.57(1H, m), 8.12(1H, m), 7.16 (1H, m), 3.96(1H, m), 1.28(6H, d)

Step B: (2-isopropylsulfanyl-pyridin-3-yl)-methanol

2-Isopropylsulfanyl-nicotinic acid obtained in Step A was dissolved in THF (50 mL), and the solution was cooled to 0~5° C. LAH (3.06 g, 80.55 mmol) was added thereto slowly, and the mixture was stirred at 0~5° C. for 30 minutes and then at room temperature for 2 hours. After the termination of the reaction, saturated sodium sulfate aqueous solution was added thereto and the mixture was stirred for 30 minutes. After the addition of EtOAc, solid material was removed by using cellite. The organic layer was dried with $MgSO_4$, filtrated and concentrated under reduced pressure. The residue was purified by column chromatography (eluent, EtOAc/Hex=1/3) to obtain the title compound (3.94 g, 67%).

$^1$H-NMR (CDCl3) δ 8.37(1H, m), 7.61(1H, m), 7.02(1H, m), 4.66(2H, s), 4.16(1H, m), 1.42(6H, d)

Step C: 3-chloromethyl-2-isopropylsulfanyl-pyridine (2-Isopropylsulfanyl-pyridin-3-yl)-methanol (3.0 g, 16.37 mmol) obtained in Step B was dissolved in $CH_3CN$ (20 mL), and $SOCl_2$(2.39 mL, 32.74 mmol) was added thereto dropwise at 0° C. The mixture was stirred at room temperature for 2 hours. After the termination of the reaction, the reactant was concentrated under reduced pressure. After the addition of EtOAc, the organic layer was washed with water, dried with $MgSO_4$, filtrated and concentrated under reduced pressure to obtain the title compound (3.04 g, 92%).

$^1$H-NMR (CDCl3) δ 8.41(1H, m), 7.61(1H, m), 7.01(1H, m), 4.6 0(2H, s), 4.17(1H, m), 1.41(6H, d)

PREPARATION EXAMPLE 2

3-(3,5-difluoro-4-hydroxy-phenyl)-propionic acid ethyl ester

Step A: 3,5-difluoro-4-hydroxy-benzaldehyde

TFA (7 mL) was added to 2,6-difluoro-phenol (1.0 g, 7.69 mmol) and hexam-ethylenetetraamine (1.08 g, 7.69 mmol), and the mixture was stirred at 75~80° C. for 12 hours. The reactant was cooled, diluted with water, and then extracted with DCM/MeOH (9:1) solution three or four times. The organic layer was concentrated under reduced pressure, and DCM was added to the residue. The mixture was dried with $MgSO_4$ and concentrated under reduced pressure. The reaction product was used in the next step without a separate purification process.

Step B: 4-benzyloxy-3,5-difluoro-benzaldehyde 3,5-Difluoro-4-hydroxy-benzaldehyde obtained in Step A was dissolved in $CH_3CN$ (15 mL), and $Cs_2CO_3$(6.3 g, 19.23 mmol) was added to the solution. The mixture was cooled to 0~5° C. Benzylbromide (1.1 mL, 9.23 mmol) was added slowly thereto, and the mixture was stirred at room temperature for 2 hours. After the termination of the reaction, the reactant was filtered and then concentrated under reduced pressure. The residue was purified by column chromatography (eluent, EtOAc/Hex=1/7) to obtain the title compound (1.76 g, 92%).

$^1$H NMR (400 MHz, CDCl$_3$) δ 9.81(t, 1H), 7.46-7.31(m, 7H), 5.32(s, 2H)

Step C: (E)-3-(4-benzyloxy-3,5-difluoro-phenyl)-acrylic acid ethyl ester

4-Benzyloxy-3,5-difluoro-benzaldehyde (1.2 g, 4.83 mmol) obtained in Step B and carbethoxymethylene triphenylphosphorane (2.0 g, 5.78 mmol) was dissolved in THF (10 mL), and the solution was stirred at 65~75° C. for 1 hour. After the termination of the reaction, the reactant was cooled and concentrated under reduced pressure. The residue was purified by column chromatography (eluent, EtOAc/Hex=1/10) to obtain the title compound (1.2 g, 78%).

$^1$H NMR (400 MHz, CDCl$_3$) δ 7.48(d, 1H), 7.45-7.40(m, 2H), 7.39-7.29(m, 3H), 7.02(d, 2H), 6.29(d, 1H), 5.21(s, 2H), 4.25(q, 2H), 1.32(t, 3H)

Step D: 3-(3,5-difluoro-4-hydroxy-phenyl)-propionic acid ethyl ester (E)-3-(4-Benzyloxy-3,5-difluoro-phenyl)-acrylic acid ethyl ester (1.2 g, 3.77 mmol) obtained in Step C was dissolved in EtOH (20 mL), and 10% Pd/C (120 mg) was added to the solution. The mixture was stirred at room temperature under hydrogen atmosphere for 12 hours. The reactant was filtered by using celite and concentrated under reduced pressure to obtain the title compound (0.85 g, 98%).

$^1$H NMR (400 MHz, CDCl$_3$) δ 6.77(d, 2H), 4.11(q, 2H), 2.83(t, 2H), 2.59(t, 2H), 1.22(t, 3H)

PREPARATION EXAMPLE 3

3-(4-hydroxy-phenyl)-2-methyl-propionic acid ethyl ester

Step A: (E)-3-(4-benzyloxy-phenyl)-2-methyl-acrylic acid ethyl ester

Carbethoxyethylidene triphenylphosphorane (1.02 g, 2.81 mmol) was dissolved in anhydrous THF (25 mL), and 4-benzyloxy-benzaldehyde (0.5 g, 2.36 mmol)/THF (10 mL) solution was added dropwise thereto at −78° C. The mixture was heated slowly to room temperature and then stirred for 12 hours. After the termination of the reaction, the reactant was concentrated under reduced pressure. The residue was added with water and then extracted with EtOAc. The organic layer was dried with MgSO$_4$ and purified by column chromatography (eluent, EtOAc/Hex=1/9) to obtain the title compound (0.68 g, 97.4%).

$^1$H NMR (400 MHz, CDCl$_3$) δ 1.28 and 1.34 (2t, 3H), 2.05 and 2.13 (2s, 3H), 4.18-4.30 (2q, 2H), 5.10 (s, 2H), 6.97-7.02 (m, 2H), 7.31-7.45 (m, 7H), 7.64 (br. s, 1H)

Step B: 3-(4-hydroxy-phenyl)-2-methyl-propionic acid ethyl ester (E)-3-(4-Benzyloxy-phenyl)-2-methyl-acrylic acid ethyl ester (0.68 g, 2.29 mmol) obtained in Step A was reacted in the same manner as in Step D of Preparation Example 2 to obtain the title compound (0.47 g, 98.4%).

$^1$H NMR (400 MHz, CDCl$_3$) δ 1.14 (d, 3H), 1.19 (t, 3H), 2.57-2.75 (m, 2H), 2.85-2.30 (m, 1H), 4.09 (d, 2H), 6.74(d, 2H), 7.03 (d, 2H)

PREPARATION EXAMPLE 4

3-(4-hydroxy-phenyl)-propionic acid methyl ester

After 3-(4-hydroxy-phenyl)propionic acid (3 g, 18 mmol) was added with MeOH (6 mL), 4M HCl/dioxane solution (18 mL, 72 mmol) was added thereto, and the mixture was stirred at room temperature for 3 hours. The reactant was concentrated, added with EtOAc, and then washed with NaCl aqueous solution. The organic layer was separated, dried with MgSO$_4$, and filtered to obtain the title compound (3.26 g, 99%).

$^1$H-NMR (CDCl$_3$) δ 7.06(2H, m), 6.75(2H, m), 4.79(1H, brs, OH), 3.66(3H, s), 2.88(2H, t), 2.59(2H, t)

PREPARATION EXAMPLE 5

2-sec-butylsulfanyl-6-chloromethyl-pyridine

Step A: 6-sec-butylsulfanyl-pyridine-2-carboxylic acid ethyl ester

6-Mercapto-pyridine-2-carboxylic acid ethyl ester (0.25 g, 1.3 mmol) was added with DMF (7 mL), and the mixture was cooled to 0° C. NaH (0.065 g, 1.56 mmol) was added thereto, and the mixture was stirred for 30 minutes. 2-Iodobutane (0.2 mL, 1.56 mmol) was added thereto, and the mixture was stirred at room temperature for 3 hours. The reactant was added with water and then extracted with EtOAc. The organic layer was separated, dried with MgSO$_4$, and purified by column chromatography to obtain the title compound (0.17 g, 52%).

$^1$H-NMR (CDCl$_3$) δ 7.74(1H, d), 7.56(1H, t), 7.28(1H, d), 4.40(2H, q), 3.96(1H, m), 1.80(1H, m), 1.70(1H, m), 1.40 (3H+3H), 1.03(3H, t)

Step B: (6-sec-butylsulfanyl-pyridin-2-yl)-methanol 6-sec-Butylsulfanyl-pyridine-2-carboxylic acid ethyl ester (0.17 g, 0.71 mmol) obtained in Step A was dissolved in anhydrous THF (3 mL). 2.0 M LiBH$_4$ solution (0.5 mL, 1.0 mmol) was added thereto, and the mixture was stirred at 40° C. for 1 hour. After the termination of the reaction, the reactant was cooled to room temperature. The reactant was added with water and then extracted with EtOAc. The organic layer was separated, dried with MgSO$_4$, and concentrated under reduced pressure to obtain the title compound (0.126 g, 90%).

$^1$H-NMR (CDCl$_3$) δ 7.47(1H, m), 7.06(1H, m), 6.86(1H, m), 4.70(2H, d), 3.84(1H, m), 3.71(1H, t, OH), 1.76(1H, m), 1.70(1H, m), 1.40(3H, d), 1.03(3H, t)

Step C: 2-sec-butylsulfanyl-6-chloromethyl-pyridine (6-sec-Butylsulfanyl-pyridin-2-yl)-methanol (0.126 g, 0.64 mmol) obtained in Step B was reacted in the same manner as in Step C of Preparation Example 1 to obtain the title compound (0.128 g, 93%).

$^1$H-NMR (CDCl$_3$) δ 7.47(1H, m), 7.09(2H, m), 4.59(2H, s), 3.87(1H, m), 1.73(1H, m), 1.67(1H, m), 1.38(3H, d), 1.02(3H, t)

PREPARATION EXAMPLE 6

3-(3-fluoro-4-hydroxy-phenyl)-propionic acid methyl ester

Step A: 1-benzyloxy-4-bromo-2-fluoro-benzene

DMF (12 mL), K$_2$CO$_3$(1.19 g, 8.55 mmol) and benzyl bromide (0.75 mL, 6.27 mmol) was added to 4-bromo-2-fluorophenol (1.1 g, 5.7 mmol), and the mixture was stirred at room temperature for 2 hours. After the termination of the reaction, the reactant was concentrated and the residue was diluted with 20 mL water. The mixture was extracted with EtOAc. The organic layer was separated and dried with MgSO$_4$ to obtain the title compound (1.62 g, 100%).

Step B: (E)-3-(4-benzyloxy-3-fluoro-phenyl)-acrylic acid methyl ester

1-Benzyloxy-4-bromo-2-fluoro-benzene (1.62 g, 5.7 mmol) obtained in Step A was added with methyl acrylate (1 mL), 1,4-dioxane (19 mL), Pd$_2$(dba)$_3$(0.1 g, 0.11 mmol), TEA (1.6 mL, 11.4 mmol) and tri-t-butylphosphine tetrafluoroborate (0.16 g, 0.57 mmol), and the mixture was stirred at 100° C. for 6 hours. The reactant was filtered by using celite, and the filtrate was washed with EtOAc and purified by column chromatography to obtain the title compound (0.37 g, 22%).
$^1$H-NMR (CDCl$_3$) δ 7.58(1H, d, J=15.9 Hz), 7.44-7.28 (6H, m), 7.19(1H, m), 6.98(1H, t), 6.28(1H, d, J=15.9 Hz), 5.18(2H, s), 3.79(3H, s)

Step C: 3-(3-fluoro-4-hydroxy-phenyl)-propionic acid methyl ester (E)-3-(4-Benzyloxy-3-fluoro-phenyl)-acrylic acid methyl ester (0.37 g, 1.2 mmol) obtained in Step B was dissolved in EtOAc (4 mL) and MeOH (2 mL). The solution was added with 10% Pd/C (0.03 g), and the mixture was stirred under hydrogen atmosphere for 18 hours. The reactant was filtered by using celite, and the filtrate was washed with EtOAc to obtain the title compound (0.25 g, 98%).
$^1$H-NMR (CDCl$_3$) δ 6.93(1H, m), 6.91(1H, m), 6.85(1H, m), 5.02(1H, brs, OH), 3.67(3H, s), 2.87(2H, t), 2.59(2H, t)

PREPARATION EXAMPLE 7

3-(2-fluoro-4-hydroxy-phenyl)-propionic acid ethyl ester

Step A: (E)-3-(2-fluoro-4-methoxy-phenyl)-acrylic acid ethyl ester

2-Fluoro-4-methoxy-benzaldehyde (2 g, 12.98 mmol) was reacted in the same manner as in Step C of Preparation Example 2 to obtain the title compound (2.90 g, 99.7%).
$^1$H NMR (400 MHz, CDCl$_3$) δ 7.75(1H, d, 16Hz), 7.45 (1H, t, 8Hz), 6.71(1H, dd, 8 and 2 Hz), 6.64(1H, dd, 12 and 2 Hz), 6.41(1H, d, 16Hz), 4.26(2H, q, 7Hz), 3.83(3H, s), 1.33(3H, t, 7Hz)

Step B: 3-(2-fluoro-4-methoxy-phenyl)-propionic acid ethyl ester (E)-3-(2-Fluoro-4-methoxy-phenyl)-acrylic acid ethyl ester (2.90 g, 12.93 mmol) obtained in Step A was reacted in the same manner as in Step D of Preparation Example 2 to obtain the title compound (2.85 g, 97%).
$^1$H NMR (400 MHz, CDCl$_3$) δ 7.10(1H, t, 8Hz), 6.63-6.57(2H, m), 4.12(2H, q, 7Hz), 3.83(3H, s), 2.90(2H, t, 8Hz), 2.58(2H, t, 8Hz), 1.23(3H, t, 7Hz)

Step C: 3-(2-fluoro-4-hydroxy-phenyl)-propionic acid ethyl ester 3-(2-Fluoro-4-methoxy-phenyl)-propionic acid ethyl ester (2.5 g, 11.05 mmol) obtained in Step B was dissolved in anhydrous DCM (10 mL). 1M BBr$_3$ solution (33 mL, 33.15 mmol) was added thereto at −78° C., and the mixture was stirred at room temperature for 3 hours. After the termination of the reaction, MeOH was added to the reactant. The mixture was concentrated under reduced pressure and purified by column chromatography (eluent, EtOAc/Hex=1/2) to obtain the title compound (1.88 g, 80%).
$^1$H NMR (400 MHz, CDCl$_3$) δ 7.03(1H, t, 8Hz), 6.55-6.51(2H, m), 5.38(1H, brs), 4.13(2H, q, 7Hz), 2.89(2H, t, 8Hz), 2.59(2H, t, 8Hz), 1.24(3H, t, 7Hz)

PREPARATION EXAMPLE 8

3-chloromethyl-2-cyclopentylsulfanyl-pyridine

Step A: 2-cyclopentylsulfanyl-nicotinic acid

2-Mercapto-nicotinic acid (1.0 g, 6.44 mmol) and bromo-cyclopentane (2 mL, 19.33 mmol) were reacted in the same manner as in Step A of Preparation Example 1 to obtain the title compound, which was used in the next step without a separate purification process.

Step B: (2-cyclopentylsulfanyl-pyridin-3-yl)-methanol

2-Cyclopentylsulfanyl-nicotinic acid obtained in Step A was reacted in the same manner as in Step B of Preparation Example 1 to obtain the title compound (0.65 g, 47%).
$^1$H-NMR (CDCl$_3$) δ 8.41-8.40(1H, m), 7.64-7.62(1H, m), 7.06-7.03(1H, q), 4.70-4.69(2H, d), 4.27-4.20(1H, m), 2.28-2.19(2H, m), 1.81-1.78(2H, m), 1.69-1.63(4H, m)

Step C: 3-chloromethyl-2-cyclopentylsulfanyl-pyridine (2-Cyclopentylsulfanyl-pyridin-3-yl)-methanol (0.6 g, 2.87 mmol) obtained in Step B was dissolved in CH$_3$CN (5 mL), and SOCl$_2$(0.42 mL, 5.74 mmol) was added thereto at 0° C. The mixture was stirred at room temperature for 2 hours. After the termination of the reaction, the reactant was concentrated under reduced pressure to obtain the title compound, which was used in the next step without a separate purification process.

PREPARATION EXAMPLE 9

3-chloromethyl-2-isopropylsulfanyl-6-methyl-pyridine

Step A: 2-chloro-6-methyl-nicotinic acid methyl ester

2-Chloro-6-methyl-nicotinic acid (3.58 g, 20.86 mmol) was dissolved in DMF (34 mL). MeI (5.8 mL, 93.88 mmol) and K$_2$CO$_3$(7.78 g, 56.33 mmol) were added thereto, and the mixture was stirred at room temperature for 2 hours. The reactant was distilled under reduced pressure to remove the solvent and extracted with EtOAc. The organic layer was dried with MgSO$_4$, filtered and concentrated under reduced pressure. The obtained residue was purified by column chromatography (eluent EtOAc/Hex=1/2) to obtain the title compound (3.68 g, 94%).
NMR: $^1$H-NMR (CDCl$_3$) 8.08(1H, d), 7.16(1H, d), 3.92 (3H, s), 2.57(3H, s)

Step B: 2-isopropylsulfanyl-6-methyl-nicotinic acid methyl ester

2-Chloro-6-methyl-nicotinic acid methyl ester (1.39 g, 7.44 mmol) obtained in Step A was dissolved in DMF (15 mL). Cs$_2$CO$_3$(4.88 g, 14.99 mmol) and propane-2-thiol (1.39 mL, 14.99 mmol) were added to the solution, and the mixture was stirred at room temperature for 2 hours. The reactant was concentrated under reduced pressure to remove the solvent. The residue was added with water and then extracted with EtOAc. The organic layer was dried with MgSO$_4$, filtered and concentrated under reduced pressure. The obtained residue was purified by column chromatography (eluent EtOAc/Hex=1/5) to obtain the title compound (1.17 g, 69%).
NMR: $^1$H-NMR (CDCl$_3$) 8.06(1H, d), 6.86(1H, d), 4.15 (1H, m), 3.90(3H, s), 2.53(3H, s), 1.40(6H, d)

Step C: (2-isopropylsulfanyl-6-methyl-nicotinic acid-3-yl)-methanol

2-Isopropylsulfanyl-6-methyl-nicotinic acid methyl ester (498 mg, 2.35 mmol) obtained in Step B was reacted in the same manner as in Step B of Preparation Example 1 to obtain the title compound (384 mg, 82%).
NMR: $^1$H-NMR (CDCl$_3$) 7.46(1H, d), 6.86(1H, d), 4.63 (2H, d), 4.17(1H, m), 2.49(3H, s), 2.01(1H, t), 1.40(6H, d)

Step D: 3-chloromethyl-2-isopropylsulfanyl-6-methyl-pyridine (2-Isopropylsulfanyl-6-methyl-nicotinic acid-3-yl)-methanol (184 mg, 0.931 mmol) obtained in Step C was reacted in the same manner as in Step C of Preparation Example 8 to obtain the title compound, which was used in the next step without a separate purification process.

PREPARATION EXAMPLE 10

2-butylsulfanyl-3-chloromethyl-pyridine

Step A: 2-butylsulfanyl-nicotinic acid

After MeOH (20 mL) was added to 2-mercapto-nicotinic acid (1 g, 6 mmol), the mixture was cooled to 0° C., and 6 M NaOH aqueous solution (3.2 mL) was added slowly thereto. The reactant was stirred at 0° C. for 30 minutes. 1-Iodobutane (0.74 mL, 6 mmol) was added to the reactant, and the mixture was stirred under reflux at 80° C. for 16 hours. The reactant was concentrated under reduced pressure, and 6 M HCl aqueous solution was added thereto to adjust the pH of the solution to 7. The resulting precipitate was filtered and dried to obtain the title compound (1.27 g, 93%).
$^1$H-NMR (DMSO-d$_6$) δ 13.3(1H, brs), 8.61(1H, m), 8.18 (1H, m), 7.21(1H, m), 3.08(2H, t), 1.59(2H, m), 1.44(2H, m), 0.90(3H, t)

Step B: (2-butylsulfanyl-pyridin-3-yl)-methanol

Anhydrous THF (30 mL) in dried flask was cooled to 0° C., LAH (1.14 g, 30 mmol) was added slowly thereto, and the mixture was stirred for 30 minutes. 2-Butylsulfanyl-nicotinic acid (1.27 g, 5.58 mmol) obtained in Step A which is dissolved in anhydrous THF (10 mL) was added slowly thereto, and the mixture was stirred at room temperature for 2 hours. After the termination of the reaction, water (10 mL) was added slowly thereto at 0° C., and the mixture was stirred for 30 minutes. The reactant was extracted with EtOAc, and the organic layer was separated, dried with MgSO$_4$, and concentrated under reduced pressure to obtain the title compound (0.85 g, 77%).

$_1$H-NMR (CDCl$_3$) δ 8.36(1H, m), 7.60(1H, m), 7.00(1H, m), 4.68(2H, s), 3.25(2H, t), 2.10(1H, brs), 1.68(2H, m), 1.47(2H, m), 0.94(3H, t)

Step C: 2-butylsulfanyl-3-chloromethyl-pyridine (2-Butylsulfanyl-pyridin-3-yl)-methanol (0.85 g, 4.3 mmol) obtained in Step B was dissolved in CH$_3$CN (20 mL). SOCl$_2$(0.63 mL, 8.6 mmol) was added thereto, and the mixture was stirred at room temperature for 2 hours. After the termination of the reaction, the reactant was concentrated under reduced pressure to remove the solvent and then added with EtOAc. The organic layer was washed with water, dried with MgSO$_4$, and concentrated under reduced pressure to obtain the title compound (0.77 g, 82%).
$^1$H-NMR (CDCl$_3$) δ 8.39(1H, m), 7.58(1H, m), 7.02(1H, m), 4.62(2H, s), 3.26(2H, t), 1.70(2H, m), 1.47(2H, m), 0.95(3H, t)

PREPARATION EXAMPLE 11 chloromethyl-2-ethylsulfanyl-pyridine

Step A: 2-ethylsulfanyl-nicotinic acid

2-Mercapto-nicotinic acid (2 g, 12.8 mmol) and bromoethane were reacted in the same manner as in Step A of Preparation Example 1 to obtain the title compound (1.9 g, 80%).
$^1$H-NMR (CDCl$_3$) δ 8.61(1H, m), 8.31(1H, m), 7.08(1H, m), 3.20(2H, q), 1.38(3H, t)

Step B: (2-ethylsulfanyl-pyridin-3-yl)-methanol

2-Ethylsulfanyl-nicotinic acid (0.44 g, 2.4 mmol) obtained in Step A was reacted in the same manner as in Step B of Preparation Example 10 to obtain the title compound (0.2 g, 49%).
$^1$H-NMR (CDCl$_3$) δ 8.37(1H, m), 7.60(1H, m), 7.02(1H, m), 4.68(2H, s), 3.26(2H, q), 2.00(1H, brs, OH), 1.38(3H, t)

Step C: 3-chloromethyl-2-ethylsulfanyl-pyridine (2-Ethylsulfanyl-pyridin-3-yl)-methanol (0.2 g, 1.1 mmol) obtained in Step B was reacted in the same manner as in Step C of Preparation Example 10 to obtain the title compound (0.2 g, 90%).
$^1$H-NMR (CDCl$_3$) δ 8.40(1H, m), 7.60(1H, m), 7.02(1H, m), 4.61(2H, s), 3.27(2H, q), 1.38(3H, t)

PREPARATION EXAMPLE 12

3-chloromethyl-2-isobutylsulfanyl-pyridine

Step A: 2-isobutylsulfanyl-nicotinic acid

2-Mercapto-nicotinic acid (2 g, 12.8 mmol) and isobutyliodide were reacted in the same manner as in Step A of Preparation Example 10 to obtain the title compound (2.175 g, 92%).
$^1$H-NMR (CDCl$_3$) δ 8.59(1H, m), 8.29(1H, m), 7.07(1H, m), 3.12(2H, d), 1.97(1H, m), 1.07(6H, d)

Step B: (2-isobutylsulfanyl-pyridin-3-yl)-methanol

2-Isobutylsulfanyl-nicotinic acid (0.43 g, 2 mmol) obtained in Step A was reacted in the same manner as in Step B of Preparation Example 10 to obtain the title compound (0.18 g, 46%).

¹H-NMR (CDCl₃) δ 8.36(1H, m), 7.61(1H, m), 7.01(1H, m), 4.72(2H, s), 3.20(2H, d), 1.95(1H, m), 1.06(6H, d)

Step C: 3-chloromethyl-2-isobutylsulfanyl-pyridine (2-Isobutylsulfanyl-pyridin-3-yl)-methanol (0.18 g, 0.9 mmol) obtained in Step B was reacted in the same manner as in Step C of Preparation Example 10 to obtain the title compound (0.18 g, 92%).
¹H-NMR (CDCl₃) δ 8.38(1H, m), 7.58(1H, m), 7.01(1H, m), 4.64(2H, s), 3.19(2H, d), 1.96(1H, m), 1.06(6H, d)

PREPARATION EXAMPLE 13

4-(4-hydroxy-phenyl)-butyric acid ethyl ester

Step A: (4-benzyloxy-phenyl)-acetic acid methyl ester (4-Hydroxy-phenyl)-acetic acid methyl ester (1.0 g, 6.02 mmol) was dissolved in DMF (10 mL), and K₂CO₃(2.5 g, 18.06 mmol) was added thereto. Benzyl chloride (0.83 mL, 7.22 mmol) was added slowly thereto, and the mixture was stirred at 40~50° C. for 12 hours. The reactant was cooled and concentrated under reduced pressure. The residue was added with water and then extracted with EtOAc. The organic layer was concentrated under reduced pressure, and the residue was purified by column chromatography (eluent, EtOAc/Hex=1/4) to obtain the title compound (1.4 g, 91%).
¹H NMR (400 MHz, CDCl₃) δ 7.43-7.27(m, 5H), 7.18(d, 2H), 6.92(d, 2H), 5.02(s, 2H), 3.66(s, 3H), 3.55(s, 2H)

Step B: 2-(4-benzyloxy-phenyl)-ethanol (4-Benzyloxy-phenyl)-acetic acid methyl ester (1.4 g, 5.46 mmol) obtained in Step A was reacted in the same manner as in Step B of Preparation Example 1 to obtain the title compound (0.71 g, 57%).
¹H NMR (400 MHz, CDCl₃) δ 7.45-7.29(m, 5H), 7.14(d, 2H), 6.93(d, 2H), 5.04(s, 2H), 3.82(q, 2H), 2.81(t, 2H), 1.39(t, 1H)

Step C: (4-benzyloxy-phenyl)-acetaldehyde 2-(4-Benzyloxy-phenyl)-ethanol (0.64 g, 2.80 mmol) obtained in Step B was dissolved in DCM (10 mL), and Dess-Martin periodinane (2.38 g, 5.60 mmol) was added thereto. The reactant was stirred at room temperature for 2 hours, diluted with DCM, and washed with Na₂S₂O₃.5H₂O aqueous solution. The remained organic solution was dried with MgSO₄ and concentrated under reduced pressure. The residue was purified by column chromatography (eluent, EtOAc/Hex=1/5) to obtain the title compound (0.50 g, 79%).
¹H NMR (400 MHz, CDCl₃) δ 9.70(t, 1H), 7.44-7.29(m, 5H), 7.12(d, 2H), 6.97(d, 2H), 5.02(s, 2H), 3.61(d, 2H)

Step D: (E)-4-(4-benzyloxy-phenyl)-2-betenoic acid ethyl ester (4-Benzyloxy-phenyl)-acetaldehyde (0.5 g, 2.21 mmol) obtained in Step C was reacted in the same manner as in Step C of Preparation Example 2 to obtain the title compound (0.55 g, 84%).

Step E: 4-(4-hydroxy-phenyl)-butyric acid ethyl ester (E)-4-(4-Benzyloxy-phenyl)-2-betenoic acid ethyl ester (0.55 g, 1.86 mmol) obtained in Step D was reacted in the same manner as in Step D of Preparation Example 2 to obtain the title compound (0.37 g, 96%).
¹H NMR (400 MHz, CDCl₃) δ 7.02(d, 2H), 6.75(d, 2H), 4.13(q, 2H), 2.57(t, 2H), 2.31(t, 2H), 1.91(m, 2H), 1.25(t, 3H)

PREPARATION EXAMPLE 14

3-chloromethyl-2-propylsulfanyl-pyridine

Step A: 2-propylsulfanyl-nicotinic acid

2-Mercapto-nicotinic acid (1 g, 6.4 mmol) and 1-iodopropane were reacted in the same manner as in Step A of Preparation Example 10 to obtain the title compound (1.22 g, 96%).
¹H-NMR (DMSO-d₆) δ 13.3(1H, brs), 8.60(1H, dd), 8.18(1H, dd), 7.20(1H, dd), 3.06(2H, t), 1.66(2H, m), 1.00 (3H, t)

Step B: (2-propylsulfanyl-pyridin-3-yl)-methanol

2-Propylsulfanyl-nicotinic acid (1.22 g, 6.2 mmol) obtained in Step A was reacted in the same manner as in Step B of Preparation Example 10 to obtain the title compound (0.9 g, 80%).
¹H-NMR (CDCl₃) δ 8.37(1H, m), 7.60(1H, m), 7.02(1H, m), 4.69(2H, s), 3.24(2H, t), 1.74(2H, m), 1.05(3H, t)

Step C: 3-chloromethyl-2-propylsulfanyl-pyridine (2-Propylsulfanyl-pyridin-3-yl)-methanol (0.9 g, 4.9 mmol) obtained in Step B was reacted in the same manner as in Step C of Preparation Example 10 to obtain the title compound (0.9 g, 91%).
¹H-NMR (CDCl₃) δ 8.40(1H, m), 7.59(1H, m), 7.01(1H, m), 4.62(2H, s), 3.24(2H, t), 1.74(2H, m), 1.05(3H, t)

PREPARATION EXAMPLE 15

3-chloromethyl-2-phenylsulfanyl-pyridine

Step A: 2-phenylsulfanyl-nicotinic acid

2-Mercapto-nicotinic acid (100 mg, 0.64 mmol) was dissolved in DMF (5 mL), and then Cu powder (82 mg, 1.28 mmol) and Cs₂CO₃(630 mg, 1.92 mmol) were added in turn thereto. The mixture was stirred at 150~160° C. for 2 hours, cooled to room temperature, and concentrated under reduced pressure. After the residue was diluted with water, 1N HCl was added to adjust the pH of the solution to 2~3. EtOAc was added to the solution, and the mixture was stirred and then filtered. The organic layer was separated, dried with MgSO₄, and concentrated under reduced pressure to obtain the title compound, which was used in the next step without a separate purification process.

Step B: (2-phenylsulfanyl-pyridin-3-yl)-methanol

2-Phenylsulfanyl-nicotinic acid obtained in Step A was reacted in the same manner as in Step B of Preparation Example 1 to obtain the title compound (20 mg, 14%).
¹H NMR (400 MHz, CDCl₃) δ 8.37-8.32(m, 1H), 7.76-7.71(m, 1H), 7.49-7.44(m, 2H), 7.40-7.32(m, 3H), 7.15-7.10 (m, 1H), 4.79(d, 2H), 2.14(t, 1H)

Step C: 3-chloromethyl-2-phenylsulfanyl-pyridine (2-Phenylsulfanyl-pyridin-3-yl)-methanol (20 mg, 0.09 mmol) obtained in Step B was dissolved in CH₃CN (20 mL), and SOCl$_2$(13 uL, 0.18 mmol) was added dropwise thereto at 0° C. The mixture was stirred at room temperature for 2 hours. After the termination of the reaction, the reactant was concentrated under reduced pressure to obtain the title compound, which was used in the next step without a separate purification process.

PREPARATION EXAMPLE 16

2-chloromethyl-6-isopropylsulfanyl)-pyridine

Step A: 6-isopropylsulfanyl-pyridine-2-carboxylic acid methyl ester

6-Bromo-pyridine-2-carboxylic acid methyl ester (0.15 g, 0.69 mmol) was added with DMF (2.3 mL), Cs$_2$CO$_3$(0.45 g, 1.38 mmol) and 2-propanethiol (0.064 mL, 0.69 mmol) in turn, and the mixture was stirred at room temperature for 18 hours. After the termination of the reaction, the reactant was filtered and concentrated under reduced pressure to obtain the title compound (0.13 g, 88%).
$^1$H-NMR (CDCl$_3$) δ 7.76(1H, d), 7.58(1H, t), 7.30(1H, d), 4.07(1H, m), 3.96(3H, s), 1.40(6H, d)

Step B: (6-isopropylsulfanyl-pyridin-2-yl)-methanol

6-Isopropylsulfanyl-pyridine-2-carboxylic acid methyl ester (0.13 g, 0.61 mmol) obtained in Step A was dissolved in anhydrous THF (3 mL). 2.0M LiBH$_4$ solution (0.5 mL, 1 mmol) was added thereto, and the mixture was stirred at 40° C. for 1 hour. After the termination of the reaction, the reactant was cooled to room temperature, added with water, and extracted with EtOAc. The organic layer was separated, dried with MgSO$_4$, and concentrated under reduced pressure to obtain the title compound (0.08 g, 70%).
$^1$H-NMR (CDCl$_3$) δ 7.47(1H, t), 7.07(1H, d), 6.89(1H, d), 4.71(2H, s), 4.01(1H, m), 3.70(1H, brs, OH), 1.42(6H, d)

Step C: 2-chloromethyl-6-isopropylsulfanyl-pyridine (6-Isopropylsulfanyl-pyridin-2-yl)-methanol (0.08 g, 0.43 mmol) obtained in Step B was reacted in the same manner as in Step C of Preparation Example 10 to obtain the title compound (0.081 g, 92%).
$^1$H-NMR (CDCl$_3$) δ 7.49(1H, t), 7.13(1H, d), 7.08(1H, d), 4.61(2H, s), 4.00(1H, m), 1.40(6H, d)

PREPARATION EXAMPLE 17

2-t-butylsulfanyl-3-chloromethyl-pyridine

Step A: 2-t-butylsulfanyl-nicotinic acid ethyl ester

2-Chloro-nicotinic acid ethyl ester (0.23 g, 1.2 mmol) and t-butylthiol were reacted in the same manner as in Step B of Preparation Example 9 to obtain the title compound (0.125 g, 42%).
$^1$H-NMR (CDCl$_3$) δ 8.53(1H, m), 8.11(1H, m), 7.00(1H, m), 4.36(2H, q), 1.63(9H, s), 1.39(3H, t)

Step B: (2-t-butylsulfanyl-pyridin-3-yl)-methanol 2-t-Butylsulfanyl-nicotinic acid ethyl ester (0.125 g, 0.52 mmol) obtained in Step A was reacted in the same manner as in Step C of Preparation Example 9 to obtain the title compound (0.094 g, 91%).
$^1$H-NMR (CDCl$_3$) δ 8.42(1H, m), 7.62(1H, m), 7.07(1H, m), 4.70(2H, s), 1.58(9H, s)

Step C: 2-t-butylsulfanyl-3-chloromethyl-pyridine (2-t-Butylsulfanyl-pyridin-3-yl)-methanol (0.093 g, 0.47 mmol) obtained in Step B was reacted in the same manner as in Step C of Preparation Example 8 to obtain the title compound (0.082 g, 80%).
$^1$H-NMR (CDCl$_3$) δ 8.44(1H, m), 7.64(1H, m), 7.06(1H, m), 4.68(2H, s), 1.58(9H, s)

PREPARATION EXAMPLE 18

3-chloromethyl-2-cyclopropylmethylsulfanyl-pyridine

Step A: 2-cyclopropylmethylsulfanyl-nicotinic acid

2-Mercapto-nicotinic acid (1 g, 6.4 mmol) and bromomethyl cyclopropane were reacted in the same manner as in Step A of Preparation Example 10 to obtain the title compound (1.19 g, 88%).
$^1$H-NMR (DMSO-d$_6$) δ 8.61(1H, m), 8.20(1H, m), 7.22 (1H, m), 3.01(2H, d), 1.07(1H, m), 0.53(2H, m), 0.27(2H, m)

Step B: (2-cyclopropylmethylsulfanyl-pyridin-3-yl)-methanol

2-Cyclopropylmethylsulfanyl-nicotinic acid (0.53 g, 2.5 mmol) obtained in Step A was reacted in the same manner as in Step B of Preparation Example 10 to obtain the title compound (0.45 g, 90%).
$^1$H-NMR (CDCl$_3$) δ 8.36(1H, m), 7.62(1H, m), 7.03(1H, m), 4.70(2H, s), 3.21(2H, d), 2.06(1H, brs, OH), 1.15(1H, m), 0.58(2H, m), 0.32(2H, m)

Step C: 3-chloromethyl-2-cyclopropylmethylsulfanyl-pyridine (2-Cyclopropylmethylsulfanyl-pyridin-3-yl)-methanol (0.427 g, 2.1 mmol) obtained in Step B was reacted in the same manner as in Step C of Preparation Example 10 to obtain the title compound (0.044 g, 94%).
$^1$H-NMR (CDCl$_3$) δ 8.39(1H, m), 7.60(1H, m), 7.03(1H, m), 4.64(2H, s), 3.21(2H, d), 1.17(1H, m), 0.61(2H, m), 0.34(2H, m)

PREPARATION EXAMPLE 19

3-chloromethyl-2-(2,2,2-trifluoro-ethylsulfanyl)-pyridine

Step A: 2-(2,2,2-trifluoro-ethylsulfanyl)-nicotinic acid

2-Mercapto-nicotinic acid (1 g, 6.4 mmol) was reacted in the same manner as in Step A of Preparation Example 10 to obtain the title compound (0.46 g, 30%)
$^1$H-NMR (DMSO-d$_6$) δ 13.69(1H, brs), 8.70(1H, m), 8.30(1H, m), 7.36(1H, m), 4.30(2H, q)

Step B: [2-(2,2,2-trifluoro-ethylsulfanyl)-pyridin-3-yl]-methanol 2-(2,2,2-trifluoro-ethylsulfanyl)-nicotinic acid (0.46 g, 1.93 mmol) obtained in Step A was reacted in the same manner as in Step B of Preparation Example 10 to obtain the title compound (0.38 g, 89%).

$^1$H-NMR (CDCl$_3$) δ 8.38(1H, m), 7.70(1H, m), 7.11(1H, m), 4.70(2H, s), 4.12(2H, q), 1.91(1H, brs, OH)

Step C: 3-chloromethyl-2-(2,2,2-trifluoro-ethylsulfanyl)-pyridine

[2-(2,2,2-trifluoro-ethylsulfanyl)-pyridin-3-yl]-methanol (0.38 g, 1.7 mmol) obtained in Step B was reacted in the same manner as in Step C of Preparation Example 10 to obtain the title compound (0.039 g, 95%).

$^1$H-NMR (CDCl$_3$) δ 8.42(1H, m), 7.65(1H, m), 7.10(1H, m), 4.60(2H, s), 4.14(2H, q)

PREPARATION EXAMPLE 20

2-chloromethyl-6-cyclopropylmethylsulfanyl-pyridine

Step A: 6-mercapto-pyridine-2-carboxylic acid ethyl ester

6-Hydroxy-pyridine-2-carboxylic acid ethyl ester (1.8 g, 10.7 mmol) was dissolved in THF (50 mL), and Lawesson's reagent (2.18 g, 5.35 mmol) was added thereto. The mixture was stirred at room temperature for 24 hours. After the termination of the reaction, the reactant was added with water and then extracted with DCM. The organic layer was separated, dried with MgSO$_4$, concentrated under reduced pressure and then separated by column chromatography to obtain the title compound (1.17 g, 59%).

$^1$H-NMR (DMSO-d$_6$) δ 13.0(1H, brs), 7.47(2H, d), 7.29 (1H, m), 4.33(2H, q), 1.32(3H, t)

Step B: 6-cyclopropylmethylsulfanyl-pyridine-2-carboxylic acid ethyl ester

6-Mercapto-pyridine-2-carboxylic acid ethyl ester (0.54 g, 2.94 mmol) obtained in Step A and bromomethyl cyclopropane were reacted in the same manner as in Step A of Preparation Example 16 to obtain the title compound (0.568 g, 81%).

$^1$H-NMR (CDCl$_3$) δ 7.76(1H, d), 7.59(1H, t), 7.33(1H, d), 4.42(2H, q), 3.22(2H, d), 1.43(3H, t), 1.20(1H, m), 0.60(2H, m), 0.39(2H, m)

Step C: (6-cyclopropylmethylsulfanyl-pyridin-2-yl)-methanol

6-Cyclopropylmethylsulfanyl-pyridine-2-carboxylic acid ethyl ester (0.56 g, 2.35 mmol) obtained in Step B was reacted in the same manner as in Step B of Preparation Example 16 to obtain the title compound (0.446 g, 95%).

$^1$H-NMR (CDCl$_3$) δ 7.48(1H, t), 7.11(1H, d), 6.90(1H, d), 4.72(2H, d), 3.68(1H, t, OH), 3.13(2H, d), 1.16(1H, d), 0.62(2H, d), 0.32(2H, d)

Step D: 2-chloromethyl-6-cyclopropylmethylsulfanyl-pyridine (6-Cyclopropylmethylsulfanyl-pyridin-2-yl)-methanol (0.446 g, 2.28 mmol) obtained in Step C was reacted in the same manner as in Step C of Preparation Example 16 to obtain the title compound (0.43 g, 88%).

$^1$H-NMR (CDCl$_3$) δ 7.49(1H, t), 7.12(2H, m), 4.60(2H, s), 3.12(2H, d), 1.25(1H, m), 0.58(2H, m), 0.32(2H, m)

PREPARATION EXAMPLE 21

2-chloromethyl-3-isopropylsulfanyl-pyrazine

Step A: 3-mercapto-pyrazine-2-carboxylic acid methyl ester

After 3-chloro-pyrazine-2-carboxylic acid methyl ester (0.4 g, 2.3 mmol) was dissolved in MeOH (46 mL), sodium hydrosulfide monohydrate (0.65 g, 6.9 mmol) was added thereto, and the mixture was stirred at room temperature for 9 hours. After the termination of the reaction, the reactant was concentrated under reduced pressure, and 1N HCl aqueous solution was used to adjust the pH of the reactant to 3. The reactant was extracted with EtOAc, and the organic layer was separated to obtain the title compound (0.35 g, 89%).

$^1$H-NMR (CDCl$_3$) δ 8.43(1H, m), 8.42(1H, m), 5.18(1H, brs), 4.04(3H, s)

Step B: 3-isopropylsulfanyl-pyrazine-2-carboxylic acid methyl ester

3-Mercapto-pyrazine-2-carboxylic acid methyl ester (0.35 g, 2.0 mmol) obtained in Step A and 2-iodopropane were reacted in the same manner as in Step A of Preparation Example 5 to obtain the title compound (0.267 g, 61%).

$^1$H-NMR (CDCl$_3$) δ 8.57(1H, d), 8.35(1H, d), 4.12(1H, m), 4.05(3H, s), 1.45(6H, d)

Step C: (3-isopropylsulfanyl-pyrazin-2-yl)-methanol

3-Isopropylsulfanyl-pyrazine-2-carboxylic acid methyl ester (0.135 g, 0.63 mmol) obtained in Step B was reacted in the same manner as in Step B of Preparation Example 16 to obtain the title compound (0.08 g, 65%).

$^1$H-NMR (CDCl$_3$) δ 8.32(1H, d), 8.18(1H, d), 4.62(2H, s), 4.12(1H, m), 3.96(1H, brs, OH), 1.42(6H, d)

Step D: 2-chloromethyl-3-isopropylsulfanyl-pyrazine (3-Isopropylsulfanyl-pyrazin-2-yl)-methanol (0.08 g, 0.4 mmol) obtained in Step C was reacted in the same manner as in Step C of Preparation Example 16 to obtain the title compound (0.04 g, 49%).

$^1$H-NMR (CDCl$_3$) δ 8.35(1H, d), 8.21(1H, d), 4.68(2H, s), 2.10(1H, m), 1.43(6H, d)

PREPARATION EXAMPLE 22

3-chloromethyl-2-cyclohexylsulfanyl-pyridine

Step A: 2-cyclohexylsulfanyl-nicotinic acid

2-Mercapto-nicotinic acid (0.5 g, 3.22 mmol) was dissolved in DMF (5 mL), and the solution was cooled to 0~5° C. NaH (0.64 g, 16.11 mmol) was added slowly thereto, and the mixture was stirred at 0~5° C. for 30 minutes. Bromocyclohexane (1.19 mL, 9.66 mmol) was added thereto, and the mixture was stirred at room temperature for 12 hours. After the termination of the reaction, the reactant was concentrated under reduced pressure, and the residue was diluted with water. 3N HCl was used to adjust the pH of the solution to 2~3, and the solution was extracted with EtOAc. The organic layer was dried with $MgSO_4$ and concentrated under reduced pressure to obtain the title compound, which was used in the next step without a separate purification process.

Step B:
(2-cyclohexylsulfanyl-pyridin-3-yl)-methanol

2-Cyclohexylsulfanyl-nicotinic acid obtained in Step A was reacted in the same manner as in Step B of Preparation Example 1 to obtain the title compound (0.29 g, 40%).

$^1$H NMR (400 MHz, $CDCl_3$) δ 8.36(d, 1 H), 7.59(d, 1H), 7.03-6.98(m, 1H), 4.66(d, 2H), 4.07-3.97(m, 1H), 2.31-2.24 (m, 1H), 2.12-2.01(m, 2H), 1.82-1.71(m, 2H), 1.69-1.60(m, 1H), 1.56-1.40(m, 3H), 1.38-1.23(m, 2H)

Step C:
3-chloromethyl-2-cyclohexylsulfanyl-pyridine (2-Cyclohexylsulfanyl-pyridin-3-yl)-methanol (0.25 g, 1.12 mmol) obtained in Step B was reacted in the same manner as in Step C of Preparation Example 14 to obtain the title compound, which was used in the next step without a separate purification process.

PREPARATION EXAMPLE 23

3-chloromethyl-2-cyclobutylsulfanyl-pyridine

Step A: 2-cyclobutylsulfanyl-nicotinic acid

2-Mercapto-nicotinic acid (0.1 g, 0.64 mmol) was dissolved in DMF (2 mL), and the solution was cooled to 0~5° C. NaH (0.13 g, 3.2 mmol) was added slowly thereto, and the mixture was stirred at 0~5° C. for 30 minutes. Bromocyclobutane (0.12 mL, 1.28 mmol) was added thereto, and the mixture was stirred at 55~65° C. for 3 hours, and then stirred at room temperature for 12 hours. After the termination of the reaction, the reactant was concentrated under reduced pressure. The residue was diluted with water, and then 3N HCl was used to adjust the pH of the solution to 2~3. The solution was extracted with EtOAc. The organic layer was dried with $MgSO_4$ and concentrated under reduced pressure to obtain the title compound, which was used in the next step without a separate purification process.

Step B:
(2-cyclobutylsulfanyl-pyridin-3-yl)-methanol

2-Cyclobutylsulfanyl-nicotinic acid obtained in Step A was reacted in the same manner as in Step B of Preparation Example 1 to obtain the title compound (0.066 g, 52%).

$^1$H NMR (400 MHz, $CDCl_3$) δ 8.36-8.30(m, 1 H), 7.62-7.57(m, 1H), 7.02-6.97(m, 1H), 4.63(d, 2H), 4.54-4.45(m, 1H), 2.59-2.47(m, 3H), 2.18-1.98(m, 4H)

Step C:
3-chloromethyl-2-cyclobutylsulfanyl-pyridine (2-Cyclobutylsulfanyl-pyridin-3-yl)-methanol (0.06 g, 0.31 mmol) obtained in Step B was reacted in the same manner as in Step C of Preparation Example 14 to obtain the title compound, which was used in the next step without a separate purification process.

PREPARATION EXAMPLE 24

(2-isopropylsulfanyl-pyrimidin-4-yl)-methanol

Step A: 2-chloropyrimidine-4-carboxylic acid ethyl ester

After 2-chloropyrimidin-4-carboxylic acid (0.223 g, 1.4 mmol) was dissolved in DCM (7 mL), dicyclohexylcarbodiimide (0.29 g, 1.4 mmol), DMAP (0.017 g, 0.14 mmol) and EtOH (0.1 mL, 1.4 mmol) were added thereto, and the mixture was stirred at room temperature for 24 hours. After the termination of the reaction, the reactant was filtered and separated by column chromatography to obtain the title compound (0.13 g, 50%).

Step B: 2-isopropylsulfanyl-pyrimidine-4-carboxylic acid ethyl ester

2-Chloropyrimidine-4-carboxylic acid ethyl ester (0.024 g, 0.13 mmol) obtained in Step A and 2-propanethiol were reacted in the same manner as in Step A of Preparation Example 16 to obtain the title compound (0.02 g, 68%).

$^1$H-NMR ($CDCl_3$) δ 8.72(1H, d), 7.57(1H, d), 4.46(2H, q), 3.99(1H, m), 1.44(6H, d), 1.42(3H, t)

Step C:
(2-isopropylsulfanyl-pyrimidin-4-yl)-methanol

After 2-isopropylsulfanyl-pyrimidine-4-carboxylic acid ethyl ester (0.1 g, 0.44 mmol) obtained in Step B was dissolved in MeOH (4 mL), $NaBH_4$(0.033 g, 0.9 mmol) was added to the solution, and the mixture was stirred at room temperature for 2 hours. After the termination of the reaction, the reactant was added with water, and then extracted with EtOAc. The separated organic layer was dried with $MgSO_4$ and separated by column chromatography to obtain the title compound (0.063 g, 77%).

$^1$H-NMR ($CDCl_3$) δ 8.46(1H, d), 6.92(1H, d), 4.68(2H, d), 3.96(1H, m), 3.24(1H, t, OH), 1.44(6H, d)

PREPARATION EXAMPLE 25

3-chloromethyl-2-(3,3,3-trifluoro-propylsulfanyl)-pyridine

Step A: 2-(3,3,3-trifluoro-propylsulfanyl)-nicotinic acid

2-Mercapto-nicotinic acid (1 g, 6.4 mmol) and 3-bromo-1,1,1-trifluoropropane were reacted in the same manner as in Step A of Preparation Example 10 to obtain the title compound (0.16 g, 10%).

$^1$H-NMR (DMSO-$d_6$) δ 8.65(1H, m), 8.22(1H, m), 7.25 (1H, m), 3.26(2H, m), 2.63(2H, m)

Step B: [2-(3,3,3-trifluoro-propylsulfanyl)-pyridin-3-yl]-methanol 2-(3,3,3-Trifluoro-propylsulfanyl)-nicotinic acid (0.16 g, 0.64 mmol) obtained in Step A was reacted in the same manner as in Step B of Preparation Example 10 to obtain the title compound (0.12 g, 79%).

$^1$H-NMR ($CDCl_3$) δ 8.37(1H, m), 7.65(1H, m), 7.06(1H, m), 4.72(2H, s), 3.40(2H, m), 2.57(2H, m), 2.06(1H, brs, OH)

Step C: 3-chloromethyl-2-(3,3,3-trifluoro-propylsulfanyl)-pyridine

[2-(3,3,3-trifluoro-propylsulfanyl)-pyridin-3-1]-methanol obtained in Step B was reacted in the same manner as in Step C of Preparation Example 10 to obtain the title compound (0.12 g, 92%).

$^1$H-NMR (CDCl$_3$) δ 8.41(1H, m), 7.61(1H, m), 7.05(1H, m), 4.58(2H, s), 3.41(2H, m), 2.57(2H, m)

PREPARATION EXAMPLE 26

3-chloromethyl-2-(2,2-dimethyl-propylsulfanyl)-pyridine

Step A: 2-(2,2-dimethyl-propylsulfanyl)pyridine-3-carboxylic acid

2-Mercapto-nicotinic acid (0.5 g, 3.2 mmol) and 1-iodo-2,2-dimethyl-propanol were reacted in the same manner as in Step A of Preparation Example 10 to obtain the title compound (0.12 g, 16%).

$^1$H-NMR (DMSO-d$_6$) δ 8.60(1H, m), 8.18(1H, m), 7.20 (1H, m), 3.17(2H, s), 1.00(9H, s)

Step B: [2-(2,2-dimethyl-propylsulfanyl)pyridin-3-yl]-methanol 2-(2,2-dimethyl-propylsulfanyl)pyridine-3-carboxylic acid (0.12 g, 0.53 mmol) obtained in Step A was reacted in the same manner as in Step B of Preparation Example 10 to obtain the title compound (0.1 g, 89%).

$^1$H-NMR (CDCl$_3$) δ 8.35(1H, m), 7.60(1H, m), 7.02(1H, m), 4.73(2H, s), 3.30(2H, s), 1.00(9H, s)

Step C: 3-chloromethyl-2-(2,2-dimethyl-propylsulfanyl)-pyridine

[2-(2,2-dimethyl-propylsulfanyl)pyridin-3-yl]-methanol (0.1 g, 0.47 mmol) obtained in Step B was reacted in the same manner as in Step C of Preparation Example 10 to obtain the title compound (0.035 g, 32%).

$^1$H-NMR (CDCl$_3$) δ 8.37(1H, m), 7.60(1H, m), 7.00(1H, m), 4.67(2H, s), 3.31(2H, s), 1.05(9H, s)

PREPARATION EXAMPLE 27

2-chloromethyl-6-cyclopentylsulfanyl-pyridine

Step A: 6-cyclopentylsulfanyl-pyridine-2-carboxylic acid methyl ester

6-Bromo-pyridine-2-carboxylic acid methyl ester (0.5 g, 2.3 mmol) and bromocy-clopentane were reacted in the same manner as in Step A of Preparation Example 16 to obtain the title compound (0.45 g, 77%).

$^1$H-NMR (CDCl$_3$) δ 7.76(1H, dd), 7.59(1H, t), 7.32(1H, dd), 4.08(1H, m), 3.97(3H, s), 2.25(2H, m), 1.78(2H, m), 1.65(4H, m)

Step B: (6-cyclopentylsulfanyl-pyridin-2-yl)-methanol

6-Cyclopentylsulfanyl-pyridine-2-carboxylic acid methyl ester (0.45 g, 1.9 mmol) obtained in Step A was reacted in the same manner as in Step B of Preparation Example 16 to obtain the title compound (0.276 g, 73%).

$^1$H-NMR (CDCl$_3$) δ 7.47(1H, t), 7.07(1H, d), 6.87(1H, d), 4.70(2H, d), 4.04(1H, m), 3.79(1H, t, OH), 2.20(2H, m), 1.79(2H, m), 1.66(4H, m)

Step C: 2-chloromethyl-6-cyclopentylsulfanyl-pyridine (6-Cyclopentylsulfanyl-pyridin-2-yl)-methanol (0.276 g, 1.3 mmol) obtained in Step B was reacted in the same manner as in Step C of Preparation Example 16 to obtain the title compound (0.276 g, 92%).

$^1$H-NMR (CDCl$_3$) δ 7.49(1H, t), 7.12(1H, d), 7.09(1H, d), 4.60(2H, s), 4.02(1H, m), 2.21(2H, m), 1.78(2H, m), 1.64 (4H, m)

PREPARATION EXAMPLE 28

2-chloromethyl-6-cyclohexylsulfanyl-pyridine

Step A: 6-cyclohexylsulfanyl-pyridine-2-carboxylic acid methyl ester

After 6-bromo-pyridine-2-carboxylic acid methyl ester (0.30 g, 1.39 mmol) was dissolved in DMF (4 mL), K$_2$CO$_3$ (0.575 g, 4.16 mmol) and cyclohexanethiol (0.25 mL, 2.08 mmol) were added thereto in turn, and the mixture was stirred at 70° C. for 18 hours. After the termination of the reaction, the reactant was concentrated under reduced pressure, extracted with EtOAc, and purified by column chromatography (eluent, EtOAc/Hex=1/5) to obtain the title compound (0.162 g, 46%).

$^1$H-NMR (CDCl$_3$) δ 7.77-7.75(1H, d), 7.60-7.56(1H, t), 7.31-7.29(1H, d), 3.97(3H, s), 3.90-3.89(1H, m), 2.12-2.09 (2H, m), 1.79-1.77(2H, m), 1.66-1.63(1H, m), 1.56-1.43(4H, m), 1.34-1.32(1H, m)

Step B: (6-cyclohexylsulfanyl-pyridin-2-yl)-methanol

6-Cyclohexylsulfanyl-pyridine-2-carboxylic acid methyl ester (0.162 g, 0.64 mmol) obtained in Step A was reacted in the same manner as in Step B of Preparation Example 1 to obtain the title compound (0.025 g, 17%).

$^1$H-NMR (CDCl$_3$) δ 7.48-7.42(1H, t), 7.08-7.06(1H, d), 6.89-6.87(1H, d), 4.70(2H, s), 3.83-3.78(1H, m), 2.11-2.07 (2H, m), 1.81-1.77(2H, m), 1.63-1.62(1H, m), 1.53-1.31(5H, m)

Step C: 2-chloromethyl-6-cyclohexylsulfanyl)-pyridine (6-Cyclohexylsulfanyl-pyridin-2-yl)-methanol (0.025 g, 0.11 mmol) obtained in Step B was reacted in the same manner as in Step C of Preparation Example 1 to obtain the title compound, which was used in the next step without a separate purification process.

PREPARATION EXAMPLE 29

3-chloromethyl-6-ethyl-2-isopropylsulfanyl-pyridine

Step A: 6-ethyl-2-isopropylsulfanyl-nicotinic acid methyl ester

After 2-isopropylsulfanyl-6-methyl-nicotinic acid methyl ester (105 mg, 0.46 mmol) was dissolved in THF (3 mL), KHMDS (1 mL, 0.51 mmol) was added slowly thereto at −78° C., and the mixture was stirred for 30 minutes. MeI (72 mg, 0.51 mmol) was added slowly to the reactant at −78° C., and the mixture was stirred at room temperature for 1 hour. The reactant was cooled, diluted with water, and extracted with EtOAc. The organic layer was dried with $MgSO_4$, filtered, and concentrated under reduced pressure. The residue was purified by column chromatography (eluent EtOAc/Hex=1/5) to obtain the title compound (60 mg, 54%).

NMR: $^1$H-NMR ($CDCl_3$) 8.09(1H, d), 6.85(1H, d), 4.15 (1H, m), 3.90(3H, s), 2.80(2H, q), 1.40(6H, d), 1.32(3H, t)

Step B: (6-ethyl-2-isopropylsulfanyl-pyridin-3-yl)-methanol

6-Ethyl-2-isopropylsulfanyl-nicotinic acid methyl ester (60 mg, 0.25 mmol)) obtained in Step A was reacted in the same manner as in Step B of Preparation Example 16 to obtain the title compound (29 mg, 55%).

NMR: $^1$H-NMR ($CDCl_3$) 7.47(1H, d), 6.85(1H, d), 4.63 (1H, d), 4.19(1H, m), 2.76(2H, q), 1.99(1H, t), 1.41(6H, d), 1.29(3H, t)

Step C: 3-chloromethyl-6-ethyl-2-isopropylsulfanyl-pyridine (6-Ethyl-2-isopropylsulfanyl-pyridin-3-yl)-methanol (29 mg, 0.13 mmol) obtained in Step B was reacted in the same manner as in Step C of Preparation Example 16 to obtain the title compound, which was used in the next step without a separate purification process.

PREPARATION EXAMPLE 30

3-chloromethyl-2-isopropylsulfanyl-5-methyl-pyridine

Step A: 2-isopropylsulfanyl-5-methyl-pyridine-3-carbonitrile

5-Methyl-2-sulfanyl-pyridine-3-carbonitrile (0.2 g, 1.3 mmol) and 2-bromopropane were reacted in the same manner as in Step A of Preparation Example 5 to obtain the title compound (0.18 g, 70%).

$^1$H-NMR ($CDCl_3$) δ 8.42(1H, dd), 7.60(1H, dd), 4.10(1H, m), 2.31(3H, s), 1.42(6H, d)

Step B: 2-isopropylsulfanyl-5-methyl-nicotinic acid

After 2-isopropylsulfanyl-5-methyl-pyridine-3-carbonitrile (0.186 g, 0.97 mmol) obtained in Step A was dissolved in water (0.4 mL) and DMSO (0.04 mL), KOH (0.76 g) was added thereto, and the mixture was stirred at 100° C. for 16 hours. After the termination of the reaction, 6N HCl aqueous solution was added thereto to adjust the pH of the reactant to 2, and the mixture was extracted with EtOAc. The organic layer was separated, dried with $MgSO_4$, and concentrated under reduced pressure to obtain the title compound (0.15 g, 73%).

$^1$H-NMR (DMSO-$d_6$) δ 13.29(1H, brs), 8.46(1H, d), 8.01(1H, d), 3.97(1H, m), 2.28(3H, s), 1.30(6H, d)

Step C: (2-isopropylsulfanyl-5-methyl-pyridin-3-yl)-methanol

2-Isopropylsulfanyl-5-methyl-nicotinic acid (0.075 g, 0.35 mmol) obtained in Step B was reacted in the same manner as in Step B of Preparation Example 10 to obtain the title compound (0.038 g, 54%).

$^1$H-NMR ($CDCl_3$) δ 8.23(1H, m), 7.44(1H, m), 4.65(2H, d), 4.11(1H, m), 2.29(3H, s), 2.07(1H, brs, OH), 1.39(6H, d)

Step D: 3-chloromethyl-2-isopropylsulfanyl-5-methyl-pyridine (2-Isopropylsulfanyl-5-methyl-pyridin-3-yl)-methanol (0.037 g, 0.18 mmol) obtained in Step C was reacted in the same manner as in Step C of Preparation Example 10 to obtain the title compound (0.031 g, 77%).

$^1$H-NMR ($CDCl_3$) δ 8.25(1H, s), 7.43(1H, s), 4.59(3H, s), 4.10(1H, m), 2.29(3H, s), 1.40(6H, d)

PREPARATION EXAMPLE 31

2-(3,5-difluoro-4-hydroxy-phenyl)-cyclopropane-carboxylic acid ethyl ester

Step A: 2-(4-benzyloxy-3,5-difluoro-phenyl)-cyclopropane-carboxylic acid ethyl ester After (E)-3-(4-benzyloxy-3,5-difluoro-phenyl)-acrylic acid ethyl ester (2.5 g, 7.85 mmol) obtained in Step C of Preparation Example 2 was dissolved in THF (10 mL), diazomethane solution (94 mL, 23.55 mmol, 0.25M ether) was added thereto. After the reactant was cooled to 0~5° C., palladium(II) acetate (0.29 g, 1.30 mmol) was added slowly thereto, and the mixture was stirred at room temperature for 5 hours. After the termination of the reaction, the reactant was added with water and then extracted. The organic layer was concentrated under reduced pressure and the residue was purified by column chromatography (eluent EtOAc/Hex=1/10) to obtain the title compound (2.27 g, 87%).

$^1$H NMR (400 MHz, $CDCl_3$) δ 7.45-7.40(m, 2H), 7.38-7.29(m, 3H), 6.62(d, 2H), 5.11(s, 2H), 4.16(q, 2H), 2.44-2.38(m, 1H), 1.85-1.79(m, 1H), 1.60-1.54(m, 1H), 1.28(t, 3H), 1.23-1.18(m, 1H)

Step B: 2-(3,5-difluoro-4-hydroxy-phenyl)-cyclopropane-carboxylic acid ethyl ester 2-(4-Benzyloxy-3,5-difluoro-phenyl)-cyclopropane-carboxylic acid ethyl ester (0.65 g, 1.96 mmol) obtained in Step A was dissolved in EtOH (15 mL), and 10% Pd/C (65 mg) was added thereto. The mixture was stirred at room temperature under hydrogen atmosphere for 3 hours. The reactant was filtered by using celite and concentrated under reduced pressure to obtain the title compound (0.46 g, 97%).

$^1$H NMR (400 MHz, $CDCl_3$) δ 6.66(d, 2H), 4.18(q, 2H), 2.47-2.38(m, 1H), 1.84-1.78(m, 1H), 1.60-1.53(m, 1H), 1.28 (t, 3H), 1.25-1.18(m, 1H)

PREPARATION EXAMPLE 32

3-(3-fluoro-4-hydroxy-phenyl]-2-methyl-propionic acid methyl ester

Step A: (E)-3-(3-fluoro-4-methoxy-phenyl)-2-methyl-acrylic acid ethyl ester

After 3-fluoro-4-methoxy-benzaldehyde (0.50 g, 3.24 mmol) was dissolved in anhydrous THF (10 mL), carbethoxyethylidene triphenylphosphorane (1.75 g, 4.86 mmol) was added thereto at 0° C., and the mixture was stirred at room temperature for 3 hours. After the termination of the reaction, the reactant was concentrated under reduced pressure and purified by column chromatography (eluent, EtOAc/Hex=1/2) to obtain the title compound (0.768 g, 99%).

$^1$H-NMR (CDCl$_3$) δ 7.57(1H, s), 7.21-7.14(2H, m), 7.06-6.99(1H, t), 4.29-4.20(2H, q), 3.92(3H, s), 2.12(3H, s), 1.36-1.33(3H, t)

Step B: 3-(3-fluoro-4-methoxy-phenyl)-2-methyl-propionic acid ethyl ester

After (E)-3-(3-fluoro-4-methoxy-phenyl)-2-methyl-acrylic acid ethyl ester (0.728 g, 3.0 mmol) obtained in Step A was dissolved in EtOH (10 mL), 10% Pd/C (0.073 g) was added thereto, and the mixture was stirred at room temperature under hydrogen atmosphere for 12 hours. After the termination of the reaction, the reactant was filtered by using celite, concentrated under reduced pressure, and purified by column chromatography (eluent, EtOAc/Hex=1/2) to obtain the title compound (0.726 g, 98%).

$^1$H-NMR (CDCl$_3$) δ 6.91-6.84(3H, m), 4.15-4.08(2H, q), 3.86(3H, s), 2.95-2.91(1H, q), 2.71-2.58(2H, m), 1.23-1.20 (3H, t), 1.15-1.14(3H, d)

Step C: 3-(3-fluoro-4-hydroxy-phenyl]-2-methyl-propionic acid methyl ester

After 3-(3-fluoro-4-methoxy-phenyl)-2-methyl-propionic acid ethyl ester (0.728 g, 3.03 mmol) obtained in Step B was dissolved in anhydrous DCM (10 mL), 1M BBr3 solution (4.5 mL, 4.5 mmol) was added thereto at −78° C., and the mixture was stirred at room temperature for 3 hours. After the termination of the reaction, the reactant was added with MeOH, concentrated under reduced pressure, and purified by column chromatography (eluent, EtOAc/Hex=1/2) to obtain the title compound (0.64 g, 99%).

$^1$H-NMR (CDCl$_3$) δ 6.91-6.80(2H, m), 6.69-6.67(1H, m), 5.29-5.28(1H, d), 3.64(3H, s), 2.95-2.90(1H, q), 2.73-2.65 (1H, m), 2.62-2.57(1H, m), 1.16-1.14(3H, d)

PREPARATION EXAMPLE 33

2-sec-butylsulfanyl-3-chloromethyl-pyridine

Step A: 2-sec-butylsulfanyl-nicotinic acid

2-Mercapto-nicotinic acid (1.0 g, 6.4 mmol) was reacted in the same manner as in Step A of Preparation Example 10 to obtain the title compound (0.89 g, 66%).

$^1$H-NMR (DMSO-d$_6$) δ 13.32(1H, brs), 8.59(1H, m), 8.17(1H, m), 7.19(1H, m), 3.91(1H, m), 1.70(1H, m), 1.58 (1H, m), 1.29(3H, d), 0.95(3H, t)

Step B: (2-sec-butylsulfanyl-pyridin-3-yl)-methanol 2-sec-Butylsulfanyl-nicotinic acid (0.89 g, 4.2 mmol) obtained in Step A was reacted in the same manner as in Step B of Preparation Example 10 to obtain the title compound (0.76 g, 90%).

$^1$H-NMR (CDCl$_3$) δ 8.36(1H, m), 7.61(1H, m), 7.01(1H, m), 4.67(2H, s), 4.04(1H, m), 2.20(1H, brs, OH), 1.76(1H, m), 1.69(1H, m), 1.39(3H, d), 1.04(3H, t)

Step C: 2-sec-butylsulfanyl-3-chloromethyl-pyridine (2-sec-Butylsulfanyl-pyridin-3-yl)-methanol (0.76 g, 3.8 mmol) obtained in Step B was reacted in the same manner as in Step C of Preparation Example 10 to obtain the title compound (0.072 g, 87%).

$^1$H-NMR (CDCl$_3$) δ 8.40(1H, m), 7.60(1H, m), 7.01(1H, m), 4.62(2H, s), 4.06(1H, m), 1.76(1H, m), 1.69(1H, m), 1.42(3H, d), 1.03(3H, t)

PREPARATION EXAMPLE 34

3-(3,5-difluoro-4-hydroxy-phenyl)-2-methyl-propionic acid ethyl ester

Step A: (E)-3-(4-benzyloxy-3,5-difluoro-phenyl)-2-methyl-acrylic acid ethyl ester 4-Benzyloxy-3,5-difluoro-benzaldehyde (1.68 g, 6.77 mmol) was reacted in the same manner as in Step A of Preparation Example 3 to obtain the title compound (2.19 g, 97%).

$^1$H NMR (400 MHz, CDCl$_3$) δ 7.50-7.43(3H, m), 7.39-7.31(3H, m), 6.97-6.90(2H, m), 5.21(2H, s), 4.26(2H, q, 7 Hz), 2.10(3H, s), 1.34(3H, t, 7 Hz)

Step B: 3-(3,5-difluoro-4-hydroxy-phenyl)-2-methyl-propionic acid ethyl ester (E)-3-(4-Benzyloxy-3,5-difluoro-phenyl)-2-methyl-acrylic acid ethyl ester (2.19 g, 6.59 mmol) obtained in Step A was reacted in the same manner as in Step D of Preparation Example 2 to obtain the title compound (1.60 g, 99%).

$^1$H NMR (400 MHz, DMSO-d$_6$) δ 9.93(1H, brs), 6.89-6.81(2H, m), 4.01(2H, q, 7 Hz), 2.79-2.65(2H, m), 2.58(1H, dd, 12 and 6 Hz), 1.11(3H, t, 7 Hz), 1.04(3H, d, 7 Hz)

PREPARATION EXAMPLE 35

3-chloromethyl-2-isopropylsulfanyl-6-methoxy-pyridine

Step A: 2-chloro-6-methoxy-nicotinic acid

Potassium botoxide (483 mg, 4.31 mmol) and MeOH (8 mL) were added to 2,6-dichloro-nicotinic acid (207 mg, 1.07 mmol), and the mixture was stirred using microwave at 60° C. for 1 hour. After the termination of the reaction, the reactant was filtered, and 1N HCl was added thereto at 0° C. to adjust the pH to 3. The solid was dried by N$_2$ gas to obtain the title compound (106 mg, 52%).

$^1$H-NMR (DMSO-d$_6$) δ 8.17(1H, d), 6.92(1H, d), 3.92 (3H, s)

Step B: 2-chloro-6-methoxy-nicotinic acid methyl ester

2-Chloro-6-methoxy-nicotinic acid (106 mg, 0.56 mmol) obtained in Step A and K$_2$ CO$_3$(156 mg, 1.13 mmol) were reacted in the same manner as in Step A of Preparation Example 9 to obtain the title compound (61 mg, 53%).

$^1$H-NMR (CDCl$_3$) δ 8.13(1H, d), 6.70(1H, d), 4.00(3H, s), 3.91(3H, s)

Step C: 2-isopropylsulfanyl-6-methoxy-nicotinic acid methyl ester

2-Chloro-6-methoxy-nicotinic acid methyl ester (52 mg, 0.26 mmol) obtained in Step B and isopropylthiol were reacted in the same manner as in Step B of Preparation Example 9 to obtain the title compound (54 mg, 87%).
NMR: ¹H-NMR (CDCl₃) 8.10(1H, d), 6.42(1H, d), 4.13 (1H, m), 4.00(3H, s), 3.87(3H, s), 1.43(6H, d)

Step D: (2-isopropylsulfanyl-6-methoxy-pyridin-3-yl)-methanol

2-Isopropylsulfanyl-6-methoxy-nicotinic acid methyl ester (54 mg, 0.22 mmol) obtained in Step C was reacted in the same manner as in Step C of Preparation Example 9 to obtain the title compound (17 mg, 96%).
¹H-NMR (CDCl₃) δ 7.47(1H, d), 6.44(1H, d), 4.60(1H, d), 4.12(1H, m), 3.94(3H, s), 1.87(1H, t), 1.44(6H, d)

Step E: 3-chloromethyl-2-isopropylsulfanyl-6-methoxy-pyridin (2-Isopropylsulfanyl-6-methoxy-pyridin-3-yl)-methanol (27 mg, 0.12 mmol) obtained in Step D was reacted in the same manner as in Step C of Preparation Example 8 to obtain the title compound, which was used in the next step without a separate purification process.

PREPARATION EXAMPLE 36

3-chloromethyl-2-cyclopentylsulfanyl-6-methyl-pyridine

Step A: 2-cyclopentylsulfanyl-6-methyl-nicotinic acid methyl ester

2-Chloro-6-methyl-nicotinic acid methyl ester (511 mg, 2.75 mmol) was reacted in the same manner as in Step B of Preparation Example 9 to obtain the title compound (418 mg, 60%).
¹H-NMR (CDCl₃) δ 8.06(1H, d), 6.86(1H, d), 4.15(1H, m), 3.89(3H, s), 2.53(3H, s), 2.23(2H, m), 1.75(2H, m), 1.65(4H, m)

Step B: (2-cyclopentylsulfanyl-6-methyl-pyridin-3-yl)-methanol

2-Cyclopentylsulfanyl-6-methyl-nicotinic acid methyl ester (210 mg, 0.83 mmol) obtained in Step A was reacted in the same manner as in Step C of Preparation Example 9 to obtain the title compound (168 mg, 90%).
¹H-NMR (CDCl₃) δ 7.42(1H, d), 6.83(1H, d), 4.16(2H, d), 4.19(1H, m), 2.48(3H, s), 2.21(2H, m), 1.76(2H, m), 1.65(4H, m)

Step C: 3-chloromethyl-2-cyclopentylsulfanyl-6-methyl-pyridine (2-Cyclopentylsulfanyl-6-methyl-pyridin-3-yl)-methanol (35 mg, 0.15 mmol) obtained in Step B was reacted in the same manner as in Step C of Preparation Example 8 to obtain the title compound, which was used in the next step without a separate purification process.

PREPARATION EXAMPLE 37

2-chloromethyl-6-cyclobutylsulfanyl-pyridine

Step A: 6-cyclobutylsulfanyl-pyridine-2-carboxylic acid ethyl ester

After 6-mercapto-pyridine-2-carboxylic acid ethyl ester (0.40 g, 2.18 mmol) was dissolved in CH₃CN (9 mL), Cs₂CO₃(2.667 g, 6.54 mmol) and bromo cyclobutane (0.385 mL, 3.27 mmol) were added thereto, and the mixture was stirred at 50° C. for 18 hours. After the termination of the reaction, the reactant was filtered, concentrated under reduced pressure, and purified by column chromatography (eluent, EtOAc/Hex=1/5) to obtain the title compound (0.481 g, 92%).

Step B: (6-cyclobutylsulfanyl-pyridin-2-yl)-methanol

6-Cyclobutylsulfanyl-pyridine-2-carboxylic acid ethyl ester (0.481 g, 2.03 mmol) obtained in Step A was reacted in the same manner as in Step B of Preparation Example 16 to obtain the title compound (0.377 g, 95%).
¹H-NMR (CDCl₃) δ 7.75-7.73(1H, d), 7.59-7.56(1H, t), 7.22-7.20(1H, d), 4.45-4.33(3H, m), 2.59-2.56(2H, m), 2.21-2.03(4H, m), 1.44-1.40(3H, t)

Step C: 2-chloromethyl-6-cyclobutylsulfanyl-pyridin (6-Cyclobutylsulfanyl-pyridin-2-yl)-methanol (0.04 g, 0.20 mmol) obtained in Step B was reacted in the same manner as in Step C of Preparation Example 16 to obtain the title compound, which was used in the next step without a separate purification process.
¹H-NMR (CDCl₃) δ 7.49-7.45(1H, t), 7.01-6.99(1H, d), 6.88-6.86(1H, d), 4.70-4.69(2H, d), 4.35-4.27(1H, m), 3.78-3.75(1H, t), 2.60-2.53(2H, m), 2.21-2.03(4H, m)

PREPARATION EXAMPLE 38

3-(4-hydroxy-3-methoxy-phenyl]-propionic acid ethyl ester

Step A: 4-benzyloxy-3-methoxy-benzaldehyde

4-Hydroxy-3-methoxy-benzaldehyde (2.17 g, 14.26 mmol) was reacted in the same manner as in Step B of Preparation Example 2 to obtain the title compound (3.40 g, 98%).
¹H-NMR (CDCl₃) δ 9.87(1H, s), 7.52~7.31(7H, m), 6.99 (1H, d), 5.30(2H, s), 3.95(3H, s)

Step B: (E)-3-(4-benzyloxy-3-methoxy-phenyl)-acrylic acid ethyl ester

4-Benzyloxy-3-methoxy-benzaldehyde (1.17 g, 4.85 mmol) obtained in Step A was reacted in the same manner as in Step C of Preparation Example 2 to obtain the title compound (1.0 g, 66%).
¹H-NMR (CDCl₃) δ 7.70(1H, d), 7.52~7.29(5H, m), 7.07~7.02(2H, m), 6.97(1H, d), 6.30(1H, d), 5.19(2H, s), 4.25(2H, q), 3.92(3H, s), 1.25(3H, t)

Step C: 3-(4-hydroxy-3-methoxy-phenyl)-propionic acid ethyl ester (E)-3-(4-Benzyloxy-3-methoxy-phenyl)-acrylic acid ethyl ester (1.0 g, 3.20 mmol) obtained in Step B was reacted in the same manner as in Step D of Preparation Example 2 to obtain the title compound (679 mg, 94%).
¹H-NMR (CDCl₃) δ 7.00(1H, d), 6.69(2H, m), 5.47(1H, s), 4.13(2H, q), 3.87(3H, s), 2.88(2H, t), 2.59(2H, t), 1.24 (3H, t)

PREPARATION EXAMPLE 39

3-(4-hydroxy-phenyl)-2,2-dimethyl-propionic acid ethyl ester

Step A: 4-benzyloxy-benzaldehyde

4-Hydroxy-benzaldehyde (1.0 g, 8.19 mmol) was reacted in the same manner as in Step B of Preparation Example 2 to obtain the title compound (1.70 g, 98%).

Step B: 3-(4-benzyloxy-phenyl)-3-hydroxy-2,2-dimethyl-propionic acid ethyl ester Ethyl isobutyrate (2.5 mL, 18.42 mmol) was dissolved in THF (8 mL), and the solution was cooled to −78° C. LDA (9.2 mL, 18.42 mmol) was added thereto, and the mixture was stirred at the corresponding temperature for 2 hours. After 4-benzyloxy-benzaldehyde (1.7 g, 8.01 mmol) obtained in Step A was added thereto at −78° C., the mixture was heated to room temperature, and then stirred for 2 days. The reactant was added with water, and then extracted with EtOAc. The organic layer was concentrated under reduced pressure. The residue was purified by column chromatography (eluent, EtOAc/Hex=1/5) to obtain the title compound (1.77 g, 67%).

$^1$H NMR (400 MHz, CDCl$_3$) δ 7.42-7.38(m, 2H), 7.37-7.32(m, 2H), 7.31-7.26(m, 1H), 7.19(d, 2H), 6.89(d, 2H), 5.00(s, 2H), 4.81(d, 1H), 4.13(q, 2H), 3.26(d, 1H), 1.23(t, 3H), 1.11(s, 3H), 1.06(s, 3H)

Step C: 3-(4-benzyloxy-phenyl)-2,2-dimethyl-propionic acid ethyl ester 3-(4-Benzyloxy-phenyl)-3-hydroxy-2,2-dimethyl-propionic acid ethyl ester (1.5 g, 4.57 mmol) obtained in Step B was dissolved in DCM (20 mL). Triethylsilane (0.81 mL, 5.03 mmol) was added thereto, and the reactant was cooled to 0~5° C. After boron trifluoride diethylether (0.62 mL, 5.03 mmol) was added thereto at 0~5° C., the mixture was heated to room temperature and stirred for 2 hours. Saturated sodium bicarbonate was added thereto, and the reactant was stirred. The separated organic layer was concentrated under reduced pressure, and the residue was purified by column chromatography (eluent, EtOAc/Hex=1/5) to obtain the title compound (1.34 g, 94%).

Step D: 3-(4-hydroxy-phenyl)-2,2-dimethyl-propionic acid ethyl ester 3-(4-benzyloxy-phenyl)-2,2-dimethyl-propionic acid ethyl ester (1.3 g, 4.16 mmol) obtained in Step C was reacted in the same manner as in Step D of Preparation Example 2 to obtain the title compound (0.92 g, 99%).

$^1$H NMR (400 MHz, CDCl$_3$) δ 6.96(d, 2H), 6.70(d, 2H), 4.11(q, 2H), 2.78(s, 2H), 1.24(t, 3H), 1.16(s, 6H)

PREPARATION EXAMPLE 40

(4-isopropylsulfanyl-2-methyl-pyrimidin-5-yl)-methanol

Step A: 4-isopropylsulfanyl-2-methyl-pyrimidine-5-carboxylic acid methyl ester 4-Chloro-2-methyl-pyrimidine-5-carboxylic acid methyl ester (0.105 g, 0.56 mmol) and 2-propanethiol were reacted in the same manner as in Step A of Preparation Example 16 to obtain the title compound (0.114 g, 90%).

$^1$H-NMR (CDCl$_3$) δ 8.89(1H, s), 4.17(1H, m), 3.92(3H, s), 2.69(3H, s), 1.41(6H, d)

Step B: (4-isopropylsulfanyl-2-methyl-pyrimidin-5-yl)-methanol

4-Isopropylsulfanyl-2-methyl-pyrimidine-5-carboxylic acid methyl ester (0.057 g, 0.25 mmol) obtained in Step A was reacted in the same manner as in Step B of Preparation Example 16 to obtain the title compound (0.006 g, 12%).

$^1$H-NMR (CDCl$_3$) δ 8.30(1H, s), 4.61(2H, d), 4.22(1H, m), 2.65(3H, s), 1.94(1H, brs, OH), 1.43(6H, d)

PREPARATION EXAMPLE 41

(2-cyclopentylsulfanyl-6-methoxy-pyridin-3-yl)-methanol

Step A: 2-cyclopentylsulfanyl-6-methoxy-nicotinic acid methyl ester

2-Chloro-6-methoxy-nicotinic acid methyl ester (54 mg, 0.26 mmol) and cyclopen-tanethiol were reacted in the same manner as in Step A of Preparation Example 16 to obtain the title compound (55 mg, 77%).

$^1$H-NMR (CDCl$_3$) δ 8.09(1H, d), 6.42(1H, d), 4.16(1H, m), 4.00(3H, s), 3.87(3H, s), 2.22(2H, m), 1.82~1.60(6H, m)

Step B: (2-cyclopentylsulfanyl-6-methoxy-pyridin-3-yl)-methanol

2-Cyclopentylsulfanyl-6-methoxy-nicotinic acid methyl ester (55 mg, 0.20 mmol) obtained in Step A was reacted in the same manner as in Step B of Preparation Example 16 to obtain the title compound (36 mg, 73%).

$^1$H-NMR (CDCl$_3$) δ 7.46(1H, d), 6.43(1H, d), 4.60(1H, d), 4.17(1H, m), 3.94(3H, s), 2.22(2H, m), 1.82~1.60(6H, m)

PREPARATION EXAMPLE 42

3-(3-chloro-4-hydroxy-phenyl)-propionic acid ethyl ester

Step A: 4-benzyloxy-3-chloro-benzaldehyde

4-Hydroxy-3-chloro-benzaldehyde (1.13 g, 14.26 mmol) was reacted in the same manner as in Step B of Preparation Example 2 to obtain the title compound (2.12 g, 99%).

$^1$H-NMR (CDCl$_3$) δ 9.84(1H, s), 7.93(1H, s), 7.73(1H, d), 7.52-7.31(5H, m), 7.07(1H, d), 5.25(2H, s)

Step B: (E)-3-(4-benzyloxy-3-chloro-phenyl)-acrylic acid ethyl ester

4-Benzyloxy-3-chloro-benzaldehyde (814 mg, 3.29 mmol) obtained in Step A was reacted in the same manner as in Step C of Preparation Example 2 to obtain the title compound (843 mg, 80%).

$^1$H-NMR (CDCl$_3$) δ 7.60~7.50(2H, m), 7.47~7.29(6H, m), 6.94(1H, d), 6.30(1H, d), 5.19(2H, s), 4.23(2H, q), 1.32(3H, t)

Step C: 3-(3-chloro-4-hydroxy-phenyl)-propionic acid ethyl ester (E)-3-(4-Benzyloxy-3-chloro-phenyl)-acrylic acid ethyl ester (1.1 g, 3.32 mmol) obtained in Step B was reacted in the same manner as in Step D of Preparation Example 2 to obtain the title compound (807 mg, 99%).

$^1$H-NMR (CDCl$_3$) δ 7.16(1H, s), 7.02(1H, d), 6.93(1H, d), 5.40(1H, s), 4.13(2H, q), 2.86(2H, t), 2.57(2H, t), 1.23(3H, t)

PREPARATION EXAMPLE 43

3-(4-hydroxy-2,3-dimethyl-phenyl]-propionic acid ethyl ester

Step A: 4-hydroxy-2,3-dimethyl-benzaldehyde

4-Methoxy-2,3-dimethyl-benzaldehyde (2.0 g, 12.18 mmol) was dissolved in DCM (48 mL), and the solution was cooled to −78° C. 1M BBr$_3$(24 mL, 24.13 mmol) was added slowly thereto, and the mixture was stirred at room temperature for 12 hours. After the termination of the reaction, the residue was diluted with water and extracted with DCM. The organic layer was dried with MgSO$_4$ and concentrated under reduced pressure. The residue was purified by column chromatography (eluent, EtOAc/Hex=1/5) to obtain the title compound (187 mg, 10%).

$^1$H-NMR (CDCl$_3$) δ 10.16(1H, s), 7.60(1H, d), 6.75(1H, d), 5.23(1H, s), 2.61(3H, s), 2.22(3H, s)

Step B: 4-benzyloxy-2,3-dimethyl-benzaldehyde

4-Hydroxy-2,3-dimethyl-benzaldehyde (187 mg, 1.24 mmol) obtained in Step A was reacted in the same manner as in Step B of Preparation Example 2 to obtain the title compound (256 mg, 84%).

$^1$H-NMR (CDCl$_3$) δ 10.15(1H, s), 7.64(1H, d), 7.50~7.30 (6H, m), 6.88(1H, d), 5.15(2H, s), 2.61(3H, s), 2.25(3H, s)

Step C: (E)-3-(4-benzyloxy-2,3-dimethyl-phenyl)-acrylic acid ethyl ester

4-Benzyloxy-2,3-dimethyl-benzaldehyde (256 mg, 1.05 mmol) obtained in Step A was reacted in the same manner as in Step C of Preparation Example 2 to obtain the title compound (306 mg, 93%).

$^1$H-NMR (CDCl$_3$) δ 8.03(1H, d), 7.52~7.31(6H, m), 6.78(1H, d), 6.23(1H, d), 5.10(2H, s), 4.26(2H, q), 2.36(3H, s), 2.23(3H, s), 1.34(3H, t)

Step D: 3-(4-hydroxy-2,3-dimethyl-phenyl]-propionic acid ethyl ester (E)-3-(4-Benzyloxy-2,3-dimethyl-phenyl)-acrylic acid ethyl ester (306 mg, 0.98 mmol) obtained in Step C was reacted in the same manner as in Step D of Preparation Example 2 to obtain the title compound (131 mg, 59%).

$^1$H-NMR (CDCl$_3$) δ 6.88(1H, d), 6.57(1H, d), 4.56(1H, s), 4.14(2H, q), 2.91(2H, t), 2.52(2H, t), 2.22(3H, s), 2.18(3H, s), 1.25(t, 3H)

PREPARATION EXAMPLE 44

2-[3-fluoro-4-hydroxy-phenyl]-cyclopropane carboxylic acid ethyl ester

Step A: (E)-3-(3-fluoro-4-methoxy-phenyl)-acrylic acid ethyl ester

3-Fluoro-4-methoxy-benzaldehyde (0.50 g, 3.2 mmol) was reacted in the same manner as in Step C of Preparation Example 2 to obtain the title compound (0.60 g, 82%).

$^1$H-NMR (CDCl$_3$) δ 7.60-7.56(1H, d), 7.30-7.23(2H, m), 6.97-6.93(1H, t), 6.31-6.27(1H, d), 4.28-4.23(2H, q), 3.92 (3H, s), 1.35-1.31(3H, t)

Step B: 2-(3-fluoro-4-methoxy-phenyl)-cyclopropanecarboxylic acid ethyl ester (E)-3-(3-Fluoro-4-methoxy-phenyl)-acrylic acid ethyl ester (0.39 g, 1.74 mmol) obtained in Step A was reacted in the same manner as in Step A of Preparation Example 31 to obtain the title compound (0.367 g, 88%).

$^1$H-NMR (CDCl$_3$) δ 6.89-6.80(3H, m), 4.19-4.14(2H, q), 3.86(3H, s), 2.48-2.43(1H, m), 1.84-1.79(1H, m), 1.59-1.54 (1H, m), 1.30-1.26(3H, t), 1.25-1.21(1H, m)

Step C: 2-[3-fluoro-4-hydroxy-phenyl]-cyclopropanecarboxylic acid ethyl ester After 2-(3-fluoro-4-methoxy-phenyl)-cyclopropanecarboxylic acid ethyl ester (0.494 g, 2.07 mmol) obtained in Step B was dissolved in anhydrous DCM (7 mL), BBr$_3$ 1 M DCM solution (3 mL, 3.11 mmol) was added thereto at −78° C., and the mixture was stirred at room temperature for 3 hours. After the termination of the reaction, the reactant was added with MeOH, concentrated under reduced pressure, and purified by column chromatography (eluent, EtOAc/Hex=1/2) to obtain the title compound (0.424 g, 91%).

$^1$H-NMR (CDCl$_3$) δ 6.93-6.88(1H, t), 6.84-6.78(2H, m), 5.00-5.01(1H, d), 4.19-4.13(2H, q), 2.46-2.44(1H, m), 1.82-1.79(1H, m), 1.58-1.54(1H, m), 1.30-1.26(3H, t), 1.25-1.21 (1H, m)

PREPARATION EXAMPLE 45

2-(2-chloro-4-hydroxy-phenyl)-cyclopropane carboxylic acid ethyl ester

Step A: 2-chloro-4-hydroxy-benzaldehyde

After 2-chloro-4-hydroxy-benzonitrile (2 g, 0.013 mol) was dissolved in anhydrous THF (40 mL), DIBAL-H 1M hexane solution (21.7 mL, 0.032 mol) was added thereto at −78° C., and the mixture was stirred for 1 hour, and then stirred at room temperature for 2 hours. After the termination of the reaction, the reactant was added with 1M HCl at 0° C. and then extracted with EtOAc. The organic layer was separated, dried with MgSO$_4$, and concentrated under reduced pressure to obtain the title compound, which was used in the next step without a separate purification process.

Step B: 4-benzyloxy-2-chloro-benzaldehyde

2-Chloro-4-hydroxy-benzaldehyde obtained in Step A was dissolved in CH$_3$CN (20 mL). After Cs$_2$CO$_3$(8.7 g, 0.027 mol) was added thereto, benzyl bromide (1.5 mL, 0.013 mol) was added thereto, and the mixture was stirred at room temperature for 2 hours. After the termination of the reaction, the reactant was filtered by using celite, concentrated under reduced pressure, and purified by column chromatography (eluent, EtOAc/Hex=1/5) to obtain the title compound (1.89 g, 59%).

$^1$H-NMR (CDCl$_3$) δ 10.33(1H, s), 7.91-7.88(1H, m), 7.42-7.35(5H, m), 7.02(1H, m), 6.97-6.94(1H, m), 5.18(2H, s)

Step C: (E)-3-(4-benzyloxy-2-chloro-phenyl)-acrylic acid ethyl ester

4-Benzyloxy-2-chloro-benzaldehyde (0.50 g, 2.02 mmol) obtained in Step B was reacted in the same manner as in Step C of Preparation Example 2 to obtain the title compound (0.61 g, racemic mixture, 95%).

¹H-NMR (CDCl₃) δ 8.05-8.01(1H, d), 7.57-7.55(1H, d), 7.41-7.34(5H, m), 7.03(1H, m), 6.90-6.88(1H, m), 6.35-6.31 (1H, d), 5.07(2H, s), 4.29-4.24(2H, q), 1.35-1.32(3H, t)

¹H-NMR (CDCl₃) δ 7.61-7.59(1H, d), 7.41-7.34(5H, m), 7.11-7.08(1H, d), 7.01(1H, m), 6.87-6.84(1H, m), 6.00-5.97 (1H, d), 5.06(2H, s), 4.16-4.11(2H, q), 1.23-1.20(3H, t)

Step D: 2-(4-benzyloxy-2-chloro-phenyl)-cyclopropanecarboxylic acid ethyl ester (E)-3-(4-Benzyloxy-2-chloro-phenyl)-acrylic acid ethyl ester (0.612 g, 1.93 mmol) obtained in Step C was reacted in the same manner as in Step A of Preparation Example 31 to obtain the title compound (0.415 g, 64%).

¹H-NMR (CDCl₃) δ 7.41-7.32(5H, m), 7.02-7.01(1H, m), 6.94-6.92(1H, m), 6.80-6.78(1H, m), 5.03(2H, s), 4.25-4.15 (2H, q), 2.67-2.62(1H, m), 1.77-1.72(1H, m), 1.60-1.56(1H, m), 1.31-1.24(4H, m)

Step E: 2-(2-chloro-4-hydroxy-phenyl)-cyclopropanecarboxylic acid ethyl ester 2-(4-Benzyloxy-2-chloro-phenyl)-cyclopropane carboxylic acid ethyl ester (0.415 g, 1.25 mmol) obtained in Step D was reacted in the same manner as in Step B of Preparation Example 31 to obtain the title compound (0.30 g, 99%).

¹H-NMR (CDCl₃) δ 6.91-6.89(2H, m), 6.67-6.65(1H, m), 4.85(1H, m), 4.23-4.16(2H, q), 2.66-2.61(1H, m), 1.76-1.72 (1H, m), 1.60-1.55(1H, m), 1.31-1.24(4H, m)

PREPARATION EXAMPLE 46

3-(3-chloro-4-hydroxy-phenyl)-2-methyl-propionic acid ethyl ester

Step A: (E)-3-(4-benzyloxy-3-chloro-phenyl)-2-methyl-acrylic acid ethyl ester

4-Benzyloxy-3-chloro-benzaldehyde (814 mg, 3.29 mmol) was reacted in the same manner as in Step C of Preparation Example 2 to obtain the title compound (843 mg, 80%).

¹H-NMR (CDCl₃) δ 7.60~7.50(2H, m), 7.47~7.29(6H, m), 6.94(1H, d), 6.30(1H, d), 5.19(2H, s), 4.23(2H, q), 1.32(3H, t)

Step B: 3-(3-chloro-4-hydroxy-phenyl)-2-methyl-propionic acid ethyl ester (E)-3-(4-benzyloxy-3-chloro-phenyl)-acrylic acid ethyl ester (1.1 g, 3.32 mmol) obtained in Step A was reacted in the same manner as in Step D of Preparation Example 2 to obtain the title compound (807 mg, 99%).

PREPARATION EXAMPLE 47

2-(3-chloro-4-hydroxy-phenyl)-cyclopropane carboxylic acid ethyl ester

Step A: 2-(4-benzyloxy-3-chloro-phenyl)-cyclopropanecarboxylic acid ethyl ester (E)-3-(4-benzyloxy-3-chloro-phenyl)-acrylic acid ethyl ester (1.03 g, 3.26 mmol) obtained in Step B of Preparation Example 42 was reacted in the same manner as in Step A of Preparation Example 31 to obtain the title compound (805 mg, 74%).

¹H-NMR (CDCl₃) δ 7.52~7.27(5H, m), 7.12(1H, s), 6.92 (1H, m), 6.86(1H, d), 5.13(2H, s), 4.14(2H, q), 2.44(1H, m), 1.82(1H, m), 1.57(1H, m), 1.34~1.20(4H, m)

Step B: 2-(3-chloro-4-hydroxy-phenyl)-cyclopropanecarboxylic acid ethyl ester 2-(4-Benzyloxy-3-chloro-phenyl)-cyclopropanecarboxylic acid ethyl ester (847 mg, 2.56 mmol) obtained in Step A was reacted in the same manner as in Step B of Preparation Example 31 to obtain the title compound (500 mg, 81%).

¹H-NMR (CDCl₃) δ 7.13(1H, s), 6.93(2H, s), 5.40(1H, s), 4.15(2H, q), 2.44(1H, m), 1.82(1H, m), 1.54(1H, m), 1.30~1.20(4H, m)

PREPARATION EXAMPLE 48

2-(4-hydroxy-2,3-dimethyl-phenyl)-cyclopropane carboxylic acid ethyl ester

Step A: (E)-3-(4-methoxy-2,3-dimethyl-phenyl)-acrylic acid ethyl ester

4-Methoxy-2,3-dimethyl-benzaldehyde (1.0 g, 6.09 mmol) was reacted in the same manner as in Step C of Preparation Example 2 to obtain the title compound (1.3 g, 91%).

Step B: 2-(4-methoxy-2,3-dimethyl-phenyl)-cyclopropanecarboxylic acid ethyl ester (E)-3-(4-Methoxy-2,3-dimethyl-phenyl)-acrylic acid ethyl ester (0.98 g, 4.18 mmol) obtained in Step A was reacted in the same manner as in Step A of Preparation Example 31 to obtain the title compound (0.80 g, 77%).

¹H NMR (400 MHz, CDCl₃) δ 6.86(d, 2H), 6.59(d, 2H), 4.23-4.14(m, 2H), 3.75(s, 3H), 2.5-2.43(m, 1H), 2.28(s, 3H), 2.15(s, 3H), 1.71-1.66(m, 1H), 1.56-1.50(m, 1H), 1.28(t, 3H), 1.27-1.20(m, 1H)

Step C: 2-(4-hydroxy-2,3-dimethyl-phenyl)-cyclopropanecarboxylic acid ethyl ester 2-(4-Methoxy-2,3-dimethyl-phenyl)-cyclopropane carboxylic acid ethyl ester (0.32 g, 1.29 mmol) obtained in Step B was dissolved in DCM (5 mL), and the reactant was cooled to 0~5° C. BBr₃ solution (3.90 mL, 3.87 mmol, 1M/DCM) was added dropwise thereto, and the mixture was stirred at 0~5° C. for 2 hours. After the termination of the reaction, EtOH and saturated sodium bicarbonate solution were added thereto in turn, and the mixture was stirred. The separated organic layer was concentrated under reduced pressure, and the residue was purified by column chromatography (eluent, EtOAc/Hex=1/5) to obtain the title compound (0.24 g, 79%).

¹H NMR (400 MHz, CDCl₃) δ 6.77(d, 2H), 6.56(d, 2H), 5.48(s, 1H), 4.25-4.17(m, 2H), 2.5-2.42(m, 1H), 2.29(s, 3H), 2.18(s, 3H), 1.72-1.67(m, 1H), 1.57-1.50(m, 1H), 1.30(t, 3H), 1.27-1.20(m, 1H)

PREPARATION EXAMPLE 49

2-(3,5-difluoro-4-hydroxy-benzyl]-cyclopropane-carboxylic acid ethyl ester

Step A:
(4-benzyloxy-3,5-difluoro-phenyl)-acetaldehyde

After methoxymethyl triphenyl phosphonium chloride (1.04 g, 3.02 mmol) was dissolved in anhydrous THF (9 mL), LiHMDS 1.0M THF solution (3 mL, 3.02 mmol) was added thereto at 0° C., and the mixture was stirred for 15 minutes. 4-Benzyloxy-3,5-difluoro-benzaldehyde (0.50 g, 2.01 mmol) obtained in Step B of Preparation Example 2 was dissolved in anhydrous THF (6 mL), and the solution was added thereto. The mixture was stirred at room temperature for 3 hours. After the termination of the reaction, the reactant was added with water, and then extracted with EtOAc. The organic layer was separated, dried with $MgSO_4$, concentrated under reduced pressure, and then purified by column chromatography (eluent, EtOAc/Hex=1/5). After the obtained product was dissolved in THF (7.68 mL), 2N HCl (3.84 mL) was added thereto, and the mixture was stirred at 70° C. for 5 hours. After the termination of the reaction, the reactant was concentrated under reduced pressure, added with water, and then extracted with EtOAc. The organic layer was separated, dried with $MgSO_4$, concentrated under reduced pressure, and the purified by column chromatography (eluent, EtOAc/Hex=1/5) to obtain the title compound (0.107 g, 20%).

$^1$H-NMR (CDCl$_3$) δ 9.82(1H, s), 7.45-7.30(7H, m), 5.22 (2H, s)

Step B: (E)-4-(4-benzyloxy-3,5-difluoro-phenyl)-2-butenoic acid ethyl ester (4-Benzyloxy-3,5-difluoro-phenyl)-acetaldehyde (0.107 mg, 0.40 mmol) obtained in Step A was reacted in the same manner as in Step C of Preparation Example 2 to obtain the title compound (0.10 g, 74%).

$^1$H-NMR (CDCl$_3$) δ 7.47-7.43(2H, m), 7.39-7.33(3H, m), 7.03-6.97(1H, m), 6.71-6.69(2H, m), 5.82-5.77(1H, d), 5.14 (2H, s), 4.22-4.14(2H, q), 3.43-3.41(2H, d), 1.31-1.27(3H, t)

Step C: 2-(4-benzyloxy-3,5-difluoro-benzyl)-cyclopropanecarboxylic acid ethyl ester (E)-4-(4-Benzyloxy-3,5-difluoro-phenyl)-2-butenoic acid ethyl ester (0.10 g, 0.30 mmol) obtained in Step B was reacted in the same manner as in Step A of Preparation Example 31 to obtain the title compound (0.082 g, 78%).

$^1$H-NMR (CDCl$_3$) δ 7.46-7.33(5H, m), 6.76-6.74(2H, m), 5.13(2H, s), 4.19-4.10(2H, m), 2.66-2.61(1H, m), 2.53-2.47 (1H, m), 1.60-1.58(1H, m), 1.52-1.48(1H, m), 1.28-1.24(4H, m), 0.84-0.80(1H, m)

Step D: 2-(3,5-difluoro-4-hydroxy-benzyl]-cyclopropanecarboxylic acid ethyl ester 2-(4-Benzyloxy-3,5-difluoro-benzyl)-cyclopropane carboxylic acid ethyl ester (0.082 g, 0.24 mmol) obtained in Step C was reacted in the same manner as in Step B of Preparation Example 31 to obtain the title compound (0.026 g, 43%).

$^1$H-NMR (CDCl$_3$) δ 6.78-6.77(2H, m), 4.97(1H, s), 4.19-4.10(2H, m), 2.66-2.61(1H, m), 2.53-2.47(1H, m), 1.60-1.58 (1H, m), 1.52-1.48(1H, m), 1.28-1.24(4H, m), 0.84-0.80(1H, m)

PREPARATION EXAMPLE 50

(5,7-difluoro-6-hydroxy-benzofuran-3-yl)-acetic acid methyl ester

Step A:
4-chloromethyl-6,8-difluoro-7-hydroxy-2-chromenone

Sulfuric acid (2 mL) in a flask was cooled to 0° C. After ethyl 4-chloroacetoacetate (0.62 g, 3.8 mmol) was added thereto, 2,4-difluororesorcinol (0.5 g, 3.4 mmol) was added dropwise thereto. The mixture was stirred at room temperature for 2 hours, and the reactant was placed in ice water. The precipitate was filtered, washed with water, and dried by nitrogen gas to obtain the title compound (0.2 g, 24%).

Step B:
(5,7-difluoro-6-hydroxy-benzofuran-3-yl)-acetic acid

4-Chloromethyl-6,8-difluoro-7-hydroxy-2-chromenone (0.2 g, 0.81 mmol) obtained in Step A was dissolved in 1N NaOH aqueous solution (8 mL), and the mixture was stirred under reflux for 2 hours. The reactant was acidified by the addition of sulfuric acid, and then extracted with EtOAc. The organic layer was dried with $MgSO_4$, and distilled under reduced pressure to obtain the title compound (0.16 g).

Step C:
(5,7-difluoro-6-hydroxy-benzofuran-3-yl)-acetic acid methyl ester (5,7-Difluoro-6-hydroxy-benzofuran-3-yl)-acetic acid obtained in Step B, without purification, was dissolved in MeOH (1 mL), and SOCl$_2$(0.10 mL, 1.4 mmol) was added slowly thereto. The mixture was stirred at room temperature for 30 minutes, and the reactant was distilled under reduced pressure. The residue was purified by column chromatography using EtOAc/Hex (1:4) solution to obtain the title compound (0.16 g, 89%).

$^1$H-NMR (CDCl$_3$) δ 7.62(1H, s), 7.02(1H, m), 3.70(2H, s), 2.39(3H, s)

PREPARATION EXAMPLE 51

(5,7-difluoro-6-hydroxy-2,3-dihydro-benzofuran-3-yl)-acetic acid methyl ester (5,7-Difluoro-6-hydroxy-benzofuran-3-yl)-acetic acid methyl ester (0.16 g, 0.66 mmol) obtained in Step C of Preparation Example 50 was dissolved in MeOH, and 10% Pd/C (30 mg) was added thereto. The mixture was stirred at room temperature under hydrogen atmosphere for 3 hours and then filtered. The filtrate was distilled under reduced pressure and then purified using EtOAc/Hex (1:4) solution by column chromatography to obtain the title compound (0.13 g, 81%).

¹H-NMR (CDCl₃) δ 6.73(1H, d), 4.83(1H, t), 4.35(1H, m), 3.86(1H, m), 3.72(3H, s), 2.72(1H, m), 2.60(1H, m)

PREPARATION EXAMPLE 52

(6-hydroxy-2,3-dihydro-benzofuran-3-yl)-acetic acid methyl ester

Resorcinol (1.0 g, 9.1 mmol) was reacted in the same manner as in Preparation Example 50 and Preparation Example 51 in turn to obtain the title compound (0.45 g, 24%).
¹H-NMR (CDCl₃) δ 7.07(1H, m), 6.48(2H, m), 4.78(1H, t), 4.31(1H, m), 3.82(1H, m), 3.72(3H, s), 2.80(1H, m), 2.65(1H, m)

PREPARATION EXAMPLE 53

[2-(3-fluoro-4-hydroxy-phenyl)-cyclopropyl]-acetic acid methyl ester

Step A: [2-(3-fluoro-4-methoxy-phenyl)-cyclopropyl]-methanol

After 2-(3-fluoro-4-methoxy-phenyl)-cyclopropane carboxylic acid-ethyl ester (0.71 g, 2.98 mmol) was dissolved in anhydrous THF (10 mL), LiBH₄-2.0M THF solution (3 mL, 5.96 mmol) was added thereto, and the mixture was stirred at 50° C. for 2 hours. After the termination of the reaction, the reactant was cooled to room temperature, added with water, and then extracted with EtOAc. The organic layer was separated, dried with MgSO₄, and then concentrated under reduced pressure to obtain the title compound (0.519 g, 88%).
¹H-NMR (CDCl₃) δ 6.88-6.77(3H, m), 3.86(3H, s), 3.63-3.60(2H, m), 1.80-1.75(1H, m), 1.40-1.35(2H, m), 0.92-0.88(2H, m)

Step B: 2-(3-fluoro-4-methoxy-phenyl)-cyclopropanecarbaldehyde

After [2-(3-fluoro-4-methoxy-phenyl)-cyclopropyl]-methanol (0.30 g, 1.52 mmol) obtained in Step A was dissolved in DMSO (5 mL), 2-iodoxybenzoic acid (1.248 g, 4.58 mmol) was added thereto at 0° C., and the mixture was stirred at room temperature for 3 hours. After the termination of the reaction, the reactant was concentrated under reduced pressure, added with water, and then extracted with EtOAc. The organic layer was separated, dried with MgSO₄, concentrated under reduced pressure, and then purified by column chromatography (eluent, EtOAc/Hex=1/3) to obtain the title compound (0.265 g, 89%).
¹H-NMR (CDCl₃) δ 9.34(1H, s), 6.90-6.81(3H, m), 3.87 (3H, s), 2.57-2.55(1H, m), 2.12-2.09(1H, m), 1.73-1.68(1H, m), 1.48-1.43(1H, m)

Step C: [2-(3-fluoro-4-methoxy-phenyl)-cyclopropyl]-acetaldehyde 2-(3-Fluoro-4-methoxy-phenyl)-cyclopropanecarbaldehyde (0.265 g, 1.36 mmol) obtained in Step B was reacted in the same manner as in Step C of Preparation Example 48 to obtain the title compound (0.088 g, 31%).
¹H-NMR (CDCl₃) δ 9.84(1H, s), 6.88-6.80(3H, m), 3.86 (3H, s), 2.50(2H, m), 1.72-1.68(1H, m), 1.26(1H, m), 1.02-0.97(1H, m), 0.87-0.82(1H, m)

Step D: [2-(3-fluoro-4-methoxy-phenyl)-cyclopropyl]-acetic acid

[2-(3-Fluoro-4-methoxy-phenyl)-cyclopropyl]-acetaldehyde (0.088 g, 0.42 mmol) obtained in Step C was dissolved in EtOH (2 mL). AgNO₃(0.143 g, 0.84 mmol) dissolved in water (0.26 mL) and NaOH (0.067 g, 1.69 mmol) dissolved in water (0.26 mL) was added thereto in turn, and the mixture was stirred for 3 hours. After the termination of the reaction, the reactant was filtered by using celite to remove solid material, and 1N HCl aqueous solution was added to adjust the pH of the solution to 2. The organic layer obtained by the extraction with EtOAc was separated, dried with MgSO₄, and concentrated under reduced pressure to obtain the title compound (0.075 g, 79%).
¹H-NMR (CDCl₃) δ 6.88-6.81(3H, m), 3.85(3H, s), 2.45-2.43(2H, dd), 1.76-1.71(1H, m), 1.33-1.29(1H, m), 0.98-0.93(1H, m), 0.88-0.83(1H, m)

Step E: [2-(3-fluoro-4-methoxy-phenyl)-cyclopropyl]-acetic acid methyl ester

After [2-(3-fluoro-4-methoxy-phenyl)-cyclopropyl]-acetic acid (0.075 g, 0.33 mmol) obtained in Step D was dissolved in THF (1 mL), diazomethane (2.7 ml, 0.66 mmol, 0.25M ether) was added thereto, and the mixture was stirred at room temperature for 2 hours. After the termination of the reaction, the reactant was concentrated under reduced pressure and purified by column chromatography (eluent, EtOAc/Hex=1/2) to obtain the title compound (0.063 g, 79%).
¹H-NMR (CDCl₃) δ 6.87-6.80(3H, m), 3.85(3H, s), 3.70 (3H, s), 2.40-2.38(2H, dd), 1.72-1.68(1H, m), 1.31-1.27(1H, m), 0.95-0.90(1H, m), 0.85-0.80(1H, m)

Step F: [2-(3-fluoro-4-hydroxy-phenyl)-cyclopropyl]-acetic acid methyl ester

After [2-(3-fluoro-4-methoxy-phenyl)-cyclopropyl]-acetic acid methyl ester (0.067 g, 0.28 mmol) obtained in Step E was dissolved in anhydrous DCM (2 mL), BBr₃ 1M DCM solution (0.42 mL, 0.42 mmol) was added thereto at −78° C., and the mixture was stirred at room temperature for 3 hours. After the termination of the reaction, the reactant was added with MeOH, concentrated under reduced pressure, and then purified by column chromatography (eluent, EtOAc/Hex=1/2) to obtain the title compound (0.053 g, 84%).
¹H-NMR (CDCl₃) δ 6.90-6.78(3H, m), 4.92-4.91(1H, d), 3.71(3H, s), 2.40-2.38(2H, dd), 1.71-1.67(1H, m), 1.29-1.26 (1H, m), 0.94-0.89(1H, m), 0.84-0.79(1H, m)

PREPARATION EXAMPLE 54

(6-hydroxy-7-methyl-benzofuran-3-yl)-acetic acid methyl ester

2-Methyl resorcinol (1.2 g, 9.7 mmol) was reacted in the same manner as in Preparation Example 50 to obtain the title compound (0.6 g, 28%).
¹H-NMR (CDCl₃) δ 7.53(1H, s), 7.22(1H, d), 6.77(1H, d), 4.79(1H, s), 3.71(3H, s), 3.65(2H, s), 2.38(3H, s)

PREPARATION EXAMPLE 55

((R)-6-hydroxy-2,3-dihydro-benzofuran-3-yl)-acetic acid methyl ester (6-Hydroxy-2,3-dihydro-benzofuran-3-yl)-acetic acid methyl ester (40 mg, 0.19 mmol) obtained in Preparation Example 52 was separated by Prep-HPLC (CHIRALPAK AD, hexane/2-propanol (90/10)) to obtain the title compound (18 mg, 45%) eluted at 27 minute of elution time.

$^1$H-NMR (CDCl$_3$) δ 7.07(1H, m), 6.48(2H, m), 4.78(1H, t), 4.31(1H, m), 3.82(1H, m), 3.72(3H, s), 2.80(1H, m), 2.65(1H, m)

PREPARATION EXAMPLE 56

((S)-6-hydroxy-2,3-dihydro-benzofuran-3-yl)-acetic acid methyl ester (6-Hydroxy-2,3-dihydro-benzofuran-3-yl)-acetic acid methyl ester (40 mg, 0.19 mmol) obtained in Preparation Example 52 was separated by Prep-HPLC (CHIRALPAK AD, hexane/2-propanol (90/10)) to obtain the title compound (18 mg, 45%) eluted at 29 minute of elution time.

$^1$H-NMR (CDCl$_3$) δ 7.07(1H, m), 6.48(2H, m), 4.78(1H, t), 4.31(1H, m), 3.82(1H, m), 3.72(3H, s), 2.80(1H, m), 2.65(1H, m)

PREPARATION EXAMPLEs 57 and 58

(R)-4-benzyl-3-[2-(4-benzyloxy-3,5-difluoro-phenyl)-cyclopropanecarbonyl]-oxazolidin-2-on (57, more polar) (58, less polar)

Step A: 2-(4-benzyloxy-3,5-difluoro-phenyl)-cyclopropanecarbonyl chloride

After 2-(4-benzyloxy-3,5-difluoro-phenyl)-cyclopropanecarboxylic acid (75 mg, 0.246 mmol) was dissolved in anhydrous MC (5 ml), SOCl$_2$ (0.58 g, 4.92 mmol) was added thereto, and the mixture was stirred at room temperature for 18 hours. After the termination of the reaction, the reactant was concentrated under reduced pressure to obtain the title compound, which was used in the next step without a separate purification process.

Step B: (R)-4-benzyl-3-[2-(4-benzyloxy-3,5-difluoro-phenyl)-cyclopropane carbonyl]-oxazolidin-2-on (57, more polar). (58, less polar)

After (R)-4-benzyl-oxazolidin-2-on (52 mg, 0.295 mmol) was dissolved in anhydrous THF (2 ml), NaH (60%, 14 mg, 0.344 mmol) was added thereto, and the mixture was stirred for 30 minutes. Next, 2-(4-benzyloxy-3,5-difluoro-phenyl)-cyclopropanecarnoyl chloride obtained in Step A was added thereto at −78° C., and the mixture was stirred for 15 minutes, and then stirred at room temperature for 1 hour. After the termination of the reaction, NH$_4$Cl solution was added thereto and the mixture was extracted with ethyl acetate. The organic layer was separated, dried with anhydrous magnesium sulfate, concentrated under reduced pressure, and purified by column chromatography (eluent, EtOAc/Hex=1/2) to obtain each title compound [(more polar, 41 mg, 36%), (less polar, 44 mg, 38%)].

(57, more polar) NMR (400 MHz, CDCl3) 1.32-1.38 (m, 1H), 1.71-1.77 (m, 1H), 2.57-2.63 (m, 1H), 2.80 (dd, 13.2 and 9.6 Hz, 1H), 3.30 (dd, 13.2 and 3.2 Hz, 1H), 3.46-3.51 (m, 1H), 4.17-4.26 (m, 2H), 4.65-4.73 (m, 1H), 5.13 (s, 2H), 6.71-6.77 (m, 2H), 7.18-7.22 (m, 2H), 7.27-7.39 (m, 6H), 7.42-7.46 (m, 2H) ppm.

(58, less polar) NMR (400 MHz, CDCl3) 1.37-1.43 (m, 1H), 1.75-1.81 (m, 1H), 2.54-2.60 (m, 1H), 2.79 (dd, 13.2 and 9.6 Hz, 1H), 3.30 (dd, 13.2 and 3.2 Hz, 1H), 3.46-3.52 (m, 1H), 4.16-4.25 (m, 2H), 4.66-4.72 (m, 1H), 5.12 (s, 2H), 6.67-6.73 (m, 2H), 7.18-7.22 (m, 2H), 7.27-7.39 (m, 6H), 7.42-7.46 (m, 2H) ppm.

PREPARATION EXAMPLE 59

2-(3,5-difluoro-4-hydroxy-phenyl)-cyclopropane carboxylic acid methyl ester (less polar)

Step A: 2-(4-benzyloxy-3,5-difluoro-phenyl)-cyclopropane carboxylic acid

After LiOH (6.4 mg, 0.152 mmol) was dissolved in water (1 mL), H$_2$O$_2$ (35%, 37 mg, 0.38 mmol) was added thereto, and the mixture was stirred at room temperature for 30 minutes, and then cooled to 0° C. The reactant was added to the solution of (R)-4-benzyl-3-[2-(4-benzyloxy-3,5-difluoro-phenyl)-cyclopropanecarbonyl]-oxazolidin-2-on (less polar, 44 mg, 0.095 mmol) obtained in Step B of Preparation Example 58 dissolved in THF/H$_2$O (2 mL/0.5 mL), and the mixture was stirred for 1 hour. After the termination of the reaction, Na$_2$SO$_3$ solution (0.1 g in 1 mL of H$_2$O) was added thereto, and the mixture was stirred at 0° C. for 1 hour, and then concentrated under reduced pressure. The residue was added with water, and 6N HCl aqueous solution was added to adjust the pH of the solution to 2. The organic layer obtained by the extraction with ethyl acetate was separated, dried with anhydrous magnesium sulfate, and concentrated under reduced pressure to obtain the mixture (41 mg) of the title compound and 4-benzyloxazolidin-2-on, which was used in the next step without a separate purification process.

Step B: 2-(4-benzyloxy-3,5-difluoro-phenyl)-cyclopropane carboxylic acid methyl ester Mixture (41 mg) of 2-(4-benzyloxy-3,5-difluoro-phenyl)-cyclopropane carboxylic acid obtained in Step A and 4-benzyloxazolidine-2-on was dissolved in THF (2 mL), and CH$_2$N$_2$ (0.25M in Et$_2$O, 1 mL, 0.158 mmol) was added thereto. The mixture was reacted at room temperature for 1 hour, and then the reactant was concentrated under reduced pressure. The residue was purified by column chromatography (eluent, EtOAc/Hex=1/2) to obtain the title compound (22.7 mg, two-step yield 75%).

NMR (400 MHz, CDCl$_3$) 1.20-1.26 (m, 1H), 1.56-1.62 (m, 1H), 1.80-1.86 (m, 1H), 2.39-2.45 (m, 1H), 3.72 (s, 3H), 5.12 (s, 2H), 6.58-6.66 (m, 2H), 7.30-7.39 (m, 3H), 7.42-7.46 (m, 2H) ppm.

Step C: 2-(3,5-difluoro-4-hydroxy-phenyl)-cyclopropane carboxylic acid methyl ester 2-(4-Benzyloxy-3,5-difluoro-phenyl)-cyclopropanecarboxylic acid methyl ester (21 mg, 0.066 mmol) obtained in Step B was dissolved in THF/MeOH (1 mL/1 mL), and Pd/C (10%, 10 mg) was added thereto. The mixture was stirred under hydroten atmosphere for 12 hours, filtered by using celite, and concentrated under reduced pressure to obtain the title compound (17 mg, 99%).

NMR (400 MHz, CDCl$_3$) 1.20-1.26 (m, 1H), 1.55-1.61 (m, 1H), 1.78-1.84 (m, 1H), 2.40-2.46 (m, 1H) 3.72 (s, 3H), ~3.8-3.9 (brs, 1H), 6.62-6.70 (m, 2H) ppm.

PREPARATION EXAMPLE 60

2-(3,5-difluoro-4-hydroxy-phenyl)-cyclopropane carboxylic acid methyl ester (more polar)

Step A:
2-(4-benzyloxy-3,5-difluoro-phenyl)-cyclopropane carboxylic acid (R)-4-Benzyl-3-[2-(4-benzyloxy-3,5-difluoro-phenyl)-cyclopropanecarbonyl]-oxazolidin-2-on (more polar, 41 mg, 0.088 mmol) obtained in Step B of Preparation Example 57 was reacted in the same manner as Step A of Preparation Example 59 to obtain the mixture (44 mg) of the title compound and 4-benzyloxazolidin-2-on, which was used in the next step without a separate purification process.

Step B:
2-(4-benzyloxy-3,5-difluoro-phenyl)-cyclopropane carboxylic acid methyl ester The mixture (44 mg) of 2-(4-benzyloxy-3,5-difluoro-phenyl)-cyclopropane carboxylic acid and 4-benzyloxazolidin-2-on obtained in Step A was reacted in the same manner as in Step B of Preparation Example 59 to obtain the title compound (26.75 mg, two-step yield 95%).

NMR (400 MHz, CDCl$_3$) 1.20-1.26 (m, 1H), 1.56-1.62 (m, 1H), 1.80-1.86 (m, 1H), 2.39-2.45 (m, 1H), 3.72 (s, 3H), 5.12 (s, 2H), 6.58-6.66 (m, 2H), 7.30-7.39 (m, 3H), 7.42-7.46 (m, 2H) ppm.

Step C:
2-(3,5-difluoro-4-hydroxy-phenyl)-cyclopropane carboxylic acid methyl ester 2-(4-Benzyloxy-3,5-difluoro-phenyl)-cyclopropane carboxylic acid methyl ester (26 mg, 0.082 mmol) obtained in Step B was reacted in the same manner as in Step C of Preparation Example 59 to obtain the title compound (17 mg, 89%).

NMR (400 MHz, CDCl$_3$) 1.20-1.26 (m, 1H), 1.55-1.61 (m, 1H), 1.78-1.84 (m, 1H), 2.40-2.46 (m, 1H), 3.72 (s, 3H), 3.8-3.9 (brs, 1H), 6.62-6.70 (m, 2H) ppm.

PREPARATION EXAMPLEs 61 and 62

(R)-4-benzyl-3-[2-(3-fluoro-4-methoxy-phenyl)-cyclopropanecarbonyl]-oxazolidin-2-on (61, more polar) (62, less polar)

Step A:
2-(3-fluoro-4-methoxy-phenyl)-cyclopropane carboxylic acid

After 2-(3-fluoro-4-methoxy-phenyl)-cyclopropane carboxylic acid ethyl ester (1.15 g, 4.83 mmol) was dissolved in THF (6 mL), methyl alcohol (1 mL) and water (1 mL), an excess amount of sodium hydroxide was added, and then the mixture was stirred at room temperature for 4 hours. After the termination of the reaction, the reactant was concentrated under reduced pressure, and 1N HCl was added to adjust the pH of the solution to 2. The organic layer obtained by the extraction with ethyl acetate was separated, dried with anhydrous magnesium sulfate, and concentrated under reduced pressure to obtain the title compound (0.985 g, 97%).

$^1$H NMR (CDCl$_3$) δ 6.90-6.81 (3H, m), 3.86 (3H, s), 2.56-2.51 (1H, m), 1.85-1.81 (1H, m), 1.65-1.61 (1H, m), 1.36-1.31 (1H, m)

Step B:
2-(3-fluoro-4-methoxy-phenyl)-cyclopropanecarbonyl chloride

After 2-(3-fluoro-4-methoxy-phenyl)-cyclopropane carboxylic acid (0.848 g, 4.03 mmol) obtained in Step A was dissolved in anhydrous MC (10 mL), SOCl$_2$ (3 mL, 40.34 mmol) was added thereto, and the mixture was stirred at room temperature for 18 hours. After the termination of the reaction, the reactant was concentrated under reduced pressure to obtain the title compound, which was used in the next step without a separate purification process Step C: (R)-4-benzyl-3-[2-(3-fluoro-4-methoxy-phenyl)-cyclopropanecarbonyl]-oxazolidin-2-on (61, more polar) (62, less polar)

After (R)-4-benzyl-oxazolidin-2-on (0.858 g, 4.84 mmol) was dissolved in anhydrous THF (15 mL), NaH (0.226 g, 5.64 mmol) was added thereto, and the mixture was stirred for 30 minutes. 2-(3-Fluoro-4-methoxy-phenyl)-cyclopropanecarbonyl chloride obtained in Step B was added thereto at −78° C., and the mixture was stirred for 15 minutes, and then stirred at room temperature for 2 hours. After the termination of the reaction, the reactant was added with NH$_4$Cl and extracted with ethyl acetate. The organic layer was separated, dried with anhydrous magnesium sulfate, concentrated under reduced pressure, and purified by column chromatography (eluent, EtOAc/Hex/MC=1/5/10) to obtain the title compounds [(more polar, 33 mg, 49%), (less polar, 33 mg, 49%)].

(61, more polar) $^1$H NMR (CDCl$_3$) δ 7.36-7.33 (2H, m), 7.30-7.28 (1H, m), 7.23-7.21 (2H, m), 6.92-6.84 (3H, m), 4.72-4.68 (1H, m), 4.24-4.17 (2H, m), 3.86 (3H, s), 3.50-3.46 (1H, m), 3.33-3.29 (1H, dd), 2.83-2.77 (1H, q), 2.63-2.60 (1H, m), 1.80-1.75 (1H, m), 1.44-1.40 (1H, m)

(62, less polar) $^1$H NMR (CDCl$_3$) δ 7.36-7.33 (2H, m), 7.30-7.28 (1H, m), 7.23-7.21 (2H, m), 6.92-6.84 (3H, m), 4.72-4.68 (1H, m), 4.24-4.17 (2H, m), 3.86 (3H, s), 3.50-3.46 (1H, m), 3.33-3.29 (1H, dd), 2.83-2.77 (1H, q), 2.63-2.60 (1H, m), 1.80-1.75 (1H, m), 1.44-1.40 (1H, m)

PREPARATION EXAMPLE 63

2-(3-fluoro-4-hydroxy-phenyl)-cyclopropane carboxylic acid methyl ester (more polar)

Step A:
2-(3-fluoro-4-methoxy-phenyl)-cyclopropane carboxylic acid

After LiOH (0.059 g, 1.40 mmol) was dissolved in water (5 mL), H$_2$O$_2$ (0.3 mL, 3.52 mmol) was added thereto, and the mixture was stirred at room temperature for 30 minutes. The reactant was added to the solution of (R)-4-benzyl-3-[2-(3-fluoro-4-methoxy-phenyl)-cyclopropanecarbonyl]-oxazolidin-2-o n (0.325 g, 0.88 mmol) obtained in Step C of Preparation Example 61 in THF/H$_2$O (17 mL/4.4 mL) at 0°

C., and the mixture was stirred for 1 hour. After the termination of the reaction, Na$_2$SO$_3$ (1 g) dissolved in water (5 mL) was added thereto, and the mixture was stirred at 0° C. for 1 hour. 6N HCl was added thereto to adjust the pH to 2, and the reactant was extracted with ethyl acetate. The organic layer was separated, dried with anhydrous magnesium sulfate, and concentrated under reduced pressure to obtain the title compound, which was used in the next step without a separate purification process $^1$H NMR (CDCl$_3$) δ 6.90-6.81 (3H, m), 3.86 (3H, s), 2.56-2.51 (1H, m), 1.85-1.81 (1H, m), 1.65-1.61 (1H, m), 1.36-1.31 (1H, m)

Step B:
2-(3-fluoro-4-methoxy-phenyl)-cyclopropane carboxylic acid methyl ester 2-(3-Fluoro-4-methoxy-phenyl)-cyclopropane carboxylic acid obtained in Step A was reacted in the same manner as in Step B of Preparation Example 59 to obtain the title compound (0.173 g, two-step yield 87%).

Step C:
2-(3-fluoro-4-hydroxy-phenyl)-cyclopropane carboxylic acid methyl ester 2-(3-Fluoro-4-methoxy-phenyl)-cyclopropane carboxylic acid methyl ester obtained in Step B was reacted in the same manner as in Step C of Preparation Example 32 to obtain the title compound (0.034 g, 21%).

$^1$H NMR (CDCl$_3$) δ 6.92-6.88 (1H, m), 6.83-6.78 (2H, m), 4.97 (1H, m), 3.71 (3H, s), 2.46 (1H, m), 1.84-1.79 (1H, m), 1.59-1.54 (1H, m), 1.25-1.21 (1H, m)

PREPARATION EXAMPLE 64

2-(3-fluoro-4-hydroxy-phenyl)-cyclopropane carboxylic acid methyl ester (less polar)

Step A:
2-(3-fluoro-4-methoxy-phenyl)-cyclopropane carboxylic acid

After LiOH (0.059 g, 1.40 mmol) was dissolved in water (5 mL), H$_2$O$_2$ (0.3 mL, 3.52 mmol) was added thereto, and the mixture was stirred at room temperature for 30 minutes. The reactant was added to the solution of (R)-4-benzyl-3-[2-(3-fluoro-4-methoxy-phenyl)-cyclopropancarbonyl]-oxazolidin-2-o n (0.325 g, 0.88 mmol) obtained in Step C of Preparation Example 62 in THF/H$_2$O (17 mL/4.4 mL) at 0° C., and the mixture was stirred for 1 hour. After the termination of the reaction, Na$_2$SO$_3$ (1 g) dissolved in water (5 mL) was added thereto, and the mixture was stirred at 0° C. for 1 hour. 6N HCl was added thereto to adjust the pH to 2, and the reactant was extracted with ethyl acetate. The organic layer was separated, dried with anhydrous magnesium sulfate, and concentrated under reduced pressure to obtain the title compound, which was used in the next step without a separate purification process $^1$H NMR (CDCl$_3$) δ 6.90-6.81 (3H, m), 3.86 (3H, s), 2.56-2.51 (1H, m), 1.85-1.81 (1H, m), 1.65-1.61 (1H, m), 1.36-1.31 (1H, m)

Step B:
2-(3-fluoro-4-methoxy-phenyl)-cyclopropane carboxylic acid methyl ester (1S,2S)-2-(3-fluoro-4-methoxy-phenyl)-cyclopropane carboxylic acid obtained in Step A was reacted in the same manner as in Step B of Preparation Example 59 to obtain the title compound (0.170 g, two-step yield 86%).

Step C:
2-(3-fluoro-4-hydroxy-phenyl)-cyclopropane carboxylic acid methyl ester (1S,2S)-2-(3-fluoro-4-methoxy-phenyl)-cyclopropane carboxylic acid methyl ester obtained in Step B was reacted in the same manner as in Step C of Preparation Example 59 to obtain the title compound (0.080 g, 50%).

$^1$H NMR (CDCl$_3$) δ 6.92-6.88 (1H, m), 6.83-6.78 (2H, m), 4.97 (1H, m), 3.71 (3H, s), 2.46 (1H, m), 1.84-1.79 (1H, m), 1.59-1.54 (1H, m), 1.25-1.21 (1H, m)

PREPARATION EXAMPLE 65

2-(3-fluoro-4-hydroxy-phenyl)-cyclopropane carboxylic acid methyl ester (more polar)

Step A:
2-(4-benzyloxy-3-chloro-phenyl)-cyclopropane carboxylic acid 2-(4-Benzyloxy-3-chloro-phenyl)-cyclopropane carboxylic acid ethyl ester (4.64 g, 14.02 mmol) was reacted in the same manner as in Step A of Preparation Example 61 to obtain the title compound (4.14 g, 97%).

$^1$H NMR (CDCl$_3$) 7.45~7.27(5H, m), 7.12(1H, s), 6.93 (1H, m), 6.86(1H, d), 5.14(2H, s), 2.52(1H, m), 1.82(1H, m), 1.62(1H, m), 1.32(1H, m)

Step B:
2-(4-benzyloxy-3-chloro-phenyl)-cyclopropane carbonyl chloride 2-(4-Benzyloxy-3-chloro-phenyl)-cyclopropanecarboxylic acid (2.02 g, 6.67 mmol) obtained in Step A was reacted in the same manner as in Step B of Preparation Example 61, and concentrated under reduced pressure to obtain the title compound, which was used in the next step without a separate purification process.

Step C: (R)-4-benzyl-3-[2-(4-benzyloxy-3-chloro-phenyl)-cyclopropane carbonyl]-oxazolidin-2-on 2-(4-Benzyloxy-3-chloro-phenyl)-cyclopropanecarbonyl chloride obtained in Step B was reacted in the same manner as in Step C of Preparation Example 61 to obtain the title compound (0.91 g, 59%).

$^1$H NMR (CDCl$_3$) 7.52~7.20(11H, m), 7.00(1H, m), 6.88 (1H, d), 5.15(2H, s), 4.70(1H, m), 4.20(2H, m), 3.47(1H, m), 3.28(1H, m), 2.81(1H, m), 2.63(1H, m), 1.74(1H, m), 1.32 (1H, m)

Step D:
2-(4-benzyloxy-3-chloro-phenyl)-cyclopropane carboxylic acid (R)-4-benzyl-3-[2-(4-benzyloxy-3-chloro-phenyl)-cyclopropanecarbonyl]-oxazolidin-2-on (918 mg, 1.98 mmol) obtained in Step C was reacted in the same manner as in Step A of Preparation Example 59 to obtain the mixture (650 mg) of the title compound and 4-benzyloxazolidin-2-on.

$^1$H NMR (CDCl$_3$) 7.45~7.27(5H, m), 7.12(1H, s), 6.93 (1H, m), 6.86(1H, d), 5.14(2H, s), 2.52(1H, m), 1.82(1H, m), 1.62(1H, m), 1.32(1H, m)

Step E:
2-(4-benzyloxy-3-chloro-phenyl)-cyclopropane carboxylic acid methyl ester The mixture (650 mg) of 2-(4-benzyloxy-3-chloro-phenyl)-cyclopropane carboxylic acid and 4-benzyloxazolidin-2-on obtained in Step D was reacted in the same manner as in Step B of Preparation Example 59 to obtain the title compound (379 mg, two-step yield 38%).
$^1$H NMR (CDCl$_3$) 7.45~7.27(5H, m), 7.12(1H, s), 6.93 (1H, m), 6.86(1H, d), 5.13(2H, s), 3.71(3H, s), 2.45(1H, m), 1.82(1H, m), 1.62(1H, m), 1.24(1H, m)

Step F:
2-(3-chloro-4-hydroxy-phenyl)-cyclopropane carboxylic acid methyl ester 2-(4-Benzyloxy-3-chloro-phenyl)-cyclopropane carboxylic acid methyl ester obtained in Step E was reacted in the same manner as in Step C of Preparation Example 59 to obtain the title compound (0.034 g, 21%).
$^1$H NMR (CDCl$_3$) 7.07(1H, s), 6.93(2H, s), 5.44(1H, s), 3.72(3H, s), 2.45(1H, m), 1.82(1H, m), 1.24(2H, m)

PREPARATION EXAMPLE 66

2-(3-fluoro-4-hydroxy-phenyl)-cyclopropane carboxylic acid methyl ester (less polar)

Step A:
2-(4-benzyloxy-3-chloro-phenyl)-cyclopropane carboxylic acid (R)-4-Benzyl-3-[2-(4-benzyloxy-3-chloro-phenyl)-cyclopropanecarbonyl]-oxazolidin-2-on (132 mg, 0.28 mmol) was reacted in the same manner as in Step A of Preparation Example 59 to obtain the mixture (85 mg) of the title compound and 4-benzyloxazolidin-2-on.
$^1$H NMR (CDCl$_3$) 7.45~7.26(5H, m), 7.14(1H, s), 6.93 (1H, m), 6.85(1H, d), 5.14(2H, s), 2.52(1H, m), 1.82(1H, m), 1.62(1H, m), 1.32(1H, m)

Step B:
2-(4-benzyloxy-3-chloro-phenyl)-cyclopropane carboxylic acid methyl ester The mixture (85 mg) of 2-(4-benzyloxy-3-chloro-phenyl)-cyclopropane carboxylic acid and 4-benzyloxazolidin-2-on obtained in Step A was reacted in the same manner as in Step B of Preparation Example 59 to obtain the title compound (54 mg, two-step yield 60%).
$^1$H NMR (CDCl$_3$) 7.45~7.27(5H, m), 7.12(1H, s), 6.93 (1H, m), 6.86(1H, d), 5.13(2H, s), 3.71(3H, s), 2.45(1H, m), 1.82(1H, m), 1.62(1H, m), 1.24(1H, m)

Step C:
2-(3-chloro-4-hydroxy-phenyl)-cyclopropane carboxylic acid methyl ester 2-(4-Benzyloxy-3-chloro-phenyl)-cyclopropane carboxylic acid methyl ester (54 mg, 0.17 mmol) obtained in Step E was reacted in the same manner as in Step C of Preparation Example 59 to obtain the title compound (37 mg, 97%).
$^1$H NMR (CDCl$_3$) 7.07(1H, s), 6.93(2H, s), 5.42(1H, s), 3.72(3H, s), 2.45(1H, m), 1.82(1H, m), 1.24(2H, m)

PREPARATION EXAMPLE 67

3-(4-amino-phenyl)-propionic acid methyl ester

SOCl$_2$(1.5 mL) was added slowly to MeOH (6 mL) at 0~5° C., and the mixture was stirred for 10 minutes. 3-(4-Amino-phenyl)-propionic acid (1 g, 6.05 mmol) was added thereto at the same temperature. After the temperature was elevated to room temperature, the mixture was stirred for 12 hours. After the termination of the reaction, the reactant was concentrated under reduced pressure, added with saturated sodium bicarbonate aqueous solution, and extracted with EtOAc. The organic layer was added with NaCl aqueous solution, extracted again, and then filtered by using celite. The filtrate was concentrated under reduced pressure. The residue was added with n-Hex, and then concentrated under reduced pressure again. n-Hex (20 mL) was added to the obtained solid, and the mixture was stirred under reflux for 1 hour, and then stirred at room temperature for 2 hours. The mixture was filtered to obtain the title compound (0.85 g, 78%).
$^1$H NMR (500 MHz, CDCl$_3$) δ 6.98(d, 2H), 6.61(d, 2H), 3.65(s, 3H), 2.83(t, 2H), 2.56(t, 2H)

PREPARATION EXAMPLE 68

2-(2-fluoro-4-hydroxy-phenyl)-cyclopropane carboxylic acid ethyl ester

Step A: (E)-3-(2-fluoro-4-methoxy-phenyl)-acrylic acid ethyl ester

2-Fluoro-4-methoxy-benzaldehyde (1.24 g, 3.56 mmol) and carbethoxy methylene triphenylphosphorane (2.0 g, 5.78 mmol) were dissolved in THF (10 mL), and the mixture was stirred at 65~75° C. for 1 hour. After the termination of the reaction, the reactant was cooled, concentrated under reduced pressure, and purified by column chromatography (eluent, EtOAc/Hex=1/10) to obtain the title compound (0.6 g, 83%).
$^1$H NMR (400 MHz, CDCl$_3$) δ 7.73(d, 1H), 7.43(t, 1H), 6.71-6.67(m, 1H), 6.64-6.59(m, 1H), 6.35(d, 1H), 4.29(q, 2H), 3.80(s, 3H), 1.33(t, 3H)

Step B:
2-(2-fluoro-4-methoxy-phenyl)-cyclopropane carboxylic acid ethyl ester (E)-3-(2-Fluoro-4-methoxy-phenyl)-acrylic acid ethyl ester (0.3 g, 1.34 mmol) obtained in Step A was dissolved in THF (10 mL), and diazomethane solution (21.4 mL, 5.36 mmol, 0.25M ether) was added thereto. After the reactant was cooled to 0~5° C., palladium(II) acetate (45 mg, 0.2 mmol) was added slowly thereto, and the mixture was stirred at room temperature for 5 hours. After the termination of the reaction, the reactant was filtered by using celite, concentrated under reduced pressure, and purified by column chromatography (eluent, EtOAc/Hex=1/10) to obtain the title compound (0.16 g, 51%).
$^1$H NMR (400 MHz, CDCl$_3$) δ 6.91-6.84(m, 1H), 6.63-6.56(m, 2H), 4.17(q, 2H), 3.76(s, 3H), 2.60-2.52(m, 1H), 1.88-1.82(m, 1H), 1.58-1.50(m, 1H), 1.31-1.25(m, 1H), 1.28 (t, 3H)

Step C:
2-(2-fluoro-4-hydroxy-phenyl)-cyclopropane carboxylic acid ethyl ester After 2-(2-fluoro-4-methoxy-phenyl)-cyclopropane carboxylic acid ethyl ester (0.16 g, 0.67 mmol) obtained in Step B was dissolved in anhydrous DCM (10 mL), 1M BBr$_3$ solution (3.36 mL, 3.35 mmol) was added thereto at −78° C., and the mixture was stirred at room temperature for 3 hours. After the termination of the reaction, EtOH was added thereto, and the mixture was stirred at room temperature for 30 minutes. The reactant was concentrated under reduced pressure, added with saturated sodium bicarbonate aqueous solution, and extracted with DCM. The organic layer was concentrated under reduced pressure and purified by column chromatography (eluent, EtOAc/Hex=1/4) to obtain the title compound (0.25 g, 97%).

$^1$H NMR (400 MHz, CDCl$_3$) δ 6.85-6.78(m, 1H), 6.59-6.51(m, 2H), 4.19(q, 2H), 2.61-2.52(m, 1H), 1.88-1.82(m, 1H), 1.59-1.52(m, 1H), 1.33-1.27(m, 1H), 1.29(t, 3H)

EXAMPLE 1

3-[3,5-difluoro-4-(2-isopropylsulfanyl-pyridin-3-ylmethoxy)-phenyl]-propionic acid

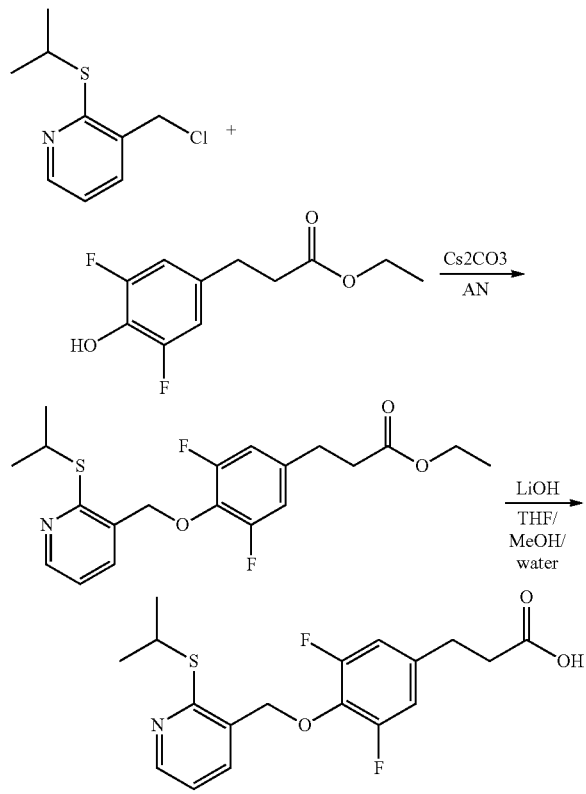

Step A: 3-[3,5-difluoro-4-(2-isopropylsulfanyl-pyridin-3-ylmethoxy)phenyl]-propionic acid ethyl ester After 3-(3,5-difluoro-4-hydroxy-phenyl)-propionic acid ethyl ester (40 mg, 0.174 mmol) obtained in Step D of Preparation Example 2 was dissolved in CH$_3$CN (5 mL), Cs$_2$CO$_3$(171 mg, 0.52 mmol) was added thereto, and then 3-chloromethyl-2-isopropyl sulfanyl-pyridin (35 mg, 0.174 mmol) obtained in Step C of Preparation Example 1 was added thereto. The mixture was stirred at 80~85° C. for 1 hour. After the termination of the reaction, the reactant was cooled and then filtered by celite. The filtrate was concentrated under reduced pressure, and purified by column chromatography (eluent, EtOAc/Hex=1/10) to obtain the title compound (66 mg, 96%).

$^1$H NMR (400 MHz, CDCl$_3$) δ 8.44-8.38(m, 1H), 7.83-7.77(m, 1H), 7.07-7.02(m, 1H), 6.76(d, 2H), 5.10(s, 2H), 4.19-4.09(m, 3H), 2.88(t, 2H), 2.58(t, 2H), 1.39(d, 6H), 1.24(t, 3H)

Step B: 3-[3,5-difluoro-4-(2-isopropylsulfanyl-pyridin-3-ylmethoxy)-phenyl]-propionic acid After 3-[3,5-difluoro-4-(2-isopropylsulfanyl-pyridin-3-ylmethoxy)phenyl]-propionic acid ethyl ester (66 mg, 0.167 mmol) obtained in Step A was dissolved in THF/MeOH/water (2:2:1, 5 mL), lithium hydroxide (12 mg, 0.50 mmol) was added thereto, and the mixture was stirred at room temperature for 2 hours. After the termination of the reaction, the reactant was concentrated under reduced pressure, and the residue was diluted with water. The aqueous layer was added with diethyl ether, stirred, and then extracted. The aqueous layer was added with 1N HCl to adjust pH to 2~3, and then extracted with EtOAc. The organic layer was dried with MgSO$_4$, and concentrated under reduced pressure to obtain the title compound (56 mg, 91%).

$^1$H NMR (400 MHz, CDCl$_3$) δ 8.45-8.40(m, 1H), 7.84-7.79(m, 1H), 7.10-7.02(m, 1H), 6.77(d, 2H), 5.12(s, 2H), 4.20-4.08(m, 1H), 2.89(t, 2H), 2.66(t, 2H), 1.39(d, 6H)

EXAMPLE 2

3-[4-(2-isopropylsulfanyl-pyridin-3-ylmethoxy)-phenyl]-propionic acid

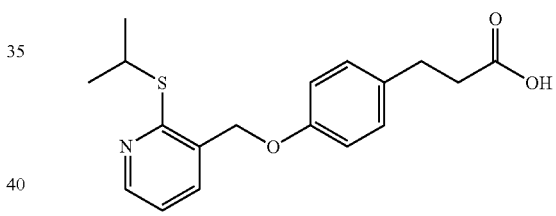

Step A: 3-[4-(2-isopropylsulfanyl-pyridin-3-ylmethoxy)phenyl]-propionic acid methyl ester 3-Chloromethyl-2-isopropylsulfanyl-pyridine (0.056 g, 0.27 mmol) obtained in Step C of Preparation Example 1 and 3-(4-hydroxy-phenyl)-propionic acid methyl ester (0.05 g, 0.27 mmol) obtained in Preparation Example 4 were reacted in the same manner as in Step A of Example 1 to obtain the title compound (0.066 g, 69%).

$^1$H-NMR (CDCl$_3$) δ 8.40(1H, m), 7.68(1H, m), 7.12(2H, d), 7.02(1H, m), 6.88(2H, d), 4.98(2H, s), 4.18(1H, m), 3.66(3H, s), 2.89(2H, t), 2.60(2H, t), 1.42(3H, t)

Step B: 3-[4-(2-isopropylsulfanyl-pyridin-3-ylmethoxy)-phenyl]-propionic acid

3-[4-(2-isopropylsulfanyl-pyridin-3-ylmethoxy)phenyl]-propionic acid methyl ester (0.064 g, 0.18 mmol) obtained in Step A was reacted in the same manner as in Step B of Example 1 to obtain the title compound (0.027 mg, 44%).

$^1$H-NMR (CDCl$_3$) δ 8.40(1H, m), 7.68(1H, m), 7.14(2H, d), 7.02(1H, m), 6.90(2H, d), 4.99(2H, s), 4.18(1H, m), 2.93(2H, t), 2.66(2H, t), 1.42(6H, d)

Mass (EI): 332(M+1)

EXAMPLE 3

3-[4-(2-isopropylsulfanyl-5-methyl-pyridin-3-yl-methoxy)-phenyl]-2-methyl-propionic acid

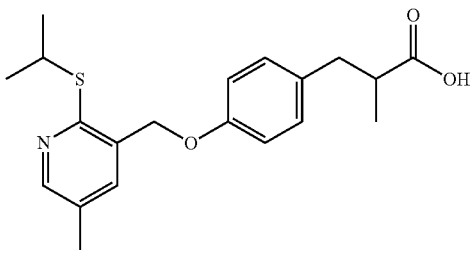 [SMILES: Cc1cnc(SC(C)C)c(COc2ccc(CC(C)C(=O)O)cc2)c1]

Step A: 3-[4-(2-isopropylsulfanyl-5-methyl-pyridin-3-ylmethoxy)phenyl]-2-methyl-propionic acid ethyl ester 3-Chloromethyl-2-isopropylsulfanyl-5-methyl-pyridine (0.02 g, 0.09 mmol) obtained in Step D of Preparation Example 30 and 3-(4-hydroxy-phenyl)-2-methyl-propionic acid ethyl ester obtained in Step B of Preparation Example 3 were reacted in the same manner as in Step A of Example 1 to obtain the title compound (0.012 g, 33%).

$^1$H-NMR (CDCl$_3$) δ 8.24(1H, s), 7.53(1H,$), 7.10(2H, d), 6.90(2H, d), 4.97(2H, s), 4.13(1H, m), 4.08(2H, q), 2.94(1H, m), 2.67(2H, m), 2.28(3H, s), 1.39(6H, d), 1.19(3H, t), 1.14(3H, d)

Step B 3-[4-(2-isopropylsulfanyl-5-methyl-pyridin-3-ylmethoxy)-phenyl]-2-methyl-propionic acid 3-[4-(2-Isopropylsulfanyl-5-methyl-pyridin-3-yl-methoxy)phenyl]-2-methyl-propionic acid ethyl ester (0.012 g, 0.03 mmol) obtained in Step A was reacted in the same manner as in Step A of Example 1 to obtain the title compound (0.007 g, 63%).

$^1$H-NMR (CDCl$_3$) δ 8.25(1H, s), 7.54(1H, s), 7.11(2H, d), 6.90(2H, d), 4.97(2H, s), 4.11(1H, m), 3.01(1H, m), 2.72(1H, m), 2.62(1H, m), 2.28(3H, s), 1.40(6H, d), 1.18(3H, d)

EXAMPLE 4

3-[4-(2-isopropylsulfanyl-pyridin-3-ylmethoxy)-phenyl]-2-methyl-propionic acid

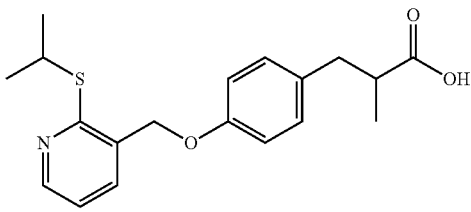 [SMILES: CC(C)Sc1ncccc1COc1ccc(CC(C)C(=O)O)cc1]

Step A: 3-[4-(2-isopropylsulfanyl-pyridin-3-yl-methoxy)-phenyl]-2-methyl-propionic acid ethyl ester 3-Chloromethyl-2-isopropylsulfanyl-pyridine (0.063 g, 0.31 mmol) obtained in Step C of Preparation Example 1 and 3-(4-hydroxy-phenyl)-2-methyl-propionic acid ethyl ester (0.065 g, 0.31 mmol) obtained in Step B of Preparation Example 3 were reacted in the same manner as in Step A of Example 1 to obtain the title compound (0.062 g, 53%).

$^1$H-NMR (CDCl$_3$) δ 8.40(1H, m), 7.70(1H, m), 7.08(2H, d), 7.02(1H, m), 6.88(2H, d), 4.98(2H, s), 4.19(1H, m), 4.06(2H, q), 2.95(1H, m), 2.63(2H, m), 1.43(6H, d), 1.20(3H, t), 1.14(3H, d)

Step B 3-[4-(2-isopropylsulfanyl-pyridin-3-yl-methoxy)-phenyl]-2-methyl-propionic acid 3-[4-(2-Isopropylsulfanyl-pyridin-3-ylmethoxy)-phenyl]-2-methyl-propionic acid ethyl ester (0.06 g 0.16 mmol) obtained in Step A was reacted in the same manner as in Step A of Example 1 to obtain the title compound (0.037 g, 66%).

$^1$H-NMR (CDCl$_3$) δ 8.40(1H, m), 7.69(1H, m), 7.11(2H, d), 7.02(1H, m), 6.89(2H, d), 4.99(2H, s), 4.18(1H, m), 3.00(1H, m), 2.72(1H, m), 2.64(1H, m), 1.43(6H, d), 1.19(3H, d)

EXAMPLE 5

3-[4-(2-isopropylsulfanyl-5-methyl-pyridin-3-yl-methoxy)-phenyl]-propionic acid

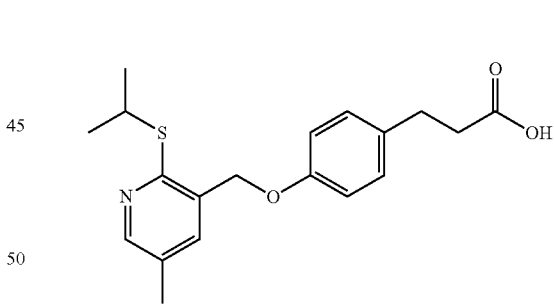

3-Chloromethyl-2-isopropylsulfanyl-5-methyl-pyridine (0.052 g, 0.24 mmol) obtained in Step D of Preparation Example 30 and 3-(4-hydroxy-phenyl)-propionic acid methyl ester (0.043 g, 0.24 mol) obtained in Preparation Example 4 were used to react sequentially in the same manner as in Steps A and B of Example 1 to obtain the title compound (55%).

$^1$H-NMR (CDCl$_3$) δ8.25(1H, s), 7.54(1H, s), 7.14(2H, d), 6.91(2H, d), 4.98(2H, s), 4.12(1H, m), 2.92(2H, t), 2.66(2H, t), 2.28(3H, s), 1.39(6H, d)

EXAMPLE 6

3-[3-fluoro-4-(2-isopropylsulfanyl-pyridin-3-yl-methoxy)-phenyl]-propionic acid

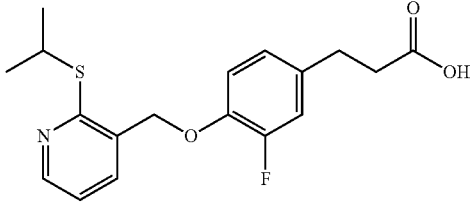 [SMILES: CC(C)Sc1ncccc1COc1ccc(CCC(=O)O)cc1F]

3-Chloromethyl-2-isopropylsulfanyl-pyridine (0.041 g, 0.2 mmol) obtained in Step C of Preparation Example 1 and 3-(3-fluoro-4-hydroxy-phenyl)-propionic acid methyl ester (0.04 g, 0.2 mmol) obtained in Step C of Preparation Example 6 were used to react sequentially in the same manner as in Steps A and B of Example 1 to obtain the title compound (47% yield).

$^1$H-NMR (CDCl$_3$) δ 8.40(1H, m), 7.74(1H, m), 7.04(1H, m), 6.95(1H, m), 6.90(2H, m), 5.05(2H, s), 4.17(1H, m), 2.88(2H, t), 2.65(2H, t), 1.42(6H, d)

EXAMPLE 7

3-[2-fluoro-4-(2-isopropylsulfanyl-pyridin-3-yl-methoxy)-phenyl]-propionic acid

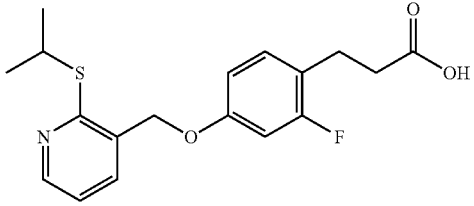 [SMILES: CC(C)Sc1ncccc1COc1ccc(CCC(=O)O)c(F)c1]

3-Chloromethyl-2-isopropylsulfanyl-pyridine (0.043 g, 0.21 mmol) obtained in Step C of Preparation Example 1 and 3-(2-fluoro-4-hydroxy-phenyl)-propionic acid ethyl ester (0.045 g, 0.21 mmol) obtained in Step D of Preparation Example 7 were used to react sequentially in the same manner as in Steps A and B of Example 1 to obtain the title compound (27% yield).

$^1$H-NMR (CDCl$_3$) δ 8.41(1H, m), 7.66(1H, m), 7.12(1H, m), 7.02(1H, m), 6.68(2H, m), 4.97(2H, s), 4.18(1H, m), 2.92(2H, t), 2.66(2H, t), 1.43(6H, d)

EXAMPLE 8

3-[4-(2-cyclopentylsulfanyl-pyridin-3-ylmethoxy)-phenyl]-2-methyl-propionic acid

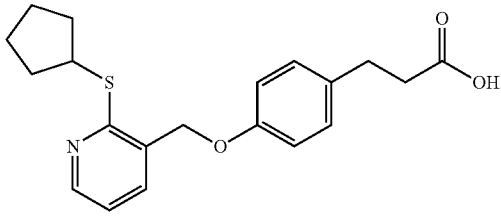 [SMILES: O=C(O)CCc1ccc(OCc2cccnc2SC2CCCC2)cc1]

3-Chloromethyl-2-cyclopentylsulfanyl-pyridine (0.205 g, 0.9 mmol) obtained in Step C of Preparation Example 8 and 3-(4-hydroxy-phenyl)-propionic acid methyl ester (0.162 g, 0.9 mmol) obtained in Preparation Example 4 were used to react sequentially in the same manner as in Steps A and B of Example 1 to obtain the title compound (0.270 g, 83%).

$^1$H-NMR (CDCl$_3$) δ 8.40-8.39(1H, m), 7.68-7.67(1H, m), 7.14-7.12(2H, d), 7.03-7.01(1H, q), 6.91-6.89(2H, d), 4.99 (2H, s), 4.26-4.18(1H, m), 2.93-2.89(2H, t), 2.67-2.63(2H, t), 2.25-2.19(2H, m), 1.79-1.77(2H, m), 1.71-1.60(4H, m)

EXAMPLE 9

3-[3,5-difluoro-4-(2-isopropylsulfanyl-6-methyl-pyridin-3-ylmethoxy)-phenyl]-propionic acid

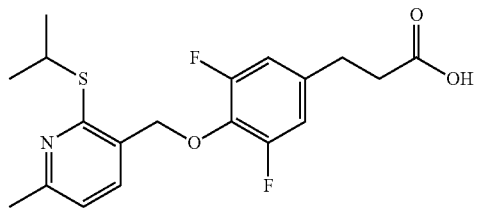 [SMILES: Cc1ccc(COc2c(F)cc(CCC(=O)O)cc2F)c(SC(C)C)n1]

3-Chloromethyl-2-isopropylsulfanyl-6-methyl-pyridine obtained in Step D of Preparation Example 9 and 3-(3,5-difluoro-4-hydroxy-phenyl)-propionic acid ethyl ester (236 mg, 1.02 mmol) obtained in Step D of Preparation Example 2 were used to react sequentially in the same manner as in Steps A and B of Example 1 to obtain the title compound (278 mg, 78%).

$^1$H-NMR (CDCl$_3$) δ 7.62(1H, d), 6.87(1H, d), 6.74(2H, m), 5.10(2H, s), 4.13(1H, m), 2.86(2H, t), 2.65(2H, t), 2.48(3H, s), 1.35(6H, d)

EXAMPLE 10

3-[4-(2-ethylsulfanyl-pyridin-3-ylmethoxy)-3,5-difluoro-phenyl]-propionic acid

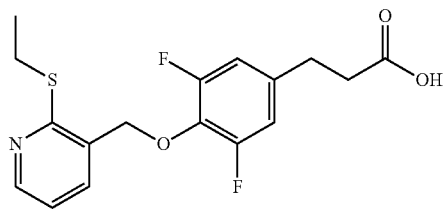 [SMILES: CCSc1ncccc1COc1c(F)cc(CCC(=O)O)cc1F]

3-Chloromethyl-2-ethylsulfanyl-pyridine (0.1 g, 0.53 mmol) obtained in Step C of Preparation Example 11 and 3-(3,5-difluoro-4-hydroxy-phenyl)-propionic acid ethyl ester (0.12 g, 0.53 mmol) obtained in Step D of Preparation Example 2 were used to react sequentially in the same manner as in Steps A and B of Example 1 to obtain the title compound (76% yield).

$^1$H-NMR (CDCl$_3$) δ 8.40(1H, m), 7.78(1H, m), 7.04(1H, m), 6.77(2H, m), 5.11(2H, s), 3.25(2H, q), 2.87(2H, t), 2.66(2H, t), 1.35(3H, t)

EXAMPLE 11

3-[3,5-difluoro-4-(2-isobutylsulfanyl-pyridin-3-yl-methoxy)-phenyl]-propionic acid

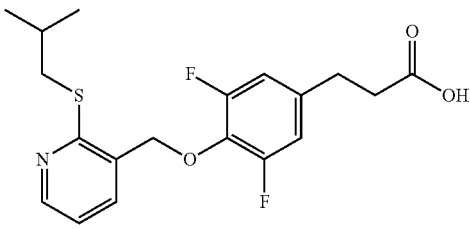 [SMILES: CC(C)CSc1ncccc1COc1c(F)cc(CCC(=O)O)cc1F]

3-Chloromethyl-2-isobutylsulfanyl-pyridine (0.048 g, 0.22 mmol) obtained in Step C of Preparation Example 12 and 3-(3,5-difluoro-4-hydroxy-phenyl)-propionic acid ethyl ester (0.051 g, 0.22 mmol) obtained in Step D of Preparation Example 2 were used to react sequentially in the same manner as in Steps A and B of Example 1 to obtain the title compound (60% yield).

$^1$H-NMR (CDCl$_3$) δ 8.38(1H, m), 7.78(1H, m), 7.03(1H, m), 6.78(2H, m), 5.14(2H, s), 3.17(2H, d), 2.88(2H, t), 2.66(2H, t), 1.92(1H, m), 1.03(6H, d)

EXAMPLE 12

3-[4-(2-cyclopentylsulfanyl-pyridin-3-ylmethoxy)-3,5-difluoro-phenyl]-propionic acid

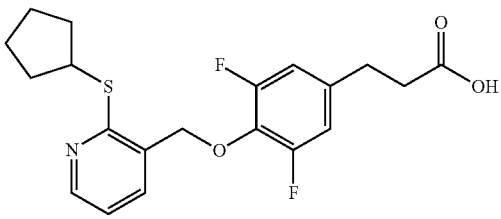 [SMILES: O=C(O)CCc1cc(F)c(OCc2cccnc2SC2CCCC2)c(F)c1]

3-Chloromethyl-2-cyclopentylsulfanyl-pyridine (0.037 g, 0.16 mmol) obtained in Step C of Preparation Example 8 and 3-(3,5-difluoro-4-hydroxy-phenyl)-propionic acid ethyl ester (0.037 g, 0.16 mmol) obtained in Step D of Preparation Example 2 were used to react sequentially in the same manner as in Steps A and B of Example 1 to obtain the title compound (0.050 g, 79%).

$^1$H-NMR (CDCl$_3$) δ 8.41-8.40(1H, m), 7.79-7.78(1H, m), 7.06-7.03(1H, q), 5.11(2H, s), 4.22-4.15(1H, m), 2.91-2.87 (2H, t), 2.68-2.64(2H, t), 2.22-2.19(2H, m), 1.76-1.75(2H, m), 1.67-1.59(4H, m)

EXAMPLE 13

4-[4-(2-isopropylsulfanyl-pyridin-3-ylmethoxy)-phenyl]-butyric acid

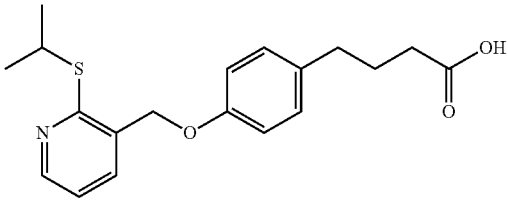 [SMILES: CC(C)Sc1ncccc1COc1ccc(CCCC(=O)O)cc1]

3-Chloromethyl-2-isopropylsulfanyl-pyridine (0.04 g, 0.20 mmol) obtained in Step C of Preparation Example 1 and 4-(4-hydroxy-phenyl)-butyric acid ethyl ester (0.041 g, 0.20 mmol) obtained in Step E of Preparation Example 13 were used to react sequentially in the same manner as in Steps A and B of Example 1 to obtain the title compound (0.06 g, 88%).

$^1$H NMR (400 MHz, CDCl$_3$) δ 8.42-8.38(m, 1H), 7.72-7.67(m, 1H), 7.10(d, 2H), 7.05-7.00(m, 1H), 6.89(d, 2H), 4.99(s, 2H), 4.23-4.12(m, 1H), 2.62(t, 2H), 2.36(t, 2H), 1.98-1.88(m, 2H), 1.42(d, 6H)

EXAMPLE 14

3-[3,5-difluoro-4-(2-propylsulfanyl-pyridin-3-yl-methoxy)-phenyl]-propionic acid

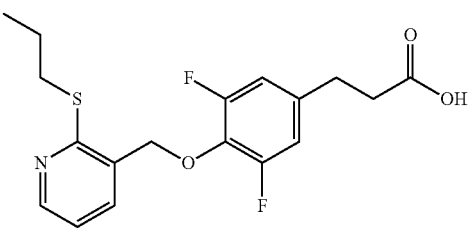 [SMILES: CCCSc1ncccc1COc1c(F)cc(CCC(=O)O)cc1F]

Step A: 3-[3,5-difluoro-4-(2-propylsulfanyl-pyridin-3-ylmethoxy)-phenyl]-propionic acid ethyl ester 3-Chloromethyl-2-propylsulfanyl-pyridine (0.1 g, 0.49 mmol) obtained in Step C of Preparation Example 14 and 3-(3,5-difluoro-4-hydroxy-phenyl)-propionic acid ethyl ester obtained in Step D of Preparation Example 2 were used to react in the same manner as in Step A of Example 1 to obtain the title compound (0.155 g, 79%).

$^1$H-NMR (CDCl$_3$) δ 8.39(1H, m), 7.78(1H, m), 7.04(1H, m), 6.76(2H, m), 5.12(2H, s), 4.13(2H, q), 3.22(2H, t), 2.87(2H, t), 2.58(2H, t), 1.73(2H, m), 1.24(3H, t), 1.03(3H, t)

Step B: 3-[3,5-difluoro-4-(2-propylsulfanyl-pyridin-3-ylmethoxy)-phenyl]-propionic acid 3-[3,5-Difluoro-4-(2-propylsulfanyl-pyridin-3-yl-methoxy)-phenyl]-propionic acid ethyl ester (0.155 g, 0.39 mmol) obtained in Step A was reacted in the same manner as in Step B of Example 1 to obtain the title compound (0.139 g, 96%).

$^1$H-NMR (CDCl$_3$) δ 8.39(1H, m), 7.78(1H, m), 7.04(1H, m), 6.77(2H, m), 5.13(2H, s), 3.22(2H, t), 2.88(2H, t), 2.68(2H, t), 1.73(2H, m), 1.03(3H, t)

EXAMPLE 15

3-[3,5-difluoro-4-(2-phenylsulfanyl-pyridin-3-yl-methoxy)-phenyl]-propionic acid

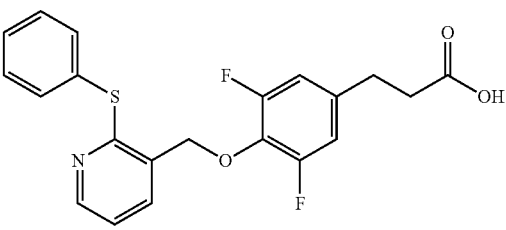 [SMILES: O=C(O)CCc1cc(F)c(OCc2cccnc2Sc2ccccc2)c(F)c1]

3-Chloromethyl-2-phenylsulfanyl-pyridine obtained in Step C of Preparation Example 15 and 3-(3,5-difluoro-4-hydroxy-phenyl)-propionic acid ethyl ester (21 mg, 0.09 mmol) obtained in Step D of Preparation Example 2 were used to react sequentially in the same manner as in Steps A and B of Example 1 to obtain the title compound (19 mg, 51%).

¹H-NMR (CDCl₃) δ 8.39(1H, d), 7.91(1H, d), 7.50(2H, m), 7.30(3H, m), 7.10(1H, m), 6.76(2H, m), 5.26(2H, s), 2.89(2H, t), 2.65(2H, t)

EXAMPLE 16

3-[4-(2-t-butylsulfanyl-pyridin-3-ylmethoxy)-3,5-difluoro-phenyl]-propionic acid

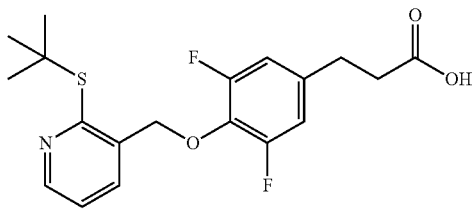 [SMILES: CC(C)(C)Sc1ncccc1COc1c(F)cc(CCC(=O)O)cc1F]

Step A: 3-[4-(2-t-butylsulfanyl-pyridin-3-yl-methoxy)-3,5-difluoro-phenyl]-propionic acid ethyl ester 2-t-Butylsulfanyl-3-chloromethyl-pyridine (0.08 g, 0.37 mmol) obtained in Step C of Preparation Example 17 and 3-(3,5-difluoro-4-hydroxy-phenyl)-propionic acid ethyl ester obtained in Step D of Preparation Example 2 were used to react in the same manner as in Step A of Example 1 to obtain the title compound (0.13 g, 86%).

¹H-NMR (CDCl₃) δ 8.45(1H, m), 7.88(1H, m), 7.11(1H, m), 6.76(2H, m), 5.17(2H, m), 4.13(2H, q), 2.87(2H, t), 2.58(2H, t), 1.54(9H, s), 1.24(3H, t)

Step B: 3-[4-(2-t-butyl-sulfanyl-pyridin-3-yl-methoxy)-3,5-difluoro-phenyl]-propionic acid 3-[4-(2-t-Butylsulfanyl-pyridin-3-ylmethoxy)-3,5-difluoro-phenyl]-propionic acid ethyl ester (0.13 g, 0.31 mmol) obtained in Step A was reacted in the same manner as in Step B of Example 1 to obtain the title compound (0.108 g, 89%).

¹H-NMR (CDCl₃) δ 8.47(1H, m), 7.89(1H, m), 7.14(1H, m), 6.76(2H, m), 5.19(2H, s), 2.87(2H, t), 2.67(2H, t), 1.53(9H, s)

EXAMPLE 17

3-[4-(2-cyclopropylmethylsulfanyl-pyridin-3-yl-methoxy)-3,5-difluoro-phenyl]-propionic acid

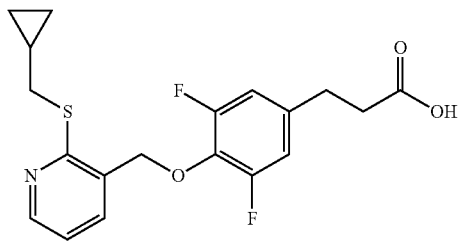 [SMILES: O=C(O)CCc1cc(F)c(OCc2cccnc2SCC2CC2)c(F)c1]

Step A: 3-[4-(2-cyclopropylmethylsulfanyl-pyridin-3-ylmethoxy)-3,5-difluoro-phenyl]-propionic acid ethyl ester 3-Chloromethyl-2-cyclopropylmethylsulfanyl-pyridine (0.07 g, 0.32 mmol) obtained in Step C of Preparation Example 18 and 3-(3,5-difluoro-4-hydroxy-phenyl)-propionic acid ethyl ester obtained in Step D of Preparation Example 2 were reacted in the same manner as in Step A of Example 1 to obtain the title compound (0.1 g, 80%).

¹H-NMR (CDCl₃) δ 8.38(1H, m), 7.80(1H, m), 7.05(1H, m), 6.75(2H, m), 5.13(2H, s), 4.13(2H, q), 3.20(2H, d), 2.88(2H, t), 2.59(2H, t), 1.24(3H, t), 1.15(1H, m), 0.58(2H, m), 0.32(2H, m)

Step B: 3-[4-(2-cyclopropylmethylsulfanyl-pyridin-3-ylmethoxy)-3,5-difluoro-phenyl]-propionic acid 3-[4-(2-Cyclopropylmethylsulfanyl-pyridin-3-yl-methoxy)-3,5-difluoro-phenyl]-propionic acid ethyl ester (0.1 g, 0.24 mmol) obtained in Step A was reacted in the same manner as in Step B of Example 1 to obtain the title compound (0.08 g, 85%).

¹H-NMR (CDCl₃) δ 8.38(1H, m), 7.80(1H, m), 7.05(1H, m), 6.76(2H, m), 5.14(2H, s), 3.18(2H, d), 2.87(2H, t), 2.66(2H, t), 1.14(1H, m), 0.56(2H, m), 0.29(2H, m)

EXAMPLE 18

3-{3,5-difluoro-4-[2-(2,2,2-trifluoro-ethylsulfanyl)-pyridin-3-ylmethoxy]-phenyl}-propionic acid

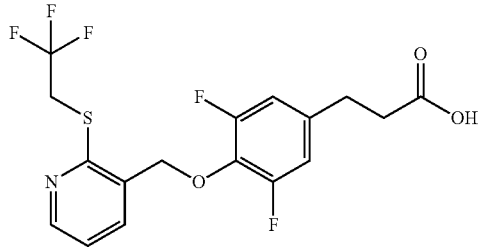 [SMILES: O=C(O)CCc1cc(F)c(OCc2cccnc2SCC(F)(F)F)c(F)c1]

Step A: 3-{3,5-difluoro-4-[2-(2,2,2-trifluoro-ethylsulfanyl)-pyridin-3-yl methoxy]-phenyl}-propionic acid ethyl ester 3-Chloromethyl-2-(2,2,2-trifluoro-ethylsulfanyl)-pyridine (0.07 g, 0.28 mmol) obtained in Step C of Preparation Example 19 and 3-(3,5-difluoro-4-hydroxy-phenyl)-propionic acid ethyl ester obtained in Step D of Preparation Example 2 were reacted in the same manner as in Step A of Example 1 to obtain the title compound (0.082 g, 65%).

¹H-NMR (CDCl₃) δ 8.42(1H, m), 7.82(1H, m), 7.14(1H, m), 6.75(2H, m), 5.14(2H, s), 4.15(2H, q), 4.12(2H, q), 2.87(2H, t), 2.58(2H, t), 1.24(3H, t)

Step B: 3-{3,5-difluoro-4-[2-(2,2,2-trifluoro-ethylsulfanyl)-pyridin-3-yl methoxy]-phenyl}-propionic acid 3-{3,5-Difluoro-4-[2-(2,2,2-trifluoro-ethylsulfanyl)-pyridin-3-ylmethoxy]-phenyl}-propionic acid ethyl ester (0.082 g, 0.18 mmol) obtained in Step A was reacted in the same manner as in Step B of Example 1 to obtain the title compound (0.043 g, 56%).

¹H-NMR (CDCl₃) δ 8.41(1H, m), 7.81(1H, m), 7.13(1H, m), 6.76(2H, m), 5.15(2H, s), 4.10(2H, q), 2.88(2H, t), 2.65(2H, t)

EXAMPLE 19

3-[4-(2-sec-butylsulfanyl-pyridin-3-ylmethoxy)-3,5-difluoro-phenyl]-propionic acid

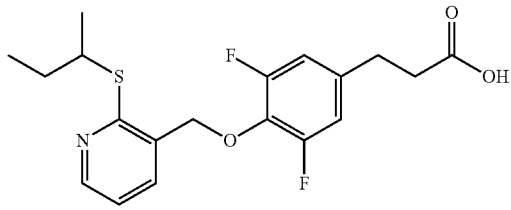 [SMILES: CCC(C)Sc1ncccc1COc1c(F)cc(CCC(=O)O)cc1F]

Step A: 3-[4-(2-sec-butylsulfanyl-pyridin-3-yl-methoxy)-3,5-difluoro-phenyl]-propionic acid ethyl ester 2-sec-Butylsulfanyl-3-chloromethyl-pyridine (0.06 g, 0.27 mmol) obtained in Step C of Preparation Example 33 and 3-(3,5-difluoro-4-hydroxy-phenyl)-propionic acid ethyl ester obtained in Step D of Preparation Example 2 were reacted in the same manner as in Step A of Example 1 to obtain the title compound (0.074 g, 65%).

¹H-NMR (CDCl₃) δ 8.39(1H, m), 7.79(1H, m), 7.04(1H, m), 6.76(2H, m), 5.11(2H, s), 4.12(2H, q), 4.03(1H, m), 2.87(2H, t), 2.58(2H, t), 1.74(1H, m), 1.66(1H, m), 1.38(3H, d), 1.24(3H, t), 1.02(3H, t)

Step B: 3-[4-(2-sec-butylsulfanyl-pyridin-3-yl-methoxy)-3,5-difluoro-phenyl]-propionic acid 3-[4-(2-sec-Butylsulfanyl-pyridin-3-ylmethoxy)-3,5-difluoro-phenyl]-propionic acid ethyl ester (0.074 g, 0.18 mmol) obtained in Step A was reacted in the same manner as in Step B of Example 1 to obtain the title compound (0.068 g, 98%).

¹H-NMR (CDCl₃) δ 8.40(1H, m), 7.79(1H, m), 7.04(1H, m), 6.77(2H, m), 5.12(2H, s), 4.04(1H, m), 2.89(2H, t), 2.65(2H, t), 1.74(1H, m), 1.66(1H, m), 1.38(3H, d), 1.01(3H, t)

EXAMPLE 20

3-[3,5-difluoro-4-(3-isopropylsulfanyl-pyrazin-2-ylmethoxy)-phenyl]-propionic acid

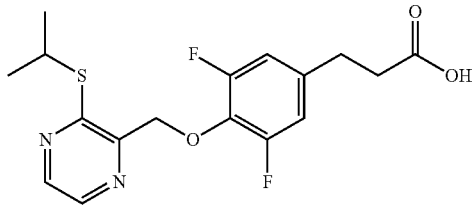 [SMILES: CC(C)Sc1nccnc1COc1c(F)cc(CCC(=O)O)cc1F]

Step A: 3-[3,5-difluoro-4-(3-isopropylsulfanyl-pyrazin-2-ylmethoxy)-phenyl]-propionic acid ethyl ester 2-Chloromethyl-3-isopropylsulfanyl-pyrazine (0.04 g, 0.2 mmol) obtained in Step D of Preparation Example 21 and 3-(3,5-difluoro-4-hydroxy-phenyl)-propionic acid ethyl ester obtained in Step D of Preparation Example 2 were reacted in the same manner as in Step A of Example 1 to obtain the title compound (0.06 g, 75%).

¹H-NMR (CDCl₃) δ 8.34(1H, d), 8.20(1H, d), 6.73(2H, m), 5.21(2H, s), 4.12(2H, q), 4.07(1H, m), 2.86(2H, t), 2.57(2H, t), 1.40(6H, d), 1.23(3H, t)

Step B: 3-[3,5-difluoro-4-(3-isopropylsulfanyl-pyrazin-2-ylmethoxy)-phenyl]-propionic acid 3-[3,5-Difluoro-4-(3-isopropylsulfanyl-pyrazin-2-yl-methoxy)-phenyl]-propionic acid ethyl ester (0.06 g, 0.15 mmol) obtained in Step A was reacted in the same manner as in Step B of Example 1 to obtain the title compound (0.05 g, 90%).

¹H-NMR (CDCl₃) δ 8.36(1H, d), 8.21(1H, d), 6.74(2H, m), 5.22(2H, s), 4.10(1H, m), 2.88(2H, t), 2.65(2H, t), 1.41(6H, d)

EXAMPLE 21

4-[4-(2-cyclopentylsulfanyl-pyridin-3-ylmethoxy)-phenyl]-butyric acid

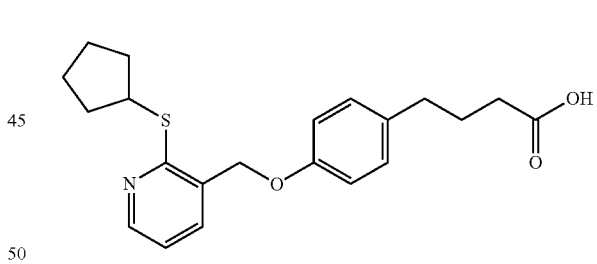

3-Chloromethyl-2-cyclopentylsulfanyl-pyridine (0.020 g, 0.09 mmol) obtained in Step C of Preparation Example 8 and 4-(4-hydroxy-phenyl)-butyric acid ethyl ester (0.018 g, 0.09 mmol) obtained in Step E of Preparation Example 13 were used to react sequentially in the same manner as in Steps A and B of Example 1 to obtain the title compound (0.031 g, 94%).

¹H-NMR (CDCl₃) δ 8.42-8.41(1H, m), 7.71-7.69(1H, m), 7.11-7.09(2H, d), 7.04-7.01(1H, q), 6.90-6.88(2H, d), 4.99 (2H, s), 4.25-4.22(1H, m), 2.63-2.59(2H, t), 2.38-2.34(2H, t), 2.24-2.22(2H, m), 1.97-1.89(2H, m), 1.89(2H, m), 1.66 (4H, m)

EXAMPLE 22

3-[4-(2-cyclohexylsulfanyl-pyridin-3-ylmethoxy)-3,5-difluoro-phenyl]-propionic acid

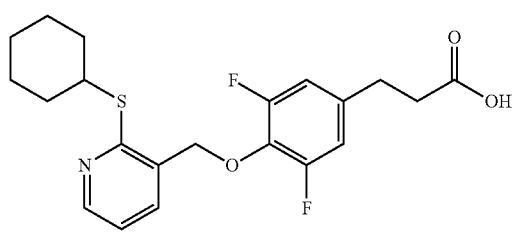 [SMILES: O=C(O)CCc1cc(F)c(OCc2cccnc2SC2CCCCC2)c(F)c1]

3-Chloromethyl-2-cyclohexylsulfanyl-pyridine (0.074 mmol) obtained in Step C of Preparation Example 22 and 3-(3,5-difluoro-4-hydroxy-phenyl)-propionic acid ethyl ester (17.5 mg, 0.074 mmol) obtained in Step D of Preparation Example 2 were used to react sequentially in the same manner as in Steps A and B of Example 1 to obtain the title compound (23 mg, 74%).

$^1$H NMR (400 MHz, CDCl$_3$) δ 8.42-8.39(m, 1H), 7.83-7.79(m, 1H), 7.08-7.01(m, 1H), 6.77(d, 2H), 5.12(s, 2H), 4.04-3.95(m, 1H), 2.89(t, 3H), 2.66(t, 3H), 2.10-2.00(m, 2H), 1.80-1.70(m, 1H), 1.69-1.58(m, 1H), 1.53-1.39(m, 4H), 1.37-1.25(m, 1H)

EXAMPLE 23

3-[4-(2-cyclobutylsulfanyl-pyridin-3-ylmethoxy)-3,5-difluoro-phenyl]-propionic acid

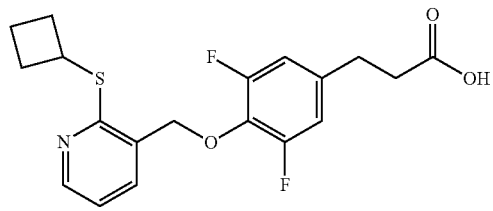 [SMILES: O=C(O)CCc1cc(F)c(OCc2cccnc2SC2CCC2)c(F)c1]

3-Chloromethyl-2-cyclobutylsulfanyl-pyridine (0.113 mmol) obtained in Step C of Preparation Example 23 and 3-(3,5-difluoro-4-hydroxy-phenyl)-propionic acid ethyl ester (26 mg, 0.113 mmol) obtained in Step D of Preparation Example 2 were used to react sequentially in the same manner as in Steps A and B of Example 1 to obtain the title compound (35 mg, 82%).

$^1$H NMR (400 MHz, CDCl$_3$) δ 8.42-8.37(m, 1H), 7.82-7.74(m, 1H), 7.09-7.00(m, 1H), 6.77(d, 2H), 5.10(s, 2H), 4.56-4.44(m, 1H), 2.89(t, 2H), 2.66(t, 2H), 2.60-2.49(m, 2H), 2.20-1.99(m, 4H)

EXAMPLE 24

3-[3,5-difluoro-4-(2-isopropylsulfanyl-pyrimidin-4-ylmethoxy)-phenyl]-propionic acid

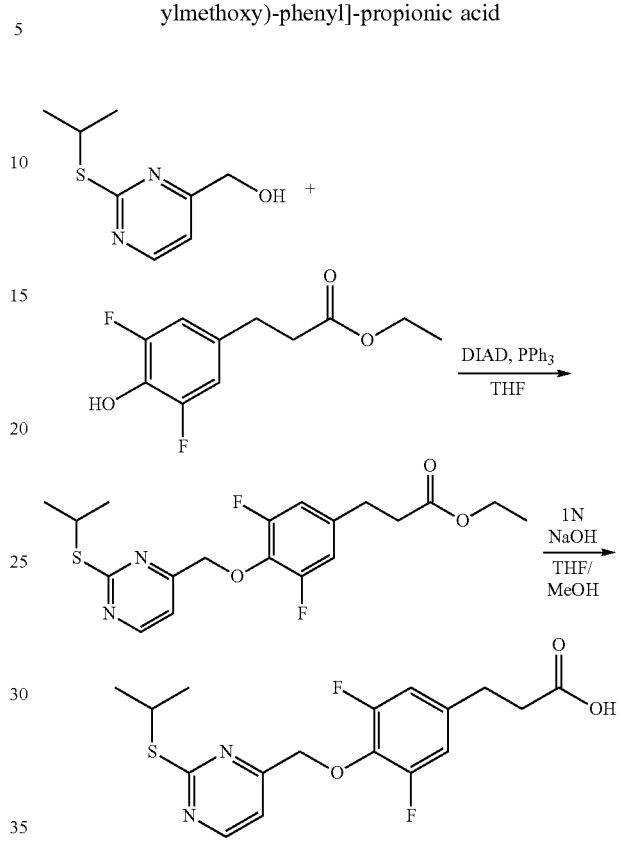

Step A: 3-[3,5-difluoro-4-(2-isopropylsulfanyl-pyrimidin-4-ylmethoxy)phenyl]-propionic acid ethyl ester (2-Isopropylsulfanyl-pyrimidin-4-yl)-methanol (0.08 g, 0.43 mmol) obtained in Step C of Preparation Example 24, 3-(3,5-difluoro-4-hydroxy-phenyl)-propionic acid ethyl ester (0.1 g, 0.43 mmol) obtained in Step D of Preparation Example 2 and triphenyl phosphine (0.114 g, 0.43 mmol) were dissolved in anhydrous THF (3 mL), and the mixture was stirred at room temperature for 10 minutes. Diisopropyl azodicarboxylate (0.085 mL, 0.43 mmol) was added slowly thereto. The mixture was stirred at room temperature for 18 hours, concentrated under reduced pressure, and separated by column chromatography (eluent: 100% DCM) to obtain the title compound (0.14 g, 81%).

$^1$H-NMR (CDCl$_3$) δ 8.56(1H, d), 7.36(1H, d), 6.78(2H, m), 5.13(2H, s), 4.14(2H, q), 3.93(1H, m), 2.88(2H, t), 2.59(2H, t), 1.41(6H, d), 1.25(3H, t)

Step B: 3-[3,5-difluoro-4-(2-isopropylsulfanyl-pyrimidin-4-ylmethoxy)-phenyl]-propionic acid 3-[3,5-Difluoro-4-(2-isopropylsulfanyl-pyrimidin-4-ylmethoxy)phenyl]-propionic acid ethyl ester (0.14 g, 0.35 mmol) obtained in Step A was reacted in the same manner as in Step B of Example 1 to obtain the title compound (0.09 g, 69%).

¹H-NMR (CDCl₃) δ 8.56(1H, d), 7.36(1H, d), 6.79(2H, m), 5.14(2H, s), 3.93(1H, m), 2.88(2H, t), 2.66(2H, t), 1.41(6H, d)

EXAMPLE 25

3-[4-(2-cyclopentylsulfanyl-pyridin-3-ylmethoxy)-phenyl]-2-methyl-propionic acid

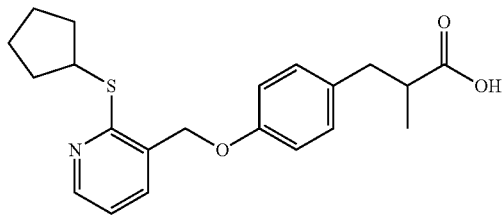 [SMILES: CC(Cc1ccc(OCc2cccnc2SC2CCCC2)cc1)C(=O)O]

3-Chloromethyl-2-cyclopentylsulfanyl-pyridine (0.056 g, 0.24 mmol) obtained in Step C of Preparation Example 8 and 3-(4-hydroxy-phenyl)-2-methyl-propionic acid ethyl ester obtained in Step B of Preparation Example 3 A were used to react sequentially in the same manner as in Steps A and B of Example 1 to obtain the title compound (0.035 g, 40%).

¹H-NMR (CDCl₃) δ 8.38(1H, m), 7.67(1H, m), 7.10(2H, d), 7.01(1H, m), 6.88(2H, d), 4.98(2H, s), 4.22(1H, m), 3.01(1H, m), 2.72(1H, m), 2.63(1H, m), 2.22(2H, m), 1.77 (2H, m), 1.65(4H, m), 1.17(3H, d)

EXAMPLE 26

3-[4-(2-butylsulfanyl-pyridin-3-ylmethoxy)-3,5-difluoro-phenyl]-propionic acid

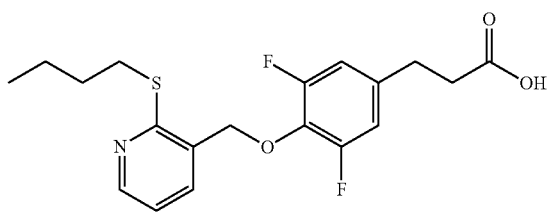 [SMILES: CCCCSc1ncccc1COc1c(F)cc(CCC(=O)O)cc1F]

Step A: 3-[4-(2-butylsulfanyl-pyridin-3-ylmethoxy)-3,5-difluoro-phenyl]-propionic acid ethyl ester 2-Butylsulfanyl-3-chloromethyl-pyridine (0.069 g, 0.32 mmol) obtained in Step C of Preparation Example 10 and 3-(3,5-difluoro-4-hydroxy-phenyl)-propionic acid ethyl ester obtained in Step D of Preparation Example 2 were reacted in the same manner as in Step A of Example 1 to obtain the title compound (0.12 g, 91%).

¹H-NMR (CDCl₃) δ 8.40(1H, m), 7.78(1H, m), 7.04(1H, m), 6.77(2H, m), 5.12(2H, s), 4.13(2H, q), 3.25(2H, t), 2.88(2H, t), 2.59(2H, t), 1.67(2H, m), 1.48(2H, m), 1.25(3H, t), 0.94(3H, t)

Step B: 3-[4-(2-butylsulfanyl-pyridin-3-ylmethoxy)-3,5-difluoro-phenyl]-propionic acid 3-[4-(2-Butylsulfanyl-pyridin-3-ylmethoxy)-3,5-difluoro-phenyl]-propionic acid ethyl ester (0.12 g, 0.29 mmol) obtained in Step A was reacted in the same manner as in Step B of Example 1 to obtain the title compound (0.071 g, 64%).

¹H-NMR (CDCl₃) δ 8.40(1H, m), 7.79(1H, m), 7.04(1H, m), 6.76(2H, m), 5.13(2H, s), 3.24(2H, t), 2.88(2H, t), 2.68(2H, t), 1.67(2H, m), 1.47(2H, m), 0.93(3H, t)

EXAMPLE 27

3-{3,5-difluoro-4-[2-(3,3,3-trifluoro-propylsulfanyl)-pyridin-3-ylmethoxy]-phenyl}-propionic acid

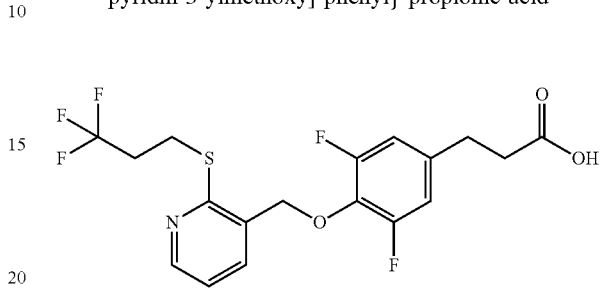

Step A: 3-{3,5-difluoro-4-[2-(3,3,3-trifluoro-propylsulfanyl)-pyridin-3-yl methoxy]-phenyl}-propionic acid ethyl ester 3-Chloromethyl-2-(3,3,3-trifluoro-propylsulfanyl)-pyridine (0.058 g, 0.22 mmol) obtained in Step C of Preparation Example 25 and 3-(3,5-difluoro-4-hydroxy-phenyl)-propionic acid ethyl ester obtained in Step D of Preparation Example 2 were reacted in the same manner as in Step A of Example 1 to obtain the title compound (0.079 g, 77%).

¹H-NMR (CDCl₃) δ 8.42(1H, m), 7.78(1H, m), 7.09(1H, m), 6.77(2H, m), 5.10(2H, s), 4.13(2H, q), 3.40(2H, m), 2.88(2H, t), 2.61(2H, t), 2.55(2H, m), 1.25(3H, t)

Step B: 3-{3,5-difluoro-4-[2-(3,3,3-trifluoro-propylsulfanyl)-pyridin-3-yl methoxyl]-phenyl}-propionic acid 3-{3,5-Difluoro-4-[2-(3,3,3-trifluoro-propylsulfanyl)-pyridin-3-ylmethoxy]-phenyl}-propionic acid ethyl ester (0.079 g, 0.17 mmol) obtained in Step A was reacted in the same manner as in Step B of Example 1 to obtain the title compound (0.035 g, 49%).

¹H-NMR (CDCl₃) δ 8.42(1H, m), 7.79(1H, m), 7.08(1H, m), 6.78(2H, m), 5.10(2H, s), 3.39(2H, m), 2.89(2H, t), 2.66(2H, t), 2.55(2H, m)

EXAMPLE 28

3-{4-[2-(2,2-dimethyl-propylsulfanyl)-pyridin-3-ylmethoxy]-3,5-difluoro-phenyl}-propionic acid

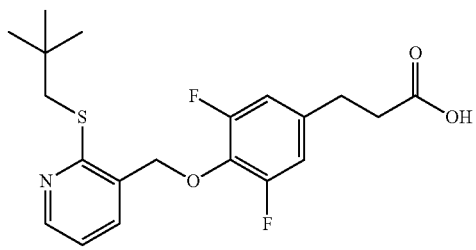 [SMILES: CC(C)(C)CSc1ncccc1COc1c(F)cc(CCC(=O)O)cc1F]

Step A: 3-{4-[2-(2,2-dimethyl-propylsulfanyl)-pyridin-3-ylmethoxy]-3,5-difluoro-phenyl}-propionic acid ethyl ester 3-Chloromethyl-2-(2,2-dimethyl-propylsulfanyl)-pyridine (0.034 g, 0.15 mmol) obtained in Step C of Preparation Example 26 and 3-(3,5-difluoro-4-hydroxy-phenyl)-propionic acid ethyl ester obtained in Step D of Preparation Example 2 were reacted in the same manner as in Step A of Example 1 to obtain the title compound (0.06 g, 95%).

$^1$H-NMR (CDCl$_3$) δ 8.38(1H, m), 7.79(1H, m), 7.03(1H, m), 6.75(2H, m), 5.16(2H, s), 4.13(2H, q), 3.29(2H, s), 2.87(2H, t), 2.58(2H, t), 1.25(3H, t), 1.02(9H, s)

Step B: 3-[4-[2-(2,2-dimethyl-propylsulfanyl)-pyridin-3-ylmethoxy]-3,5-difluoro-phenyl]-propionic acid 3-{4-[2-(2,2-Dimethyl-propylsulfanyl)-pyridin-3-ylmethoxy]-3,5-difluoro-phenyl}-propionic acid ethyl ester (0.06 g, 0.14 mmol) obtained in Step A was reacted in the same manner as in Step B of Example 1 to obtain the title compound (0.022 g, 40%).

$^1$H-NMR (CDCl$_3$) δ 8.38(1H, m), 7.79(1H, m), 7.03(1H, m), 6.78(2H, m), 5.17(2H, s), 3.29(2H, s), 2.88(2H, t), 2.66(2H, t), 1.02(9H, s)

EXAMPLE 29

3-[4-(6-cyclopentylsulfanyl)-pyridin-2-ylmethoxy]-phenyl]-propionic acid

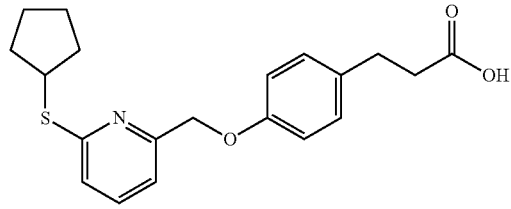 [SMILES: O=C(O)CCc1ccc(OCc2cccc(SC3CCCC3)n2)cc1]

2-Chloromethyl-6-cyclopentylsulfanyl-pyridine (0.094 mmol) obtained in Step C of Preparation Example 27 and 3-(4-hydroxy-phenyl)-propionic acid methyl ester (17 mg, 0.094 mmol) obtained in Preparation Example 4 were used to react sequentially in the same manner as in Steps A and B of Example 1 to obtain the title compound (0.03 g, 89%).

$^1$H NMR (400 MHz, CDCl$_3$) δ 7.48(t, 1H), 7.18-7.06(m, 4H), 6.90(d, 2H), 5.12(s, 2H), 4.04-3.96(m, 1H), 2.90(t, 2H), 2.64(t, 2H), 2.25-2.12(m, 2H), 1.85-1.73(m, 2H), 1.71-1.59 (m, 4H)

EXAMPLE 30

3-[4-(6-cyclopentylsulfanyl)-pyridin-2-ylmethoxy]-3,5-difluoro-phenyl]-propionic acid

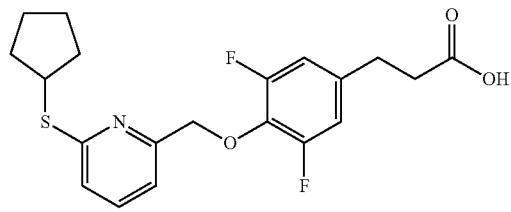 [SMILES: O=C(O)CCc1cc(F)c(OCc2cccc(SC3CCCC3)n2)c(F)c1]

2-Chloromethyl-6-cyclopentylsulfanyl-pyridine (0.096 mmol) obtained in Step C of Preparation Example 27 and 3-(3,5-difluoro-4-hydroxy-phenyl)-propionic acid ethyl ester (0.022 g, 0.096 mmol) obtained in Step D of Preparation Example 2 were used to react sequentially in the same manner as in Steps A and B of Example 1 to obtain the title compound (0.031 g, 82%).

$^1$H NMR (400 MHz, CDCl$_3$) δ 7.52(t, 1H), 7.31(d, 1H), 7.09(d, 1H), 6.76(d, 2H), 5.20(s, 2H), 4.01-3.91(m, 1H), 2.88(t, 2H), 2.65(t, 2H), 2.23-2.10(m, 2H), 1.83-1.70(m, 2H), 1.69-1.55(m, 4H)

EXAMPLE 31

3-[4-(6-cyclohexylsulfanyl)-pyridin-2-ylmethoxy]-3,5-difluoro-phenyl]-propionic acid

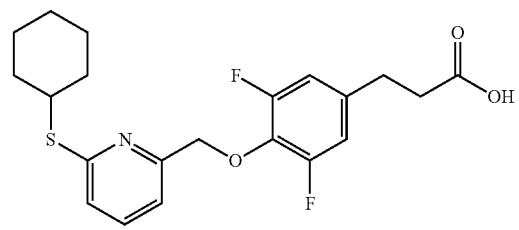 [SMILES: O=C(O)CCc1cc(F)c(OCc2cccc(SC3CCCCC3)n2)c(F)c1]

2-Chloromethyl-6-cyclohexylsulfanyl-pyridine (0.027 g, 0.11 mmol) obtained in Step C of Preparation Example 28 and 3-(3,5-difluoro-4-hydroxy-phenyl)-propionic acid ethyl ester (0.026 g, 0.11 mmol) obtained in Step D of Preparation Example 2 were used to react sequentially in the same manner as in Steps A and B of Example 1 to obtain the title compound (0.017 g, 37%).

$^1$H-NMR (CDCl$_3$) δ 7.53-7.49(1H, t), 7.32-7.30(1H, d), 7.09-7.07(1H, d), 6.79-6.74(2H, m), 5.19(2H, s), 3.75-3.74 (1H, m), 2.90-2.86(2H, t), 2.67-2.63(2H, t), 2.04-2.02(2H, m), 1.76-1.74(2H, m), 1.61(1H, m), 1.50-1.36(5H, m)

EXAMPLE 32

3-[4-(6-ethyl-2-isopropylsulfanyl)-pyridin-3-ylmethoxy]-3,5-difluoro-phenyl]-propionic acid

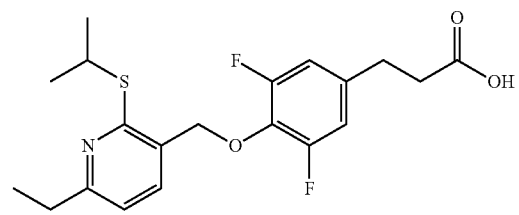 [SMILES: CCc1ccc(COc2c(F)cc(CCC(=O)O)cc2F)c(SC(C)C)n1]

3-Chloromethyl-6-ethyl-2-isopropylsulfanyl-pyridine obtained in Step C of Preparation Example 29 and 3-(3,5-difluoro-4-hydroxy-phenyl)-propionic acid ethyl ester (35 mg, 0.15 mmol) obtained in Step D of Preparation Example 2 were used to react sequentially in the same manner as in Steps A and B of Example 1 to obtain the title compound (34 mg, 63%).

$^1$H-NMR (CDCl$_3$) δ 7.66(1H, d), 6.87(1H, d), 6.76(2H, m), 5.09(2H, s), 4.17(1H, m), 2.88(2H, t), 2.78(2H, q), 2.65(2H, t), 1.39(6H, d) 1.28(3H, t)

EXAMPLE 33

3-[3,5-difluoro-4-(6-isopropylsulfanyl-pyridin-2-ylmethoxy)-phenyl]-propionic acid

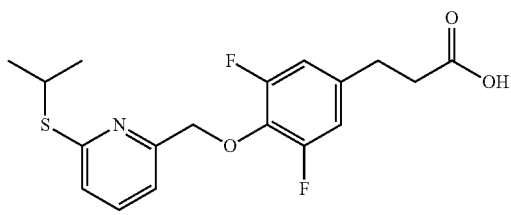 [SMILES: CC(C)Sc1cccc(COc2c(F)cc(CCC(=O)O)cc2F)n1]

2-Chloromethyl-6-isopropylsulfanyl-pyridine (0.043 g, 0.21 mmol) obtained in Step C of Preparation Example 16 and 3-(3,5-difluoro-4-hydroxy-phenyl)-propionic acid ethyl ester obtained in Step D of Preparation Example 2 were used to react sequentially in the same manner as in Steps A and B of Example 1 to obtain the title compound (0.047 g, 60%).

$^1$H-NMR (CDCl$_3$) δ 7.51(1H, m), 7.31(1H, d), 7.07(1H, d), 6.74(2H, m), 5.19(2H, s), 3.92(1H, m), 2.85(2H, t), 2.65(2H, t), 1.34(6H, d)

EXAMPLE 34

3-[4-(6-sec-butylsulfanyl-pyridin-2-ylmethoxy)-3,5-difluoro-phenyl]-propionic acid

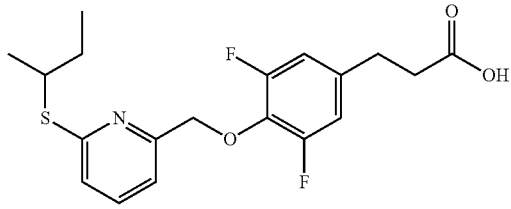 [SMILES: CCC(C)Sc1cccc(COc2c(F)cc(CCC(=O)O)cc2F)n1]

2-sec-Butylsulfanyl-6-chloromethyl-pyridine (0.06 g, 0.27 mmol) obtained in Step C of Preparation Example 5 and 3-(3,5-difluoro-4-hydroxy-phenyl)-propionic acid ethyl ester obtained in Step D of Preparation Example 2 were used to react in the same manner as in Step A Example 1 to obtain the title compound (0.074 g, 65%).

$^1$H-NMR (CDCl$_3$) δ 7.51(1H, t), 7.31(1H, d), 7.08(1H, d), 6.75(2H, m), 5.20(2H, s), 3.78(1H, m), 2.88(2H, t), 2.65(2H, t), 1.72(1H, m), 1.62(1H, m), 1.34(3H, d), 1.00(3H, t)

EXAMPLE 35

2-[4-(6-cyclopentylsulfanyl-pyridin-2-ylmethoxy)-3,5-difluoro-phenyl]-cyclopropane carboxylic acid

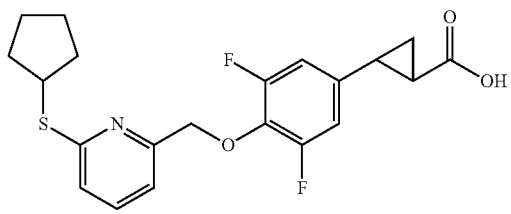 [SMILES: O=C(O)C1CC1c1cc(F)c(OCc2cccc(SC3CCCC3)n2)c(F)c1]

2-Chloromethyl-6-cyclopentylsulfanyl-pyridine (0.033 g, 0.143 mmol) obtained in Step C of Preparation Example 27 and 2-(3,5-difluoro-4-hydroxy-phenyl)-cyclopropanecarboxylic acid ethyl ester (0.033 g, 0.143 mmol) obtained in Step B of Preparation Example 31 were used to react sequentially in the same manner as in Steps A and B of Example 1 to obtain the title compound (0.045 g, 77%).

$^1$H NMR (400 MHz, CDCl$_3$) δ 7.52(t, 1H), 7.29(d, 1H), 7.09(d, 1H), 6.66(d, 2H), 5.20(s, 2H), 3.98-3.89(m, 1H), 2.54-2.47(m, 1H), 2.20-2.09(m, 2H), 1.87-1.81(m, 1H), 1.81-1.70(m, 2H), 1.69-1.54(m, 5H), 1.37-1.29(m, 1H)

EXAMPLE 36

2-[4-(2-cyclobutylsulfanyl-pyridin-3-ylmethoxy)-3,5-difluoro-phenyl]-cyclopropane carboxylic acid

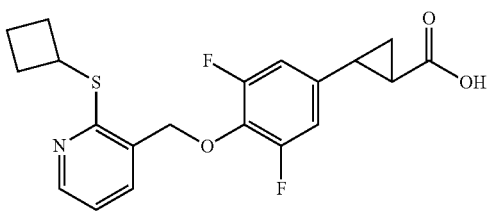 [SMILES: O=C(O)C1CC1c1cc(F)c(OCc2cccnc2SC2CCC2)c(F)c1]

3-Chloromethyl-2-cyclobutylsulfanyl-pyridine (0.024 g, 0.113 mmol) obtained in Step C of Preparation Example 23 and 2-(3,5-difluoro-4-hydroxy-phenyl)-cyclopropane carboxylic acid ethyl ester (0.026 g, 0.113 mmol) obtained in Step B of Preparation Example 31 were used to react sequentially in the same manner as in Steps A and B of Example 1 to obtain the title compound (0.036 g, 81%).

$^1$H NMR (400 MHz, CDCl$_3$) δ 8.41-8.37(m, 1H), 7.78-7.72(m, 1H), 7.07-7.00(m, 1H), 6.67(d, 2H), 5.10(s, 2H), 4.54-4.44(m, 1H), 2.59-2.48(m, 3H), 2.18-1.98(m, 4H), 1.88-1.82(m, 1H), 1.70-1.62(m, 1H), 1.37-1.29(m, 1H)

EXAMPLE 37

3-[4-(2-cyclobutylsulfanyl-pyridin-3-ylmethoxy)-3-fluoro-phenyl]-2-methyl-propionic acid

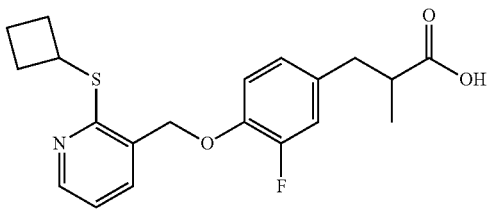 [SMILES: CC(Cc1ccc(OCc2cccnc2SC2CCC2)c(F)c1)C(=O)O]

3-Chloromethyl-2-cyclobutylsulfanyl-pyridine (0.022 g, 0.10 mmol) obtained in Step C of Preparation Example 23 and 3-(3-fluoro-4-hydroxy-phenyl)-propionic acid methyl ester (0.022 g, 0.10 mmol) obtained in Step C of Preparation Example 6 were used to react sequentially in the same manner as in Steps A and B of Example 1 to obtain the title compound (0.037 g, 97%).

$^1$H-NMR (CDCl$_3$) δ 8.38(1H, m), 7.72-7.70(1H, m), 7.03-7.00(1H, q), 6.97-6.85(3H, m), 5.04(2H, s), 4.56-4.51

(1H, m), 3.01-2.96(1H, q), 2.74-2.71(1H, m), 2.65-2.54(3H, m), 2.17-2.05(4H, m), 1.19-1.18(3H, d)

EXAMPLE 38

3-[4-(2-cyclopentylsulfanyl-pyridin-3-ylmethoxy)-3-fluoro-phenyl]-2-methyl-propionic acid

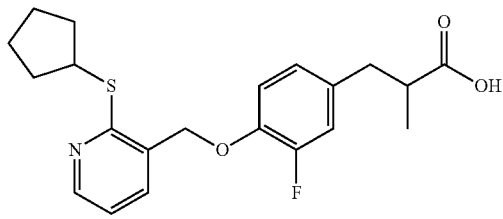 [SMILES: CC(Cc1ccc(OCc2cccnc2SC2CCCC2)c(F)c1)C(=O)O]

3-Chloromethyl-2-cyclopentylsulfanyl-pyridine (0.054 g, 0.24 mmol) obtained in Step C of Preparation Example 8 and 3-(3-fluoro-4-hydroxy-phenyl)-propionic acid methyl ester (0.050 g, 0.24 mmol) obtained in Step C of Preparation Example 6 were used to react sequentially in the same manner as in Steps A and B of Example 1 to obtain the title compound (0.091 g, 98%).

$^1$H-NMR (CDCl$_3$) δ 8.41-8.40(1H, m), 7.75-7.73(1H, m), 7.05-7.02(1H, q), 6.97-6.85(3H, m), 5.06(2H, s), 4.26-4.24(1H, m), 3.01-2.96(1H, q), 2.75-2.70(1H, m), 2.65-2.60(1H, m), 2.25-2.22(2H, m), 1.79-1.77(2H, m), 1.66-1.63(4H, m), 1.19-1.18(3H, d)

EXAMPLE 39

3-[4-(2-sec-butylsulfanyl-pyridin-3-ylmethoxy)-3-fluoro-phenyl]-2-methyl-propionic acid

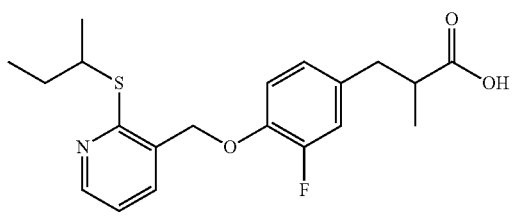 [SMILES: CCC(C)Sc1ncccc1COc1ccc(CC(C)C(=O)O)cc1F]

2-sec-Butylsulfanyl-3-chloromethyl-pyridine (0.050 g, 0.23 mmol) obtained in Step C of Preparation Example 33 and 3-(3-fluoro-4-hydroxy-phenyl)-propionic acid methyl ester (0.050 g, 0.23 mmol) obtained in Step C of Preparation Example 6 were used to react sequentially in the same manner as in Steps A and B of Example 1 to obtain the title compound (0.060 g, 64%).

$^1$H-NMR (CDCl$_3$) δ 8.40(1H, m), 7.75-7.73(1H, m), 7.05-7.02(1H, q), 6.96-6.87(3H, m), 5.07(2H, s), 4.11-4.08 (1H, m), 3.01-2.96(1H, q), 2.75-2.73(1H, m), 2.66-2.60(1H, m), 1.78-1.69(2H, m), 1.41-1.39(3H, d), 1.20-1.18(3H, d), 1.06-1.02(3H, t)

EXAMPLE 40

3-[4-(2-cyclopropylmethylsulfanyl-pyridin-3-ylmethoxy)-3-fluoro-phenyl]-2-methyl-propionic acid

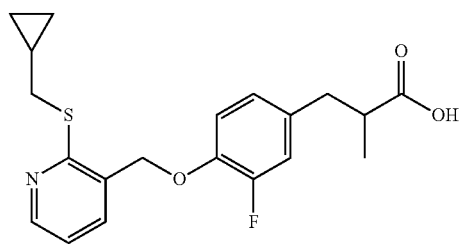 [SMILES: CC(Cc1ccc(OCc2cccnc2SCC2CC2)c(F)c1)C(=O)O]

3-Chloromethyl-2-cyclomethylsulfanyl-pyridine (0.050 g, 0.23 mmol) obtained in Step C of Preparation Example 18 and 3-(3-fluoro-4-hydroxy-phenyl)-propionic acid methyl ester (0.050 g, 0.23 mmol) obtained in Step C of Preparation Example 6 were used to react sequentially in the same manner as in Steps A and B of Example 1 to obtain the title compound (0.084 g, 96%).

$^1$H-NMR (CDCl$_3$) δ 8.39-8.38(1H, m), 7.75-7.73(1H, m), 7.05-7.02(1H, q), 6.97-6.85(3H, m), 5.09(2H, s), 3.24-3.22 (2H, d), 3.01-2.96(1H, q), 2.76-2.71(1H, m), 2.66-2.60(1H, m), 1.20-1.17(4H, m), 0.62-0.57(2H, m), 0.35-0.32(2H, m)

EXAMPLE 41

3-[3,5-difluoro-4-(2-isopropylsulfanyl-pyridin-3-ylmethoxy)-phenyl]-2-methyl-propionic acid

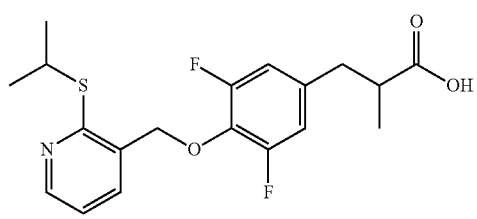 [SMILES: CC(C)Sc1ncccc1COc1c(F)cc(CC(C)C(=O)O)cc1F]

3-Chloromethyl-2-isopropylsulfanyl-pyridine (0.045 g, 0.22 mmol) obtained in Step C of Preparation Example 1 and 3-(3,5-difluoro-4-hydroxy-phenyl)-2-methyl-propionic acid ethyl ester (0.055 g, 0.22 mmol) obtained in Step B of Preparation Example 34 were used to react sequentially in the same manner as in Steps A and B of Example 1 to obtain the title compound (0.046 g, 54%).

$^1$H-NMR (CDCl$_3$) δ 8.40(1H, m), 7.80(1H, m), 7.06(1H, m), 6.74(2H, m), 5.11(2H, s), 4.14(1H, m), 2.97(1H, m), 2.72(1H, m), 2.61(1H, m), 1.39(6H, d), 1.21(3H, d)

EXAMPLE 42

3-[4-(2-sec-butylsulfanyl-pyridin-3-ylmethoxy)-3,5-difluoro-phenyl]-2-methyl-propionic acid

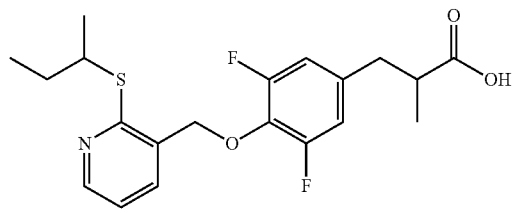 [SMILES: CCC(C)Sc1ncccc1COc1c(F)cc(CC(C)C(=O)O)cc1F]

2-sec-Butylsulfanyl-3-chloromethyl-pyridine (0.049 g, 0.22 mmol) obtained in Step C of Preparation Example 33 and 3-(3,5-difluoro-4-hydroxy-phenyl)-2-methyl-propionic acid ethyl ester (0.055 g, 0.22 mmol) obtained in Step B of Preparation Example 34 were used to react sequentially in the same manner as in Steps A and B of Example 1 to obtain the title compound (0.036 g, 56%).

$^1$H-NMR (CDCl$_3$) δ 8.40(1H, m) 7.79(1H, m), 7.05(1H, m), 6.74(2H, m), 5.12(2H, s), 4.03(1H, m), 2.97(1H, m), 2.73(1H, m), 2.64(1H, m), 1.74(1H, m), 1.65(1H, m), 1.36 (3H, d), 1.20(3H, d), 1.02(3H, t)

EXAMPLE 43

3-[3,5-difluoro-4-(2-isopropylsulfanyl-6-methoxy-pyridin-3-ylmethoxy)-phenyl]-propionic acid

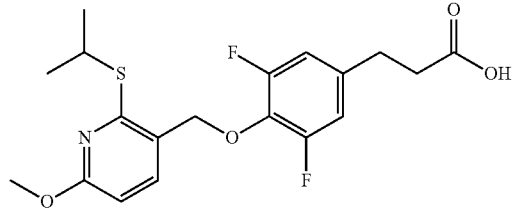 [SMILES: COc1ccc(COc2c(F)cc(CCC(=O)O)cc2F)c(SC(C)C)n1]

3-Chloromethyl-2-isopropylsulfanyl-6-methoxy-pyridine obtained in Step E of Preparation Example 35 and 3-(3,5-difluoro-4-hydroxy-phenyl)-propionic acid ethyl ester (33 mg, 0.14 mmol) obtained in Step D of Preparation Example 2 were used to react sequentially in the same manner as in Steps A and B of Example 1 to obtain the title compound (30 mg, 66%).

$^1$H-NMR (CDCl$_3$) δ 7.58(1H, d), 6.75(2H, m), 6.44(1H, d), 5.06(2H, s), 4.11(1H, m), 3.94(3H, s), 2.89(2H, t), 2.66(2H, t), 1.41(6H, d)

EXAMPLE 44

3-[4-(6-cyclopentylsulfanyl-pyridin-2-ylmethoxy)-3,5-difluoro-phenyl]-2-methyl-propionic acid

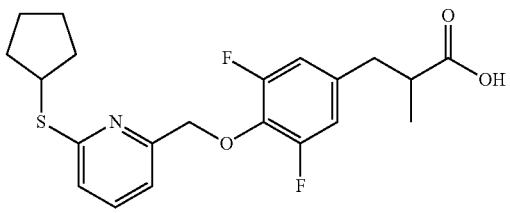

2-Chloromethyl-6-cyclopentylsulfanyl-pyridine (40 mg, 0.17 mmol) obtained in Step C of Preparation Example 27 and 3-(3,5-difluoro-4-hydroxy-phenyl)-2-methyl-propionic acid ethyl ester (43 mg, 0.17 mmol) obtained in Step B of Preparation Example 34 were used to react sequentially in the same manner as in Steps A and B of Example 1 to obtain the title compound (0.054 g, 75%).

$^1$H-NMR (CDCl$_3$) δ 8.39(1H, m), 7.78(1H, m), 7.03(1H, m), 6.73(2H, m), 5.10(2H, s), 4.27(1H, m), 4.11(2H, q), 2.97(1H, m), 2.74(1H, m), 2.60(1H, m), 2.20(2H, m), 1.74 (2H, m), 1.63(4H, m), 1.20(3H, d)

EXAMPLE 45

3-[4-(2-cyclopentylsulfanyl-6-methyl-pyridin-3-ylmethoxy)-3,5-difluoro-phenyl]-propionic acid

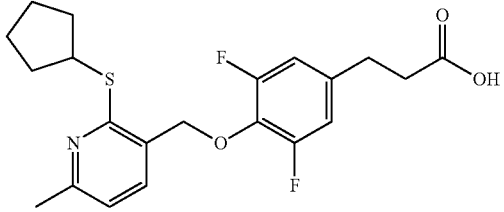 [SMILES: Cc1ccc(COc2c(F)cc(CCC(=O)O)cc2F)c(SC2CCCC2)n1]

3-Chloromethyl-2-cyclopentylsulfanyl-6-methyl-pyridine obtained in Step C of Preparation Example 36 and 3-(3,5-difluoro-4-hydroxy-phenyl)-propionic acid ethyl ester (39 mg, 0.17 mmol) obtained in Step D of Preparation Example 2 were used to react sequentially in the same manner as in Steps A and B of Example 1 to obtain the title compound (33 mg, 57%).

$^1$H-NMR (CDCl$_3$) δ 7.61(1H, d), 6.87(1H, d), 6.75(2H, m), 5.09(2H, s), 4.19(1H, m), 2.88(2H, t), 2.65(2H, t), 2.49(3H, s), 2.20(2H, m), 1.76(2H, m), 1.62(4H, m)

EXAMPLE 46

3-[4-(6-cyclobutylsulfanyl-pyridin-2-ylmethoxy)-3,5-difluoro-phenyl]-2-methyl-propionic acid

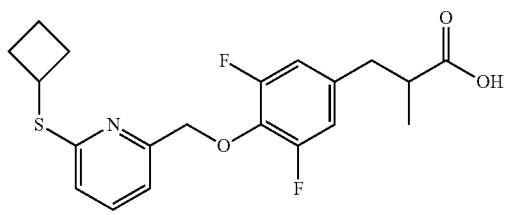 [SMILES: CC(Cc1cc(F)c(OCc2cccc(SC3CCC3)n2)c(F)c1)C(=O)O]

Step A: 3-[4-(6-cyclobutylsulfanyl-pyridin-2-yl-methoxy)-3,5-difluoro-phenyl]-2-methyl-propionic acid ethyl ester 2-Chloromethyl-6-cyclobutylsulfanyl-pyridine (0.018 g, 0.08 mmol) obtained in Step C of Preparation Example 37 and 3-(3,5-difluoro-4-hydroxy-phenyl)-2-methyl-propionic acid ethyl ester (0.021 g, 0.08 mmol) obtained in Step B of Preparation Example 34 were used to react in the same manner as in Step A of Example 1 to obtain the title compound (0.024 g, 67%).

$^1$H-NMR (CDCl$_3$) δ 7.52(1H, t), 7.32(1H, d), 7.00(1H, d), 6.72(2H, m), 5.18(2H, s), 4.25(1H, m), 4.10(2H, q), 2.92 (1H, m), 2.67(1H, m), 2.61(1H, m), 2.49(2H, m), 2.08(4H, m), 1.20(3H, t), 1.15(3H, d)

Step B: 3-[4-(6-cyclobutylsulfanyl-pyridin-2-yl-methoxy)-3,5-difluoro-phenyl]-2-methyl-propionic acid 3-[4-(6-Cyclobutylsulfanyl-pyridin-2-ylmethoxy)-3,5-difluoro-phenyl]-2-methyl-propionic acid ethyl ester (0.024 g, 0.057 mmol) obtained in Step A was reacted in the same manner as in Step B of Example 1 to obtain the title compound (0.0023 g, 10%).

$^1$H-NMR (CDCl$_3$) δ 7.52(1H, t), 7.32(1H, d), 7.00(1H, d), 6.74(2H, m), 5.19(2H, s), 4.23(1H, m), 2.97(1H, m), 2.74 (1H, m), 2.62(1H, m), 2.49(2H, m), 2.08(4H, m), 1.19(3H, d)

EXAMPLE 47

3-[4-(2-cyclopentylsulfanyl-pyridin-3-ylmethoxy)-3,5-difluoro-phenyl]-2-methyl-propionic acid

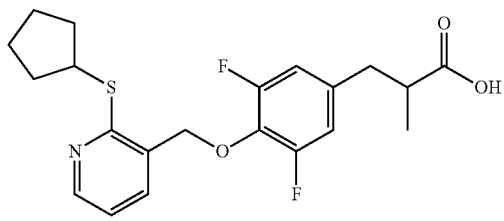 [SMILES: CC(Cc1cc(F)c(OCc2cccnc2SC2CCCC2)c(F)c1)C(=O)O]

3-Chloromethyl-2-cyclopentylsulfanyl-pyridine (0.035 g, 0.15 mmol) obtained in Step C of Preparation Example 8 and 3-(3,5-difluoro-4-hydroxy-phenyl)-2-methyl-propionic acid ethyl ester (35 mg, 0.13 mmol) obtained in Step B of Preparation Example 34 were used to react sequentially in the same manner as in Steps A and B of Example 1 to obtain the title compound (0.027 g, 46% yield).

$^1$H-NMR (CDCl$_3$) δ 8.39(1H, m), 7.78(1H, m), 7.04(1H, m), 6.73(2H, m), 5.10(2H, s), 4.18(1H, m), 2.96(1H, m), 2.72(1H, m), 2.63(1H, m), 2.19(2H, m), 1.74(2H, m), 1.63 (4H, m), 1.20(3H, d)

EXAMPLE 48

3-[4-(6-sec-butylsulfanyl-pyridin-2-ylmethoxy)-3,5-difluoro-phenyl]-2-methyl-propionic acid

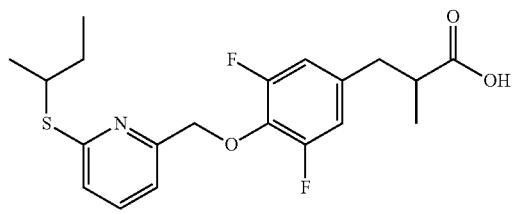 [SMILES: CCC(C)Sc1cccc(COc2c(F)cc(CC(C)C(=O)O)cc2F)n1]

Step A: 3-[4-(6-sec-butylsulfanyl-pyridin-2-yl-methoxy)-3,5-difluoro-phenyl]-2-methyl-propionic acid ethyl ester 2-sec-Butylsulfanyl-6-chloromethyl-pyridine (28 mg, 0.13 mmol) in Step C of Preparation Example 5 and 3-(3,5-difluoro-4-hydroxy-phenyl)-2-methyl-propionic acid ethyl ester (30 mg, 0.13 mmol) in Step B of Preparation Example 34 were used to react in the same manner as in Step A of Example 1 to obtain the title compound (50 mg, 96%).

Step B: 3-[4-(6-sec-butylsulfanyl-pyridin-2-yl-methoxy)-3,5-difluoro-phenyl]-2-methyl-propionic acid 3-[4-(6-sec-Butylsulfanyl-pyridin-2-ylmethoxy)-3,5-difluoro-phenyl]-2-methyl-propionic acid ethyl ester (50 mg, 0.12 mmol) obtained in Step A was reacted in the same manner as in Step B of Example 1 to obtain the title compound (35 mg, 75%).

$^1$H-NMR (CDCl$_3$) δ 7.53(1H, t), 7.31(1H, d), 7.08(1H, d), 6.74(2H, m), 5.19(2H, s), 3.81(1H, m), 2.97(1H, m), 2.73 (1H, m), 2.62(1H, m), 1.71(1H, m), 1.63(1H, m), 1.34(3H, d), 1.20(3H, d), 1.00(3H, t)

EXAMPLE 49

3-[3,5-difluoro-4-(6-isopropylsulfanyl-pyridin-2-ylmethoxy)-phenyl]-2-methyl-propionic acid

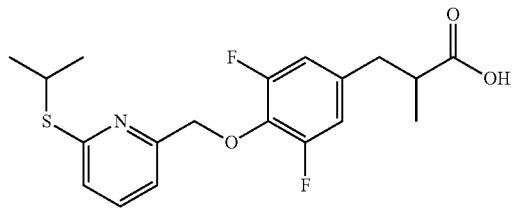 [SMILES: CC(C)Sc1cccc(COc2c(F)cc(CC(C)C(=O)O)cc2F)n1]

2-Chloromethyl-6-isopropylsulfanyl-pyridine (26 mg, 0.13 mmol) obtained in Step C of Preparation Example 16 and 3-(3,5-difluoro-4-hydroxy-phenyl)-2-methyl-propionic acid ethyl ester (30 mg, 0.13 mmol) obtained in Step B of Preparation Example 34 were used to react sequentially in the same manner as in Steps A and B of Example 1 to obtain the title compound (40 mg, 80%).

$^1$H-NMR (CDCl$_3$) δ 7.51(1H, t), 7.32(1H, d), 7.08(1H, d), 6.74(2H, m), 5.20(2H, s), 3.93(1H, m), 2.97(1H, m), 2.73 (1H, m), 2.62(1H, m), 1.36(6H, d), 1.20(3H, d)

EXAMPLE 50

3-[4-(2-cyclopropylmethylsulfanyl-pyridin-3-yl-methoxy)-3,5-difluoro-phenyl]-2-methyl-propionic acid

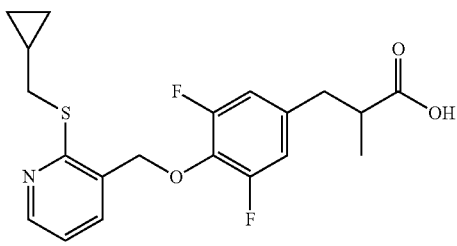

3-Chloromethyl-2-cyclopropylmethylsulfanyl-pyridine (0.037 g, 0.17 mmol) obtained in Step C of Preparation Example 18 and 3-(3,5-difluoro-4-hydroxy-phenyl)-2-methyl-propionic acid ethyl ester (39 mg, 0.17 mmol) obtained in Step B of Preparation Example 34 were used to react sequentially in the same manner as in Steps A and B of Example 1 to obtain the title compound (0.047 g, 70%).

$^1$H-NMR (CDCl$_3$) δ 8.38(1H, m), 7.80(1H, m), 7.05(1H, m), 6.76(2H, m), 5.14(2H, s), 3.20(2H, d), 2.98(1H, m), 2.73(1H, m), 2.63(1H, m), 1.21(3H, d), 1.14(1H, m), 0.58 (2H, m), 0.31(2H, m)

EXAMPLE 51

3-[3,5-difluoro-4-(2-propylsulfanyl-pyridin-3-yl-methoxy)-phenyl]-2-methyl-propionic acid

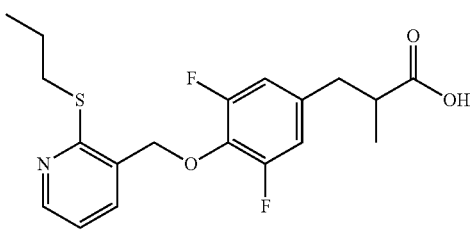 [SMILES: CCCSc1ncccc1COc1c(F)cc(CC(C)C(=O)O)cc1F]

3-Chloromethyl-2-propylsulfanyl-pyridine (0.031 g, 0.15 mmol) obtained in Step C of Preparation Example 14 and 3-(3,5-difluoro-4-hydroxy-phenyl)-2-methyl-propionic acid ethyl ester (35 mg, 0.15 mmol) obtained in Step B of Preparation Example 34 were used to react sequentially in the same manner as in Steps A and B of Example 1 to obtain the title compound (0.04 g, 68%).

$^1$H-NMR (CDCl$_3$) δ 8.39(1H, m), 7.78(1H, m), 7.04(1H, m), 6.75(2H, m), 5.13(2H, s), 3.22(2H, t), 2.97(1H, m), 2.74(1H, m), 2.63(1H, m), 1.71(2H, m), 1.21(3H, d), 1.02 (3H, t)

EXAMPLE 52

3-[3-fluoro-4-(6-isopropylsulfanyl-pyridin-2-yl-methoxy)-phenyl]-2-methyl-propionic acid

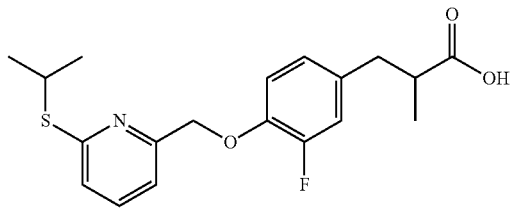 [SMILES: CC(C)Sc1cccc(COc2ccc(CC(C)C(=O)O)cc2F)n1]

2-Chloromethyl-6-isopropylsulfanyl-pyridine (0.030 g, 0.15 mmol) obtained in Step C of Preparation Example 16 and 3-(3-fluoro-4-hydroxy-phenyl)-propionic acid methyl ester (0.031 g, 0.15 mmol) obtained in Step C of Preparation Example 6 were used to react sequentially in the same manner as in Steps A and B of Example 1 to obtain the title compound (0.047 g, 87%).

$^1$H-NMR (CDCl$_3$) δ 7.52-7.48(1H, t), 7.23-7.21(1H, d), 7.09-7.07(1H, d), 6.96-6.90(2H, m), 6.85-6.83(1H, m), 5.19 (2H, s), 4.00-3.93(1H, m), 3.01-2.96(1H, q), 2.76-2.67(1H, m), 2.64-2.58(1H, m), 1.40-1.39(6H, d), 1.18-1.17(3H, d)

EXAMPLE 53

3-[4-(6-sec-butylsulfanyl-pyridin-2-ylmethoxy)-3-fluoro-phenyl]-2-methyl-propionic acid

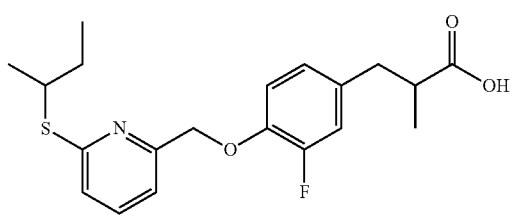 [SMILES: CCC(C)Sc1cccc(COc2ccc(CC(C)C(=O)O)cc2F)n1]

2-sec-Butylsulfanyl-6-chloromethyl-pyridine (0.030 g, 0.14 mmol) obtained in Step C of Preparation Example 5 and 3-(3-fluoro-4-hydroxy-phenyl)-propionic acid methyl ester (0.030 g, 0.14 mmol) obtained in Step C of Preparation Example 6 were used to react sequentially in the same manner as in Steps A and B of Example 1 to obtain the title compound (0.052 g, 99%).

$^1$H-NMR (CDCl$_3$) δ 7.50-7.46(1H, t), 7.21-7.19(1H, d), 7.09-7.07(1H, d), 6.96-6.89(2H, m), 6.84-6.82(1H, m), 5.17 (2H, s), 3.88-3.79(1H, m), 3.00-2.95(1H, q), 2.72-2.58(1H, m), 1.76-1.64(2H, m), 1.38-1.36(3H, d), 1.18-1.16(3H, d), 0.88-0.83(3H, t)

EXAMPLE 54

3-[4-(6-cyclopentylsulfanyl-pyridin-2-ylmethoxy)-3-fluoro-phenyl]-2-methyl-propionic acid

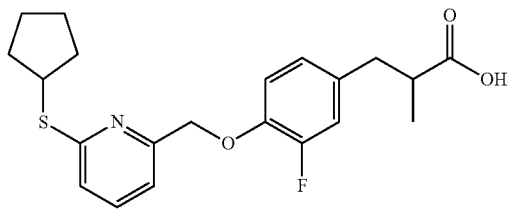 [SMILES: CC(Cc1ccc(OCc2cccc(SC3CCCC3)n2)c(F)c1)C(=O)O]

2-Chloromethyl-6-cyclopentylsulfanyl-pyridine (0.030 g, 0.13 mmol) obtained in Step C of Preparation Example 27 and 3-(3-fluoro-4-hydroxy-phenyl)-propionic acid methyl ester (0.028 g, 0.13 mmol) obtained in Step C of Preparation Example 6 were used to react sequentially in the same manner as in Steps A and B of Example 1 to obtain the title compound (0.050 g, 98%).

$^1$H-NMR (CDCl$_3$) δ 7.52-7.48(1H, t), 7.22-7.20(1H, d), 7.09-7.07(1H, d), 6.96-6.84(3H, m), 5.18(2H, s), 4.03-3.96 (1H, m), 3.00-2.97(1H, q), 2.71-2.66(1H, m), 2.63-2.60(1H, m), 2.22-2.16(2H, m), 1.79-1.76(2H, m), 1.66-1.60(4H, m), 1.19-1.16(3H, d)

EXAMPLE 55

3-[4-(6-cyclobutylsulfanyl-pyridin-2-ylmethoxy)-3-fluoro-phenyl]-2-methyl-propionic acid

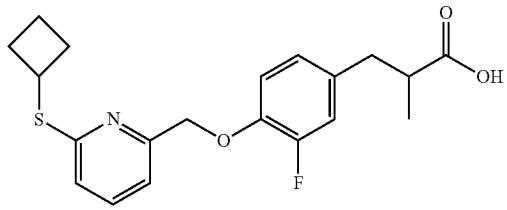

2-Chloromethyl-6-cyclobutylsulfanyl-pyridine (0.050 g, 0.23 mmol) obtained in Step C of Preparation Example 37 and 3-(3-fluoro-4-hydroxy-phenyl)-propionic acid methyl ester (0.050 g, 0.23 mmol) obtained in Step C of Preparation Example 6 were used to react sequentially in the same manner as in Steps A and B of Example 1 to obtain the title compound (0.070 g, 81%).

$^1$H-NMR (CDCl$_3$) δ 7.52-7.48(1H, t), 7.22-7.20(1H, d), 7.00-6.98(1H, d), 6.97-6.83(3H, m), 5.17(2H, s), 4.32-4.24 (1H, m), 3.00-2.95(1H, q), 2.75-2.70(1H, m), 2.64-2.59(1H, m), 2.56-2.51(2H, m), 2.16-2.00(4H, m), 1.19-1.17(3H, d)

EXAMPLE 56

3-[4-(2-cyclobutylsulfanyl-pyridin-3-ylmethoxy)-3,5-difluoro-phenyl]-2-methyl-propionic acid

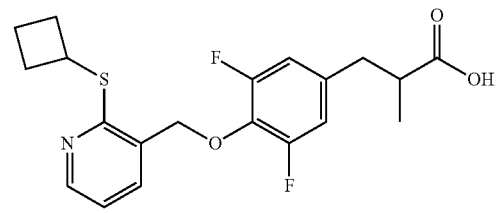 [SMILES: CC(Cc1cc(F)c(OCc2cccnc2SC2CCC2)c(F)c1)C(=O)O]

3-Chloromethyl-2-cyclobutylsulfanyl-pyridine (0.045 g, 0.21 mmol) obtained in Step C of Preparation Example 23 and 3-(3,5-difluoro-4-hydroxy-phenyl)-2-methyl-propionic acid ethyl ester (49 mg, 0.21 mmol) obtained in Step B of Preparation Example 34 were used to react sequentially in the same manner as in Steps A and B of Example 1 to obtain the title compound (0.026 g, 31%).

$^1$H-NMR (CDCl$_3$) δ 8.36(1H, m), 7.76(1H, m), 7.02(1H, m), 6.75(2H, m), 5.09(2H, s), 4.49(1H, m), 2.97(1H, m), 2.74(1H, m), 2.63(1H, m), 2.51(2H, m), 2.10(2H, m), 2.05 (2H, m), 1.20(3H, d)

EXAMPLE 57

3-[4-(2-isopropylsulfanyl-pyridin-3-ylmethoxy)-3-methoxy-phenyl]-propionic acid

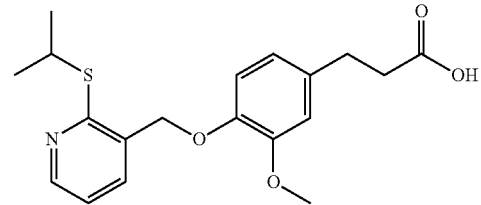 [SMILES: COc1cc(CCC(=O)O)ccc1OCc1cccnc1SC(C)C]

3-Chloromethyl-2-isopropylsulfanyl-pyridine (33 mg, 0.16 mmol) obtained in Step C of Preparation Example 1 and 3-(4-hydroxy-3-methoxy-phenyl]-propionic acid ethyl ester (40 mg, 0.17 mmol) obtained in Step C of Preparation Example 38 were used to react sequentially in the same manner as in Steps A and B of Example 1 to obtain the title compound (34 mg, 72%).

$^1$H-NMR (CDCl$_3$) δ 8.38(1H, m), 7.72(1H, d), 7.00(1H, m), 6.77(2H, m), 6.69(1H, m), 5.06(2H, s), 4.18(1H, m), 3.89(3H, s), 2.91(2H, t), 2.66(2H, t), 1.43(6H, d)

EXAMPLE 58

3-[4-(2-cyclopentylsulfanyl-pyridin-3-ylmethoxy)-3-methoxy-phenyl]-propionic acid

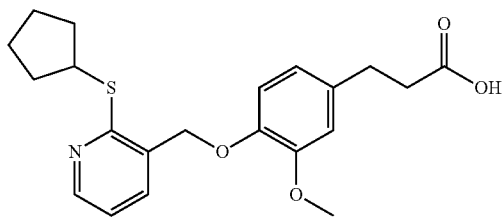 [SMILES: COc1cc(CCC(=O)O)ccc1OCc1cccnc1SC1CCCC1]

3-Chloromethyl-2-cyclopentylsulfanyl-pyridine (40 mg, 0.16 mmol) obtained in Step C of Preparation Example 8 and 3-(4-hydroxy-3-methoxy-phenyl]-propionic acid ethyl ester (48 mg, 0.21 mmol) obtained in Step C of Preparation Example 38 were used to react sequentially in the same manner as in Steps A and B of Example 1 to obtain the title compound (36 mg, 64%).

$^1$H-NMR (CDCl$_3$) δ 8.37(1H, m), 7.72(1H, d), 7.00(1H, m), 6.76(2H, m), 6.68(1H, m), 5.06(2H, s), 4.22(1H, m), 3.89(3H, s), 2.91(2H, t), 2.67(2H, t), 2.24(2H, m), 1.79(2H, m), 1.54(4H, m)

EXAMPLE 59

[6-(2-isopropylsulfanyl-pyridin-3-ylmethoxy)-2,3-dihydro-benzofuran-3-yl]-acetic acid

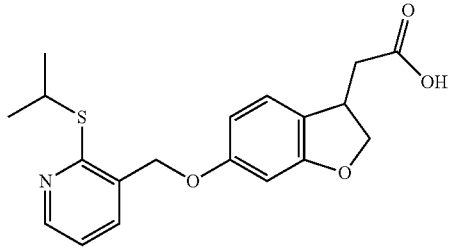 [SMILES: CC(C)Sc1ncccc1COc1ccc2c(c1)OCC2CC(=O)O]

3-Chloromethyl-2-isopropylsulfanyl-pyridine (20 mg, 0.10 mmol) obtained in Step C of Preparation Example 1 and (6-hydroxy-2,3-dihydro-benzofuran-3-yl)-acetic acid methyl ester (20 mg, 0.10 mmol) obtained in Preparation Example 52 were used to react sequentially in the same manner as in Steps A and B of Example 1 to obtain the title compound (25 mg, 70%).

$^1$H-NMR (CDCl$_3$) δ 8.41(1H, d), 7.68(1H, d), 7.07(2H, m), 6.48(2H, m), 4.97(2H, s), 4.78(1H, t), 4.31(1H, m), 4.16(1H, m), 3.82(1H, m), 2.80(1H, m), 2.65(1H, m), 1.41 (6H, d)

EXAMPLE 60

3-[3-fluoro-4-(2-isopropylsulfanyl-pyridin-3-yl-methoxy)-phenyl]-2-methyl-propionic acid

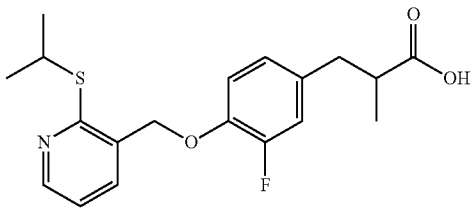 [SMILES: CC(C)Sc1ncccc1COc1ccc(CC(C)C(=O)O)cc1F]

3-Chloromethyl-2-isopropylsulfanyl-pyridine (0.028 g, 0.14 mmol) obtained in Step C of Preparation Example 1 and 3-(3-fluoro-4-hydroxy-phenyl)-propionic acid methyl ester (0.029 g, 0.14 mmol) obtained in Step C of Preparation Example 6 were used to react sequentially in the same manner as in Steps A and B of Example 1 to obtain the title compound (0.039 g, 78%).

$^1$H-NMR (CDCl$_3$) δ 8.41-8.40(1H, m), 7.75-7.73(1H, m), 7.05-7.02(1H, q), 6.97-6.84(3H, m), 5.05(2H, s), 4.22-4.15 (1H, m), 3.01-2.96(1H, q), 2.75-2.70(1H, m), 2.65-2.60(1H, m), 1.43-1.41(6H, d), 1.19-1.18(3H, d)

EXAMPLE 61

3-[4-(2-butylsulfanyl-pyridin-3-ylmethoxy)-3-fluoro-phenyl]-2-methyl-propionic acid

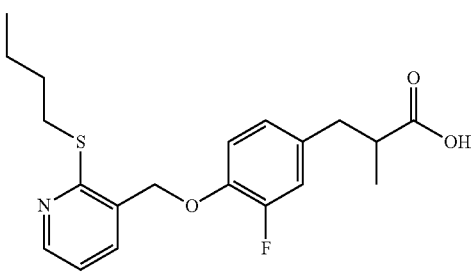 [SMILES: CCCCSc1ncccc1COc1ccc(CC(C)C(=O)O)cc1F]

2-Butylsulfanyl-3-chloromethyl-pyridine (0.020 g, 0.09 mmol) obtained in Step C of Preparation Example 10 and 3-(3-fluoro-4-hydroxy-phenyl)-propionic acid methyl ester (0.019 g, 0.09 mmol) obtained in Step C of Preparation Example 6 were used to react sequentially in the same manner as in Steps A and B of Example 1 to obtain the title compound (0.034 g, 97%).

$^1$H-NMR (CDCl$_3$) δ 8.44(1H, m), 7.77-7.75(1H, m), 7.07(1H, m), 6.97-6.85(3H, m), 5.08(2H, s), 3.33-3.29(2H, m), 3.01-2.96(1H, q), 2.75-2.70(1H, m), 2.65-2.60(1H, m), 1.73-1.67(2H, m), 1.51-1.46(2H, m), 1.19-1.18(3H, d), 0.97-0.93(3H, t)

EXAMPLE 62

2-[4-(2-cyclopentylsulfanyl-pyridin-3-ylmethoxy)-3,5-difluoro-phenyl]-cyclopropane carboxylic acid

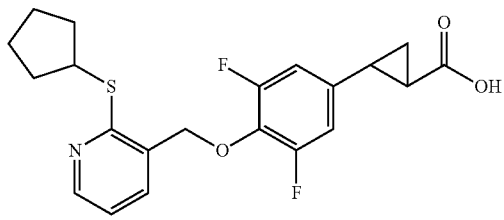 [SMILES: O=C(O)C1CC1c1cc(F)c(OCc2cccnc2SC2CCCC2)c(F)c1]

3-Chloromethyl-2-cyclopentylsulfanyl-pyridine (0.030 g, 0.13 mmol) obtained in Step C of Preparation Example 8 and 2-(3,5-difluoro-4-hydroxy-phenyl)-cyclopropane carboxylic acid ethyl ester (0.032 g, 0.13 mmol) obtained in Step B of Preparation Example 31 were used to react sequentially in the same manner as in Steps A and B of Example 1 to obtain the title compound (0.054 g, 99%).

$^1$H-NMR (CDCl$_3$) δ 8.41-8.40(1H, m), 7.77-7.75(1H, m), 7.05-7.02(1H, q), 6.68-6.66(2H, m), 5.11(2H, s), 4.21-4.19 (1H, m), 2.51-2.48(1H, m), 2.21(2H, m), 1.88-1.84(1H, m), 1.76(2H, m), 1.68-1.60(5H, m), 1.36-1.31(1H, m)

EXAMPLE 63

2-[4-(2-cyclopropylmethylsulfanyl-pyridin-3-ylmethoxy)-3,5-difluoro-phenyl]-cyclopropane carboxylic acid

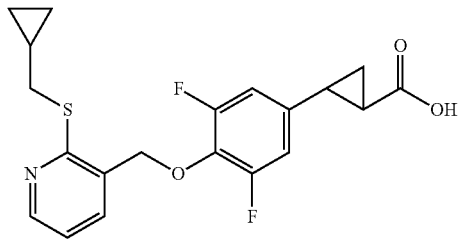 [SMILES: O=C(O)C1CC1c1cc(F)c(OCc2cccnc2SCC2CC2)c(F)c1]

3-Chloromethyl-2-cyclopropylmethylsulfanyl-pyridine (0.020 g, 0.09 mmol) obtained in Step C of Preparation Example 18 and 2-(3,5-difluoro-4-hydroxy-phenyl)-cyclopropane carboxylic acid ethyl ester (0.023 g, 0.09 mmol) obtained in Step B of Preparation Example 31 were used to react sequentially in the same manner as in Steps A and B of Example 1 to obtain the title compound (0.028 g, 77%).

$^1$H-NMR (CDCl$_3$) δ 8.40-8.39(1H, m), 7.79-7.77(1H, m), 7.06-7.03(1H, q), 6.69-6.66(2H, m), 5.15(2H, s), 3.21-3.19 (2H, d), 2.51(1H, m), 1.87-1.84(1H, m), 1.67-1.65(1H, m), 1.35-1.33(1H, m), 1.14(1H, m), 0.59-0.57(2H, m), 0.32-0.30 (2H, m)

EXAMPLE 64

2-[3,5-difluoro-4-(6-isopropylsulfanyl-pyridin-2-ylmethoxy)-phenyl]-cyclopropane carboxylic acid

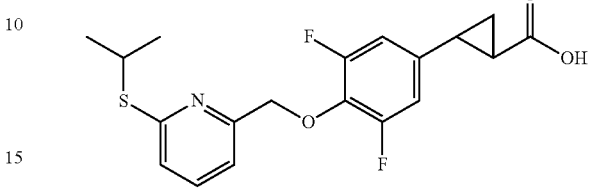

2-Chloromethyl-6-isopropylsulfanyl-pyridine (0.020 g, 0.10 mmol) obtained in Step C of Preparation Example 16 and 2-(3,5-difluoro-4-hydroxy-phenyl)-cyclopropane carboxylic acid ethyl ester (0.024 g, 0.10 mmol) obtained in Step B of Preparation Example 31 were used to react sequentially in the same manner as in Steps A and B of Example 1 to obtain the title compound (0.022 g, 59%).

$^1$H-NMR (CDCl$_3$) δ 7.53-7.50(1H, t), 7.30-7.28(1H, d), 7.09-7.07(1H, d), 6.66-6.64(2H, m), 5.19(2H, s), 3.92-3.89 (1H, m), 2.49(1H, m), 1.84(1H, m), 1.65(1H, m), 1.36-1.35 (6H, d), 1.34(1H, m)

EXAMPLE 65

2-[3,5-difluoro-4-(2-isopropylsulfanyl-pyridin-3-ylmethoxy)-phenyl]-cyclopropane carboxylic acid

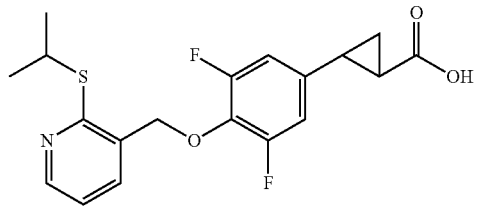 [SMILES: CC(C)Sc1ncccc1COc1c(F)cc(C2CC2C(=O)O)cc1F]

3-Chloromethyl-2-isopropylsulfanyl-pyridine (0.020 g, 0.10 mmol) obtained in Step C of Preparation Example 1 and 2-(3,5-difluoro-4-hydroxy-phenyl)-cyclopropane carboxylic acid ethyl ester (0.024 g, 0.10 mmol) obtained in Step B of Preparation Example 31 were used to react sequentially in the same manner as in Steps A and B of Example 1 to obtain the title compound (0.035 g, 94%).

$^1$H-NMR (CDCl$_3$) δ 8.43-8.42 (1H, m), 7.80-7.78 (1H, m), 7.07-7.04 (1H, q), 6.68-6.64 (2H, m), 5.11 (2H, s), 4.18-4.11 (1H, m), 2.54-2.50 (1H, m), 1.88-1.83 (1H, m), 1.68-1.64 (1H, m), 1.40-1.38 (6H, d), 1.36-1.31 (1H, m)

EXAMPLE 66

2-[4-(2-butylsulfanyl-pyridin-3-ylmethoxy)-3,5-difluoro-phenyl]-cyclopropane carboxylic acid

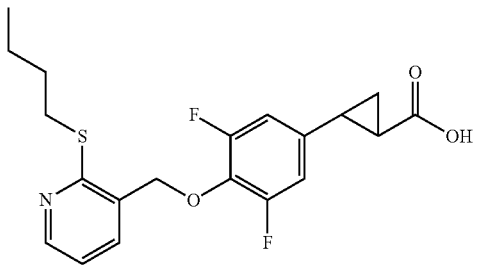 [SMILES: CCCCSc1ncccc1COc1c(F)cc(C2CC2C(=O)O)cc1F]

2-Butylsulfanyl-3-chloromethyl-pyridine (0.020 g, 0.09 mmol) obtained in Step C of Preparation Example 10 and 2-(3,5-difluoro-4-hydroxy-phenyl)-cyclopropane carboxylic acid ethyl ester (0.022 g, 0.09 mmol) obtained in Step B of Preparation Example 31 were used to react sequentially in the same manner as in Steps A and B of Example 1 to obtain the title compound (0.024 g, 66%).

$^1$H-NMR (CDCl$_3$) δ 8.42-8.41 (1H, m), 7.78-7.76 (1H, m), 7.07-7.04 (1H, q), 6.69-6.64 (2H, m), 5.12 (2H, s), 3.27-3.23 (2H, t), 2.54-2.50 (1H, m), 1.86-1.83 (1H, m), 1.69-1.65 (3H, m), 1.49-1.43 (2H, m), 1.35-1.30 (1H, m), 0.95-0.91 (3H, t)

EXAMPLE 67

[6-(6-isopropylsulfanyl-pyridin-2-ylmethoxy)-2,3-dihydro-benzofuran-3-yl]-acetic acid

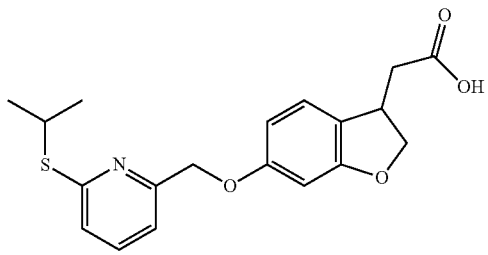 [SMILES: CC(C)Sc1cccc(COc2ccc3c(c2)OCC3CC(=O)O)n1]

2-Chloromethyl-6-isopropylsulfanyl-pyridine (20 mg, 0.10 mmol) obtained in Step C of Preparation Example 16 and (6-hydroxy-2,3-dihydro-benzofuran-3-yl)-acetic acid methyl ester (20 mg, 0.10 mmol) obtained in Preparation Example 52 were used to react sequentially in the same manner as in Steps A and B of Example 1 to obtain the title compound (30 mg, 84%).

$^1$H-NMR (CDCl$_3$) δ 7.49 (1H, t), 7.15 (1H, d), 7.07 (2H, t), 6.49 (2H, m), 5.10 (2H, s), 4.77 (1H, t), 4.28 (1H, m), 3.98 (1H, m), 3.81 (1H, m), 2.79 (1H, m), 2.64 (1H, m), 1.40 (6H, d)

EXAMPLE 68

[6-(6-cyclopentylsulfanyl-pyridin-2-ylmethoxy)-2,3-dihydro-benzofuran-3-yl]-acetic acid

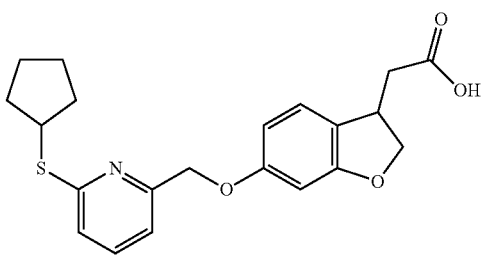 [SMILES: O=C(O)CC1COc2cc(OCc3cccc(SC4CCCC4)n3)ccc21]

2-Chloromethyl-6-cyclopentylsulfanyl-pyridine (23 mg, 0.10 mmol) obtained in Step C of Preparation Example 27 and (6-hydroxy-2,3-dihydro-benzofuran-3-yl)-acetic acid methyl ester (20 mg, 0.10 mmol) obtained in Preparation Example 52 were used to react sequentially in the same manner as in Steps A and B of Example 1 to obtain the title compound (30 mg, 78%).

$^1$H-NMR (CDCl$_3$) δ 7.49 (1H, t), 7.15 (1H, d), 7.06 (2H, m), 6.48 (2H, m), 5.09 (2H, s), 4.77 (1H, t), 4.28 (1H, m), 4.01 (1H, m), 3.81 (1H, m), 2.81 (1H, m), 2.64 (1H, m), 2.19 (2H, m), 1.78 (2H, m), 1.64 (4H, m)

EXAMPLE 69

3-[4-(2-isopropylsulfanyl-pyridin-3-ylmethoxy)-phenyl]-2,2-dimethyl-propionic acid

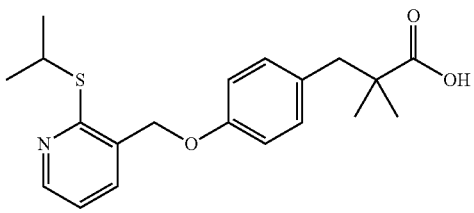 [SMILES: CC(C)Sc1ncccc1COc1ccc(CC(C)(C)C(=O)O)cc1]

3-Chloromethyl-2-isopropylsulfanyl-pyridine (0.02 g, 0.099 mmol) obtained in Step C of Preparation Example 1 and 3-(4-hydroxy-phenyl)-2,2-dimethyl-propionic acid ethyl ester (0.022 g, 0.099 mmol) obtained in Step D of Preparation Example 39 were used to react sequentially in the same manner as in Steps A and B of Example 1 to obtain the title compound (0.029 g, 81%).

$^1$H NMR (400 MHz, CDCl$_3$) δ 8.42-8.38 (m, 1H), 7.72-7.67 (m, 1H), 7.09 (d, 2H), 7.04-6.99 (m, 1H), 6.88 (d, 2H), 4.99 (s, 2H), 4.23-4.12 (m, 1H), 2.84 (s, 2H), 1.41 (d, 6H), 1.20 (s, 6H)

EXAMPLE 70

3-[4-(6-isopropylsulfanyl-pyridin-2-ylmethoxy)-phenyl]-2,2-dimethyl-propionic acid

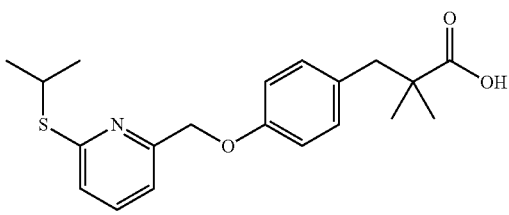 [SMILES: CC(C)Sc1cccc(COc2ccc(CC(C)(C)C(=O)O)cc2)n1]

2-Chloromethyl-6-isopropylsulfanyl-pyridine (0.02 g, 0.099 mmol) obtained in Step C of Preparation Example 16 and 3-(4-hydroxy-phenyl)-2,2-dimethyl-propionic acid ethyl ester (0.022 g, 0.099 mmol) obtained in Step D of Preparation Example 39 were used to react sequentially in the same manner as in Steps A and B of Example 1 to obtain the title compound (0.029 g, 81%).

$^1$H NMR (400 MHz, CDCl$_3$) δ 7.47 (t, 1H), 7.17 (d, 1H), 7.10-7.02 (m, 3H), 6.89 (d, 2H), 5.12 (s, 2H), 4.02-3.90 (m, 1H), 2.83 (s, 2H), 1.39 (d, 6H), 1.19 (s, 6H)

EXAMPLE 71

3-[3,5-difluoro-4-(4-isopropylsulfanyl-2-methyl-pyrimidin-5-ylmethoxy)-phenyl]-prop ionic acid

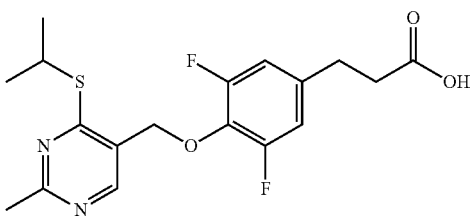 [SMILES: Cc1ncc(COc2c(F)cc(CCC(=O)O)cc2F)c(SC(C)C)n1]

Step A: 3-[3,5-difluoro-4-(4-isopropylsulfanyl-2-methyl-pyrimidin-5-yl methoxy)-phenyl]-propionic acid ethyl ester (4-Isopropylsulfanyl-2-methyl-pyrimidin-5-yl)-methanol (0.006 g, 0.03 mmol) obtained in Step B of Preparation Example 40 and 3-(3,5-difluoro-4-hydroxy-phenyl)-propionic acid ethyl ester (0.007 g, 0.03 mmol) obtained in Step D of Preparation Example 2 were reacted in the same manner as in Step A of Example 24 to obtain the title compound (0.009 g, 72%).

$^1$H-NMR (CDCl$_3$) δ 8.36 (1H, s), 6.74 (2H, m), 5.03 (2H, s), 4.21 (2H, q), 2.85 (2H, t), 2.65 (3H, s), 2.58 (2H, t), 1.42 (6H, d), 1.24 (3H, t)

Step B: 3-[3,5-difluoro-4-(4-isopropylsulfanyl-2-methyl-pyrimidin-5-yl methoxy)-phenyl]-propionic acid 3-[3,5-Difluoro-4-(4-isopropylsulfanyl-2-methyl-pyrimidin-5-ylmethoxy)-phenyl]-propionic acid ethyl ester (0.009 g, 0.02 mmol) obtained in Step A was reacted in the same manner as in Step B of Example 1 to obtain the title compound (0.0035 g, 42%).

$^1$H-NMR (CDCl$_3$) δ 8.34 (1H, s), 6.76 (2H, m), 5.02 (2H, s), 4.21 (1H, m), 2.88 (2H, t), 2.64 (3H, s), 2.63 (2H, t), 1.41 (6H, d)

EXAMPLE 72

3-[4-(6-isopropylsulfanyl-pyridin-2-ylmethoxy)-3-methoxy-phenyl]-propionic acid

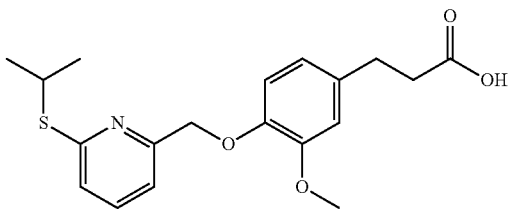 [SMILES: COc1cc(CCC(=O)O)ccc1OCc1cccc(SC(C)C)n1]

2-Chloromethyl-6-isopropylsulfanyl-pyridine (32 mg, 0.15 mmol) obtained in Step C of Preparation Example 16 and 3-(4-hydroxy-3-methoxy-phenyl)-propionic acid ethyl ester (39 mg, 0.17 mmol) obtained in Step C of Preparation Example 38 were used to react sequentially in the same manner as in Steps A and B of Example 1 to obtain the title compound (30 mg, 61%).

$^1$H-NMR (CDCl$_3$) δ 7.49 (1H, t), 7.20 (1H, d), 7.06 (1H, d), 6.77 (2H, m), 6.68 (1H, m), 5.21 (2H, s), 4.00 (1H, m), 3.90 (3H, s), 2.90 (2H, t), 2.66 (2H, t), 1.40 (6H, d)

EXAMPLE 73

3-[4-(6-cyclopentylsulfanyl-pyridin-2-ylmethoxy)-3-methoxy-phenyl]-propionic acid

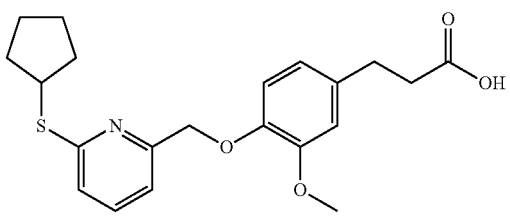 [SMILES: COc1cc(CCC(=O)O)ccc1OCc1cccc(SC2CCCC2)n1]

2-Chloromethyl-6-cyclopentylsulfanyl-pyridine (33 mg, 0.14 mmol) obtained in Step C of Preparation Example 27 and 3-(4-hydroxy-3-methoxy-phenyl)-propionic acid ethyl ester (36 mg, 0.15 mmol) obtained in Step C of Preparation Example 38 were used to react sequentially in the same manner as in Steps A and B of Example 1 to obtain the title compound (32 mg, 69%).

$^1$H-NMR (CDCl$_3$) δ 7.49 (1H, t), 7.19 (1H, d), 7.06 (1H, d), 6.77 (2H, m), 6.68 (1H, m), 5.20 (2H, s), 4.00 (1H, m), 3.90 (3H, s), 2.90 (2H, t), 2.66 (2H, t), 2.18 (2H, m), 1.79 (2H, m), 1.54 (4H, m)

EXAMPLE 74

[6-(2-cyclopentylsulfanyl-pyridin-3-ylmethoxy)-2,3-dihydro-benzofuran-3-yl]-acetic acid

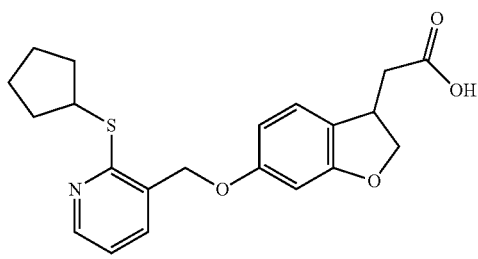 [SMILES: O=C(O)CC1COc2cc(OCc3cccnc3SC3CCCC3)ccc21]

3-Chloromethyl-2-cyclopentylsulfanyl-pyridine (0.21 g, 0.92 mmol) obtained in Step C of Preparation Example 8 and (6-hydroxy-2,3-dihydro-benzofuran-3-yl)-acetic acid methyl ester (0.19 g, 0.92 mmol) obtained in Preparation Example 52 were used to react sequentially in the same manner as in Steps A and B of Example 1 to obtain the title compound (0.25 g, 70%).

$^1$H-NMR (CDCl$_3$) δ 8.39 (1H, d), 7.66 (1H, d), 7.07 (1H, d), 7.01 (1H, m), 6.49 (2H, m), 4.97 (2H, s), 4.76 (1H, t), 4.30 (1H, m), 4.20 (1H, m), 3.82 (1H, m), 2.80 (1H, m), 2.65 (1H, m), 2.23 (2H, m), 1.77 (2H, m), 1.65 (4H, m)

EXAMPLE 75

2-[4-(6-cyclobutylsulfanyl-pyridin-2-ylmethoxy)-3,5-difluoro-phenyl]-cyclopropane carboxylic acid

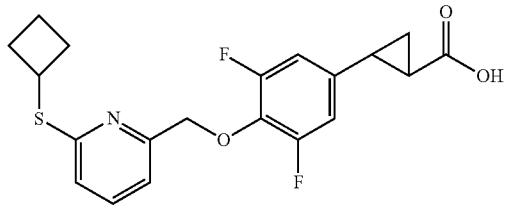 [SMILES: O=C(O)C1CC1c1cc(F)c(OCc2cccc(SC3CCC3)n2)c(F)c1]

2-Chloromethyl-6-cyclobutylsulfanyl-pyridine (0.040 g, 0.18 mmol) obtained in Step C of Preparation Example 37 and 2-(3,5-difluoro-4-hydroxy-phenyl)-cyclopropane carboxylic acid ethyl ester (0.045 g, 0.18 mmol) obtained in Step B of Preparation Example 31 were used to react sequentially in the same manner as in Steps A and B of Example 1 to obtain the title compound (0.050 g, 69%).

$^1$H-NMR (CDCl$_3$) δ 7.55-7.51 (1H, t), 7.31-7.29 (1H, d), 7.01-6.99 (1H, d), 6.68-6.64 (2H, m), 5.19 (2H, s), 4.27-4.19 (1H, m), 2.52-2.50 (3H, m), 2.13-2.05 (4H, m), 1.86-1.84 (1H, m), 1.67-1.65 (1H, m), 1.34-1.31 (1H, m)

EXAMPLE 76

3-[4-(2-cyclopentylsulfanyl-6-methoxy-pyridin-3-ylmethoxy)-3,5-difluoro-phenyl]-propionic acid

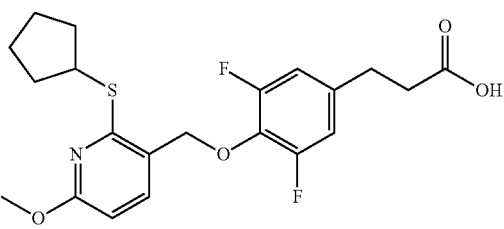 [SMILES: COc1ccc(COc2c(F)cc(CCC(=O)O)cc2F)c(SC2CCCC2)n1]

3-Chloromethyl-2-cyclopentylsulfanyl-pyridine (40 mg, 0.16 mmol) obtained in Step C of Preparation Example 8 and 3-(3,5-difluoro-4-hydroxy-phenyl)-propionic acid ethyl ester (38 mg, 0.16 mmol) obtained in Step D of Preparation Example 2 were used to react sequentially in the same manner as in Steps A and B of Example 1 to obtain the title compound (64 mg, 98%).

$^1$H-NMR (CDCl$_3$) δ 7.56 (1H, d), 6.75 (2H, m), 6.43 (1H, d), 5.06 (2H, s), 4.16 (1H, m), 3.94 (3H, s), 2.99 (2H, t), 2.65 (2H, t), 2.20 (2H, m), 1.77 (2H, m), 1.54 (4H, m)

EXAMPLE 77

3-[3-chloro-4-(2-isopropylsulfanyl-pyridin-3-ylmethoxy)-phenyl]-propionic acid

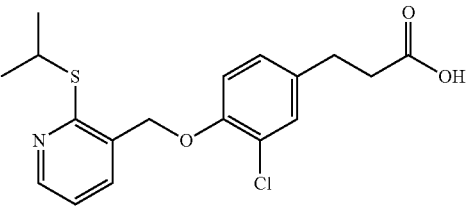 [SMILES: CC(C)Sc1ncccc1COc1ccc(CCC(=O)O)cc1Cl]

3-Chloromethyl-2-isopropylsulfanyl-pyridine (23 mg, 0.11 mmol) obtained in Step C of Preparation Example 1 and 3-(3-chloro-4-hydroxy-phenyl)-propionic acid ethyl ester (29 mg, 0.12 mmol) obtained in Step C of Preparation Example 42 were used to react sequentially in the same manner as in Steps A and B of Example 1 to obtain the title compound (41 mg, 93%).

$^1$H-NMR (CDCl$_3$) δ 8.41 (1H, m), 7.83 (1H, d), 7.27 (1H, m), 7.05 (2H, m), 6.89 (1H, d), 5.05 (2H, s), 4.20 (1H, m), 2.89 (2H, t), 2.66 (2H, t), 1.43 (6H, d)

EXAMPLE 78

3-[3-chloro-4-(2-cyclopentylsulfanyl-pyridin-3-yl-methoxy)-phenyl]-propionic acid

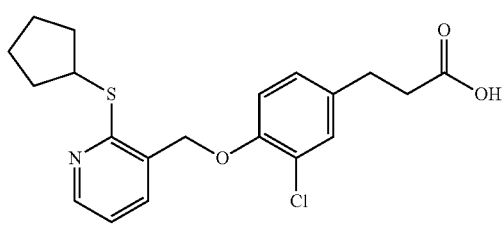 [SMILES: O=C(O)CCc1ccc(OCc2cccnc2SC2CCCC2)c(Cl)c1]

3-Chloromethyl-2-cyclopentylsulfanyl-pyridine (28 mg, 0.13 mmol) obtained in Step C of Preparation Example 8 and 3-(3-chloro-4-hydroxy-phenyl)-propionic acid ethyl ester (33 mg, 0.14 mmol) obtained in Step C of Preparation Example 42 were used to react sequentially in the same manner as in Steps A and B of Example 1 to obtain the title compound (41 mg, 91%).

$^1$H-NMR (CDCl$_3$) δ 8.40 (1H, m), 7.81 (1H, d), 7.27 (1H, m), 7.05 (2H, m), 6.89 (1H, d), 5.05 (2H, s), 4.25 (1H, m), 2.89 (2H, t), 2.65 (2H, t), 2.20 (2H, m), 1.78 (2H, m), 1.55 (4H, m)

EXAMPLE 79

3-[4-(2-isopropylsulfanyl-pyridin-3-ylmethoxy)-2,3-dimethyl-phenyl]-propionic acid

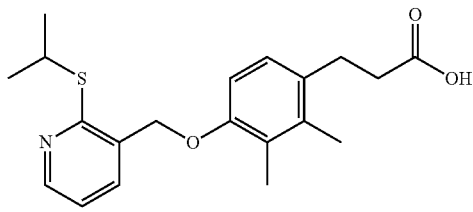 [SMILES: Cc1c(CCC(=O)O)ccc(OCc2cccnc2SC(C)C)c1C]

3-Chloromethyl-2-isopropylsulfanyl-pyridine (25 mg, 0.12 mmol) obtained in Step C of Preparation Example 1 and 3-(4-hydroxy-2,3-dimethyl-phenyl)-propionic acid ethyl ester (30 mg, 0.13 mmol) obtained in Step D of Preparation Example 43 were used to react sequentially in the same manner as in Steps A and B of Example 1 to obtain the title compound (34 mg, 85%).

$^1$H-NMR (CDCl$_3$) δ 8.41 (1H, m), 7.83 (1H, d), 7.01 (1H, m), 6.97 (1H, m), 6.69 (1H, d), 4.97 (2H, s), 4.18 (1H, m), 2.95 (2H, t), 2.60 (2H, t), 2.25 (d, 6H), 1.42 (6H, d)

EXAMPLE 80

3-[4-(2-cyclopentylsulfanyl-pyridin-3-ylmethoxy)-2,3-dimethyl-phenyl]-propionic acid

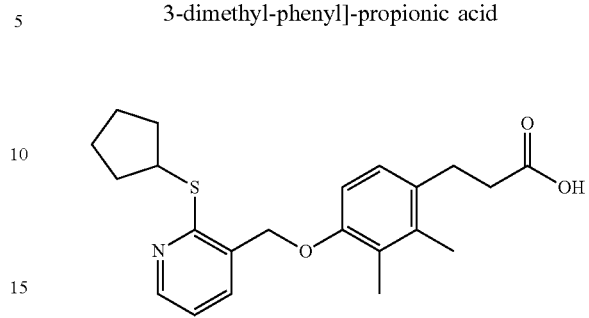

3-Chloromethyl-2-cyclopentylsulfanyl-pyridine (28 mg, 0.10 mmol) obtained in Step C of Preparation Example 8 and 3-(4-hydroxy-2,3-dimethyl-phenyl)-propionic acid ethyl ester (27 mg, 0.12 mmol) obtained in Step D of Preparation Example 43 were used to react sequentially in the same manner as in Steps A and B of Example 1 to obtain the title compound (37 mg, 84%).

$^1$H-NMR (CDCl$_3$) δ 8.39 (1H, m), 7.72 (1H, d), 7.05 (1H, m), 6.96 (1H, m), 6.70 (1H, d), 5.14 (2H, s), 4.22 (1H, m), 2.94 (2H, t), 2.59 (2H, t), 2.23 (m, 8H), 1.78 (2H, m), 1.55 (4H, m)

EXAMPLE 81

[(S)-6-(2-cyclopentylsulfanyl-pyridin-3-ylmethoxy)-2,3-dihydro-benzofuran-3-yl]-acetic acid

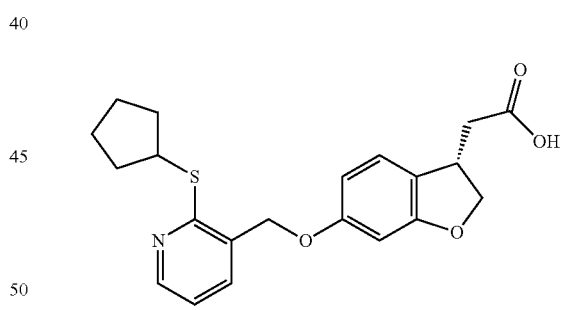

3-Chloromethyl-2-cyclopentylsulfanyl-pyridine (11 mg, 0.05 mmol) obtained in Step C of Preparation Example 8 and ((S)-6-hydroxy-2,3-dihydro-benzofuran-3-yl)-acetic acid methyl ester (10 mg, 0.05 mmol) obtained in Preparation Example 56 were used to react sequentially in the same manner as in Steps A and B of Example 1 to obtain the title compound (13 mg, 70%).

$^1$H-NMR (CDCl$_3$) δ 8.39 (1H, d), 7.66 (1H, d), 7.07 (1H, d), 7.01 (1H, m), 6.49 (2H, m), 4.97 (2H, s), 4.78 (1H, t), 4.30 (1H, m), 4.20 (1H, m), 3.82 (1H, m), 2.80 (1H, m), 2.65 (1H, m), 2.23 (2H, m), 1.77 (2H, m), 1.65 (4H, m)

EXAMPLE 82

[(R)-6-(2-cyclopentylsulfanyl-pyridin-3-ylmethoxy)-2,3-dihydro-benzofuran-3-yl]-acetic acid

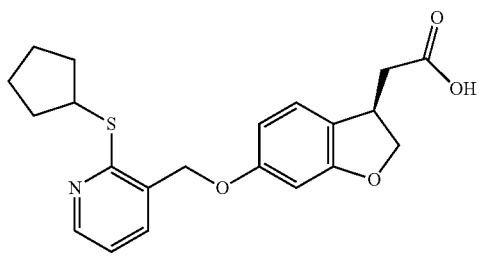 [SMILES: O=C(O)C[C@H]1COc2cc(OCc3cccnc3SC3CCCC3)ccc21]

3-Chloromethyl-2-cyclopentylsulfanyl-pyridine (11 mg, 0.05 mmol) obtained in Step C of Preparation Example 8 and ((R)-6-hydroxy-2,3-dihydro-benzofuran-3-yl)-acetic acid methyl ester (10 mg, 0.05 mmol) obtained in Preparation Example 55 were used to react sequentially in the same manner as in Steps A and B of Example 1 to obtain the title compound (15 mg, 89%).

$^1$H-NMR (CDCl$_3$) δ 8.39 (1H, d), 7.66 (1H, d), 7.07 (1H, d), 7.01 (1H, m), 6.49 (2H, m), 4.97 (2H, s), 4.78 (1H, t), 4.30 (1H, m), 4.20 (1H, m), 3.81 (1H, m), 2.84 (1H, m), 2.65 (1H, m), 2.23 (2H, m), 1.77 (2H, m), 1.65 (4H, m)

EXAMPLE 83

2-[3-fluoro-4-(2-isopropylsulfanyl-pyridin-3-ylmethoxy)-phenyl]-cyclopropane carboxylic acid

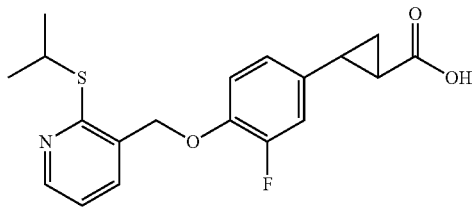 [SMILES: CC(C)Sc1ncccc1COc1ccc(C2CC2C(=O)O)cc1F]

3-Chloromethyl-2-isopropylsulfanyl-pyridine (0.040 g, 0.20 mmol) obtained in Step C of Preparation Example 1 and 2-[3-fluoro-4-hydroxy-phenyl]-cyclopropane carboxylic acid ethyl ester (0.044 g, 0.20 mmol) obtained in Step C of Preparation Example 44 were used to react sequentially in the same manner as in Steps A and B of Example 1 to obtain the title compound (0.060 g, 84%).

$^1$H-NMR (CDCl$_3$) δ 8.42-8.40 (1H, m), 7.73-7.71 (1H, m), 7.05-7.03 (1H, q), 6.94-6.81 (3H, m), 5.06 (2H, s), 4.22-4.15 (2H, m), 2.53-2.51 (1H, m), 1.85-1.81 (1H, m), 1.66-1.61 (1H, m), 1.61-1.43 (6H, d), 1.36-1.31 (1H, m)

EXAMPLE 84

2-[4-(2-cyclopropylmethylsulfanyl-pyridin-3-ylmethoxy)-3-fluoro-phenyl]-cyclopropane carboxylic acid

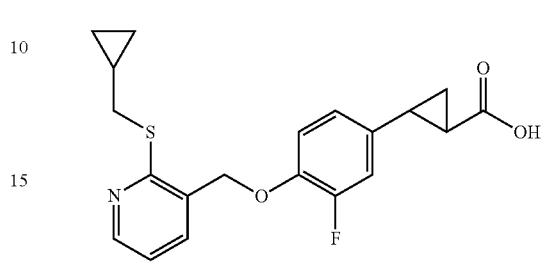

3-Chloromethyl-2-cyclopropylmethyl sulfanyl-pyridine (0.040 g, 0.18 mmol) obtained in Step C of Preparation Example 18 and 2-(3-fluoro-4-hydroxy-phenyl)-cyclopropane carboxylic acid ethyl ester (0.042 g, 0.18 mmol) obtained in Step C of Preparation Example 44 were used to react sequentially in the same manner as in Steps A and B of Example 1 to obtain the title compound (0.050 g, 72%).

$^1$H-NMR (CDCl$_3$) δ 8.39-8.38 (1H, m), 7.73-7.71 (1H, m), 7.05-7.02 (1H, q), 6.94-6.81 (3H, m), 5.09 (2H, s), 3.24-3.22 (2H, d), 2.53-2.51 (1H, m), 1.86-1.81 (1H, m), 1.66-1.61 (1H, m), 1.34-1.32 (1H, m), 1.19-1.15 (1H, m), 0.61-0.57 (2H, m), 0.35-0.32 (2H, m)

EXAMPLE 85

2-[4-(6-cyclopentylsulfanyl-pyridin-2-ylmethoxy)-3-fluoro-phenyl]-cyclopropane carboxylic acid

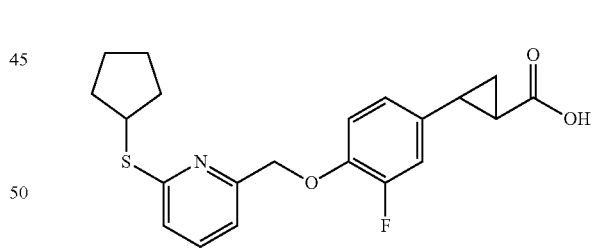

2-Chloromethyl-6-cyclopentylsulfanyl-pyridine (0.040 g, 0.17 mmol) obtained in Step C of Preparation Example 27 and 2-(3-fluoro-4-hydroxy-phenyl)-cyclopropane carboxylic acid ethyl ester (0.040 g, 0.17 mmol) obtained in Step C of Preparation Example 44 were used to react sequentially in the same manner as in Steps A and B of Example 1 to obtain the title compound (0.061 g, 89%).

$^1$H-NMR (CDCl$_3$) δ 7.52-7.48 (1H, t), 7.20-7.19 (1H, d), 7.10-7.08 (1H, d), 6.93-6.78 (3H, m), 5.19 (2H, s), 4.02-3.97 (1H, m), 2.55-2.50 (1H, m), 2.19-2.17 (2H, m), 1.84-1.79 (3H, m), 1.65-1.61 (5H, m), 1.35-1.30 (1H, m)

EXAMPLE 86

2-[4-(6-cyclobutylsulfanyl-pyridin-2-ylmethoxy)-3-fluoro-phenyl]-cyclopropane carboxylic acid

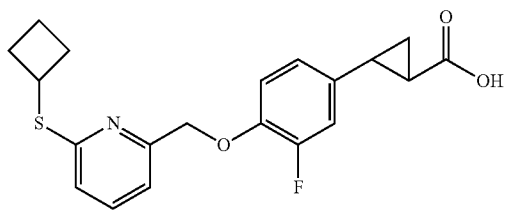 [SMILES: O=C(O)C1CC1c1ccc(OCc2cccc(SC3CCC3)n2)c(F)c1]

2-Chloromethyl-6-cyclobutylsulfanyl-pyridine (0.044 g, 0.20 mmol) obtained in Step C of Preparation Example 37 and 2-(3-fluoro-4-hydroxy-phenyl)-cyclopropane carboxylic acid ethyl ester (0.046 g, 0.20 mmol) obtained in Step C of Preparation Example 44 were used to react sequentially in the same manner as in Steps A and B of Example 1 to obtain the title compound (0.069 g, 90%).

$^1$H-NMR (CDCl$_3$) δ 7.53-7.50 (1H, t), 7.22-7.20 (1H, d), 7.01-6.99 (1H, d), 6.93-6.79 (3H, m), 5.22 (2H, s), 4.32-4.24 (1H, m), 2.56-2.50 (3H, m), 2.15-2.03 (4H, m), 1.83-1.81 (1H, m), 1.64-1.61 (1H, m), 1.35-1.30 (1H, m)

EXAMPLE 87

2-[4-(2-cyclopentylsulfanyl-pyridin-3-ylmethoxy)-3-fluoro-phenyl]-cyclopropane carboxylic acid

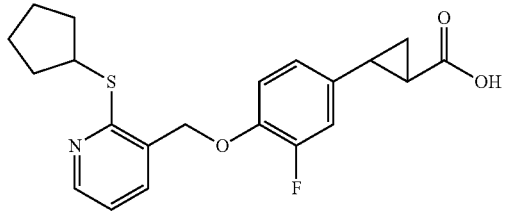 [SMILES: O=C(O)C1CC1c1ccc(OCc2cccnc2SC2CCCC2)c(F)c1]

3-Chloromethyl-2-cyclopentylsulfanyl-pyridine (0.040 g, 0.17 mmol) obtained in Step C of Preparation Example 8 and 2-(3-fluoro-4-hydroxy-phenyl)-cyclopropane carboxylic acid ethyl ester (0.040 g, 0.17 mmol) obtained in Step C of Preparation Example 44 were used to react sequentially in the same manner as in Steps A and B of Example 1 to obtain the title compound (0.067 g, 98%).

$^1$H-NMR (CDCl$_3$) δ 8.40-8.39 (1H, m), 7.71-7.70 (1H, m), 7.04-7.01 (1H, q), 6.93-6.81 (3H, m), 5.06 (2H, s), 4.24-4.21 (1H, m), 2.53 (1H, m), 2.24-2.22 (2H, m), 1.86-1.81 (3H, m), 1.65-1.62 (5H, m), 1.36-1.31 (1H, m)

EXAMPLE 88

2-[4-(2-cyclobutylsulfanyl-pyridin-3-ylmethoxy)-3-fluoro-phenyl]-cyclopropane carboxylic acid

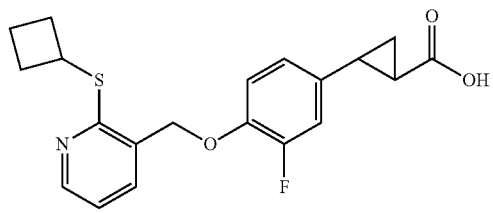 [SMILES: O=C(O)C1CC1c1ccc(OCc2cccnc2SC2CCC2)c(F)c1]

3-Chloromethyl-2-cyclobutylsulfanyl-pyridine (0.040 g, 0.18 mmol) obtained in Step C of Preparation Example 23 and 2-(3-fluoro-4-hydroxy-phenyl)-cyclopropane carboxylic acid ethyl ester (0.046 g, 0.18 mmol) obtained in Step C of Preparation Example 44 were used to react sequentially in the same manner as in Steps A and B of Example 1 to obtain the title compound (0.069 g, 98%).

$^1$H-NMR (CDCl$_3$) δ 8.38-8.37 (1H, m), 7.70-7.68 (1H, m), 7.03-7.01 (1H, q), 6.93-6.81 (3H, m), 5.04 (2H, s), 4.56-4.52 (1H, m), 2.56-2.54 (3H, m), 2.17-2.06 (4H, m), 1.86-1.82 (1H, m), 1.66-1.61 (1H, m), 1.36-1.33 (1H, m)

EXAMPLE 89

2-[2-chloro-4-(2-isopropylsulfanyl-pyridin-3-ylmethoxy)-phenyl]-cyclopropane carboxylic acid

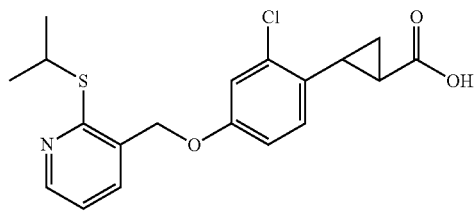 [SMILES: CC(C)Sc1ncccc1COc1ccc(C2CC2C(=O)O)c(Cl)c1]

3-Chloromethyl-2-isopropylsulfanyl-pyridine (0.040 g, 0.20 mmol) obtained in Step C of Preparation Example 1 and 2-(2-chloro-4-hydroxy-phenyl)-cyclopropane carboxylic acid ethyl ester (0.047 g, 0.20 mmol) obtained in Step E of Preparation Example 45 were used to react sequentially in the same manner as in Steps A and B of Example 1 to obtain the title compound (0.041 g, 55%).

$^1$H-NMR (CDCl$_3$) δ 8.42-8.41 (1H, m), 7.66-7.64 (1H, m), 7.04-7.03 (2H, m), 6.97-6.95 (1H, d), 6.81-6.79 (1H, m), 4.98 (2H, s), 4.21-4.17 (1H, m), 2.72 (1H, m), 1.78-1.75 (1H, m), 1.67-1.64 (1H, m), 1.44-1.42 (6H, d), 1.39-1.37 (1H, m)

EXAMPLE 90

2-[2-chloro-4-(6-chlorobutylsulfanyl-pyridin-2-yl-methoxy)-phenyl]-cyclopropane carboxylic acid

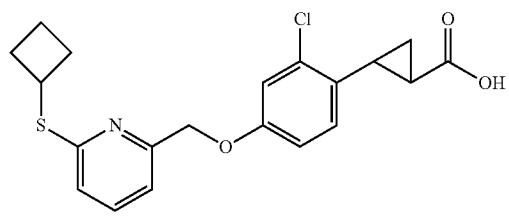 [SMILES: O=C(O)C1CC1c1ccc(OCc2cccc(SC3CCC3)n2)cc1Cl]

2-Chloromethyl-6-cyclobutylsulfanyl-pyridine (0.040 g, 0.18 mmol) obtained in Step C of Preparation Example 37 and 2-(2-chloro-4-hydroxy-phenyl)-cyclopropane carboxylic acid ethyl ester (0.045 g, 0.18 mmol) obtained in Step E of Preparation Example 45 were used to react sequentially in the same manner as in Steps A and B of Example 1 to obtain the title compound (0.042 g, 58%).

$^1$H-NMR (CDCl$_3$) δ 7.50-7.46 (1H, t), 7.12-7.10 (1H, d), 7.05 (1H, s), 7.02-7.00 (1H, d), 6.96-6.93 (1H, m), 6.81-6.78 (1H, m), 5.11 (2H, s), 4.33-4.25 (1H, m), 2.74-2.69 (1H, m), 2.55-2.50 (2H, m), 2.16-2.07 (4H, m), 1.77-1.72 (1H, m), 1.66-1.61 (1H, m), 1.39-1.34 (1H, m)

EXAMPLE 91

3-[3-chloro-4-(2-cyclopropylmethylsulfanyl-pyridin-3-ylmethoxy)-phenyl]-2-methyl-propionic acid

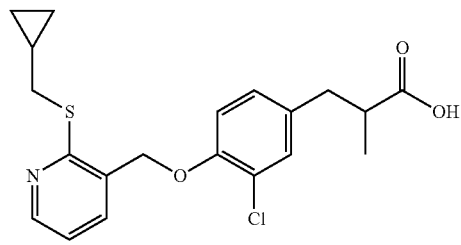 [SMILES: CC(Cc1ccc(OCc2cccnc2SCC2CC2)c(Cl)c1)C(=O)O]

3-Chloromethyl-2-cyclopropylmethyl sulfanyl-pyridine (33 mg, 0.15 mmol) obtained in Step C of Preparation Example 18 and 3-(3-chloro-4-hydroxy-phenyl)-2-methyl-propionic acid ethyl ester (42 mg, 0.17 mmol) obtained in Step B of Preparation Example 46 were used to react sequentially in the same manner as in Steps A and B of Example 1 to obtain the title compound (41 mg, 77%).

$^1$H-NMR (CDCl$_3$) δ 8.38 (1H, m), 7.83 (1H, d), 7.26 (1H, m), 7.05 (2H, m), 6.90 (1H, d), 5.04 (2H, s), 3.24 (2H, d), 3.00 (1H, m), 2.73 (1H, m), 2.61 (1H, m), 1.20 (4H, m), 0.61 (2H, m), 0.34 (2H, m)

EXAMPLE 92

3-[3-chloro-4-(2-propylsulfanyl-pyridin-3-yl-methoxy)-phenyl]-2-methyl-propionic acid

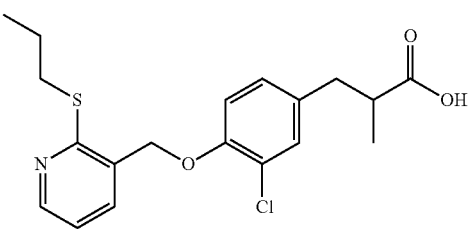 [SMILES: CCCSc1ncccc1COc1ccc(CC(C)C(=O)O)cc1Cl]

3-Chloromethyl-2-propylsulfanyl-pyridine (32 mg, 0.15 mmol) obtained in Step C of Preparation Example 14 and 3-(3-chloro-4-hydroxy-phenyl)-2-methyl-propionic acid ethyl ester (42 mg, 0.17 mmol) obtained in Step B of Preparation Example 46 were used to react sequentially in the same manner as in Steps A and B of Example 1 to obtain the title compound (40 mg, 75%).

$^1$H-NMR (CDCl$_3$) δ 8.39 (1H, m), 7.80 (1H, d), 7.26 (1H, m), 7.05 (2H, m), 6.89 (1H, d), 5.07 (2H, s), 3.28 (2H, t), 3.00 (1H, m), 2.74 (1H, m), 2.63 (1H, m), 1.76 (2H, m), 1.19 (3H, d), 1.05 (3H, t)

EXAMPLE 93

3-[3-chloro-4-(6-isopropylsulfanyl-pyridin-2-yl-methoxy)-phenyl]-2-methyl-propionic acid

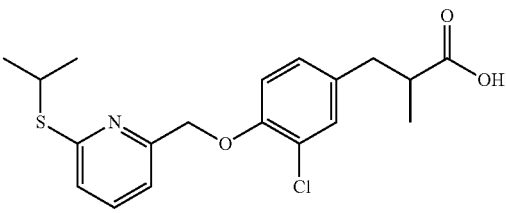

2-Chloromethyl-6-isopropylsulfanyl-pyridine (35 mg, 0.17 mmol) obtained in Step C of Preparation Example 16 and 3-(3-chloro-4-hydroxy-phenyl)-2-methyl-propionic acid ethyl ester (47 mg, 0.19 mmol) obtained in Step B of Preparation Example 46 were used to react sequentially in the same manner as in Steps A and B of Example 1 to obtain the title compound (50 mg, 89%).

$^1$H-NMR (CDCl$_3$) δ 7.51 (1H, m), 7.25 (2H, m), 7.08 (1H, m), 7.00 (1H, m), 6.89 (1H, d), 5.19 (2H, s), 3.96 (1H, m), 2.98 (1H, m), 2.75 (1H, m), 2.61 (1H, m), 1.40 (6H, d), 1.18 (3H, d)

EXAMPLE 94

3-[3-chloro-4-(6-cyclopentylsulfanyl-pyridin-2-yl-methoxy)-phenyl]-2-methyl-propionic acid

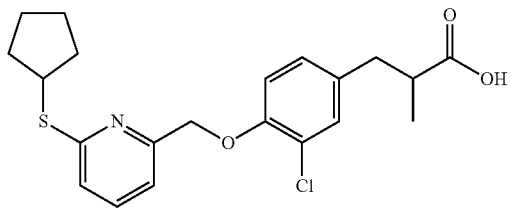 [SMILES: CC(Cc1ccc(OCc2cccc(SC3CCCC3)n2)c(Cl)c1)C(=O)O]

2-Chloromethyl-6-cyclopentylsulfanyl-pyridine (37 mg, 0.16 mmol) obtained in Step C of Preparation Example 27 and 3-(3-chloro-4-hydroxy-phenyl)-2-methyl-propionic acid ethyl ester (43 mg, 0.17 mmol) obtained in Step B of Preparation Example 46 were used to react sequentially in the same manner as in Steps A and B of Example 1 to obtain the title compound (51 mg, 85%).

$^1$H-NMR (CDCl$_3$) δ 7.51 (1H, t), 7.25 (2H, m), 7.09 (1H, d), 6.99 (1H, m), 6.88 (1H, d), 5.19 (2H, s), 4.00 (1H, m), 3.00 (1H, m), 2.98 (1H, m), 2.74 (1H, m), 2.61 (1H, m), 2.19 (2H, m), 1.79 (2H, m), 1.64 (4H, m), 1.18 (3H, d)

EXAMPLE 95

3-[3-chloro-4-(2-cyclobutylsulfanyl-pyridin-3-yl-methoxy)-phenyl]-2-methyl-propionic acid

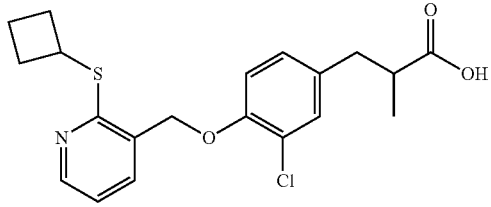 [SMILES: CC(Cc1ccc(OCc2cccnc2SC2CCC2)c(Cl)c1)C(=O)O]

3-Chloromethyl-2-cyclobutylsulfanyl-pyridine (50 mg, 0.25 mmol) obtained in Step C of Preparation Example 23 and 3-(3-chloro-4-hydroxy-phenyl)-2-methyl-propionic acid ethyl ester (60 mg, 0.28 mmol) obtained in Step B of Preparation Example 46 were used to react sequentially in the same manner as in Steps A and B of Example 1 to obtain the title compound (76 mg, 81%).

$^1$H-NMR (CDCl$_3$) δ 8.36 (1H, m), 7.80 (1H, d), 7.24 (1H, m), 7.04 (2H, m), 6.89 (1H, d), 5.04 (2H, s), 4.55 (1H, m), 2.98 (1H, m), 2.73 (1H, m), 2.69~2.65 (3H, m), 2.20~2.00 (4H, m), 1.19 (3H, d)

EXAMPLE 96

3-[3-chloro-4-(6-cyclobutylsulfanyl-pyridin-2-yl-methoxy)-phenyl]-2-methyl-propionic acid

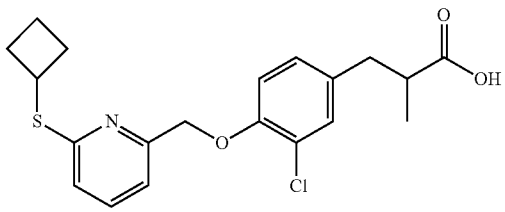 [SMILES: CC(Cc1ccc(OCc2cccc(SC3CCC3)n2)c(Cl)c1)C(=O)O]

2-Chloromethyl-6-cyclobutylsulfanyl-pyridine (50 mg, 0.25 mmol) obtained in Step C of Preparation Example 37 and 3-(3-chloro-4-hydroxy-phenyl)-2-methyl-propionic acid ethyl ester (60 mg, 0.28 mmol) obtained in Step B of Preparation Example 46 were used to react sequentially in the same manner as in Steps A and B of Example 1 to obtain the title compound (77 mg, 85%).

$^1$H-NMR (CDCl$_3$) δ 7.52 (1H, t), 7.25 (2H, m), 7.01 (2H, m), 6.89 (1H, m), 5.18 (2H, s), 4.29 (1H, m), 2.98 (1H, m), 2.73 (1H, m), 2.69~2.45 (3H, m), 2.20~2.00 (4H, m), 1.19 (3H, d)

EXAMPLE 97

2-[3-chloro-4-(2-isopropylsulfanyl-pyridin-3-yl-methoxy)-phenyl]-cyclopropane carboxylic acid

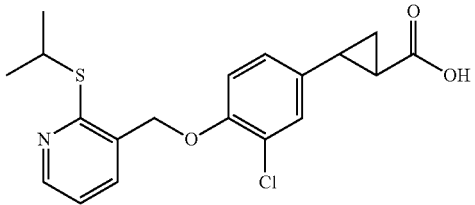 [SMILES: CC(C)Sc1ncccc1COc1ccc(C2CC2C(=O)O)cc1Cl]

3-Chloromethyl-2-isopropylsulfanyl-pyridine (33 mg, 0.16 mmol) obtained in Step C of Preparation Example 1 and 2-(3-chloro-4-hydroxy-phenyl)-cyclopropane carboxylic acid ethyl ester (43 mg, 0.17 mmol) obtained in Step B of Preparation Example 47 were used to react sequentially in the same manner as in Steps A and B of Example 1 to obtain the title compound (42 mg, 80%).

$^1$H-NMR (CDCl$_3$) δ 8.41 (1H, m), 7.80 (1H, d), 7.14 (1H, m), 7.05 (1H, m), 6.97 (1H, m), 6.87 (1H, d), 5.05 (2H, s), 4.20 (1H, m), 2.52 (1H, m), 1.83 (1H, m), 1.62 (1H, m), 1.43 (6H, d), 1.33 (1H, m)

EXAMPLE 98

2-[3-chloro-4-(6-cyclopropylmethylsulfanyl-pyridin-2-ylmethoxy)-phenyl]-cyclopropane carboxylic acid

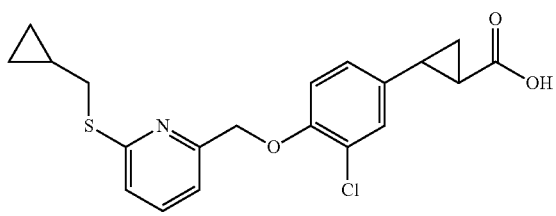 [SMILES: O=C(O)C1CC1c1ccc(OCc2cccc(SCC3CC3)n2)c(Cl)c1]

2-Chloromethyl-6-cyclopropylmethylsulfanyl-pyridine (36 mg, 0.17 mmol) obtained in Step D of Preparation Example 20 and 2-(3-chloro-4-hydroxy-phenyl)-cyclopropane carboxylic acid ethyl ester (45 mg, 0.18 mmol) obtained in Step B of Preparation Example 47 were used to react sequentially in the same manner as in Steps A and B of Example 1 to obtain the title compound (59 mg, 83%).

$^1$H-NMR (CDCl$_3$) δ 7.51 (1H, t), 7.25 (2H, m), 7.15 (1H, m), 7.10 (1H, m), 6.88 (1H, m), 5.19 (2H, s), 3.11 (2H, d), 2.52 (1H, m), 1.84 (1H, m), 1.62 (1H, m), 1.30 (1H, m), 1.10 (1H, m), 0.60 (2H, m), 0.30 (2H, m)

EXAMPLE 99

2-[3-chloro-4-(6-isopropylsulfanyl-pyridin-2-ylmethoxy)-phenyl]-cyclopropane carboxylic acid

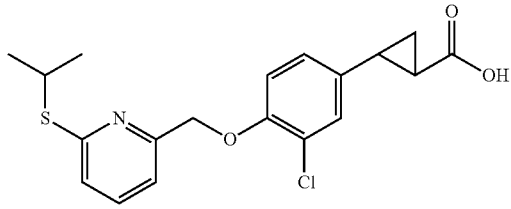 [SMILES: CC(C)Sc1cccc(COc2ccc(C3CC3C(=O)O)cc2Cl)n1]

2-Chloromethyl-6-isopropylsulfanyl-pyridine (40 mg, 0.19 mmol) obtained in Step C of Preparation Example 16 and 2-(3-chloro-4-hydroxy-phenyl)-cyclopropane carboxylic acid ethyl ester (52 mg, 0.21 mmol) obtained in Step B of Preparation Example 47 were used to react sequentially in the same manner as in Steps A and B of Example 1 to obtain the title compound (42 mg, 65%).

$^1$H-NMR (CDCl$_3$) δ 7.51 (1H, t), 7.25 (1H, m), 7.15 (1H, m), 7.08 (1H, m), 6.89 (2H, m), 5.20 (2H, s), 3.97 (1H, m), 2.52 (1H, m), 1.83 (1H, m), 1.62 (1H, m), 1.40 (6H, d), 1.34 (1H, m)

EXAMPLE 100

2-[3-chloro-4-(6-cyclopentylsulfanyl-pyridin-2-ylmethoxy)-phenyl]-cyclopropane carboxylic acid

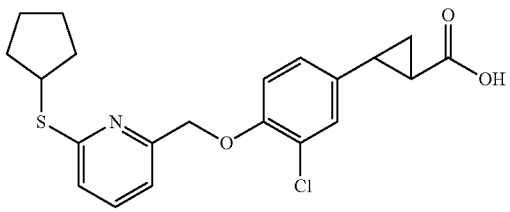 [SMILES: O=C(O)C1CC1c1ccc(OCc2cccc(SC3CCCC3)n2)c(Cl)c1]

2-Chloromethyl-6-cyclopentylsulfanyl-pyridine (42 mg, 0.18 mmol) obtained in Step C of Preparation Example 27 and 2-(3-chloro-4-hydroxy-phenyl)-cyclopropane carboxylic acid ethyl ester (49 mg, 0.20 mmol) obtained in Step B of Preparation Example 47 were used to react sequentially in the same manner as in Steps A and B of Example 1 to obtain the title compound (47 mg, 72%).

$^1$H-NMR (CDCl$_3$) δ 7.51 (1H, t), 7.25 (1H, m), 7.15 (1H, m), 7.08 (1H, m), 6.93 (1H, m), 6.89 (1H, d), 5.19 (2H, s), 3.99 (1H, m), 2.52 (1H, m), 2.18 (2H, m), 1.90~1.75 (3H, m), 1.70~50 (5H, m), 1.34 (1H, m)

EXAMPLE 101

2-[3-chloro-4-(2-cyclopentylsulfanyl-pyridin-3-ylmethoxy)-phenyl]-cyclopropane carboxylic acid

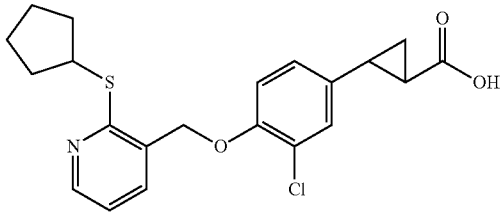 [SMILES: O=C(O)C1CC1c1ccc(OCc2cccnc2SC2CCCC2)c(Cl)c1]

3-Chloromethyl-2-cyclopentylsulfanyl-pyridine (49 mg, 0.23 mmol) obtained in Step C of Preparation Example 8 and 2-(3-chloro-4-hydroxy-phenyl)-cyclopropane carboxylic acid ethyl ester (62 mg, 0.25 mmol) obtained in Step B of Preparation Example 47 were used to react sequentially in the same manner as in Steps A and B of Example 1 to obtain the title compound (65 mg, 75%).

$^1$H-NMR (CDCl$_3$) δ 8.39 (1H, m), 7.79 (1H, d), 7.15 (1H, m), 7.05 (1H, m), 6.90 (1H, m), 6.88 (1H, d), 5.05 (2H, s), 4.13 (1H, m), 2.53 (1H, m), 2.22 (2H, m), 1.90~1.75 (3H, m), 1.70~50 (5H, m), 1.35 (1H, m)

EXAMPLE 102

2-[3-chloro-4-(2-cyclobutylsulfanyl-pyridin-3-yl-methoxy)-phenyl]-cyclopropane carboxylic acid

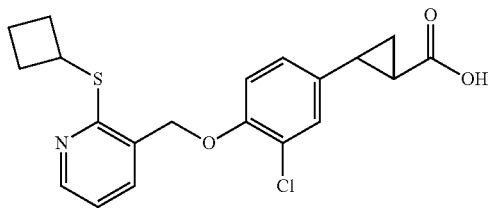 [SMILES: O=C(O)C1CC1c1ccc(OCc2cccnc2SC2CCC2)c(Cl)c1]

3-Chloromethyl-2-cyclobutylsulfanyl-pyridine (52 mg, 0.26 mmol) obtained in Step C of Preparation Example 23 and 2-(3-chloro-4-hydroxy-phenyl)-cyclopropane carboxylic acid ethyl ester (70 mg, 0.29 mmol) obtained in Step B of Preparation Example 47 were used to react sequentially in the same manner as in Steps A and B of Example 1 to obtain the title compound (77 mg, 84%).

$^1$H-NMR (CDCl$_3$) δ 8.37 (1H, m), 7.78 (1H, d), 7.15 (1H, m), 7.05 (1H, m), 6.90 (1H, m), 6.88 (1H, d), 5.04 (2H, s), 4.55 (1H, m), 2.60~2.45 (3H, m), 2.22~2.00 (4H, m), 1.84 (1H, m), 1.63 (1H, m), 1.34 (1H, m)

EXAMPLE 103

2-[3-chloro-4-(6-cyclobutylsulfanyl-pyridin-2-yl-methoxy)-phenyl]-cyclopropane carboxylic acid

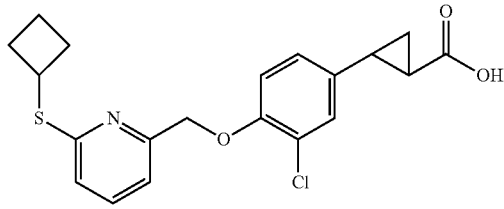

2-Chloromethyl-6-cyclobutylsulfanyl-pyridine (52 mg, 0.26 mmol) obtained in Step C of Preparation Example 37 and 2-(3-chloro-4-hydroxy-phenyl)-cyclopropane carboxylic acid ethyl ester (70 mg, 0.29 mmol) obtained in Step B of Preparation Example 47 were used to react sequentially in the same manner as in Steps A and B of Example 1 to obtain the title compound (77 mg, 84%).

$^1$H-NMR (CDCl$_3$) δ 7.51 (1H, t), 7.25 (1H, m), 7.10 (1H, m), 6.95 (2H, m), 6.87 (1H, d), 5.18 (2H, s), 4.27 (1H, m), 2.59~2.45 (3H, m), 2.22~2.00 (4H, m), 1.83 (1H, m), 1.61 (1H, m), 1.35 (1H, m)

EXAMPLE 104

2-[2-chloro-4-(6-chloropentylsulfanyl-pyridin-2-ylmethoxy)-phenyl]-cyclopropane carboxylic acid

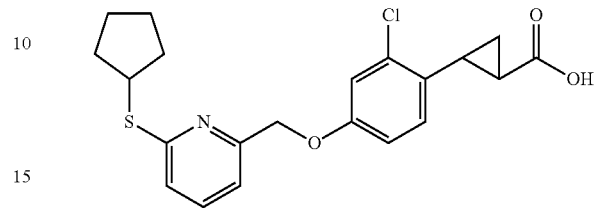

2-Chloromethyl-6-cyclopentylsulfanyl-pyridine (0.040 g, 0.17 mmol) obtained in Step C of Preparation Example 27 and 2-(2-chloro-4-hydroxy-phenyl)-cyclopropane carboxylic acid ethyl ester (0.042 g, 0.17 mmol) obtained in Step E of Preparation Example 45 were used to react sequentially in the same manner as in Steps A and B of Example 1 to obtain the title compound (0.043 g, 61%).

$^1$H-NMR (CDCl$_3$) δ 7.52-7.48 (1H, t), 7.17-7.09 (2H, q), 7.05 (1H, s), 6.95-6.93 (1H, d), 6.82-6.79 (1H, m), 5.12 (2H, s), 4.04-3.97 (1H, m), 2.74-2.69 (1H, m), 2.21-2.18 (2H, m), 1.79-1.73 (3H, m), 1.66-1.62 (5H, m), 1.39-1.34 (1H, m)

EXAMPLE 105

2-[4-(2-isopropylsulfanyl-pyridin-3-ylmethoxy)-2,3-dimethyl-phenyl]-cyclopropane carboxylic acid

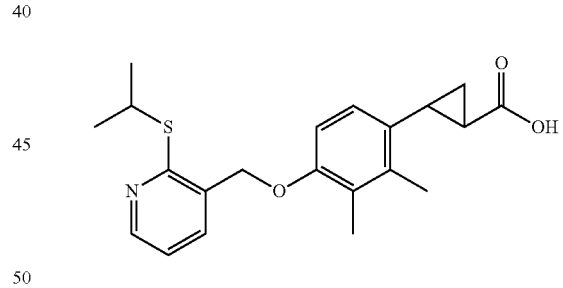

3-Chloromethyl-2-isopropylsulfanyl-pyridine (0.030 g, 0.149 mmol) obtained in Step C of Preparation Example 1 and 2-(4-hydroxy-2,3-dimethyl-phenyl)-cyclopropane carboxylic acid ethyl ester (0.035 g, 0.149 mmol) obtained in Step C of Preparation Example 48 were used to react sequentially in the same manner as in Steps A and B of Example 1 to obtain the title compound (0.045 g, 81%).

$^1$H NMR (400 MHz, CDCl$_3$) δ 8.43-8.39 (m, 1H), 7.74-7.70 (m, 1H), 7.07-7.01 (m, 1H), 6.88 (d, 1H), 6.67 (d, 1H), 4.98 (s, 2H), 4.23-4.12 (m, 1H), 2.62-2.53 (m, 1H), 2.35 (s, 3H), 2.27 (s, 3H), 1.76-1.69 (m, 1H), 1.65-1.58 (m, 1H), 1.42 (d, 6H), 1.40-1.33 (m, 1H)

EXAMPLE 106

2-[4-(2-cyclopropylmethylsulfanyl-pyridin-3-yl-methoxy)-2,3-dimethyl-phenyl]-cyclopropane carboxylic acid

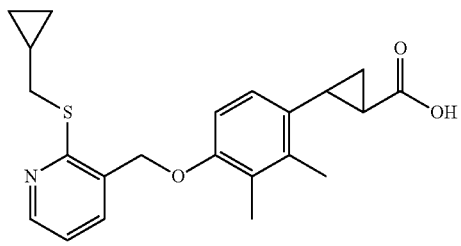 [SMILES: Cc1c(OCc2cccnc2SCC2CC2)ccc(C2CC2C(=O)O)c1C]

2-Chloromethyl-6-cyclopropylmethylsulfanyl-pyridine (0.032 g, 0.149 mmol) obtained in Step D of Preparation Example 20 and 2-(4-hydroxy-2,3-dimethyl-phenyl)-cyclopropane carboxylic acid ethyl ester (0.035 g, 0.149 mmol) obtained in Step C of Preparation Example 48 were used to react sequentially in the same manner as in Steps A and B of Example 1 to obtain the title compound (0.044 g, 77%).

$^1$H NMR (400 MHz, CDCl$_3$) δ 8.42-8.38 (m, 1H), 7.77-7.69 (m, 1H), 7.09-7.01 (m, 1H), 6.88 (d, 1H), 6.69 (d, 1H), 5.01 (s, 2H), 3.23 (d, 2H), 2.63-2.55 (m, 1H), 2.35 (s, 3H), 2.27 (s, 3H), 1.77-1.69 (m, 1H), 1.67-1.59 (m, 1H), 1.42-1.33 (m, 1H), 1.23-1.11 (m, 1H), 0.65-0.57 (m, 1H), 0.40-0.30 (m, 1H)

EXAMPLE 107

2-[3-chloro-4-(2-cyclopropylmethylsulfanyl-pyridin-3-ylmethoxy)-phenyl]-cyclopropane carboxylic acid

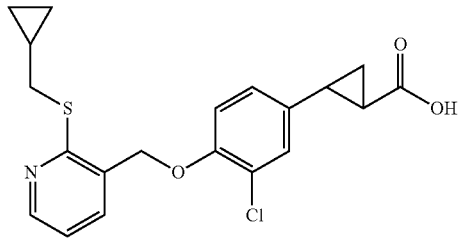 [SMILES: O=C(O)C1CC1c1ccc(OCc2cccnc2SCC2CC2)c(Cl)c1]

3-Chloromethyl-2-cyclopropylmethylsulfanyl-pyridine (41 mg, 0.19 mmol) obtained in Step C of Preparation Example 18 and 2-(3-chloro-4-hydroxy-phenyl)-cyclopropane carboxylic acid ethyl ester (50 mg, 0.21 mmol) obtained in Step B of Preparation Example 47 were used to react sequentially in the same manner as in Steps A and B of Example 1 to obtain the title compound (72 mg, 90%).

$^1$H-NMR (CDCl$_3$) δ 8.37 (1H, m), 7.88 (1H, d), 7.14 (1H, m), 7.05 (1H, m), 6.99 (1H, m), 6.98 (1H, m), 5.08 (2H, s), 3.23 (2H, d), 2.52 (1H, m), 1.83 (1H, m), 1.62 (1H, m), 1.34 (1H, m), 1.16 (1H, m), 0.60 (2H, m), 0.32 (2H, m)

EXAMPLE 108

2-[3-chloro-4-(2-propylsulfanyl-pyridin-3-yl-methoxy)-phenyl]-cyclopropane carboxylic acid

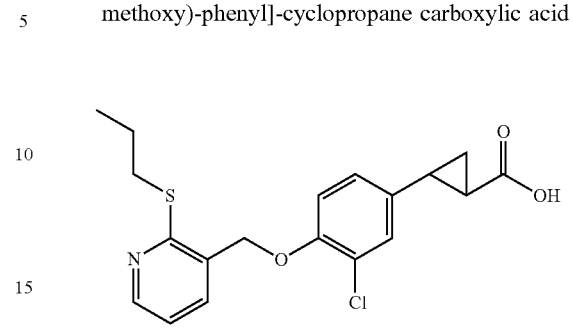

3-Chloromethyl-2-propylsulfanyl-pyridine (47 mg, 0.23 mmol) obtained in Step C of Preparation Example 14 and 2-(3-chloro-4-hydroxy-phenyl)-cyclopropane carboxylic acid ethyl ester (61 mg, 0.25 mmol) obtained in Step B of Preparation Example 47 were used to react sequentially in the same manner as in Steps A and B of Example 1 to obtain the title compound (60 mg, 73%).

$^1$H-NMR (CDCl$_3$) δ 8.39 (1H, m), 7.79 (1H, d), 7.15 (1H, m), 7.05 (1H, m), 6.96 (1H, m), 6.89 (1H, d), 5.08 (2H, s), 3.27 (2H, t), 2.51 (1H, m), 1.84 (1H, m), 1.75 (2H, m), 1.62 (1H, m), 1.34 (1H, m), 1.16 (1H, m), 1.60 (3H, t)

EXAMPLE 109

2-[3-chloro-4-(2-isopropylsulfanyl-6-methoxy-pyridin-3-ylmethoxy)-phenyl]-cyclopropane carboxylic acid

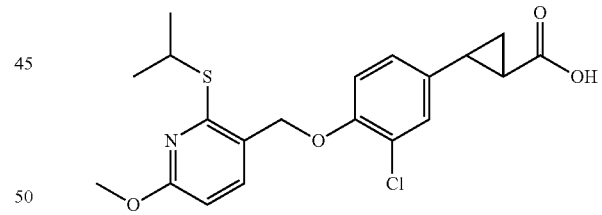

3-Chloromethyl-2-isopropylsulfanyl-6-methoxy-pyridine (20 mg, 0.09 mmol) obtained in Step E of Preparation Example 36 and 3-(3,5-difluoro-4-hydroxy-phenyl)-propionic acid ethyl ester (21 mg, 0.09 mmol) obtained in Step D of Preparation Example 2 were used to react sequentially in the same manner as in Steps A and B of Example 1 to obtain the title compound (19 mg, 66%).

$^1$H-NMR (CDCl$_3$) δ 7.64 (1H, d), 7.12 (1H, m), 6.95 (1H, m), 6.88 (1H, d), 6.47 (1H, d), 5.01 (2H, s), 4.15 (1H, m), 3.94 (3H, s), 2.52 (1H, m), 1.83 (1H, m), 1.62 (1H, m), 1.44 (6H, d), 1.35 (1H, m)

EXAMPLE 110

2-[4-(6-cyclopentylsulfanyl-pyridin-2-ylmethoxy)-3,5-difluoro-benzyl]-cyclopropane carboxylic acid

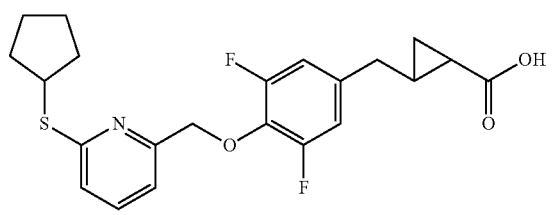 [SMILES: O=C(O)C1CC1Cc1cc(F)c(OCc2cccc(SC3CCCC3)n2)c(F)c1]

2-Chloromethyl-6-cyclopentylsulfanyl-pyridine (0.023 g, 0.10 mmol) obtained in Step C of Preparation Example 27 and 2-(3,5-difluoro-4-hydroxy-benzyl)-cyclopropane carboxylic acid ethyl ester (0.026 g, 0.10 mmol) obtained in Step D of Preparation Example 49 were used to react sequentially in the same manner as in Steps A and B of Example 1 to obtain the title compound (0.037 g, 88%).

$^1$H-NMR (CDCl$_3$) δ 7.54-7.51 (1H, t), 7.33-7.31 (1H, d), 7.10-7.08 (1H, d), 6.78-6.76 (2H, m), 5.20 (2H, s), 3.98-3.94 (1H, m), 2.68-2.62 (1H, m), 2.57-2.51 (1H, m), 2.15 (2H, m), 1.70 (2H, m), 1.67 (1H, m), 1.62 (4H, m), 1.54-1.51 (1H, m), 1.36-1.32 (1H, m), 0.94-0.89 (1H, m)

EXAMPLE 111

[6-(2-cyclobutylsulfanyl-pyridin-3-ylmethoxy)-5,7-difluoro-2,3-dihydro-benzofuran-3-yl]-acetic acid

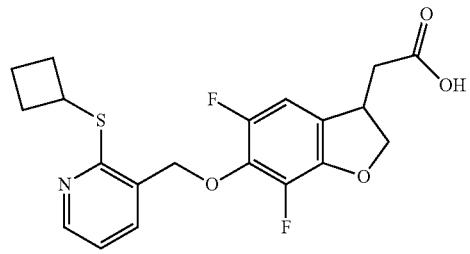 [SMILES: O=C(O)CC1COc2c1cc(F)c(OCc1cccnc1SC1CCC1)c2F]

3-Chloromethyl-2-cyclobutylsulfanyl-pyridine (18 mg, 0.08 mmol) obtained in Step C of Preparation Example 23 and (5,7-difluoro-6-hydroxy-2,3-dihydro-benzofuran-3-yl)-acetic acid methyl ester (20 mg, 0.08 mmol) obtained in Preparation Example 51 were used to react sequentially in the same manner as in Steps A and B of Example 1 to obtain the title compound (26 mg, 78%).

$^1$H-NMR (CDCl$_3$) δ 8.38 (1H, d), 7.77 (1H, d), 7.04 (1H, m), 6.78 (1H, d), 5.13 (2H, s), 4.86 (1H, t), 4.49 (1H, m), 4.38 (1H, m), 3.90 (1H, m), 2.82 (1H, m), 2.69 (1H, m), 2.53 (2H, m), 2.11 (2H, m), 2.03 (2H, m)

EXAMPLE 112

2-[2,3-dimethyl-4-(2-propylsulfanyl-pyridin-3-ylmethoxy)-phenyl]-cyclopropane carboxylic acid

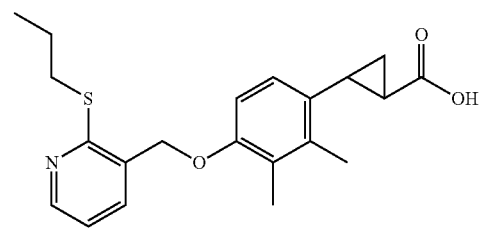 [SMILES: CCCSc1ncccc1COc1ccc(C2CC2C(=O)O)c(C)c1C]

2-Chloromethyl-6-cyclopropylmethylsulfanyl-pyridine (0.03 g, 0.149 mmol) obtained in Step D of Preparation Example 20 and 2-(4-hydroxy-2,3-dimethyl-phenyl)-cyclopropane carboxylic acid ethyl ester (0.035 g, 0.149 mmol) obtained in Step C of Preparation Example 48 were used to react sequentially in the same manner as in Steps A and B of Example 1 to obtain the title compound (0.046 g, 83%).

$^1$H NMR (400 MHz, CDCl$_3$) δ 8.43-8.37 (m, 1H), 7.74-7.68 (m, 1H), 7.06-7.00 (m, 1H), 6.88 (d, 1H), 6.68 (d, 1H), 5.00 (s, 2H), 3.26 (t, 2H), 2.62-2.54 (m, 1H), 2.35 (s, 3H), 2.27 (s, 3H), 1.80-1.69 (m, 3H), 1.65-1.58 (m, 1H), 1.40-1.32 (m, 1H), 1.05 (t, 3H)

EXAMPLE 113

2-[4-(2-cyclobutylsulfanyl-pyridin-3-ylmethoxy)-2,3-dimethyl-phenyl]-cyclopropane carboxylic acid

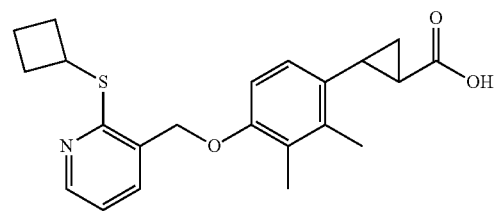 [SMILES: Cc1c(OCc2cccnc2SC2CCC2)ccc(C2CC2C(=O)O)c1C]

3-Chloromethyl-2-cyclobutylsulfanyl-pyridine (0.032 g, 0.149 mmol) obtained in Step C of Preparation Example 23 and 2-(4-hydroxy-2,3-dimethyl-phenyl)-cyclopropane carboxylic acid ethyl ester (0.035 g, 0.149 mmol) obtained in Step C of Preparation Example 48 were used to react sequentially in the same manner as in Steps A and B of Example 1 to obtain the title compound (0.047 g, 82%).

$^1$H NMR (400 MHz, CDCl$_3$) δ 8.40-8.37 (m, 1H), 7.72-7.67 (m, 1H), 7.05-6.99 (m, 1H), 6.88 (d, 1H), 6.67 (d, 1H), 4.97 (s, 2H), 4.59-4.49 (m, 1H), 2.62-2.51 (m, 3H), 2.35 (s, 3H), 2.26 (s, 3H), 2.20-2.10 (m, 2H), 2.10-2.00 (m, 2H), 1.75-1.69 (m, 1H), 1.66-1.58 (m, 1H), 1.40-1.33 (m, 1H)

EXAMPLE 114

2-[4-(6-isopropylsulfanyl-pyridin-2-ylmethoxy)-2,3-dimethyl-phenyl]-cyclopropane carboxylic acid

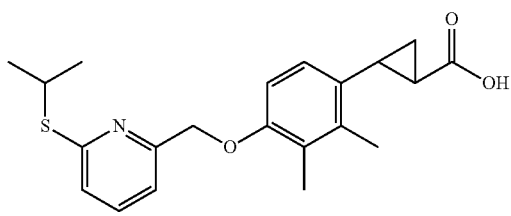 [SMILES: Cc1c(OCc2cccc(SC(C)C)n2)ccc(C2CC2C(=O)O)c1C]

2-Chloromethyl-6-isopropylsulfanyl-pyridine (0.030 g, 0.149 mmol) obtained in Step C of Preparation Example 16 and 2-(4-hydroxy-2,3-dimethyl-phenyl)-cyclopropane carboxylic acid ethyl ester (0.035 g, 0.149 mmol) obtained in Step C of Preparation Example 48 were used to react sequentially in the same manner as in Steps A and B of Example 1 to obtain the title compound (0.046 g, 83%).

$^1$H NMR (400 MHz, CDCl$_3$) δ 7.49 (t, 1H), 7.19 (d, 1H), 7.07 (d, 1H), 6.86 (d, 1H), 6.67 (d, 1H), 5.12 (s, 2H), 4.03-3.92 (m, 1H), 2.61-2.53 (m, 1H), 2.34 (s, 3H), 2.28 (s, 3H), 1.73-1.67 (m, 1H), 1.64-1.57 (m, 1H), 1.40 (d, 6H), 1.38-1.31 (m, 1H)

EXAMPLE 115

2-[4-(6-cyclobutylsulfanyl-pyridin-2-ylmethoxy)-3,5-difluoro-benzyl]-cyclopropane carboxylic acid

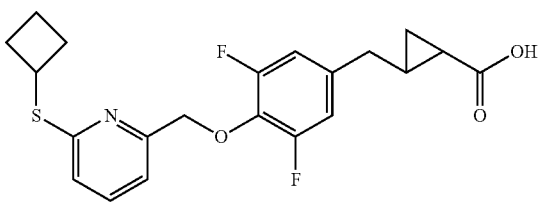 [SMILES: O=C(O)C1CC1Cc1cc(F)c(OCc2cccc(SC3CCC3)n2)c(F)c1]

2-Chloromethyl-6-cyclobutylsulfanyl-pyridine (0.021 g, 0.10 mmol) obtained in Step C of Preparation Example 37 and 2-(3,5-difluoro-4-hydroxy-benzyl)-cyclopropane carboxylic acid ethyl ester (0.024 g, 0.10 mmol) obtained in Step D of Preparation Example 49 were used to react sequentially in the same manner as in Steps A and B of Example 1 to obtain the title compound (0.026 g, 66%).

$^1$H-NMR (CDCl$_3$) δ 7.55-7.51 (1H, t), 7.34-7.32 (1H, d), 7.02-7.00 (1H, d), 6.78-6.76 (2H, m), 5.20 (2H, s), 4.27-4.23 (1H, m), 2.68-2.63 (1H, m), 2.57-2.47 (3H, m), 2.14-2.02 (4H, m), 1.70 (1H, m), 1.54-1.52 (1H, m), 1.37-1.34 (1H, m), 0.94-0.89 (1H, m)

EXAMPLE 116

2-[3,5-difluoro-4-(2-isopropylsulfanyl-pyridin-3-ylmethoxy)-benzyl]-cyclopropane carboxylic acid

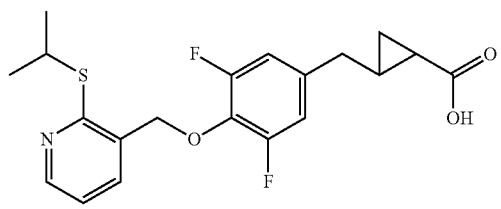 [SMILES: CC(C)Sc1ncccc1COc1c(F)cc(CC2CC2C(=O)O)cc1F]

3-Chloromethyl-2-isopropylsulfanyl-pyridine (0.019 g, 0.09 mmol) obtained in Step C of Preparation Example 1 and 2-(3,5-difluoro-4-hydroxy-benzyl)-cyclopropane carboxylic acid ethyl ester (0.023 g, 0.09 mmol) obtained in Step D of Preparation Example 49 were used to react sequentially in the same manner as in Steps A and B of Example 1 to obtain the title compound (0.028 g, 75%).

$^1$H-NMR (CDCl$_3$) δ 8.42-8.41 (1H, m), 7.82-7.80 (1H, m), 7.07-7.04 (1H, q), 6.80-6.75 (2H, m), 5.12 (2H, s), 4.18-4.10 (1H, m), 2.64-2.52 (2H, m), 1.71-1.69 (1H, m), 1.55-1.51 (1H, m), 1.40-1.38 (6H, d), 1.37-1.32 (1H, m), 0.94-0.89 (1H, m)

EXAMPLE 117

2-[3,5-difluoro-4-(2-propylsulfanyl-pyridin-3-ylmethoxy)-benzyl]-cyclopropane carboxylic acid

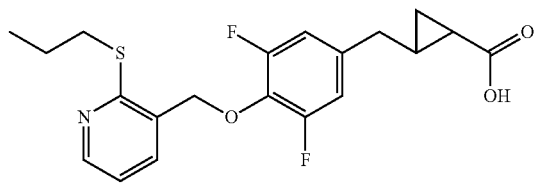 [SMILES: CCCSc1ncccc1COc1c(F)cc(CC2CC2C(=O)O)cc1F]

3-chloromethyl-2-propylsulfanyl-pyridine (0.016 g, 0.08 mmol) obtained in Step C of Preparation Example 14 and 2-(3,5-difluoro-4-hydroxy-benzyl)-cyclopropane carboxylic acid ethyl ester (0.02 g, 0.08 mmol) obtained in Step D of Preparation Example 49 were used to react sequentially in the same manner as in Steps A and B of Example 1 to obtain the title compound (0.024 g, 77%).

$^1$H-NMR (CDCl$_3$) δ 8.41-8.40 (1H, m), 7.81-7.79 (1H, m), 7.07-7.04 (1H, q), 6.81-6.74 (2H, m), 5.14 (2H, s), 3.25-3.21 (2H, m), 2.66-2.56 (2H, m), 1.75-1.68 (3H, m), 1.54-1.52 (1H, m), 1.37-1.32 (1H, m), 1.05-1.01 (1H, t), 0.94-0.89 (1H, m)

EXAMPLE 118

[6-(2-cyclopentylsulfanyl-pyridin-3-ylmethoxy)-7-methyl-benzofuran-3-yl]-acetic acid

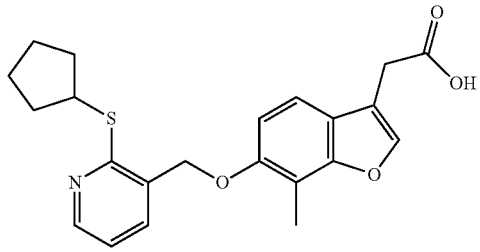 [SMILES: Cc1c(OCc2cccnc2SC2CCCC2)ccc2c(CC(=O)O)coc12]

3-Chloromethyl-2-cyclopentylsulfanyl-pyridine (21 mg, 0.09 mmol) obtained in Step C of Preparation Example 8 and (6-hydroxy-7-methyl-benzofuran-3-yl)-acetic acid methyl ester (21 mg, 0.09 mmol) obtained in Preparation Example 54 were used to react sequentially in the same manner as in Steps A and B of Example 1 to obtain the title compound (30 mg, 83%).

$^1$H-NMR (CDCl$_3$) δ 8.41 (1H, d), 7.73 (1H, d), 7.57 (1H, s), 7.29 (1H, d), 7.04 (1H, m), 6.91 (1H, d), 5.06 (2H, s), 4.24 (1H, m), 3.70 (2H, s), 2.44 (3H, s), 2.22 (2H, m), 1.78 (2H, m), 1.66 (4H, m)

EXAMPLE 119

2-[3-fluoro-4-(2-propylsulfanyl-pyridin-3-yl-methoxy)-phenyl]-cyclopropane carboxylic acid (less polar)

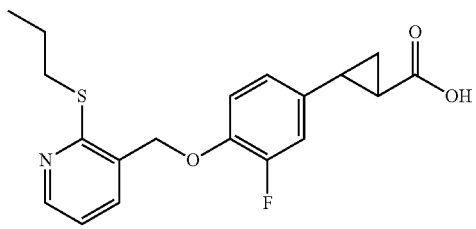 [SMILES: CCCSc1ncccc1COc1ccc(C2CC2C(=O)O)cc1F]

3-Chloromethyl-2-propylsulfanyl-pyridine (0.016 g, 0.08 mmol) obtained in Step C of Preparation Example 14 and 2-(3-fluoro-4-hydroxy-phenyl)-cyclopropane carboxylic acid methyl ester (less polar) (0.017 g, 0.08 mmol) obtained in Step C of Preparation Example 64 were used to react sequentially in the same manner as in Steps A and B of Example 1 to obtain the title compound (0.014 g, 48%).

$^1$H-NMR (CDCl$_3$) δ 8.42-8.41 (1H, m), 7.74-7.72 (1H, m), 7.06-7.03 (1H, q), 6.94-6.81 (3H, m), 5.08 (2H, s), 3.29-3.25 (2H, t), 2.55-2.52 (1H, m), 1.84-1.81 (1H, m), 1.78-1.72 (2H, m), 1.66-1.61 (1H, m), 1.36-1.31 (1H, m), 1.07-1.04 (3H, t)

EXAMPLE 120

{2-[4-(6-cyclopentylsulfanyl-pyridin-2-ylmethoxy)-3-fluoro-phenyl]-cyclopropyl}-acetic acid

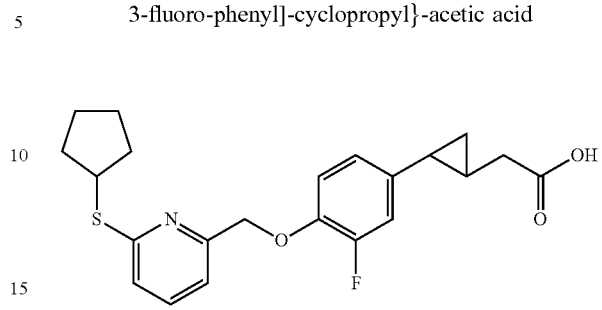

2-Chloromethyl-6-cyclopentylsulfanyl-pyridine (0.026 g, 0.11 mmol) obtained in Step C of Preparation Example 27 and [2-(3-fluoro-4-hydroxy-phenyl)-cyclopropyl]-acetic acid methyl ester (0.026 g, 0.11 mmol) obtained in Step F of Preparation Example 53 were used to react sequentially in the same manner as in Steps A and B of Example 1 to obtain the title compound (0.040 g, 87%).

$^1$H-NMR (CDCl$_3$) δ 7.51-7.47 (1H, t), 7.21-7.19 (1H, d), 7.09-7.07 (1H, d), 6.90-6.76 (3H, m), 5.17 (2H, s), 4.00-3.97 (1H, m), 2.44-2.42 (2H, m), 2.19-2.17 (2H, m), 1.79 (2H, m), 1.73-1.70 (1H, m), 1.66-1.63 (4H, m), 1.31-1.30 (1H, m), 0.95-0.93 (1H, m), 0.86-0.84 (1H, m)

EXAMPLE 121

{2-[3-fluoro-4-(2-propylsulfanyl-pyridin-3-yl-methoxy)-phenyl]-cyclopropyl}-acetic acid

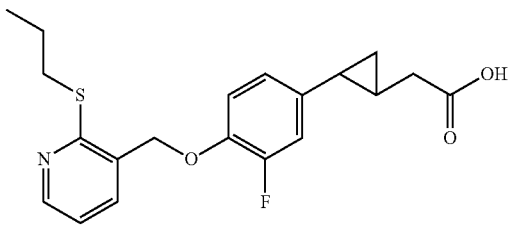 [SMILES: CCCSc1ncccc1COc1ccc(C2CC2CC(=O)O)cc1F]

3-Chloromethyl-2-propylsulfanyl-pyridine (0.024 g, 0.12 mmol) obtained in Step C of Preparation Example 14 and [2-(3-fluoro-4-hydroxy-phenyl)-cyclopropyl]-acetic acid methyl ester (0.027 g, 0.12 mmol) obtained in Step F of Preparation Example 53 were used to react sequentially in the same manner as in Steps A and B of Example 1 to obtain the title compound (0.043 g, 96%).

$^1$H-NMR (CDCl$_3$) δ 8.40-8.39 (1H, m), 7.73-7.71 (1H, m), 7.04-7.01 (1H, q), 6.91-6.79 (3H, m), 5.07 (2H, s), 3.27-3.23 (2H, m), 2.45-2.43 (2H, m), 1.77-1.71 (3H, m), 1.31-1.28 (1H, m), 1.07-1.02 (3H, m), 0.96-0.94 (1H, m), 0.87-0.85 (1H, m)

EXAMPLE 122

[6-(2-cyclopentylsulfanyl-pyridin-3-ylmethoxy)-5,7-difluoro-benzofuran-3-yl]-acetic acid

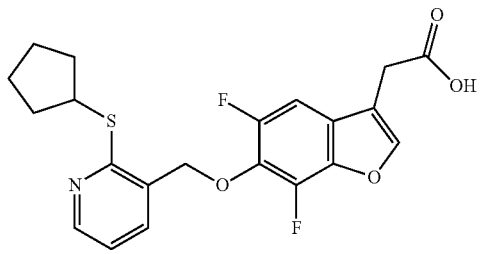 [SMILES: O=C(O)Cc1coc2c(F)c(OCc3cccnc3SC3CCCC3)c(F)cc12]

3-Chloromethyl-2-cyclopentylsulfanyl-pyridine (19 mg, 0.08 mmol) obtained in Step C of Preparation Example 8 and (5,7-difluoro-6-hydroxy-benzofuran-3-yl)-acetic acid methyl ester (20 mg, 0.08 mmol) obtained in Step C of Preparation Example 50 were used to react sequentially in the same manner as in Steps A and B of Example 1 to obtain the title compound (28 mg, 81%).

$^1$H-NMR (CDCl$_3$) δ 8.42 (1H, d), 7.82 (1H, d), 7.66 (1H, s), 7.06 (2H, m), 5.17 (2H, s), 4.18 (1H, m), 3.69 (2H, s), 2.19 (2H, m), 1.74 (2H, m), 1.62 (4H, m)

EXAMPLE 123

[6-(2-cyclopentylsulfanyl-pyridin-3-ylmethoxy)-5,7-difluoro-2,3-dihydro-benzofuran-3-yl]-acetic acid

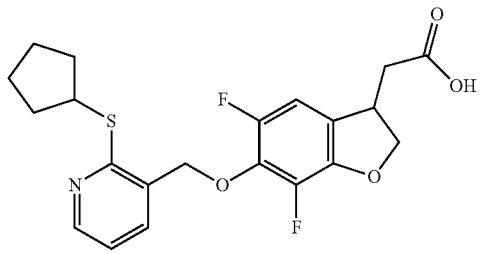 [SMILES: O=C(O)CC1COc2c1cc(F)c(OCc1cccnc1SC1CCCC1)c2F]

3-Chloromethyl-2-cyclopentylsulfanyl-pyridine (19 mg, 0.08 mmol) obtained in Step C of Preparation Example 8 and (5,7-difluoro-6-hydroxy-2,3-dihydro-benzofuran-3-yl)-acetic acid methyl ester (20 mg, 0.08 mmol) obtained in Preparation Example 51 were used to react sequentially in the same manner as in Steps A and B of Example 1 to obtain the title compound (0.25 mg, 72%).

$^1$H-NMR (CDCl$_3$) δ 8.40 (1H, d), 7.79 (1H, d), 7.05 (1H, m), 6.77 (1H, d), 5.12 (2H, s), 4.86 (1H, t), 4.38 (1H, m), 4.19 (1H, m), 3.88 (1H, m), 2.82 (1H, m), 2.69 (1H, m), 2.20 (2H, m), 1.75 (2H, m), 1.64 (4H, m)

EXAMPLE 124

2-[3-chloro-4-(2-cyclobutylsulfanyl-pyridin-3-ylmethoxy)-phenyl]-cyclopropane carboxylic acid (less polar)

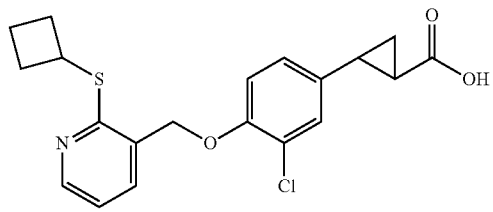 [SMILES: O=C(O)C1CC1c1ccc(OCc2cccnc2SC2CCC2)c(Cl)c1]

3-Chloromethyl-2-cyclobutylsulfanyl-pyridine (27 mg, 0.13 mmol) obtained in Step C of Preparation Example 23 and 2-(3-fluoro-4-hydroxy-phenyl)-cyclopropane carboxylic acid methyl ester (less polar) (37 mg, 0.15 mmol) obtained in Preparation Example 66 were used to react sequentially in the same manner as in Steps A and B of Example 1 to obtain the title compound (36 mg, 80%).

$^1$H NMR (CDCl$_3$) 8.37 (1H, m), 7.77 (1H, d), 7.15 (1H, m), 7.03 (1H, m), 6.97 (1H, m), 6.87 (1H, d), 5.04 (2H, s), 4.55 (1H, m), 2.60~2.45 (3H, m), 2.22~2.00 (4H, m), 1.84 (1H, m), 1.63 (1H, m), 1.34 (1H, m)

EXAMPLE 125

2-[3-chloro-4-(2-cyclobutylsulfanyl-pyridin-3-ylmethoxy)-phenyl]-cyclopropane carboxylic acid (more polar)

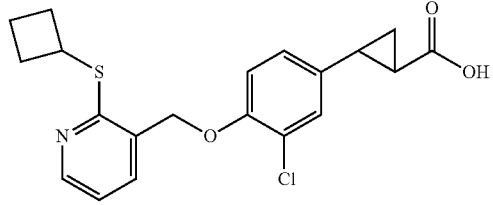 [SMILES: O=C(O)C1CC1c1ccc(OCc2cccnc2SC2CCC2)c(Cl)c1]

3-Chloromethyl-2-cyclobutylsulfanyl-pyridine (26 mg, 0.13 mmol) obtained in Step C of Preparation Example 23 and 2-(3-fluoro-4-hydroxy-phenyl)-cyclopropane carboxylic acid methyl ester (more polar) (33 mg, 0.14 mmol) obtained in Step F of Preparation Example 65 were used to react sequentially in the same manner as in Steps A and B of Example 1 to obtain the title compound (39 mg, 90%).

$^1$H NMR (CDCl$_3$) 8.37 (1H, m), 7.77 (1H, d), 7.15 (1H, m), 7.03 (1H, m), 6.97 (1H, m), 6.87 (1H, d), 5.04 (2H, s), 4.55 (1H, m), 2.60~2.45 (3H, m), 2.22~2.00 (4H, m), 1.84 (1H, m), 1.63 (1H, m), 1.34 (1H, m)

EXAMPLE 126

2-[3-chloro-4-(2-isopropylsulfanyl-pyridin-3-yl-methoxy)-phenyl]-cyclopropane carboxylic acid (more polar)

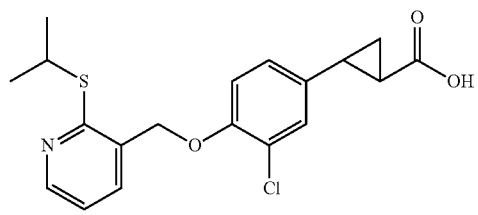 [SMILES: CC(C)Sc1ncccc1COc1ccc(C2CC2C(=O)O)cc1Cl]

3-Chloromethyl-2-isopropylsulfanyl-pyridine (17 mg, 0.08 mmol) obtained in Step C of Preparation Example 1 and 2-(3-fluoro-4-hydroxy-phenyl)-cyclopropane carboxylic acid methyl ester (more polar) (20 mg, 0.09 mmol) obtained in Step F of Preparation Example 65 were used to react sequentially in the same manner as in Steps A and B of Example 1 to obtain the title compound (23 mg, 79%).

$^1$H NMR (CDCl$_3$) 8.39 (1H, d), 7.79 (1H, d), 7.13 (1H, m), 7.04 (1H, m), 6.87 (1H, m), 6.86 (1H, d), 5.04 (2H, s), 4.18 (1H, m), 2.52 (1H, m), 1.82 (1H, m), 1.61 (1H, m), 1.41 (6H, d), 1.33 (1H, m)

EXAMPLE 127

2-[3-chloro-4-(2-cyclopropylmethylsulfanyl-pyridin-3-ylmethoxy)-phenyl]-cyclopropane carboxylic acid (more polar)

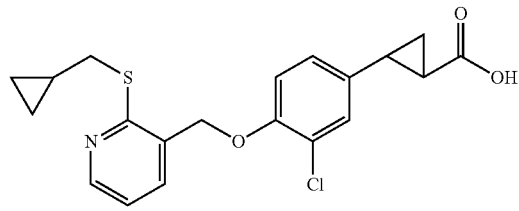 [SMILES: O=C(O)C1CC1c1ccc(OCc2cccnc2SCC2CC2)c(Cl)c1]

3-Chloromethyl-2-cyclopropylmethylsulfanyl-pyridine (21 mg, 0.10 mmol) obtained in Step C of Preparation Example 18 and 2-(3-fluoro-4-hydroxy-phenyl)-cyclopropane carboxylic acid methyl ester (more polar) (25 mg, 0.11 mmol) obtained in Step F of Preparation Example 65 were used to react sequentially in the same manner as in Steps A and B of Example 1 to obtain the title compound (24 mg, 74%).

$^1$H NMR (CDCl$_3$) 8.38 (1H, m), 7.80 (1H, d), 7.14 (1H, m), 7.05 (1H, m), 6.99 (1H, m), 6.88 (1H, m), 5.09 (2H, s), 3.24 (2H, d), 2.52 (1H, m), 1.85 (1H, m), 1.62 (1H, m), 1.35 (1H, m), 1.17 (1H, m), 0.61 (2H, m), 0.33 (2H, m)

EXAMPLE 128

2-[3-chloro-4-(6-cyclopropylmethylsulfanyl-pyridin-2-ylmethoxy)-phenyl]-cyclopropane carboxylic acid (more polar)

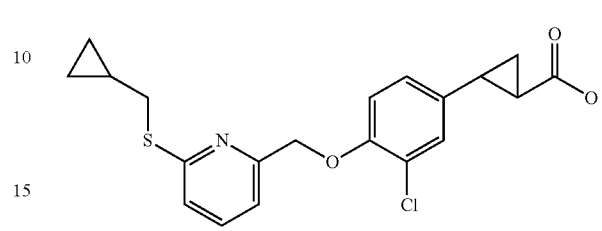

2-Chloromethyl-6-cyclopropylmethylsulfanyl-pyridine (21 mg, 0.10 mmol) obtained in Step D of Preparation Example 20 and 2-(3-fluoro-4-hydroxy-phenyl)-cyclopropane carboxylic acid methyl ester (more polar) (25 mg, 0.11 mmol) obtained in Step F of Preparation Example 65 were used to react sequentially in the same manner as in Steps A and B of Example 1 to obtain the title compound (21 mg, 77%).

$^1$H NMR (CDCl$_3$) 7.51 (1H, t), 7.25 (1H, m), 7.15 (2H, m), 7.00 (1H, m), 6.88 (1H, m), 5.19 (2H, s), 3.11 (2H, d), 2.51 (1H, m), 1.82 (1H, m), 1.62 (1H, m), 1.32 (1H, m), 1.15 (1H, m), 0.58 (2H, m), 0.31 (2H, m)

EXAMPLE 129

2-[4-(2-cyclopropylmethylsulfanyl-pyridin-3-yl-methoxy)-3-fluoro-phenyl]-cyclopropane carboxylic acid (less polar)

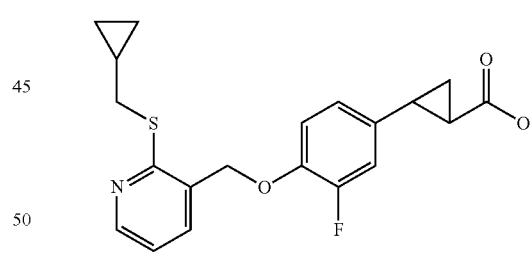

3-Chloromethyl-2-cyclopropylmethylsulfanyl-pyridine (0.026 g, 0.12 mmol) obtained in Step C of Preparation Example 18 and 2-(3-fluoro-4-hydroxy-phenyl)-cyclopropane carboxylic acid methyl ester (less polar) (0.025 g, 0.12 mmol) obtained in Step C of Preparation Example 64 were used to react sequentially in the same manner as in Steps A and B of Example 1 to obtain the title compound (0.042 g, 95%).

$^1$H NMR (CDCl$_3$) δ 8.38 (1H, m), 7.72 (1H, m), 7.04 (1H, m), 6.92 (1H, t), 6.90–6.80 (2H, m), 5.09 (2H, s), 3.23 (2H, d), 2.53 (1H, m), 1.84 (1H, m), 1.63 (1H, m), 1.33 (1H, m), 1.17 (1H, m), 0.59 (2H, m), 0.33 (2H, m)

EXAMPLE 130

2-[4-(2-cyclopentylsulfanyl-pyridin-3-ylmethoxy)-3-fluoro-phenyl]-cyclopropane carboxylic acid (less polar)

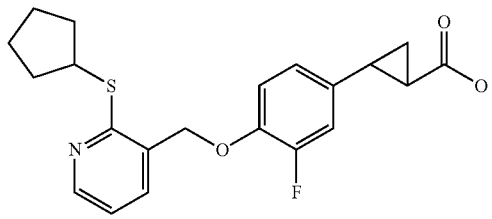 [SMILES: O=C(O)C1CC1c1ccc(OCc2cccnc2SC2CCCC2)c(F)c1]

3-Chloromethyl-2-cyclopentylsulfanyl-pyridine (0.032 g, 0.14 mmol) obtained in Step C of Preparation Example 8 and 2-(3-fluoro-4-hydroxy-phenyl)-cyclopropane carboxylic acid methyl ester (less polar) (0.030 g, 0.14 mmol) obtained in Step C of Preparation Example 64 were used to react sequentially in the same manner as in Steps A and B of Example 1 to obtain the title compound (0.033 g, 71%).

$^1$H NMR (CDCl$_3$) δ 8.40 (1H, m), 7.70 (1H, m), 7.03 (1H, m), 6.90 (1H, t), 6.88~6.80 (2H, m), 5.05 (2H, s), 4.22 (1H, m), 2.52 (1H, m), 2.23 (2H, m), 1.83 (1H, m), 1.79 (2H, m), 1.65 (5H, m), 1.33 (1H, m)

EXAMPLE 131

2-[3-fluoro-4-(6-isopropylsulfanyl-pyridin-2-ylmethoxy)-phenyl]-cyclopropane carboxylic acid (less polar)

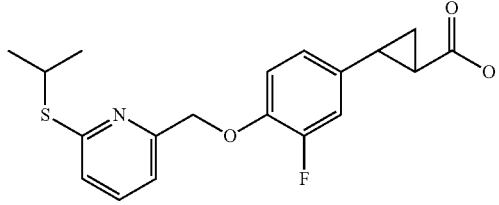 [SMILES: CC(C)Sc1cccc(COc2ccc(C3CC3C(=O)O)cc2F)n1]

2-Chloromethyl-6-isopropylsulfanyl-pyridine (0.029 g, 0.14 mmol) obtained in Step C of Preparation Example 16 and 2-(3-fluoro-4-hydroxy-phenyl)-cyclopropane carboxylic acid methyl ester (less polar) (0.030 g, 0.14 mmol) obtained in Step C of Preparation Example 64 were used to react sequentially in the same manner as in Steps A and B of Example 1 to obtain the title compound (0.048 g, 93%).

$^1$H NMR (CDCl$_3$) δ 7.49 (1H, t), 7.19 (1H, d), 7.07 (1H, d), 6.90 (1H, t), 6.84 (1H, m), 6.80 (1H, m), 5.18 (2H, s), 3.96 (1H, m), 2.52 (1H, m), 1.82 (1H, m), 1.63 (1H, m), 1.39 (6H, d), 1.32 (1H, m)

EXAMPLE 132

2-[3-chloro-4-(6-cyclobutylsulfanyl-pyridin-2-ylmethoxy)-phenyl]-cyclopropane carboxylic acid (more polar)

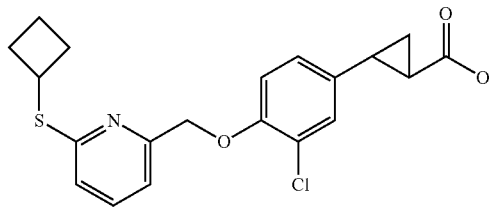 [SMILES: O=C(O)C1CC1c1ccc(OCc2cccc(SC3CCC3)n2)c(Cl)c1]

2-Chloromethyl-6-cyclobutylsulfanyl-pyridine (32 mg, 0.16 mmol) obtained in Step C of Preparation Example 37 and 2-(3-fluoro-4-hydroxy-phenyl)-cyclopropane carboxylic acid methyl ester (more polar) (41 mg, 0.18 mmol) obtained in Step F of Preparation Example 65 were used to react sequentially in the same manner as in Steps A and B of Example 1 to obtain the title compound (32 mg, 68%).

$^1$H NMR (CDCl$_3$) 7.51 (1H, t), 7.25 (1H, m), 7.15 (1H, m), 7.08 (1H, m), 6.93 (1H, m), 6.89 (1H, d), 5.18 (2H, s), 4.27 (1H, m), 2.53 (3H, m), 2.20~2.00 (4H, m), 1.84 (1H, m), 1.61 (1H, m), 1.33 (1H, m)

EXAMPLE 133

2-[4-(2-cyclobutylsulfanyl-pyridin-3-ylmethoxy)-3-fluoro-phenyl]-cyclopropane carboxylic acid (less polar)

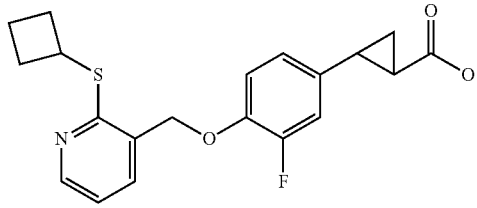 [SMILES: O=C(O)C1CC1c1ccc(OCc2cccnc2SC2CCC2)c(F)c1]

3-Chloromethyl-2-cyclobutylsulfanyl-pyridine (0.032 g, 0.15 mmol) obtained in Step C of Preparation Example 23 and 2-(3-fluoro-4-hydroxy-phenyl)-cyclopropane carboxylic acid methyl ester (less polar) (0.030 g, 0.14 mmol) obtained in Step C of Preparation Example 64 were used to react sequentially in the same manner as in Steps A and B of Example 1 to obtain the title compound (0.037 g, 84%).

$^1$H NMR (CDCl$_3$) δ 8.37 (1H, m), 7.68 (1H, m), 7.02 (1H, m), 6.90 (1H, t), 6.88~6.80 (2H, m), 5.04 (2H, s), 4.53 (1H, m), 2.55 (3H, m), 2.20~2.05 (4H, m), 1.83 (1H, m), 1.64 (1H, m), 1.34 (1H, m)

EXAMPLE 134

2-[4-(6-cyclopentylsulfanyl-pyridin-2-ylmethoxy)-3-fluoro-phenyl]-cyclopropane carboxylic acid (less polar)

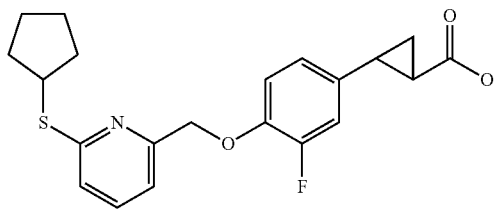 [SMILES: O=C(O)C1CC1c1ccc(OCc2cccc(SC3CCCC3)n2)c(F)c1]

2-Chloromethyl-6-cyclopentylsulfanyl-pyridine (0.033 g, 0.14 mmol) obtained in Step C of Preparation Example 27 and 2-(3-fluoro-4-hydroxy-phenyl)-cyclopropane carboxylic acid methyl ester (less polar) (0.030 g, 0.14 mmol) obtained in Step C of Preparation Example 64 were used to react sequentially in the same manner as in Steps A and B of Example 1 to obtain the title compound (0.043 g, 77%).

$^1$H NMR (CDCl$_3$) δ 7.50 (1H, t), 7.19 (1H, d), 7.09 (1H, d), 6.90 (1H, t), 6.84 (1H, m), 6.80 (1H, m), 5.18 (2H, s), 4.00 (1H, m), 2.53 (1H, m), 2.19 (2H, m), 1.80 (3H, m), 1.64 (5H, m), 1.33 (1H, m)

EXAMPLE 135

2-[4-(6-cyclobutylsulfanyl-pyridin-2-ylmethoxy)-3-fluoro-phenyl]-cyclopropane carboxylic acid (less polar)

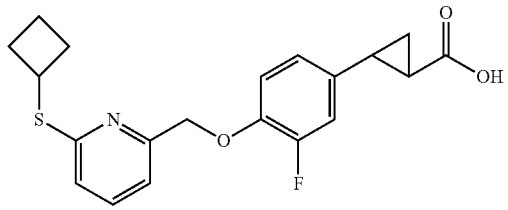 [SMILES: O=C(O)C1CC1c1ccc(OCc2cccc(SC3CCC3)n2)c(F)c1]

2-Chloromethyl-6-cyclobutylsulfanyl-pyridine (0.018 g, 0.08 mmol) obtained in Step C of Preparation Example 37 and 2-(3-fluoro-4-hydroxy-phenyl)-cyclopropane carboxylic acid methyl ester (less polar) (0.018 g, 0.08 mmol) obtained in Step C of Preparation Example 64 were used to react sequentially in the same manner as in Steps A and B of Example 1 to obtain the title compound (0.022 g, 71%).

$^1$H NMR (CDCl$_3$) δ 7.53-7.50 (1H, t), 7.22-7.20 (1H, d), 7.01-6.99 (1H, d), 6.93-6.79 (3H, m), 5.22 (2H, s), 4.32-4.24 (1H, m), 2.56-2.50 (3H, m), 2.15-2.03 (4H, m), 1.83-1.81 (1H, m), 1.64-1.61 (1H, m), 1.35-1.30 (1H, m)

EXAMPLE 136

2-[4-(2-cyclopropylmethylsulfanyl-pyridin-3-ylmethoxy)-3,5-difluoro-phenyl]-cyclopropane carboxylic acid (less polar)

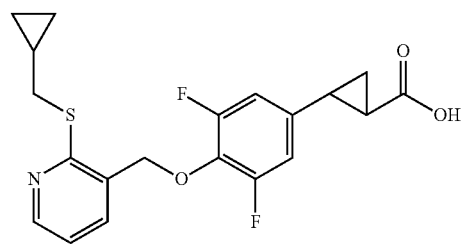 [SMILES: O=C(O)C1CC1c1cc(F)c(OCc2cccnc2SCC2CC2)c(F)c1]

Step A:

2-[4-(2-cyclopropylmethylsulfanyl-pyridin-3-ylmethoxy)-3,5-difluoro-phenyl]-cyclopropane carboxylic acid methyl ester 2-(3,5-Difluoro-4-hydroxy-phenyl)-cyclopropane carboxylic acid methyl ester (less polar) (8 mg, 0.035 mmol) obtained in Step C of Preparation Example 59 and 3-chloromethyl-2-cyclopropylmethylsulfanyl-pyridine (7.5 mg, 0.035 mmol) obtained in Step C of Preparation Example 18 were used to react in the same manner as in Step A of Example 1 to obtain the title compound (13 mg, 90%).

NMR (400 MHz, CDCl3): 0.28-0.33 (m., 2H), 0.55-0.60 (m., 2H), 1.12-1.16 (m., 1H), 1.22-1.27 (m., 1H), 1.57-1.63 (m., 1H), 1.82-1.87 (m., 1H), 2.42-2.47 (m., 1H), 3.20 (d., 7.2 Hz, 2H), 3.72 (s., 3H), 5.14 (s., 2H), 6.62-6.70 (m., 2H), 7.04 (d.d., 7.6 and 4.8 Hz, 1H), 7.77 (d.d., 7.6 and 1.6 Hz, 1H), 8.39 (d.d., 4.8 and 1.6 Hz, 1H) ppm.

Step B:

2-[4-(2-cyclopropylmethylsulfanyl-pyridin-3-ylmethoxy)-3,5-difluoro-phenyl]-cyclopropane carboxylic acid After 2-[4-(2-cyclopropylmethylsulfanyl-pyridin-3-ylmethoxy)-3,5-difluoro-phenyl]-cyclopropane carboxylic acid methyl ester (13 mg, 0.031 mmol) obtained in Step A was dissolved in THF/MeOH (1 mL/1 mL), 10N sodium hydroxide solution (30 mg, 0.31 mmol) was added thereto, and the mixture was stirred at room temperature for 12 hours. After the termination of the reaction, the reactant was concentrated under reduced pressure, and the residue was diluted with water. The aqueous layer was added with 1N HCl to adjust the pH to 2~3, and then extracted with EtOAc. The organic layer was dried with MgSO$_4$, concentrated under reduced pressure, and purified by column chromatography (eluent, MeOH/DCM=5/95) to obtain the title compound (12 mg, 97%).

NMR (400 MHz, CDCl$_3$): 0.28-0.33 (m., 2H), 0.55-0.60 (m., 2H), 1.09-1.19 (m., 1H), 1.28-1.35 (m., 1H), 1.63-1.68 (m., 1H), 1.83-1.88 (m., 1H), 2.49-2.53 (m., 1H), 3.20 (d., 7.2 Hz, 2H), 5.14 (s., 2H), 6.64-6.70 (m., 2H), 7.05 (d.d., 7.6 and 4.8 Hz, 1H), 7.78 (d.d., 7.6 and 1.6 Hz, 1H), 8.39 (d.d., 4.8 and 1.6 Hz, 1H) ppm.

EXAMPLE 137

2-[4-(2-cyclopropylmethylsulfanyl-pyridin-3-yl-methoxy)-3,5-difluoro-phenyl]-cyclopropane carboxylic acid (more polar)

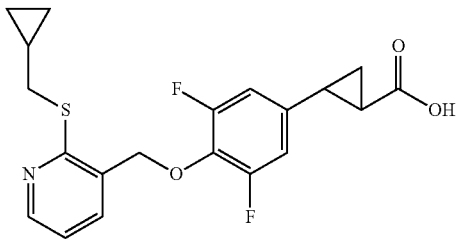 [SMILES: O=C(O)C1CC1c1cc(F)c(OCc2cccnc2SCC2CC2)c(F)c1]

Step A:

2-[4-(2-cyclopropylmethylsulfanyl-pyridin-3-yl-methoxy)-3,5-difluoro-phenyl]-cyclopropanecarboxylic acid methyl ester 2-(3,5-Difluoro-4-hydroxy-phenyl)-cyclopropane carboxylic acid methyl ester (more polar) (8 mg, 0.035 mmol) obtained in Step C of Preparation Example 60 and 3-chloromethyl-2-cyclopropylmethylsulfanyl-pyridine (7.5 mg, 0.035 mmol) obtained in Step C of Preparation Example 18 were used to react in the same manner as in Step A of Example 1 to obtain the title compound (15 mg, 99%).

NMR (400 MHz, CDCl$_3$): 0.28-0.33 (m., 2H), 0.55-0.60 (m., 2H), 1.12-1.16 (m., 1H), 1.22-1.27 (m., 1H), 1.57-1.63 (m., 1H), 1.82-1.87 (m., 1H), 2.42-2.47 (m., 1H), 3.20 (d., 7.2 Hz, 2H), 3.72 (s., 3H), 5.14 (s., 2H), 6.62-6.70 (m., 2H), 7.04 (d.d., 7.6 and 4.8 Hz, 1H), 7.77 (d.d., 7.6 and 1.6 Hz, 1H), 8.39 (d.d., 4.8 and 1.6 Hz, 1H) ppm.

Step B:

2-[4-(2-cyclopropylmethylsulfanyl-pyridin-3-yl-methoxy)-3,5-difluoro-phenyl]-cyclopropane carboxylic acid 2-[4-(2-Cyclopropylmethylsulfanyl-pyridin-3-yl-methoxy)-3,5-difluoro-phenyl]-cyclo propane carboxylic acid methyl ester (15 mg, 0.035 mmol) obtained in Step A was reacted in the same manner as in Step B of Example 1 to obtain the title compound (12 mg, 85%).

NMR (400 MHz, CDCl$_3$): 0.28-0.33 (m., 2H), 0.55-0.60 (m., 2H), 1.09-1.19 (m., 1H), 1.28-1.35 (m., 1H), 1.63-1.68 (m., 1H), 1.83-1.88 (m., 1H), 2.49-2.53 (m., 1H), 3.20 (d., 7.2 Hz, 2H), 5.14 (s., 2H), 6.64-6.70 (m., 2H), 7.05 (d.d., 7.6 and 4.8 Hz, 1H), 7.78 (d.d., 7.6 and 1.6 Hz, 1H), 8.39 (d.d., 4.8 and 1.6 Hz, 1H) ppm.

EXAMPLE 138

2-[3,5-difluoro-4-(2-isopropylsulfanyl-pyridin-3-ylmethoxy)-phenyl]-cyclopropane carboxylic acid (more polar)

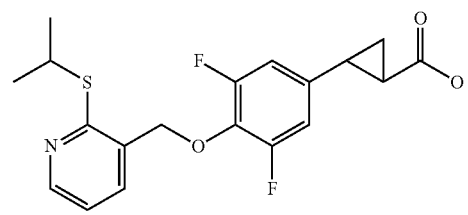 [SMILES: CC(C)Sc1ncccc1COc1c(F)cc(C2CC2C(=O)O)cc1F]

Step A:

2-[3,5-difluoro-4-(2-isopropylsulfanyl-pyridin-3-ylmethoxy)-phenyl]-cyclopropane carboxylic acid methyl ester 2-(3,5-Difluoro-4-hydroxy-phenyl)-cyclopropane carboxylic acid methyl ester (more polar) (22.5 mg, 0.1 mmol) obtained in Step C of Preparation Example 60 was used to react in the same manner as in Step A of Example 1 to obtain the title compound (38.5 mg, 98%).

NMR (400 MHz, CDCl$_3$): 1.22-1.27 (m., 1H), 1.39 (d., 6.4 Hz, 6H), 1.57-1.63 (m., 1H), 1.82-1.87 (m., 1H), 2.41-2.47 (m., 1H), 3.72 (s., 3H), 4.13 (sep., 6.4 Hz, 1H), 5.10 (s., 2H), 6.62-6.70 (m., 2H), 7.04 (d.d., 7.6 and 4.8 Hz, 1H), 7.77 (d.d., 7.6 and 1.6 Hz, 1H), 8.40 (d.d., 4.8 and 1.6 Hz, 1H) ppm.

Step B:

2-[3,5-difluoro-4-(2-isopropylsulfanyl-pyridin-3-ylmethoxy)-phenyl]-cyclopropane carboxylic acid 2-[3,5-Difluoro-4-(2-isopropylsulfanyl-pyridin-3-yl-methoxy)-phenyl]-cyclopropane carboxylic acid methyl ester (38 mg, 0.098 mmol) obtained in Step A was reacted in the same manner as in Step B of Example 1 to obtain the title compound (28 mg, 76%).

NMR (400 MHz, CDCl$_3$): 1.22-1.27 (m., 1H), 1.38 (d., 6.4 Hz, 6H), 1.55-1.65 (m., 1H), 1.79-1.87 (m., 1H), 2.44-2.50 (m., 1H), 4.15 (sep., 6.4 Hz, 1H), 5.10 (s., 2H), 6.62-6.70 (m., 2H), 7.03 (d.d., 7.6 and 4.8 Hz, 1H), 7.77 (d.d., 7.6 and 1.6 Hz, 1H), 8.40 (d.d., 4.8 and 1.6 Hz, 1H) ppm.

EXAMPLE 139

2-[3,5-difluoro-4-(2-propylsulfanyl-pyridin-3-yl-methoxy)-phenyl]-cyclopropane carboxylic acid (more polar)

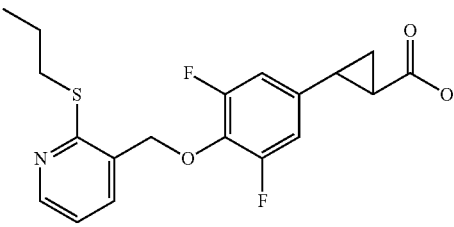 [SMILES: CCCSc1ncccc1COc1c(F)cc(C2CC2C(=O)O)cc1F]

Step A:

2-[3,5-difluoro-4-(2-propylsulfanyl-pyridin-3-yl-methoxy)-phenyl]-cyclopropane carboxylic acid methyl ester 2-(3,5-Difluoro-4-hydroxy-phenyl)-cyclopropane carboxylic acid methyl ester (more polar) (20 mg, 0.088 mmol) obtained in Step C of Preparation Example 60 and 3-chloromethyl-2-propylsulfanyl-pyridine (17.7 mg, 0.088 mmol) obtained in Step C of Preparation Example 14 were used to react in the same manner as in Step A of Example 1 to obtain the title compound (33.5 mg, 97%).

NMR (400 MHz, CDCl₃): 1.03 (t., 7.6 Hz., 3H), 1.22-1.27 (m., 1H), 1.57-1.63 (m., 1H), 1.71 (sex., 7.6 Hz, 2H), 1.82-1.87 (m., 1H), 2.41-2.47 (m., 1H), 3.22 (t., 7.6 Hz, 2H), 3.72 (s., 3H), 5.12 (s., 2H), 6.62-6.69 (m., 2H), 7.03 (d.d., 7.6 and 4.8 Hz, 1H), 7.74 (d.d., 7.6 and 1.6 Hz, 1H), 8.39 (d.d., 4.8 and 1.6 Hz, 1H) ppm.

Step B:

2-[3,5-difluoro-4-(2-propylsulfanyl-pyridin-3-yl-methoxy)-phenyl]-cyclopropane carboxylic acid 2-[3,5-difluoro-4-(2-propylsulfanyl-pyridin-3-yl-methoxy)-phenyl]-cyclopropane carboxylic acid methyl ester (33 mg, 0.085 mmol) obtained in Step A was reacted in the same manner as in Step B of Example 1 to obtain the title compound (25 mg, 77%).

NMR (400 MHz, CDCl₃): 1.01 (t., 7.6 Hz., 3H), 1.22-1.27 (m., 1H), 1.52-1.62 (m., 1H), 1.69 (sex., 7.6 Hz, 2H), 1.75-1.85 (m., 1H), 2.38-2.47 (m., 1H), 3.19 (t., 7.6 Hz, 2H), 5.10 (s., 2H), 6.62-6.69 (m., 2H), 7.00 (d.d., 7.6 and 4.8 Hz, 1H), 7.73 (d.d., 7.6 and 1.6 Hz, 1H), 8.38 (d.d., 4.8 and 1.6 Hz, 1H) ppm.

EXAMPLE 140

2-[4-(2-cyclopentylsulfanyl-pyridin-3-ylmethoxy)-3,5-difluoro-phenyl]-cyclopropane carboxylic acid (more polar)

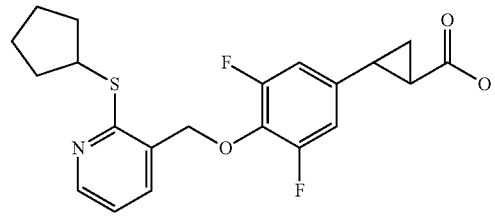 [SMILES: O=C(O)C1CC1c1cc(F)c(OCc2cccnc2SC2CCCC2)c(F)c1]

Step A: 2-[4-(2-cyclopentylsulfanyl-pyridin-3-yl-methoxy)-3,5-difluoro-phenyl]-cyclopropane carboxylic acid methyl ester 2-(3,5-Difluoro-4-hydroxy-phenyl)-cyclopropane carboxylic acid methyl ester (more polar) (20.8 mg, 0.091 mmol) obtained in Step C of Preparation Example 60 and 3-chloromethyl-2-cyclopentylsulfanyl-pyridine (20.76 mg, 0.091 mmol) obtained in Step C of Preparation Example 8 were used to react in the same manner as in Step A of Example 1 to obtain the title compound (38 mg, 99%).

NMR (400 MHz, CDCl₃): 1.23-1.27 (m., 1H), 1.57-1.70 (m., 5H), 1.70-1.80 (m., 2H), 1.82-1.87 (m., 1H), 2.17-2.22 (m., 2H), 2.41-2.47 (m., 1H), 3.72 (s., 3H), 4.15-4.22 (m., 1H), 5.10 (s., 2H), 6.62-6.69 (m., 2H), 7.03 (d.d., 7.6 and 4.8 Hz, 1H), 7.73 (d.d., 7.6 and 1.6 Hz, 1H), 8.39 (d.d., 4.8 and 1.6 Hz, 1H) ppm.

Step B:

2-[4-(2-cyclopentylsulfanyl-pyridin-3-ylmethoxy)-3,5-difluoro-phenyl]-cyclopropane carboxylic acid 2-[4-(2-Cyclopentylsulfanyl-pyridin-3-ylmethoxy)-3,5-difluoro-phenyl]-cyclopropane carboxylic acid methyl ester (38 mg, 0.09 mmol) obtained in Step A was reacted in the same manner as in Step B of Example 1 to obtain the title compound (34 mg, 93%).

NMR (400 MHz, CDCl₃): 1.23-1.27 (m., 1H), 1.55-1.86 (m., 8H), 2.17-2.22 (m., 2H), 2.45-2.51 (m., 1H), 4.15-4.22 (m., 1H), 5.10 (s., 2H), 6.62-6.69 (m., 2H), 7.03 (d.d., 7.6 and 4.8 Hz, 1H), 7.75 (d.d., 7.6 and 1.6 Hz, 1H), 8.39 (d.d., 4.8 and 1.6 Hz, 1H) ppm.

EXAMPLE 141

3-[3-chloro-4-(6-isopropylsulfanyl-pyridin-2-yl-methoxy)-phenyl]-propionic acid

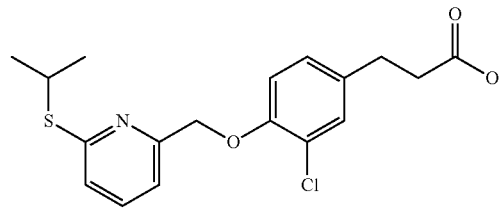 [SMILES: CC(C)Sc1cccc(COc2ccc(CCC(=O)O)cc2Cl)n1]

2-Chloromethyl-6-isopropylsulfanyl-pyridine (41 mg, 0.20 mmol) obtained in Step C of Preparation Example 16 and 3-(3-chloro-4-hydroxy-phenyl)-propionic acid ethyl ester (51 mg, 0.22 mmol) obtained in Step C of Preparation Example 42 were used to react sequentially in the same manner as in Steps A and B of Example 1 to obtain the title compound (38 mg, 59%).

$^1$H NMR (CDCl$_3$) 7.52 (1H, t), 7.26 (1H, m), 7.08 (1H, m), 6.90 (1H, m), 6.88 (1H, d), 5.19 (2H, s), 3.97 (1H, m), 2.88 (2H, t), 2.65 (2H, t), 1.40 (6H, d)

EXAMPLE 142

3-[3-chloro-4-(6-cyclopropylmethylsulfanyl-pyridin-2-ylmethoxy)-phenyl]-propionic acid

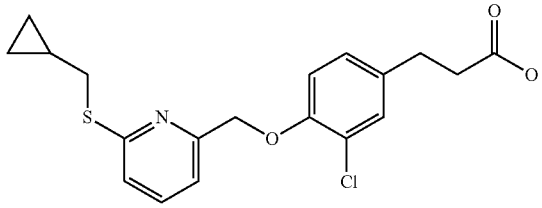 [SMILES: O=C(O)CCc1ccc(OCc2cccc(SCC3CC3)n2)c(Cl)c1]

2-Chloromethyl-6-cyclopropylmethylsulfanyl-pyridine (43 mg, 0.20 mmol) obtained in Step D of Preparation Example 20 and 3-(3-chloro-4-hydroxy-phenyl)-propionic acid ethyl ester (51 mg, 0.22 mmol) obtained in Step C of Preparation Example 42 were used to react sequentially in the same manner as in Steps A and B of Example 1 to obtain the title compound (48 mg, 72%).

$^1$H NMR (CDCl$_3$) 7.50 (1H, t), 7.25 (2H, m), 7.11 (1H, m), 6.90 (1H, m), 6.88 (1H, m), 5.19 (2H, s), 3.11 (2H, d), 2.89 (2H, t), 2.65 (2H, t), 1.15 (1H, m), 0.60 (1H, m), 0.32 (1H, m)

EXAMPLE 143

3-[3-chloro-4-(6-cyclopentylsulfanyl-pyridin-2-yl-methoxy)-phenyl]-propionic acid

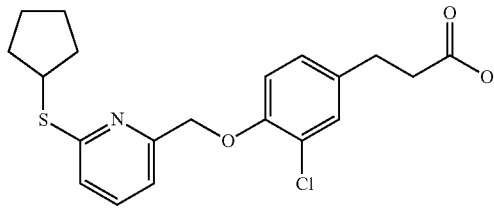 [SMILES: O=C(O)CCc1ccc(OCc2cccc(SC3CCCC3)n2)c(Cl)c1]

2-Chloromethyl-6-cyclopentylsulfanyl-pyridine (46 mg, 0.20 mmol) obtained in Step C of Preparation Example 27 and 3-(3-chloro-4-hydroxy-phenyl)-propionic acid ethyl ester (51 mg, 0.22 mmol) obtained in Step C of Preparation Example 42 were used to react sequentially in the same manner as in Steps A and B of Example 1 to obtain the title compound (45 mg, 71%).

$^1$H NMR (CDCl$_3$) 7.51 (1H, t), 7.25 (1H, m), 7.09 (1H, m), 6.99 (1H, m), 6.88 (1H, d), 5.19 (2H, s), 4.00 (1H, m), 2.88 (2H, m), 2.64 (2H, m), 2.19 (2H, m), 1.67 (3H, m), 1.64 (4H, m)

EXAMPLE 144

3-[3-fluoro-4-(2-propylsulfanyl-pyridin-3-yl-methoxy)-phenyl]-propionic acid

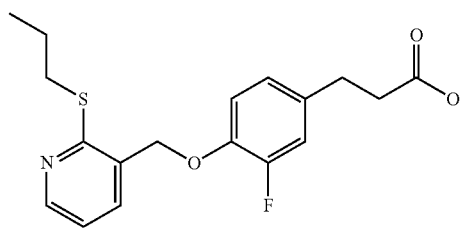 [SMILES: CCCSc1ncccc1COc1ccc(CCC(=O)O)cc1F]

3-Chloromethyl-2-propylsulfanyl-pyridine (0.030 g, 0.15 mmol) obtained in Step C of Preparation Example 14 and 3-(3-fluoro-4-hydroxy-phenyl)-propionic acid methyl ester (0.031 g, 0.15 mmol) obtained in Step C of Preparation Example 6 were used to react sequentially in the same manner as in Steps A and B of Example 1 to obtain the title compound (0.038 g, 73%).

$^1$H NMR (CDCl$_3$) δ 8.40-8.39 (1H, m), 7.74-7.72 (1H, m), 7.05-7.01 (1H, q), 6.99-6.87 (3H, m), 5.08 (2H, s), 3.27-3.24 (2H, t), 2.91-2.88 (2H, t), 2.67-2.63 (2H, t), 1.79-1.70 (2H, m), 1.07-1.03 (3H, m)

EXAMPLE 145

3-[4-(2-cyclobutylsulfanyl-pyridin-3-ylmethoxy)-3-fluoro-phenyl]-propionic acid

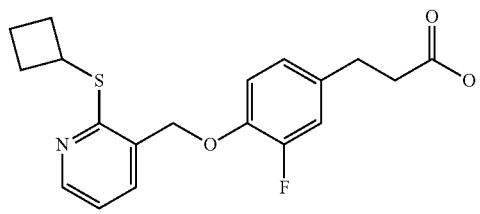

3-Chloromethyl-2-cyclobutylsulfanyl-pyridine (0.030 g, 0.14 mmol) obtained in Step C of Preparation Example 23 and 3-(3-fluoro-4-hydroxy-phenyl)-propionic acid methyl ester (0.030 g, 0.14 mmol) obtained in Step C of Preparation Example 6 were used to react sequentially in the same manner as in Steps A and B of Example 1 to obtain the title compound (0.041 g, 82%).

$^1$H NMR (CDCl$_3$) δ 8.38-8.37 (1H, m), 7.72-7.70 (1H, m), 7.03-7.00 (1H, q), 6.99-6.87 (3H, m), 5.04 (2H, s), 4.58-4.50 (1H, m), 2.92-2.88 (2H, t), 2.67-2.63 (2H, t), 2.60-2.53 (2H, m), 2.20-2.02 (4H, m)

EXAMPLE 146

3-[4-(2-cyclopentylsulfanyl-pyridin-3-ylmethoxy)-3-fluoro-phenyl]-propionic acid

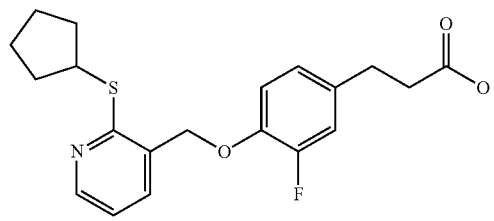 [SMILES: O=C(O)CCc1ccc(OCc2cccnc2SC2CCCC2)c(F)c1]

3-Chloromethyl-2-cyclopentylsulfanyl-pyridine (0.032 g, 0.14 mmol) obtained in Step C of Preparation Example 8 and 3-(3-fluoro-4-hydroxy-phenyl)-propionic acid methyl ester (0.030 g, 0.14 mmol) obtained in Step C of Preparation Example 6 were used to react sequentially in the same manner as in Steps A and B of Example 1 to obtain the title compound (0.045 g, 84%).

$^1$H NMR (CDCl$_3$) δ 8.40-8.39 (1H, m), 7.73-7.71 (1H, m), 7.04-7.01 (1H, q), 6.98-6.87 (3H, m), 5.05 (2H, s), 4.22 (1H, m), 2.92-2.88 (2H, t), 2.67-2.63 (2H, t), 2.24 (2H, m), 1.79 (2H, m), 1.66 (4H, m)

EXAMPLE 147

3-[4-(2-cyclopropylmethylsulfanyl-pyridin-3-yl-methoxy)-3-fluoro-phenyl]-propionic acid

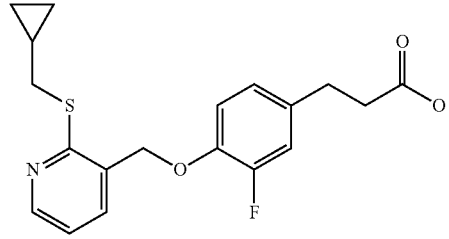

3-Chloromethyl-2-cyclopropylmethylsulfanyl-pyridine (0.030 g, 0.14 mmol) obtained in Step C of Preparation Example 18 and 3-(3-fluoro-4-hydroxy-phenyl)-propionic acid ethyl ester (0.031 g, 0.14 mmol) obtained in Step C of Preparation Example 6 were used to react sequentially in the same manner as in Steps A and B of Example 1 to obtain the title compound (0.044 g, 86%).

$^1$H NMR (CDCl$_3$) δ 8.39 (1H, m), 7.74-7.72 (1H, m), 7.03-7.02 (1H, q), 6.99-6.87 (3H, m), 5.09 (2H, s), 3.24-3.22 (2H, d), 2.92-2.88 (2H, t), 2.67-2.63 (2H, t), 1.17 (1H, m), 0.61-0.59 (2H, m), 0.34-0.32 (2H, m)

EXAMPLE 148

3-[4-(6-cyclobutylsulfanyl-pyridin-2-ylmethoxy)-3-fluoro-phenyl]-propionic acid

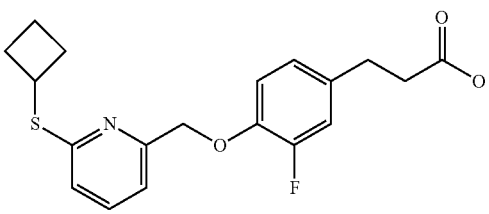 [SMILES: O=C(O)CCc1ccc(OCc2cccc(SC3CCC3)n2)c(F)c1]

2-Chloromethyl-6-cyclobutylsulfanyl-pyridine (0.030 g, 0.14 mmol) obtained in Step C of Preparation Example 37 and 3-(3-fluoro-4-hydroxy-phenyl)-propionic acid ethyl ester (0.030 g, 0.14 mmol) obtained in Step C of Preparation Example 6 were used to react sequentially in the same manner as in Steps A and B of Example 1 to obtain the title compound (0.043 g, 84%).

$^1$H NMR (CDCl$_3$) δ 7.52-7.48 (1H, t), 7.21-7.19 (1H, d), 7.00-6.98 (1H, d), 6.96-6.85 (3H, m), 5.17 (2H, s), 4.30-4.24 (1H, m), 2.91-2.87 (2H, t), 2.66-2.62 (2H, t), 2.56-2.51 (2H, m), 2.17-2.02 (4H, m)

EXAMPLE 149

3-[3-fluoro-4-(6-isopropylsulfanyl-pyridin-2-yl-methoxy)-phenyl]-propionic acid

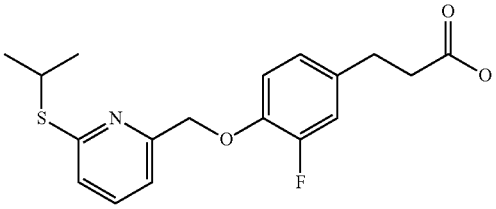

2-Chloromethyl-6-isopropylsulfanyl-pyridine (0.028 g, 0.14 mmol) obtained in Step C of Preparation Example 16 and 3-(3-fluoro-4-hydroxy-phenyl)-propionic acid ethyl ester (0.030 g, 0.14 mmol) obtained in Step C of Preparation Example 6 were used to react sequentially in the same manner as in Steps A and B of Example 1 to obtain the title compound (0.041 g, 83%).

$^1$H NMR (CDCl$_3$) δ 7.52-7.48 (1H, t), 7.22-7.20 (1H, d), 7.09-7.07 (1H, d), 6.99-6.85 (3H, m), 5.18 (2H, s), 4.00-3.93 (1H, m), 2.91-2.87 (2H, t), 2.66-2.62 (2H, t), 1.40-1.39 (6H, d)

EXAMPLE 150

3-[4-(6-cyclopentylsulfanyl-pyridin-2-ylmethoxy)-3-fluoro-phenyl]-propionic acid

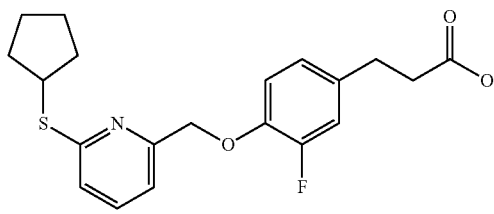

2-Chloromethyl-6-cyclopentylsulfanyl-pyridine (0.032 g, 0.14 mmol) obtained in Step C of Preparation Example 27 and 3-(3-fluoro-4-hydroxy-phenyl)-propionic acid ethyl ester (0.030 g, 0.14 mmol) obtained in Step C of Preparation Example 6 were used to react sequentially in the same manner as in Steps A and B of Example 1 to obtain the title compound (0.045 g, 84%).

$^1$H NMR (CDCl$_3$) δ 7.52-7.48 (1H, t), 7.21-7.20 (1H, d), 7.09-7.07 (1H, d), 6.98-6.85 (3H, m), 5.18 (2H, s), 4.01-3.98 (1H, m), 2.90-2.87 (2H, t), 2.66-2.62 (2H, t), 2.21-2.19 (2H, m), 1.79 (2H, m), 1.67-1.63 (4H, m)

EXAMPLE 151

3-[4-(6-cyclopropylmethylsulfanyl-pyridin-2-ylmethoxy)-3-fluoro-phenyl]-propionic acid 2-Chloromethyl-6-cyclopropylmethylsulfanyl-pyridine (0.030 g, 0.14 mmol) obtained in Step D of Preparation Example 20 and 3-(3-fluoro-4-hydroxy-phenyl)-propionic acid ethyl ester (0.030 g, 0.14 mmol) obtained in Step C of Preparation Example 6 were used to react sequentially in the same manner as in Steps A and B of Example 1 to obtain the title compound (0.043 g, 86%).

$^1$H NMR (CDCl$_3$) δ 7.51-7.47 (1H, t), 7.22-7.20 (1H, d), 7.11-7.09 (1H, d), 6.99-6.85 (3H, m), 5.18 (2H, s), 3.12-3.10 (2H, d), 2.91-2.87 (2H, t), 2.66-2.62 (2H, t), 1.15 (1H, m), 0.61-0.56 (2H, m), 0.33-0.29 (2H, m)

EXAMPLE 152

2-[3,5-difluoro-4-(6-isopropylsulfanyl-pyridin-2-ylmethoxy)-phenyl]-cyclopropane carboxylic acid (more polar)

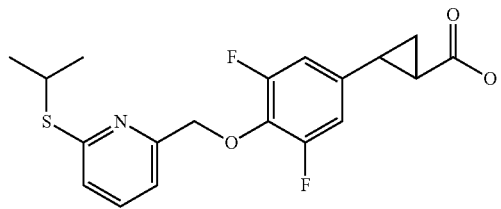 [SMILES: CC(C)Sc1cccc(COc2c(F)cc(C3CC3C(=O)O)cc2F)n1]

Step A:

2-[3,5-difluoro-4-(6-isopropylsulfanyl-pyridin-2-ylmethoxy)-phenyl]-cyclopropane carboxylic acid methyl ester 2-(3,5-Difluoro-4-hydroxy-phenyl)-cyclopropane carboxylic acid methyl ester (more polar) (20.3 mg, 0.089 mmol) obtained in Step C of Preparation Example 60 and 2-chloromethyl-6-isopropylsulfanyl-pyridine (17.94 mg, 0.089 mmol) obtained in Step C of Preparation Example 16 were used to react in the same manner as in Step A of Example 1 to obtain the title compound (32 mg, 91%).

NMR (400 MHz, CDCl$_3$): 1.22-1.27 (m., 1H), 1.35 (d., 6.8 Hz, 6H), 1.57-1.63 (m., 1H), 1.82-1.87 (m., 1H), 2.41-2.46 (m., 1H), 3.72 (s., 3H), 3.91 (sep., 6.8 Hz, 1H), 5.19 (s., 2H), 6.62-6.70 (m., 2H), 7.08 (d., 8 Hz, 1H), 7.29 (d., 8 Hz, 1H), 7.51 (t., 8 Hz, 1H) ppm.

Step B:

2-[3,5-difluoro-4-(6-isopropylsulfanyl-pyridin-2-ylmethoxy)-phenyl]-cyclopropanecarboxylic acid 2-[3,5-Difluoro-4-(6-isopropylsulfanyl-pyridin-2-ylmethoxy)-phenyl]-cyclopropane carboxylic acid methyl ester (32 mg, 0.081 mmol) obtained in Step A was reacted in the same manner as in Step B of Example 1 to obtain the title compound (27 mg, 87%).

NMR (400 MHz, CDCl$_3$): 1.22-1.36 (m.+d. (overlaps), 7H), 1.62-1.68 (m., 1H), 1.82-1.87 (m., 1H), 2.48-2.53 (m., 1H), 3.91 (sep., 6.8 Hz, 1H), 5.20 (s., 2H), 6.62-6.70 (m., 2H), 7.08 (d., 8 Hz, 1H), 7.29 (d., 8 Hz, 1H), 7.51 (t., 8 Hz, 1H) ppm.

EXAMPLE 153

2-[4-(6-cyclopropylmethylsulfanyl-pyridin-2-ylmethoxy)-3,5-difluoro-phenyl]-cyclopropane carboxylic acid (more polar)

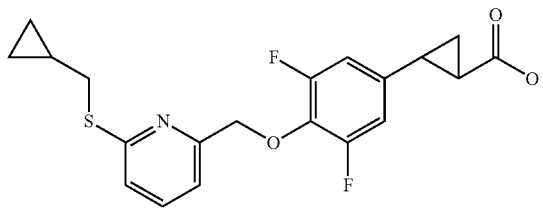 [SMILES: O=C(O)C1CC1c1cc(F)c(OCc2cccc(SCC3CC3)n2)c(F)c1]

Step A:

2-[4-(6-cyclopropylmethylsulfanyl-pyridin-2-yl-methoxy)-3,5-difluoro-phenyl]-cyclopropane carboxylic acid methyl ester 2-(3,5-Difluoro-4-hydroxy-phenyl)-cyclopropane carboxylic acid methyl ester (more polar) (21 mg, 0.092 mmol) obtained in Step C of Preparation Example 60 and 2-chloromethyl-6-cyclopropylmethylsulfanyl-pyridine (19.67 mg, 0.092 mmol) obtained in Step D of Preparation Example 20 were used to react in the same manner as in Step A of Example 1 to obtain the title compound (37 mg, 99%).

NMR (400 MHz, CDCl$_3$): 0.26-0.30 (m., 2H), 0.53-0.58 (m., 2H), 1.08-1.13 (m., 1H), 1.22-1.27 (m., 1H), 1.57-1.63 (m., 1H), 1.82-1.87 (m., 1H), 2.41-2.46 (m., 1H), 3.05 (d., 7.2 Hz, 2H), 3.72 (s., 3H), 5.18 (s., 2H), 6.62-6.68 (m., 2H), 7.10 (d., 8 Hz, 1H), 7.29 (d., 8 Hz, 1H), 7.51 (t., 8 Hz, 1H) ppm.

Step B:

2-[4-(6-cyclopropylmethylsulfanyl-pyridin-2-yl-methoxy)-3,5-difluoro-phenyl]-cyclopropanecarboxylic acid 2-[4-(6-Cyclopropylmethylsulfanyl-pyridin-2-yl-methoxy)-3,5-difluoro-phenyl]-cyclo propane carboxylic acid methyl ester (37 mg, 0.091 mmol) obtained in Step A was reacted in the same manner as in Step B of Example 1 to obtain the title compound (31.5 mg, 88%).

NMR (400 MHz, CDCl$_3$): 0.26-0.30 (m., 2H), 0.53-0.58 (m., 2H), 1.06-1.16 (m., 1H), 1.29-1.35 (m., 1H), 1.62-1.68 (m., 1H), 1.82-1.87 (m., 1H), 2.48-2.53 (m., 1H), 3.05 (d., 7.2 Hz, 2H), 5.19 (s., 2H), 6.62-6.69 (m., 2H), 7.10 (d., 8 Hz, 1H), 7.28 (d., 8 Hz, 1H), 7.51 (t., 8 Hz, 1H) ppm.

EXAMPLE 154

2-[4-(6-cyclopentylsulfanyl-pyridin-2-ylmethoxy)-3,5-difluoro-phenyl]-cyclopropane carboxylic acid (more polar)

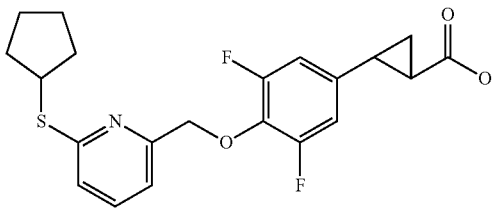 [SMILES: O=C(O)C1CC1c1cc(F)c(OCc2cccc(SC3CCCC3)n2)c(F)c1]

Step A: 2-[4-(6-cyclopentylsulfanyl-pyridin-2-yl-methoxy)-3,5-difluoro-phenyl]-cyclopropane carboxylic acid methyl ester 2-(3,5-Difluoro-4-hydroxy-phenyl)-cyclopropane carboxylic acid methyl ester (more polar) (21.7 mg, 0.095 mmol) obtained in Step C of Preparation Example 60 and 2-chloromethyl-6-cyclopentylsulfanyl-pyridine (21.66 mg, 0.095 mmol) obtained in Step C of Preparation Example 27 were used to react in the same manner as in Step A of Example 1 to obtain the title compound (37 mg, 93%).

NMR (400 MHz, CDCl$_3$): 1.23-1.27 (m., 1H), 1.57-1.70 (m., 5H), 1.70-1.80 (m., 2H), 1.82-1.87 (m., 1H), 2.10-2.18 (m., 2H), 2.41-2.46 (m., 1H), 3.72 (s., 3H), 3.90-3.97 (m., 1H), 5.18 (s., 2H), 6.62-6.68 (m., 2H), 7.08 (d., 8 Hz, 1H), 7.29 (d., 8 Hz, 1H), 7.51 (t., 8 Hz, 1H) ppm.

Step B: 2-[4-(6-cyclopentylsulfanyl-pyridin-2-yl-methoxy)-3,5-difluoro-phenyl]-cyclopropanecarboxylic acid 2-[4-(6-Cyclopentylsulfanyl-pyridin-2-ylmethoxy)-3,5-difluoro-phenyl]-cyclopropane carboxylic acid methyl ester (37 mg, 0.089 mmol) obtained in Step A was reacted in the same manner as in Step B of Example 1 to obtain the title compound (33 mg, 92%).

NMR (400 MHz, CDCl$_3$): 1.29-1.35 (m., 1H), 1.55-1.68 (m., 5H), 1.70-1.80 (m., 2H), 1.82-1.88 (m., 1H), 2.10-2.18 (m., 2H), 2.48-2.53 (m., 1H), 3.90-3.97 (m., 1H), 5.19 (s., 2H), 6.62-6.69 (m., 2H), 7.09 (d., 8 Hz, 1H), 7.29 (d., 8 Hz, 1H), 7.52 (t., 8 Hz, 1H) ppm.

EXAMPLE 155

2-[4-(6-cyclobutylsulfanyl-pyridin-2-ylmethoxy)-3,5-difluoro-phenyl]-cyclopropane carboxylic acid (more polar)

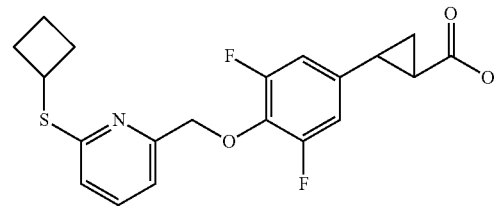 [SMILES: O=C(O)C1CC1c1cc(F)c(OCc2cccc(SC3CCC3)n2)c(F)c1]

2-Chloromethyl-6-cyclobutylsulfanyl-pyridine (0.018 g, 0.08 mmol) obtained in Step C of Preparation Example 37 and 2-(3,5-difluoro-4-hydroxy-phenyl)-cyclopropane carboxylic acid methyl ester (more polar) (0.020 g, 0.08 mmol) obtained in Step C of Preparation Example 60 were used to react sequentially in the same manner as in Steps A and B of Example 1 to obtain the title compound (0.030 g, 88%).

$^1$H-NMR (CDCl$_3$) δ 7.54-7.50 (1H, t), 7.30-7.29 (1H, d), 7.01-6.99 (1H, d), 6.70-6.64 (2H, m), 5.18 (2H, s), 4.27-4.19 (1H, m), 2.53-2.48 (3H, m), 2.13-2.04 (4H, m), 1.86-1.84 (1H, m), 1.67-1.64 (1H, m), 1.34-1.32 (1H, m)

EXAMPLE 156

2-[4-(2-cyclobutylsulfanyl-pyridin-3-ylmethoxy)-3,5-difluoro-phenyl]-cyclopropane carboxylic acid (more polar)

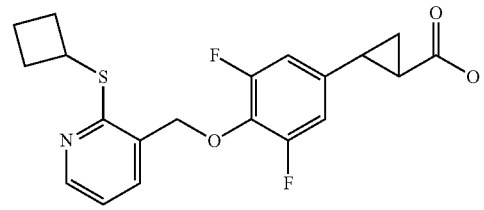

3-Chloromethyl-2-cyclobutylsulfanyl-pyridine (0.018 g, 0.08 mmol) obtained in Step C of Preparation Example 23 and 2-(3,5-difluoro-4-hydroxy-phenyl)-cyclopropane carboxylic acid methyl ester (more polar) (0.020 g, 0.08 mmol) obtained in Step C of Preparation Example 60 were used to react sequentially in the same manner as in Steps A and B of Example 1 to obtain the title compound (0.030 g, 88%).

$^1$H-NMR (CDCl$_3$) δ 8.39-8.38 (1H, m), 8.05-8.03 (1H, m), 7.05-7.02 (1H, q), 6.70-6.65 (2H, m), 5.10 (2H, s), 4.54-4.46 (1H, m), 2.54-2.50 (3H, m), 2.14-2.03 (4H, m), 1.87-1.84 (1H, m), 1.67-1.65 (1H, m), 1.34-1.32 (1H, m)

EXAMPLE 157

3-[3-chloro-4-(2-cyclopropylmethylsulfanyl-pyridin-3-ylmethoxy)-phenyl]-propionic acid

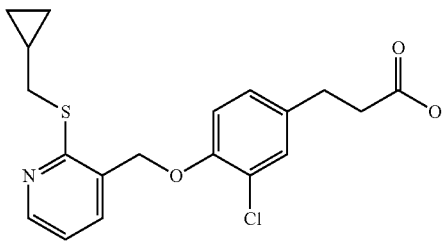 [SMILES: O=C(O)CCc1ccc(OCc2cccnc2SCC2CC2)c(Cl)c1]

3-Chloromethyl-2-cyclopropylmethylsulfanyl-pyridine (35 mg, 0.16 mmol) obtained in Step C of Preparation Example 18 and 3-(3-chloro-4-hydroxy-phenyl)-propionic acid ethyl ester (42 mg, 0.18 mmol) obtained in Step C of Preparation Example 42 were used to react sequentially in the same manner as in Steps A and B of Example 1 to obtain the title compound (38 mg, 74%).

$^1$H NMR (CDCl$_3$) 8.38 (1H, m), 7.82 (1H, d), 7.26 (1H, m), 7.05 (2H, m), 6.90 (1H, d), 5.09 (2H, s), 3.24 (2H, d), 2.91 (2H, t), 2.66 (2H, t), 1.17 (1H, m), 0.59 (2H, m), 0.34 (2H, m)

EXAMPLE 158

3-[3-chloro-4-(2-cyclobutylsulfanyl-pyridin-3-yl-methoxy)-phenyl]-propionic acid

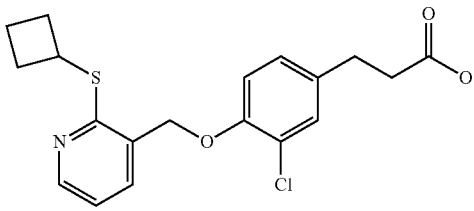 [SMILES: O=C(O)CCc1ccc(OCc2cccnc2SC2CCC2)c(Cl)c1]

3-Chloromethyl-2-cyclobutylsulfanyl-pyridine (34 mg, 0.17 mmol) obtained in Step C of Preparation Example 23 and 3-(3-chloro-4-hydroxy-phenyl)-propionic acid ethyl ester (43 mg, 0.19 mmol) obtained in Step C of Preparation Example 42 were used to react sequentially in the same manner as in Steps A and B of Example 1 to obtain the title compound (39 mg, 73%).

$^1$H NMR (CDCl$_3$) 8.37 (1H, m), 7.80 (1H, d), 7.26 (1H, m), 7.04 (2H, m), 6.88 (1H, d), 5.04 (2H, s), 4.55 (1H, m), 2.98 (2H, t), 2.64 (2H, t), 2.55 (2H, m), 2.20~2.00 (4H, m)

EXAMPLE 159

3-[3-chloro-4-(6-cyclobutylsulfanyl-pyridin-2-yl-methoxy)-phenyl]-propionic acid

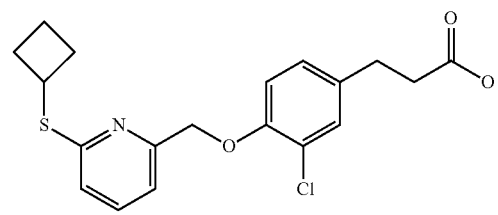 [SMILES: O=C(O)CCc1ccc(OCc2cccc(SC3CCC3)n2)c(Cl)c1]

2-Chloromethyl-6-cyclobutylsulfanyl-pyridine (34 mg, 0.17 mmol) obtained in Step C of Preparation Example 37 and 3-(3-chloro-4-hydroxy-phenyl)-propionic acid ethyl ester (43 mg, 0.19 mmol) obtained in Step C of Preparation Example 42 were used to react sequentially in the same manner as in Steps A and B of Example 1 to obtain the title compound (35 mg, 63%).

$^1$H NMR (CDCl$_3$) 7.52 (1H, m), 7.25 (2H, m), 7.04 (2H, m), 6.88 (1H, m), 5.18 (2H, s), 4.27 (1H, m), 2.89 (2H, m), 2.65 (2H, m), 2.54 (2H, m), 2.12 (4H, m)

EXAMPLE 160

3-[3-chloro-4-(2-isopropylsulfanyl-6-methyl-pyridin-3-ylmethoxy)-phenyl]-propionic acid

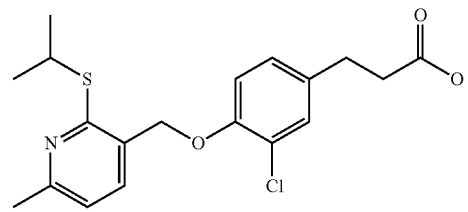 [SMILES: Cc1ccc(COc2ccc(CCC(=O)O)cc2Cl)c(SC(C)C)n1]

3-Chloromethyl-2-isopropylsulfanyl-6-methyl-pyridine (34 mg, 0.17 mmol) obtained in Step D of Preparation Example 9 and 3-(3-chloro-4-hydroxy-phenyl)-propionic acid ethyl ester (43 mg, 0.18 mmol) obtained in Step C of Preparation Example 42 were used to react sequentially in the same manner as in Steps A and B of Example 1 to obtain the title compound (32 mg, 58%).

$^1$H NMR (CDCl$_3$) 7.66 (1H, m), 7.26 (1H, m), 7.02 (1H, m), 6.88 (2H, m), 5.04 (2H, s), 4.20 (1H, m), 2.88 (2H, t), 2.65 (2H, t), 2.50 (3H, s), 1.42 (6H, d)

EXAMPLE 161

3-[3-chloro-4-(2-cyclopentylsulfanyl-6-methyl-pyridin-3-ylmethoxy)-phenyl]-propionic acid

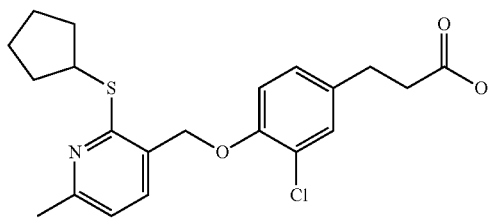 [SMILES: Cc1ccc(COc2ccc(CCC(=O)O)cc2Cl)c(SC2CCCC2)n1]

3-Chloromethyl-2-cyclopentylsulfanyl-6-methyl-pyridine (35 mg, 0.15 mmol) obtained in Step C of Preparation Example 36 and 3-(3-chloro-4-hydroxy-phenyl)-propionic acid ethyl ester (36 mg, 0.17 mmol) obtained in Step C of Preparation Example 42 were used to react sequentially in the same manner as in Steps A and B of Example 1 to obtain the title compound (30 mg, 58%).

$^1$H NMR (CDCl$_3$) 7.66 (1H, m), 7.26 (2H, m), 7.02 (1H, m), 6.89 (2H, d), 5.04 (2H, s), 4.24 (1H, m), 2.88 (2H, t), 2.65 (2H, t), 2.50 (3H, s), 2.23 (2H, m), 1.78 (2H, m), 1.55 (4H, m)

EXAMPLE 162

2-[3-fluoro-4-(2-isopropylsulfanyl-pyridin-3-ylmethoxy)-phenyl]-cyclopropane carboxylic acid (more polar)

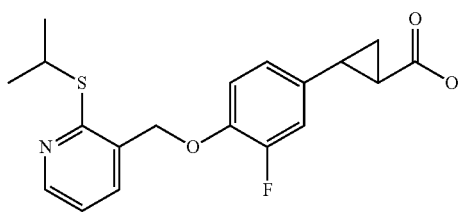 [SMILES: CC(C)Sc1ncccc1COc1ccc(C2CC2C(=O)O)cc1F]

Step A:

2-[3-fluoro-4-(2-isopropylsulfanyl-pyridin-3-ylmethoxy)-phenyl]-cyclopropane carboxylic acid methyl ester 2-(3-Fluoro-4-hydroxy-phenyl)-cyclopropane carboxylic acid methyl ester (more polar) (32 mg, 0.153 mmol) obtained in Step C of Preparation Example 63 and 3-chloromethyl-2-isopropylsulfanyl-pyridine (31 mg, 0.153 mmol) obtained in Step C of Preparation Example 1 were used to react in the same manner as in Step A of Example 1 to obtain the title compound (56 mg, 97%).

NMR (400 MHz, CDCl$_3$): 1.22-1.27 (m., 1H), 1.42 (d., 6.4 Hz, 6H), 1.54-1.60 (m., 1H), 1.80-1.85 (m., 1H), 2.43-2.49 (m., 1H), 3.72 (s., 3H), 4.18 (sep., 6.4 Hz, 1H), 5.05 (s., 2H), 6.77-6.88 (m., 2H), 6.92 (t., 8.4 Hz, 1H), 7.02 (d.d., 7.6 and 4.8 Hz, 1H), 7.71 (d.d., 7.6 and 1.6 Hz, 1H), 8.40 (d.d., 4.8 and 1.6 Hz, 1H) ppm.

Step B:

2-[3-fluoro-4-(2-isopropylsulfanyl-pyridin-3-ylmethoxy)-phenyl]-cyclopropane carboxylic acid 2-[3-Fluoro-4-(2-isopropylsulfanyl-pyridin-3-ylmethoxy)-phenyl]-cyclopropane carboxylic acid methyl ester (56 mg, 0.148 mmol) obtained in Step A was reacted in the same manner as in Step B of Example 1 to obtain the title compound (52 mg, 97%).

NMR (400 MHz, CDCl$_3$): 1.27-1.35 (m., 1H), 1.42 (d., 6.4 Hz, 6H), 1.60-1.66 (m., 1H), 1.81-1.85 (m., 1H), 2.51-2.56 (m., 1H), 4.18 (sep., 6.4 Hz, 1H), 5.06 (s., 2H), 6.80-6.88 (m., 2H), 6.91 (t., 8.4 Hz, 1H), 7.03 (d.d., 7.6 and 4.8 Hz, 1H), 7.72 (d.d., 7.6 and 1.6 Hz, 1H), 8.40 (d.d., 4.8 and 1.6 Hz, 1H) ppm.

EXAMPLE 163

2-[3-fluoro-4-(2-propylsulfanyl-pyridin-3-ylmethoxy)-phenyl]-cyclopropane carboxylic acid (more polar)

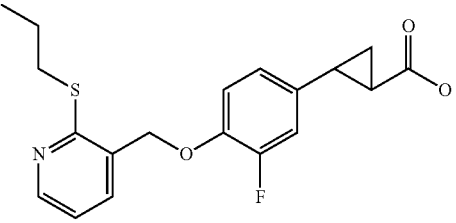 [SMILES: CCCSc1ncccc1COc1ccc(C2CC2C(=O)O)cc1F]

Step A: 2-[3-fluoro-4-(2-propylsulfanyl-pyridin-3-ylmethoxy)-phenyl]-cyclopropane carboxylic acid methyl ester 2-(3-Fluoro-4-hydroxy-phenyl)-cyclopropane carboxylic acid methyl ester (more polar) (30 mg, 0.142 mmol) obtained in Step C of Preparation Example 63 and 3-chloromethyl-2-propylsulfanyl-pyridine (28.79 mg, 0.142 mmol) obtained in Step C of Preparation Example 14 were used to react in the same manner as in Step A of Example 1 to obtain the title compound (50 mg, 95%).

NMR (400 MHz, CDCl$_3$): 1.05 (t., 7.6 Hz., 3H), 1.22-1.27 (m., 1H), 1.55-1.60 (m., 1H), 1.74 (sex., 7.6 Hz, 2H), 1.82-1.87 (m., 1H), 2.43-2.49 (m., 1H), 3.26 (t., 7.6 Hz, 2H), 3.72 (s., 3H), 5.07 (s., 2H), 6.77-6.89 (m., 2H), 6.92 (t., 8.4 Hz, 1H), 7.02 (d.d., 7.6 and 4.8 Hz, 1H), 7.71 (d.d., 7.6 and 1.6 Hz, 1H), 8.39 (d.d., 4.8 and 1.6 Hz, 1H) ppm.

Step B: 2-[3-fluoro-4-(2-propylsulfanyl-pyridin-3-ylmethoxy)-phenyl]-cyclopropane carboxylic acid 2-[3-Fluoro-4-(2-propylsulfanyl-pyridin-3-ylmethoxy)-phenyl]-cyclopropane carboxylic acid methyl ester (51 mg, 0.135 mmol) obtained in Step A was reacted in the same manner as in Step B of Example 1 to obtain the title compound (47 mg, 97%).

NMR (400 MHz, CDCl$_3$): 1.05 (t., 7.6 Hz., 3H), 1.31-1.36 (m., 1H), 1.61-1.66 (m., 1H), 1.74 (sex., 7.6 Hz, 2H), 1.81-1.86 (m., 1H), 2.51-2.56 (m., 1H), 3.26 (t., 7.6 Hz, 2H), 5.08 (s., 2H), 6.81-6.87 (m., 2H), 6.92 (t., 8.4 Hz, 1H), 7.02

(d.d., 7.6 and 4.8 Hz, 1H), 7.71 (d.d., 7.6 and 1.6 Hz, 1H), 8.39 (d.d., 4.8 and 1.6 Hz, 1H) ppm.

EXAMPLE 164

2-[4-(2-cyclopentylsulfanyl-pyridin-3-ylmethoxy)-3-fluoro-phenyl]-cyclopropane carboxylic acid (more polar)

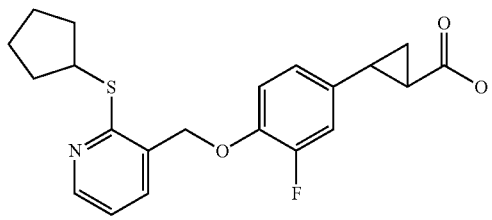 [SMILES: O=C(O)C1CC1c1ccc(OCc2cccnc2SC2CCCC2)c(F)c1]

Step A:

2-[4-(2-cyclopentylsulfanyl-pyridin-3-ylmethoxy)-3-fluoro-phenyl]-cyclopropane carboxylic acid methyl ester 2-(3-Fluoro-4-hydroxy-phenyl)-cyclopropane carboxylic acid methyl ester (more polar) (33 mg, 0.158 mmol) obtained in Step C of Preparation Example 63 and 3-chloromethyl-2-cyclopentylsulfanyl-pyridine (35.76 mg, 0.158 mmol) obtained in Step C of Preparation Example 8 were used to react in the same manner as in Step A of Example 1 to obtain the title compound (61 mg, 97%).

NMR (400 MHz, CDCl$_3$): 1.23-1.27 (m., 1H), 1.56-1.72 (m., 5H), 1.72-1.84 (m., 3H), 2.17-2.22 (m. 2H), 2.43-2.49 (m., 1H), 3.71 (s., 3H), 4.19-4.26 (m., 1H), 5.05 (s., 2H), 6.77-6.89 (m., 2H), 6.92 (t., 8.4 Hz, 1H), 7.02 (d.d., 7.6 and 4.8 Hz, 1H), 7.70 (d.d., 7.6 and 1.6 Hz, 1H), 8.39 (d.d., 4.8 and 1.6 Hz, 1H) ppm.

Step B:

2-[4-(2-cyclopentylsulfanyl-pyridin-3-ylmethoxy'-3-fluoro-phenyl]-cyclopropane carboxylic acid 2-[4-(2-Cyclopentylsulfanyl-pyridin-3-ylmethoxy)-3-fluoro-phenyl]-cyclopropane carboxylic acid methyl ester (61 mg, 0.153 mmol) obtained in Step A was reacted in the same manner as in Step B of Example 1 to obtain the title compound (58 mg, 97%).

NMR (400 MHz, CDCl$_3$): 1.32-1.36 (m., 1H), 1.58-1.72 (m., 5H), 1.72-1.84 (m., 3H), 2.17-2.25 (m., 2H), 2.51-2.56 (m., 1H), 4.19-4.26 (m., 1H), 5.06 (s., 2H), 6.80-6.87 (m., 2H), 6.91 (t., 8.4 Hz, 1H), 7.02 (d.d., 7.6 and 4.8 Hz, 1H), 7.70 (d.d., 7.6 and 1.6 Hz, 1H), 8.39 (d.d., 4.8 and 1.6 Hz, 1H) ppm.

EXAMPLE 165

2-[4-(2-cyclopropylmethylsulfanyl-pyridin-3-yl-methoxy)-3-fluoro-phenyl]-cyclopropane carboxylic acid (more polar)

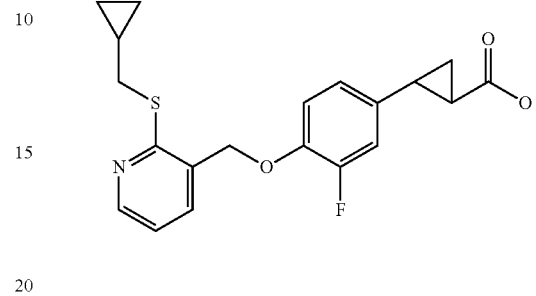

Step A:

2-[4-(2-cyclopropylmethylsulfanyl-pyridin-3-yl-methoxy)-3-fluoro-phenyl]-cyclopropane carboxylic acid methyl ester 2-(3-Fluoro-4-hydroxy-phenyl)-cyclopropane carboxylic acid methyl ester (more polar) (32 mg, 0.152 mmol) obtained in Step C of Preparation Example 63 and 3-chloromethyl-2-cyclopropylmethylsulfanyl-pyridine (32.54 mg, 0.152 mmol) obtained in Step C of Preparation Example 18 were used to react in the same manner as in Step A of Example 1 to obtain the title compound (56 mg, 95%).

NMR (400 MHz, CDCl$_3$): 0.31-0.35 (m., 2H), 0.57-0.62 (m., 2H), 1.13-1.20 (m., 1H), 1.22-1.27 (m., 1H), 1.55-1.60 (m., 1H), 1.81-1.86 (m., 1H), 2.43-2.49 (m., 1H), 3.23 (d., 7.2 Hz, 2H), 3.72 (s., 3H), 5.09 (s., 2H), 6.77-6.89 (m., 2H), 6.91 (t., 8.4 Hz, 1H), 7.03 (d.d., 7.6 and 4.8 Hz, 1H), 7.71 (d.d., 7.6 and 1.6 Hz, 1H), 8.38 (d.d., 4.8 and 1.6 Hz, 1H) ppm.

Step B:

2-[4-(2-cyclopropylmethylsulfanyl-pyridin-3-yl-methoxy)-3-fluoro-phenyl]-cyclopropane carboxylic acid 2-[4-(2-Cyclopropylmethylsulfanyl-pyridin-3-yl-methoxy)-3-fluoro-phenyl]-cyclopropane carboxylic acid methyl ester (56 mg, 0.144 mmol) obtained in Step A was reacted in the same manner as in Step B of Example 1 to obtain the title compound (47 mg, 87%).

NMR (400 MHz, CDCl$_3$): 0.31-0.35 (m., 2H), 0.57-0.62 (m., 2H), 1.12-1.21 (m., 1H), 1.31-1.36 (m., 1H), 1.61-1.66 (m., 1H), 1.81-1.86 (m., 1H), 2.51-2.56 (m., 1H), 3.23 (d., 7.2 Hz, 2H), 5.09 (s., 2H), 6.80-6.87 (m., 2H), 6.92 (t., 8.4 Hz, 1H), 7.03 (d.d., 7.6 and 4.8 Hz, 1H), 7.71 (d.d., 7.6 and 1.6 Hz, 1H), 8.38 (d.d., 4.8 and 1.6 Hz, 1H) ppm.

EXAMPLE 166

2-[3-fluoro-4-(6-isopropylsulfanyl-pyridin-2-yl-methoxy)-phenyl]-cyclopropane carboxylic acid (more polar)

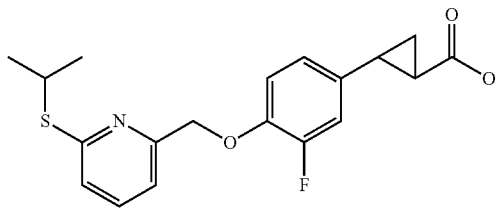 [SMILES: CC(C)Sc1cccc(COc2ccc(C3CC3C(=O)O)cc2F)n1]

Step A:

2-[3-fluoro-4-(6-isopropylsulfanyl-pyridin-2-yl-methoxy)-phenyl]-cyclopropane carboxylic acid methyl ester 2-(3-Fluoro-4-hydroxy-phenyl)-cyclopropane carboxylic acid methyl ester (more polar) (29 mg, 0.140 mmol) obtained in Step C of Preparation Example 63 was reacted in the same manner as in Step A of Example 1 to obtain the title compound (50 mg, 96%).

NMR (400 MHz, CDCl$_3$): 1.22-1.27 (m., 1H), 1.39 (d., 6.8 Hz, 6H), 1.54-1.59 (m., 1H), 1.80-1.84 (m., 1H), 2.43-2.48 (m., 1H), 3.71 (s., 3H), 3.96 (sep., 6.8 Hz, 1H), 5.18 (s., 2H), 6.77-6.85 (m., 2H), 6.90 (t., 8.4 Hz, 1H), 7.07 (d., 8 Hz, 1H), 7.19 (d., 8 Hz, 1H), 7.49 (t., 8 Hz, 1H) ppm.

Step B:

2-[3-fluoro-4-(6-isopropylsulfanyl-pyridin-2-yl-methoxy)-phenyl]-cyclopropanecarboxylic acid 2-[3-Fluoro-4-(6-isopropylsulfanyl-pyridin-2-yl-methoxy)-phenyl]-cyclopropane carboxylic acid methyl ester (50 mg, 0.134 mmol) obtained in Step A was reacted in the same manner as in Step B of Example 1 to obtain the title compound (39 mg, 81%).

NMR (400 MHz, CDCl$_3$): 1.30-1.35 (m., 1H), 1.39 (d., 6.8 Hz, 6H), 1.60-1.65 (m., 1H), 1.80-1.85 (m., 1H), 2.50-2.55 (m., 1H), 3.96 (sep., 6.8 Hz, 1H), 5.18 (s., 2H), 6.78-6.87 (m., 2H), 6.91 (t., 8.4 Hz, 1H), 7.07 (d., 8 Hz, 1H), 7.19 (d., 8 Hz, 1H), 7.49 (t., 8 Hz, 1H) ppm.

EXAMPLE 167

2-[4-(6-cyclobutylsulfanyl-pyridin-2-ylmethoxy)-3-fluoro-phenyl]-cyclopropane carboxylic acid (more polar)

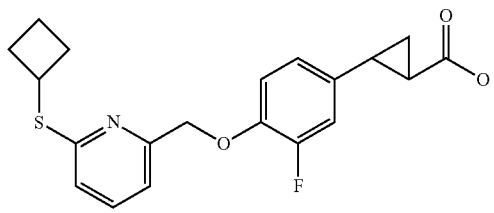 [SMILES: O=C(O)C1CC1c1ccc(OCc2cccc(SC3CCC3)n2)c(F)c1]

Step A:

2-[4-(6-cyclobutylsulfanyl-pyridin-2-ylmethoxy'-3-fluoro-phenyl]-cyclopropane carboxylic acid methyl ester 2-(3-Fluoro-4-hydroxy-phenyl)-cyclopropane carboxylic acid methyl ester (more polar) (30 mg, 0.143 mmol) obtained in Step C of Preparation Example 63 and 2-chloromethyl-6-cyclobutylsulfanyl-pyridine (30.5 mg, 0.143 mmol) obtained in Step C of Preparation Example 37 were used to react in the same manner as in Step A of Example 1 to obtain the title compound (52 mg, 95%).

NMR (400 MHz, CDCl$_3$): 1.23-1.27 (m., 1H), 1.54-1.59 (m., 1H), 1.80-1.84 (m., 1H), 2.02-2.20 (m., 4H), 2.42-2.47 (m., 1H), 2.47-2.55 (m., 2H), 3.71 (s., 3H), 4.28 (quin., 7.6 Hz, 1H), 5.16 (s., 2H), 6.77-6.86 (m., 2H), 6.90 (t., 8.4 Hz, 1H), 6.98 (d., 8 Hz, 1H), 7.18 (d., 8 Hz, 1H), 7.49 (t., 8 Hz, 1H) ppm.

Step B:

2-[4-(6-cyclobutylsulfanyl-pyridin-2-ylmethoxy'-3-fluoro-phenyl]-cyclopropane carboxylic acid 2-[4-(6-cyclobutylsulfanyl-pyridin-2-ylmethoxy)-3-fluoro-phenyl]-cyclopropane carboxylic acid methyl ester (52 mg, 0.135 mmol) obtained in Step A was reacted in the same manner as in Step B of Example 1 to obtain the title compound (44 mg, 87%).

NMR (400 MHz, CDCl$_3$): 1.30-1.35 (m., 1H), 1.60-1.65 (m., 1H), 1.80-1.85 (m., 1H), 2.02-2.20 (m., 4H), 2.50-2.58 (m., 3H), 4.28 (quin., 7.6 Hz, 1H), 5.17 (s., 2H), 6.78-6.87 (m., 2H), 6.91 (t., 8.4 Hz, 1H), 6.99 (d., 8 Hz, 1H), 7.18 (d., 8 Hz, 1H), 7.49 (t., 8 Hz, 1H) ppm.

EXAMPLE 168

2-[4-(6-cyclopentylsulfanyl-pyridin-2-ylmethoxy)-3-fluoro-phenyl]-cyclopropane carboxylic acid (more polar)

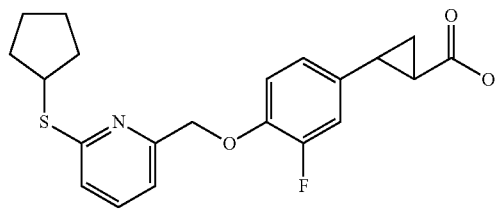 [SMILES: O=C(O)C1CC1c1ccc(OCc2cccc(SC3CCCC3)n2)c(F)c1]

Step A:

2-[4-(6-cyclopentylsulfanyl-pyridin-2-ylmethoxy'-3-fluoro-phenyl]-cyclopropane carboxylic acid methyl ester 2-(3-Fluoro-4-hydroxy-phenyl)-cyclopropane carboxylic acid methyl ester (more polar) (33 mg, 0.159 mmol) obtained in Step C of Preparation Example 63 and 2-chloromethyl-6-cyclopentylsulfanyl-pyridine (35.76 mg, 0.159 mmol) obtained in Step C of Preparation Example 27 were used to react in the same manner as in Step A of Example 1 to obtain the title compound (59 mg, 93%).

NMR (400 MHz, CDCl₃): 1.23-1.27 (m., 1H), 1.54-1.70 (m., 5H), 1.70-1.87 (m., 3H), 2.12-2.22 (m., 2H), 2.43-2.48 (m., 1H), 3.71 (s., 3H), 3.95-4.03 (m., 1H), 5.17 (s., 2H), 6.77-6.85 (m., 2H), 6.90 (t., 8.4 Hz, 1H), 7.08 (d., 8 Hz, 1H), 7.18 (d., 8 Hz, 1H), 7.49 (t., 8 Hz, 1H) ppm.

Step B:

2-[4-(6-cyclopentylsulfanyl-pyridin-2-ylmethoxy'-3-fluoro-phenyl]-cyclopropane carboxylic acid 2-[4-(6-Cyclopentylsulfanyl-pyridin-2-ylmethoxy)-3-fluoro-phenyl]-cyclopropane carboxylic acid methyl ester (59 mg, 0.148 mmol) obtained in Step A was reacted in the same manner as in Step B of Example 1 to obtain the title compound (52 mg, 91%).

NMR (400 MHz, CDCl₃): 1.30-1.35 (m., 1H), 1.58-1.70 (m., 5H), 1.70-1.85 (m., 3H), 2.13-2.22 (m., 2H), 2.50-2.55 (m., 1H), 3.95-4.03 (m., 1H), 5.18 (s., 2H), 6.77-6.86 (m., 2H), 6.91 (t., 8.4 Hz, 1H), 7.08 (d., 8 Hz, 1H), 7.18 (d., 8 Hz, 1H), 7.49 (t., 8 Hz, 1H) ppm.

EXAMPLE 169

2-[4-(2-cyclobutylsulfanyl-pyridin-3-ylmethoxy)-3-fluoro-phenyl]-cyclopropane carboxylic acid (more polar)

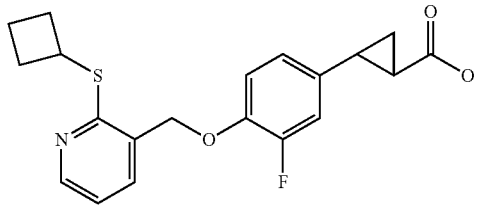 [SMILES: O=C(O)C1CC1c1ccc(OCc2cccnc2SC2CCC2)c(F)c1]

Step A:

2-[4-(2-cyclobutylsulfanyl-pyridin-3-ylmethoxy)-3-fluoro-phenyl]-cyclopropanecarboxylic acid methyl ester 2-(3-Fluoro-4-hydroxy-phenyl)-cyclopropane carboxylic acid methyl ester (more polar) (31 mg, 0.149 mmol) obtained in Step C of Preparation Example 63 and 3-chloromethyl-2-cyclobutylsulfanyl-pyridine (31.52 mg, 0.149 mmol) obtained in Step C of Preparation Example 23 were used to react in the same manner as in Step A of Example 1 to obtain the title compound (57 mg, 99%).

NMR (400 MHz, CDCl₃): 1.22-1.27 (m., 1H), 1.57-1.60 (m., 1H), 1.81-1.85 (m., 1H), 2.03-2.20 (m., 4H), 2.42-2.47 (m., 1H), 2.53-2.58 (m., 2H), 3.72 (s., 3H), 4.54 (quin., 7.6 Hz, 1H), 5.04 (s., 2H), 6.78-6.86 (m., 2H), 6.90 (t., 8.4 Hz, 1H), 7.01 (d.d., 7.6 and 4.8 Hz, 1H), 7.68 (d.d., 7.6 and 1.6 Hz, 1H), 8.37 (d.d., 4.8 and 1.6 Hz, 1H) ppm.

Step B:

2-[4-(2-cyclobutylsulfanyl-pyridin-3-ylmethoxy'-3-fluoro-phenyl]-cyclopropane carboxylic acid 2-[4-(2-cyclobutylsulfanyl-pyridin-3-ylmethoxy)-3-fluoro-phenyl]-cyclopropane carboxylic acid methyl ester (57 mg, 0.148 mmol) obtained in Step A was reacted in the same manner as in Step B of Example 1 to obtain the title compound (52 mg, 94%).

NMR (400 MHz, CDCl₃): 1.31-1.36 (m., 1H), 1.61-1.66 (m., 1H), 1.81-1.86 (m., 1H), 2.03-2.20 (m., 4H), 2.53-2.60 (m., 3H), 4.54 (quin., 7.6 Hz, 1H), 5.04 (s., 2H), 6.80-6.87 (m., 2H), 6.91 (t., 8.4 Hz, 1H), 7.01 (d.d., 7.6 and 4.8 Hz, 1H), 7.69 (d.d., 7.6 and 1.6 Hz, 1H), 8.37 (d.d., 4.8 and 1.6 Hz, 1H) ppm.

EXAMPLE 170

2-[4-(6-cyclopropylmethylsulfanyl-pyridin-2-ylmethoxy)-3-fluoro-phenyl]-cyclopropane carboxylic acid (more polar)

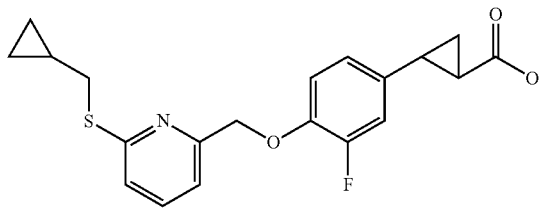 [SMILES: O=C(O)C1CC1c1ccc(OCc2cccc(SCC3CC3)n2)c(F)c1]

Step A:

2-[4-(6-cyclopropylmethylsulfanyl-pyridin-2-ylmethoxy)-3-fluoro-phenyl]-cyclopropane carboxylic acid methyl ester 2-(3-Fluoro-4-hydroxy-phenyl)-cyclopropanecarboxylic acid methyl ester (more polar) (31 mg, 0.146 mmol) obtained in Step C of Preparation Example 63 and 2-chloromethyl-6-cyclopropylmethylsulfanyl-pyridine (31.52 mg, 0.146 mmol) obtained in Step D of Preparation Example 20 were used to react in the same manner as in Step A of Example 1 to obtain the title compound (50 mg, 89%).

NMR (400 MHz, CDCl₃): 0.29-0.33 (m., 2H), 0.56-0.61 (m., 2H), 1.11-1.17 (m., 1H), 1.22-1.28 (m., 1H), 1.54-1.59 (m., 1H), 1.80-1.84 (m., 1H), 2.43-2.48 (m., 1H), 3.10 (d., 7.2 Hz, 2H), 3.71 (s., 3H), 5.18 (s., 2H), 6.77-6.85 (m., 2H), 6.90 (t., 8.4 Hz, 1H), 7.10 (d., 8 Hz, 1H), 7.18 (d., 8 Hz, 1H), 7.49 (t., 8 Hz, 1H) ppm.

Step B:

2-[4-(6-cyclopropylmethylsulfanyl-pyridin-2-ylmethoxy)-3-fluoro-phenyl]-cyclopropane carboxylic acid 2-[4-(6-cyclopropylmethylsulfanyl-pyridin-2-ylmethoxy)-3-fluoro-phenyl]-cyclopropane carboxylic acid methyl ester (50 mg, 0.130 mmol) obtained in Step A was reacted in the same manner as in Step B of Example 1 to obtain the title compound (38 mg, 79%).

NMR (400 MHz, CDCl₃): 0.29-0.33 (m., 2H), 0.56-0.61 (m., 2H), 1.11-1.17 (m., 1H), 1.30-1.35 (m., 1H), 1.60-1.65 (m., 1H), 1.80-1.85 (m., 1H), 2.50-2.55 (m., 1H), 3.11 (d., 7.2 Hz, 2H), 5.18 (s., 2H), 6.78-6.87 (m., 2H), 6.91 (t., 8.4 Hz, 1H), 7.10 (d., 8 Hz, 1H), 7.18 (d., 8 Hz, 1H), 7.49 (t., 8 Hz, 1H) ppm.

EXAMPLE 171

3-{4-[(2-cyclopentylsulfanyl-pyridin-3-ylmethyl)-amino]-phenyl}-propionic acid

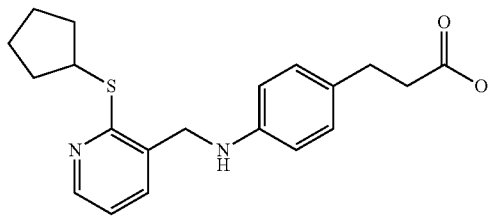 [SMILES: O=C(O)CCc1ccc(NCc2cccnc2SC2CCCC2)cc1]

Step A: 3-{4-[(2-cyclopentylsulfanyl-pyridin-3-ylmethyl)-aminol-phenyl]-propionic acid methyl ester 3-(4-Amino-phenyl)-propionic acid methyl ester (50 mg, 0.28 mmol) obtained in Preparation Example 67 was dissolved in $CH_3CN$ (5 mL), and $Cs_2CO_3$ (227 mg, 0.7 mmol) was added thereto. After 3-chloromethyl-2-cyclopentylsulfanyl-pyridine (64 mg, 0.28 mmol) obtained in Step C of Preparation Example 8 was added thereto, the mixture was stirred at 80~85° C. for 5 hours. After the termination of the reaction, the reactant was cooled and then filtered by using celite. The filtrate was concentrated under reduced pressure, and purified by column chromatography (eluent, EtOAc/Hex=1/7) to obtain the title compound (28 mg, 27%).

$^1$H NMR (400 MHz, $CDCl_3$) δ 8.37-8.31 (m, 1H), 7.54-7.48 (m, 1H), 6.99 (d, 2H), 6.97-6.90 (m, 1H), 6.52 (d, 2H), 4.25 (s, 2H), 4.25-4.18 (m, 1H), 4.12 (s, 1H), 3.66 (s, 3H), 2.83 (t, 2H), 2.56 (t, 2H), 2.30-2.18 (m, 2H), 1.85-1.72 (m, 2H), 1.72-1.59 (m, 4H)

Step B: 3-{4-[(2-cyclopentylsulfanyl-pyridin-3-ylmethyl)-aminol-phenyl]-propionic acid 3-{4-[(2-Cyclopentylsulfanyl-pyridin-3-ylmethyl)-amino]-phenyl}-propionic acid methyl ester (28 mg, 0.076 mmol) obtained in Step A was reacted in the same manner as in Step B of Example 1 to obtain the title compound (26 mg, 97%).

$^1$H NMR (400 MHz, $CDCl_3$) δ 8.49-8.43 (m, 1H), 7.79-7.71 (m, 1H), 7.10-7.02 (m, 1H), 7.06 (d, 2H), 6.65 (d, 2H), 4.40-4.33 (m, 1H), 4.33 (s, 2H), 2.85 (t, 2H), 2.62 (t, 2H), 2.32-2.21 (m, 2H), 1.83-1.57 (m, 6H)

EXAMPLE 172

3-{4-[(6-cyclopentylsulfanyl-pyridin-2-ylmethyl)-amino]-phenyl}-propionic acid

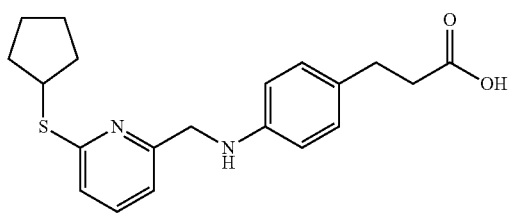 [SMILES: O=C(O)CCc1ccc(NCc2cccc(SC3CCCC3)n2)cc1]

3-(4-Amino-phenyl)-propionic acid methyl ester (50 mg, 0.28 mmol) obtained in Preparation Example 67 and 2-chloromethyl-6-cyclopentylsulfanyl-pyridine (64 mg, 0.28 mmol) obtained in Step C of Preparation Example 27 were used to react sequentially in the same manner as in Steps A and B of Example 171 to obtain the title compound (36 mg, 36%).

$^1$H NMR (500 MHz, $CDCl_3$) δ 7.42 (t, 1H), 7.07-7.00 (m, 3H), 6.98-6.94 (m, 1H), 6.63-6.58 (m, 2H), 4.36 (s, 2H), 4.05-3.97 (m, 1H), 2.84 (t, 2H), 2.61 (t, 2H), 2.26-2.14 (m, 2H), 1.84-1.74 (m, 2H), 1.72-1.60 (m, 4H)

EXAMPLE 173

3-[4-[(2-cyclopentylsulfanyl-pyridin-3-ylmethoxy)-2-fluoro-phenyl]-propionic acid

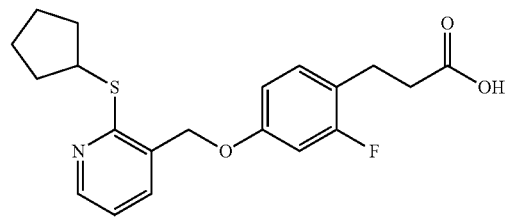 [SMILES: O=C(O)CCc1ccc(OCc2cccnc2SC2CCCC2)cc1F]

Step A:

3-[4-[(2-cyclopentylsulfanyl-pyridin-3-ylmethoxy)-2-fluoro-phenyl]-propionic acid ethyl ester 3-(2-Fluoro-4-hydroxy-phenyl)-propionic acid ethyl ester (28 mg, 0.13 mmol) obtained in Step C of Preparation Example 7 and 3-chloromethyl-2-cyclopentylsulfanyl-pyridine (30 mg, 0.13 mmol) obtained in Step C of Preparation Example 8 were used to react in the same manner as in Step A of Example 1 to obtain the title compound (45 mg, 85%).

$^1$H NMR (400 MHz, $CDCl_3$) δ 8.42-8.37 (m, 1H), 7.67-7.61 (m, 1H), 7.11 (t, 1H), 7.04-6.99 (m, 1H), 6.77-6.63 (m, 2H), 4.97 (s, 2H), 4.28-4.18 (m, 1H), 4.12 (q, 2H), 2.90 (t, 2H), 2.58 (t, 2H), 2.29-2.18 (m, 2H), 1.83-1.73 (m, 2H), 1.71-1.59 (m, 4H), 1.23 (t, 3H)

Step B:

3-[4-[(2-cyclopentylsulfanyl-pyridin-3-ylmethoxy)-2-fluoro-phenyl]-propionic acid 3-[4-[(2-cyclopentylsulfanyl-pyridin-3-ylmethoxy)-2-fluoro-phenyl]-propionic acid ethyl ester (45 mg, 0.11 mmol) obtained in Step A was reacted in the same manner as in Step B of Example 1 to obtain the title compound (41 mg, 98%).

$^1$H NMR (400 MHz, $CDCl_3$) δ 8.45-8.39 (m, 1H), 7.69-7.61 (m, 1H), 7.12 (t, 1H), 7.06-7.00 (m, 1H), 6.75-6.65 (m, 2H), 4.97 (s, 2H), 4.28-4.18 (m, 1H), 2.92 (t, 2H), 2.65 (t, 2H), 2.33-2.18 (m, 2H), 1.87-1.73 (m, 2H), 1.73-1.59 (m, 4H)

EXAMPLE 174

2-[4-[(2-cyclopentylsulfanyl-pyridin-3-ylmethoxy)-2-fluoro-phenyl]-cyclopropane carboxylic acid

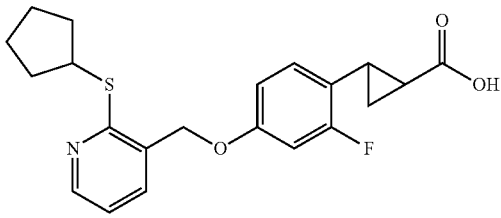 [SMILES: O=C(O)C1CC1c1ccc(OCc2cccnc2SC2CCCC2)cc1F]

Step A:

2-[4-[(2-cyclopentylsulfanyl-pyridin-3-ylmethoxy)-2-fluoro-phenyl]-cyclopropane carboxylic acid ethyl ester 2-(2-Fluoro-4-hydroxy-phenyl)-cyclopropane carboxylic acid ethyl ester (29.5 mg, 0.13 mmol) obtained in Step C of Preparation Example 68 and 3-chloromethyl-2-cyclopentyl-sulfanyl-pyridine (30 mg, 0.13 mmol) obtained in Step C of Preparation Example 8 were used to react in the same manner as in Step A of Example 1 to obtain the title compound (52 mg, 95%).

$^1$H NMR (400 MHz, CDCl$_3$) δ 8.42-8.37 (m, 1H), 7.65-7.60 (m, 1H), 7.04-6.98 (m, 1H), 6.88 (t, 1H), 6.70-6.63 (m, 2H), 4.99 (s, 2H), 4.28-4.18 (m, 1H), 4.17 (q, 2H), 2.60-2.52 (m, 1H), 2.28-2.17 (m, 2H), 1.89-1.81 (m, 1H), 1.81-1.71 (m, 2H), 1.71-1.59 (m, 4H), 1.59-1.51 (m, 1H), 1.31-1.22 (m, 1H), 1.28 (t, 3H)

Step B:

2-[4-[(2-cyclopentylsulfanyl-pyridin-3-ylmethoxy)-2-fluoro-phenyl]-cyclopropane carboxylic acid 2-[4-[(2-Cyclopentylsulfanyl-pyridin-3-ylmethoxy)-2-fluoro-phenyl]-cyclopropane carboxylic acid ethyl ester (52 mg, 0.125 mmol) obtained in Step A was reacted in the same manner as in Step B of Example 1 to obtain the title compound (48 mg, 99%).

$^1$H NMR (400 MHz, CDCl$_3$) δ 8.44-8.38 (m, 1H), 7.67-7.60 (m, 1H), 7.07-6.99 (m, 1H), 6.90 (t, 1H), 6.71-6.63 (m, 2H), 4.98 (s, 2H), 4.28-4.18 (m, 1H), 2.69-2.60 (m, 1H), 2.30-2.17 (m, 2H), 1.90-1.82 (m, 1H), 1.82-1.71 (m, 2H), 1.71-1.59 (m, 4H), 1.45-1.34 (m, 1H), 1.30-1.20 (m, 1H)

EXAMPLE 175

3-[4-[(2-cyclobutylsulfanyl-pyridin-3-ylmethoxy)-2-fluoro-phenyl]-propionic acid

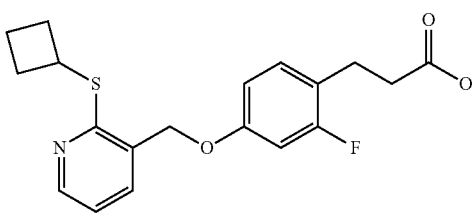 [SMILES: O=C(O)CCc1ccc(OCc2cccnc2SC2CCC2)cc1F]

Step A:

3-[4-[(2-cyclobutylsulfanyl-pyridin-3-ylmethoxy)-2-fluoro-phenyl]-propionic acid ethyl ester 3-(2-Fluoro-4-hydroxy-phenyl)-propionic acid ethyl ester (20 mg, 0.094 mmol) obtained in Step C of Preparation Example 7 and 3-chloromethyl-2-cyclobutylsulfanyl-pyridine (20.14 mg, 0.094 mmol) obtained in Step C of Preparation Example 23 were used to react in the same manner as in Step A of Example 1 to obtain the title compound (35 mg, 95%).

$^1$H NMR (400 MHz, CDCl$_3$) δ 8.40-8.34 (m, 1H), 7.67-7.60 (m, 1H), 7.11 (t, 1H), 7.03-6.98 (m, 1H), 6.71-6.65 (m, 2H), 4.96 (s, 2H), 4.59-4.49 (m, 1H), 4.12 (q, 2H), 2.91 (t, 2H), 2.59 (t, 2H), 2.59-2.50 (m, 2H), 2.20-2.09 (m, 2H), 2.09-2.00 (m, 2H), 1.23 (t, 3H)

Step B:

3-[4-[(2-cyclobutylsulfanyl-pyridin-3-ylmethoxy)-2-fluoro-phenyl]-propionic acid 3-[4-[(2-Cyclobutylsulfanyl-pyridin-3-ylmethoxy)-2-fluoro-phenyl]-propionic acid ethyl ester (35 mg, 0.09 mmol) obtained in Step A was reacted in the same manner as in Step B of Example 1 to obtain the title compound (31 mg, 95%).

$^1$H NMR (400 MHz, CDCl$_3$) δ 8.41-8.36 (m, 1H), 7.67-7.61 (m, 1H), 7.12 (t, 1H), 7.05-6.99 (m, 1H), 6.72-6.65 (m, 2H), 4.96 (s, 2H), 4.58-4.49 (m, 1H), 2.92 (t, 2H), 2.66 (t, 2H), 2.61-2.50 (m, 2H), 2.20-2.00 (m, 4H)

EXAMPLE 176

3-[4-[(6-cyclobutylsulfanyl-pyridin-2-ylmethoxy)-2-fluoro-phenyl]-propionic acid

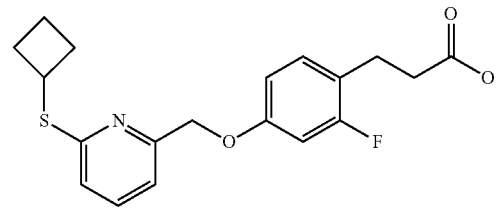 [SMILES: O=C(O)CCc1ccc(OCc2cccc(SC3CCC3)n2)cc1F]

Step A:

3-[4-[(6-cyclobutylsulfanyl-pyridin-2-ylmethoxy)-2-fluoro-phenyl]-propionic acid ethyl ester 3-(2-Fluoro-4-hydroxy-phenyl)-propionic acid ethyl ester (20 mg, 0.094 mmol) obtained in Step C of Preparation Example 7 and 2-chloromethyl-6-cyclobutylsulfanyl-pyridine (20.14 mg, 0.094 mmol) obtained in Step C of Preparation Example 37 were used to react in the same manner as in Step A of Example 1 to obtain the title compound (36 mg, 98%).

$^1$H NMR (400 MHz, CDCl$_3$) δ 7.49 (t, 1H), 7.16-7.05 (m, 2H), 6.99 (d, 1H), 6.72-6.65 (m, 2H), 5.09 (s, 2H), 4.35-4.25 (m, 1H), 4.12 (q, 2H), 2.90 (t, 2H), 2.58 (t, 2H), 2.58-2.49 (m, 2H), 2.20-2.00 (m, 4H), 1.23 (t, 3H)

153

Step B:

3-[4-[(6-cyclobutylsulfanyl-pyridin-2-ylmethoxy)-2-fluoro-phenyl]-propionic acid 3-[4-[(6-cyclobutylsulfanyl-pyridin-2-ylmethoxy)-2-fluoro-phenyl]-propionic acid ethyl ester (36 mg, 0.092 mmol) obtained in Step A was reacted in the same manner as in Step B of Example 1 to obtain the title compound (32 mg, 96%).

$^1$H NMR (400 MHz, CDCl$_3$) δ 7.49 (t, 1H), 7.17-7.08 (m, 2H), 6.99 (d, 1H), 6.72-6.66 (m, 2H), 5.09 (s, 2H), 4.33-4.23 (m, 1H), 2.91 (t, 2H), 2.64 (t, 2H), 2.60-2.49 (m, 2H), 2.20-1.99 (m, 4H)

EXAMPLE 177

3-[4-[(6-cyclopentylsulfanyl-pyridin-2-ylmethoxy)-2-fluoro-phenyl]-propionic acid

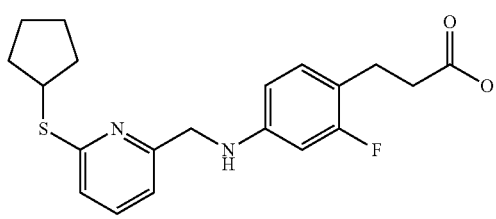 [SMILES: O=C(O)CCc1ccc(NCc2cccc(SC3CCCC3)n2)cc1F]

Step A:

3-[4-[(6-cyclopentylsulfanyl-pyridin-2-ylmethoxy)-2-fluoro-phenyl]-propionic acid ethyl ester 3-(2-Fluoro-4-hydroxy-phenyl)-propionic acid ethyl ester (20 mg, 0.094 mmol) obtained in Step C of Preparation Example 7 and 2-chloromethyl-6-cyclopentyl sulfanyl-pyridine (21.46 mg, 0.094 mmol) obtained in Step C of Preparation Example 27 were used to react in the same manner as in Step A of Example 1 to obtain the title compound (34 mg, 89%).

$^1$H NMR (400 MHz, CDCl$_3$) δ 7.48 (t, 1H), 7.16-7.05 (m, 3H), 6.71-6.65 (m, 2H), 5.10 (s, 2H), 4.12 (q, 2H), 4.06-3.97 (m, 1H), 2.90 (t, 2H), 2.58 (t, 2H), 2.24-2.13 (m, 2H), 1.83-1.71 (m, 2H), 1.70-1.58 (m, 4H), 1.23 (t, 3H)

Step B:

3-[4-[(6-cyclopentylsulfanyl-pyridin-2-ylmethoxy)-2-fluoro-phenyl]-propionic acid 3-[4-[(6-Cyclopentylsulfanyl-pyridin-2-ylmethoxy)-2-fluoro-phenyl]-propionic acid ethyl ester (34 mg, 0.082 mmol) obtained in Step A was reacted in the same manner as in Step B of Example 1 to obtain the title compound (30 mg, 95%).

$^1$H NMR (400 MHz, CDCl$_3$) δ 7.49 (t, 1H), 7.16-7.07 (m, 3H), 6.72-6.66 (m, 2H), 5.11 (s, 2H), 4.05-3.96 (m, 1H), 2.90 (t, 2H), 2.64 (t, 2H), 2.25-2.11 (m, 2H), 1.84-1.71 (m, 2H), 1.71-1.58 (m, 4H)

154

EXAMPLE 178

3-[4-[(2-cyclopropylmethylsulfanyl-pyridin-3-ylmethoxy)-2-fluoro-phenyl]-propionic acid

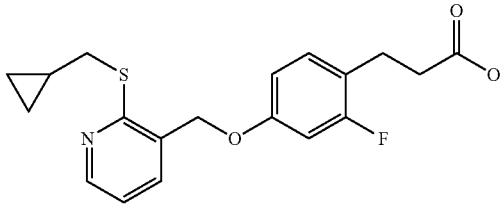 [SMILES: O=C(O)CCc1ccc(OCc2cccnc2SCC2CC2)cc1F]

Step A:

3-[4-[(2-cyclopropylmethylsulfanyl-pyridin-3-ylmethoxy)-2-fluoro-phenyl]-propionic acid ethyl ester 3-(2-Fluoro-4-hydroxy-phenyl)-propionic acid ethyl ester (20 mg, 0.094 mmol) obtained in Step C of Preparation Example 7 and 3-chloromethyl-2-cyclopropylmethyl sulfanyl-pyridine (20.14 mg, 0.094 mmol) obtained in Step C of Preparation Example 18 were used to react in the same manner as in Step A of Example 1 to obtain the title compound (36 mg, 98%).

$^1$H NMR (400 MHz, CDCl$_3$) δ 8.41-8.37 (m, 1H), 7.69-7.63 (m, 1H), 7.11 (t, 1H), 7.05-6.99 (m, 1H), 6.72-6.65 (m, 2H), 5.01 (s, 2H), 4.12 (q, 2H), 3.23 (d, 2H), 2.91 (t, 2H), 2.59 (t, 2H), 1.23 (t, 3H), 1.20-1.11 (m, 1H), 0.63-0.57 (m, 2H), 0.36-0.30 (m, 2H)

Step B:

3-[4-[(2-cyclopropylmethylsulfanyl-pyridin-3-ylmethoxy)-2-fluoro-phenyl]-propionic acid 3-[4-[(2-Cyclopropylmethylsulfanyl-pyridin-3-ylmethoxy)-2-fluoro-phenyl]-propionic acid ethyl ester (36 mg, 0.092 mmol) obtained in Step A was reacted in the same manner as in Step B of Example 1 to obtain the title compound (33 mg, 99%).

$^1$H NMR (400 MHz, CDCl$_3$) δ 8.42-8.37 (m, 1H), 7.70-7.62 (m, 1H), 7.12 (t, 1H), 7.08-7.00 (m, 1H), 6.74-6.65 (m, 2H), 5.01 (s, 2H), 3.23 (d, 2H), 2.92 (t, 2H), 2.66 (t, 2H), 1.22-1.10 (m, 1H), 0.64-0.56 (m, 2H), 0.37-0.30 (m, 2H)

EXAMPLE 179

3-[4-[(6-cyclopropylmethylsulfanyl-pyridin-2-ylmethoxy)-2-fluoro-phenyl]-propionic acid

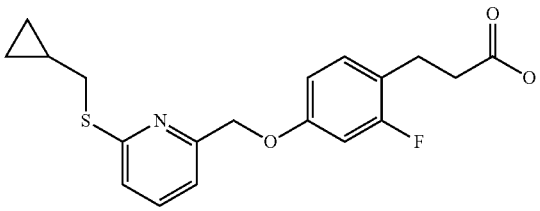 [SMILES: O=C(O)CCc1ccc(OCc2cccc(SCC3CC3)n2)cc1F]

Step A:

3-[4-[(6-cyclopropylmethylsulfanyl-pyridin-2-yl-methoxy)-2-fluoro-phenyl]-propionic acid ethyl ester 3-(2-Fluoro-4-hydroxy-phenyl)-propionic acid ethyl ester (20 mg, 0.094 mmol) obtained in Step C of Preparation Example 7 and 2-chloromethyl-6-cyclopropylmethyl sulfanyl-pyridine (20.14 mg, 0.094 mmol) obtained in Step D of Preparation Example 20 were used to react in the same manner as in Step A of Example 1 to obtain the title compound (36 mg, 98%).

$^1$H NMR (400 MHz, CDCl$_3$) δ 7.48 (t, 1H), 7.15-7.06 (m, 3H), 6.71-6.66 (m, 2H), 5.10 (s, 2H), 4.12 (q, 2H), 3.12 (d, 2H), 2.90 (t, 2H), 2.58 (t, 2H), 1.23 (t, 3H), 1.20-1.10 (m, 1H), 0.62-0.55 (m, 2H), 0.35-0.29 (m, 2H)

Step B:

3-[4-[(6-cyclopropylmethylsulfanyl-pyridin-2-yl-methoxy)-2-fluoro-phenyl]-propionic acid 3-[4-[(6-Cyclopropylmethylsulfanyl-pyridin-2-yl-methoxy)-2-fluoro-phenyl]-propionic acid ethyl ester (36 mg, 0.092 mmol) obtained in Step A was reacted in the same manner as in Step B of Example 1 to obtain the title compound (33 mg, 99%).

$^1$H NMR (400 MHz, CDCl$_3$) δ 7.48 (t, 1H), 7.16-7.07 (m, 3H), 6.72-6.66 (m, 2H), 5.10 (s, 2H), 3.12 (d, 2H), 2.91 (t, 2H), 2.64 (t, 2H), 1.20-1.10 (m, 1H), 0.63-0.55 (m, 2H), 0.35-0.28 (m, 2H)

EXAMPLE 180

3-[4-[(2-cyclobutylsulfanyl-pyridin-3-ylmethoxy)-phenyl]-propionic acid

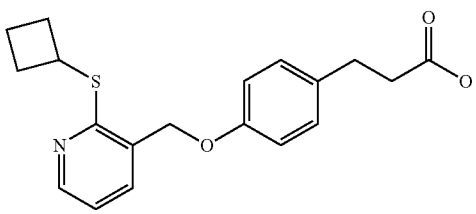 [SMILES: O=C(O)CCc1ccc(OCc2cccnc2SC2CCC2)cc1]

Step A:

3-[4-[(2-cyclobutylsulfanyl-pyridin-3-ylmethoxy)-phenyl]-propionic acid methyl ester 3-(4-Hydroxy-phenyl)-propionic acid methyl ester (20 mg, 0.11 mmol) obtained in Preparation Example 4 and 3-chloromethyl-2-cyclobutylsulfanyl-pyridine (23.72 mg, 0.11 mmol) obtained in Step C of Preparation Example 23 were used to react in the same manner as in Step A of Example 1 to obtain the title compound (35 mg, 88%).

$^1$H NMR (400 MHz, CDCl$_3$) δ 8.39-8.33 (m, 1H), 7.68-7.62 (m, 1H), 7.15-7.09 (m, 2H), 7.01-6.97 (m, 1H), 6.92-6.87 (m, 2H), 4.97 (s, 2H), 4.59-4.49 (m, 1H), 3.66 (s, 3H), 2.90 (t, 2H), 2.60 (t, 2H), 2.59-2.51 (m, 2H), 2.20-2.09 (m, 2H), 2.09-2.00 (m, 2H)

Step B: 3-[4-[(2-cyclobutylsulfanyl-pyridin-3-yl-methoxy)-phenyl]-propionic acid 3-[4-[(2-Cyclobutylsulfanyl-pyridin-3-ylmethoxy)-phenyl]-propionic acid methyl ester (35 mg, 0.098 mmol) obtained in Step A was reacted in the same manner as in Step B of Example 1 to obtain the title compound (31 mg, 95%).

$^1$H NMR (500 MHz, CDCl$_3$) δ 8.40-8.34 (m, 1H), 7.69-7.63 (m, 1H), 7.18-7.09 (m, 2H), 7.04-6.97 (m, 1H), 6.94-6.86 (m, 2H), 4.97 (s, 2H), 4.57-4.48 (m, 1H), 2.90 (t, 2H), 2.65 (t, 2H), 2.60-2.49 (m, 2H), 2.20-2.08 (m, 2H), 2.08-1.97 (m, 2H)

EXAMPLE 181

3-[4-[(6-cyclobutylsulfanyl-pyridin-2-ylmethoxy)-phenyl]-propionic acid

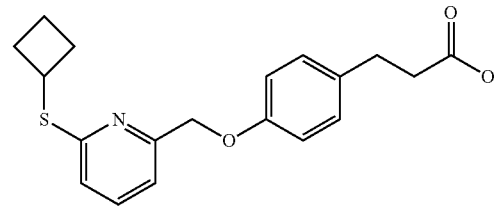 [SMILES: O=C(O)CCc1ccc(OCc2cccc(SC3CCC3)n2)cc1]

Step A: 3-[4-[(6-cyclobutylsulfanyl-pyridin-2-yl-methoxy)-phenyl]-propionic acid methyl ester 3-(4-Hydroxy-phenyl)-propionic acid methyl ester (20 mg, 0.11 mmol) obtained in Preparation Example 4 and 2-chloromethyl-6-cyclobutylsulfanyl-pyridine (23.72 mg, 0.11 mmol) obtained in Step C of Preparation Example 37 were used to react in the same manner as in Step A of Example 1 to obtain the title compound (37 mg, 93%).

$^1$H NMR (400 MHz, CDCl$_3$) δ 7.47 (t, 1H), 7.18-7.13 (m, 1H), 7.13-7.08 (m, 2H), 6.99-6.95 (m, 1H), 6.92-6.87 (m, 2H), 5.11 (s, 2H), 4.33-4.24 (m, 1H), 3.66 (s, 3H), 2.89 (t, 2H), 2.59 (t, 2H), 2.58-2.49 (m, 2H), 2.20-2.00 (m, 4H)

Step B: 3-[4-[(6-cyclobutylsulfanyl-pyridin-2-yl-methoxy)-phenyl]-propionic acid 3-[4-[(6-Cyclobutylsulfanyl-pyridin-2-ylmethoxy)-phenyl]-propionic acid methyl ester (37 mg, 0.092 mmol) obtained in Step A was reacted in the same manner as in Step B of Example 1 to obtain the title compound (33 mg, 93%).

$^1$H NMR (500 MHz, CDCl$_3$) δ 7.48 (t, 1H), 7.18-7.13 (m, 1H), 7.13-7.08 (m, 2H), 7.00-6.95 (m, 1H), 6.93-6.86 (m, 2H), 5.11 (s, 2H), 4.32-4.23 (m, 1H), 2.89 (t, 2H), 2.64 (t, 2H), 2.60-2.47 (m, 2H), 2.20-1.98 (m, 4H)

EXAMPLE 182

3-[4-[(2-cyclopropylmethylsulfanyl-pyridin-3-yl-methoxy)-phenyl]-propionic acid

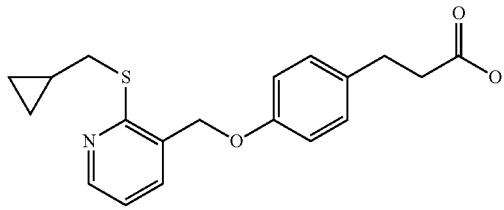 [SMILES: O=C(O)CCc1ccc(OCc2cccnc2SCC2CC2)cc1]

Step A: 3-[4-[(2-cyclopropylmethylsulfanyl-pyridin-3-ylmethoxy)-phenyl]-propionic acid methyl ester 3-(4-Hydroxy-phenyl)-propionic acid methyl ester (20 mg, 0.11 mmol) obtained in Preparation Example 4 and 3-chloromethyl-2-cyclopropylmethyl sulfanyl-pyridine (23.72 mg, 0.11 mmol) obtained in Step C of Preparation Example 18 were used to react in the same manner as in Step A of Example 1 to obtain the title compound (37 mg, 93%).
$^1$H NMR (400 MHz, CDCl$_3$) δ 8.40-8.34 (m, 1H), 7.70-7.65 (m, 1H), 7.15-7.10 (m, 2H), 7.05-6.99 (m, 1H), 6.93-6.88 (m, 2H), 5.02 (s, 2H), 3.66 (s, 3H), 3.23 (d, 2H), 2.90 (t, 2H), 2.60 (t, 2H), 1.22-1.10 (m, 1H), 0.63-0.56 (m, 2H), 0.38-0.30 (m, 2H)

Step B: 3-[4-[(2-cyclopropylmethylsulfanyl-pyridin-3-ylmethoxy)-phenyl]-propionic acid 3-[4-[(2-Cyclopropylmethylsulfanyl-pyridin-3-yl-methoxy)-phenyl]-propionic acid methyl ester (37 mg, 0.104 mmol) obtained in Step A was reacted in the same manner as in Step B of Example 1 to obtain the title compound (34 mg, 96%).
$^1$H NMR (500 MHz, CDCl$_3$) δ 8.41-8.35 (m, 1H), 7.71-7.66 (m, 1H), 7.18-7.10 (m, 2H), 7.05-6.99 (m, 1H), 6.95-6.86 (m, 2H), 5.02 (s, 2H), 3.22 (d, 2H), 2.90 (t, 2H), 2.64 (t, 2H), 1.21-1.10 (m, 1H), 0.64-0.54 (m, 2H), 0.37-0.27 (m, 2H)

EXAMPLE 183

3-[4-[(6-cyclopropylmethylsulfanyl-pyridin-2-yl-methoxy)-phenyl]-propionic acid

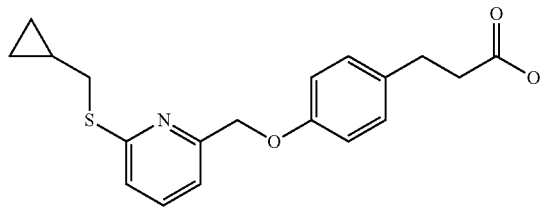 [SMILES: O=C(O)CCc1ccc(OCc2cccc(SCC3CC3)n2)cc1]

Step A: 3-[4-[(6-cyclopropylmethylsulfanyl-pyridin-2-ylmethoxy)-phenyl]-propionic acid methyl ester 3-(4-Hydroxy-phenyl)-propionic acid methyl ester (20 mg, 0.11 mmol) obtained in Preparation Example 4 and 2-chloromethyl-6-cyclopropylmethyl sulfanyl-pyridine (23.72 mg, 0.11 mmol) obtained in Step D of Preparation Example 20 were used to react in the same manner as in Step A of Example 1 to obtain the title compound (36 mg, 91%).
$^1$H NMR (400 MHz, CDCl$_3$) δ 7.47 (t, 1H), 7.17-7.14 (m, 1H), 7.13-7.07 (m, 3H), 6.93-6.88 (m, 2H), 5.12 (s, 2H), 3.66 (s, 3H), 3.12 (d, 2H), 2.89 (t, 2H), 2.59 (t, 2H), 1.20-1.10 (m, 1H), 0.62-0.56 (m, 2H), 0.35-0.29 (m, 2H)

Step B: 3-[4-[(6-cyclopropylmethylsulfanyl-pyridin-2-ylmethoxy)-phenyl]-propionic acid 3-[4-[(6-Cyclopropylmethylsulfanyl-pyridin-2-yl-methoxy)-phenyl]-propionic acid methyl ester (36 mg, 0.10 mmol) obtained in Step A was reacted in the same manner as in Step B of Example 1 to obtain the title compound (34 mg, 98%).
$^1$H NMR (500 MHz, CDCl$_3$) δ 7.47 (t, 1H), 7.19-7.14 (m, 1H), 7.14-7.06 (m, 3H), 6.93-6.87 (m, 2H), 5.11 (s, 2H), 3.12 (d, 2H), 2.89 (t, 2H), 2.64 (t, 2H), 1.20-1.10 (m, 1H), 0.62-0.54 (m, 2H), 0.35-0.28 (m, 2H)

EXAMPLE 184

3-[4-[(2-cyclopentylsulfanyl-6-methyl-pyridin-3-ylmethoxy)-phenyl]-propionic acid

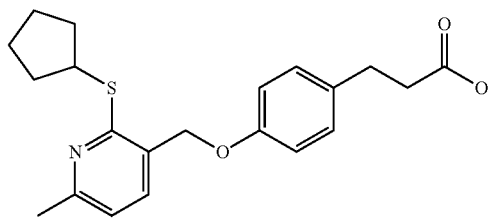 [SMILES: Cc1ccc(COc2ccc(CCC(=O)O)cc2)c(SC2CCCC2)n1]

3-Chloromethyl-2-cyclopentylsulfanyl-6-methyl-pyridine (31 mg, 0.13 mmol) obtained in Step C of Preparation Example 36 and 3-(4-hydroxy-phenyl)-propionic acid methyl ester (27 mg, 0.15 mmol) obtained in Preparation Example 4 were used to react sequentially in the same manner as in Steps A and B of Example 1 to obtain the title compound (32 mg, 63%).
$^1$H NMR (CDCl$_3$) 7.53 (1H, m), 7.13 (2H, m), 6.87 (3H, m), 4.97 (2H, s), 4.22 (1H, m), 2.91 (2H, t), 2.65 (2H, t), 2.49 (3H, s), 2.22 (2H, m), 1.78 (2H, m), 1.55 (4H, m)

EXAMPLE 185

3-[4-[(2-isopropylsulfanyl-6-methyl-pyridin-3-yl-methoxy)-phenyl]-propionic acid

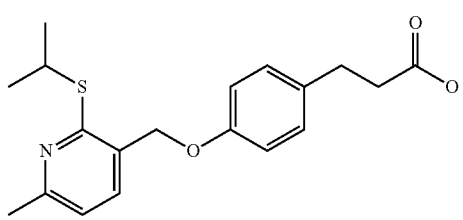 [SMILES: Cc1ccc(COc2ccc(CCC(=O)O)cc2)c(SC(C)C)n1]

3-Chloromethyl-2-isopropylsulfanyl-6-methyl-pyridine (30 mg, 0.15 mmol) obtained in Step D of Preparation Example 9 and 3-(4-hydroxy-phenyl)-propionic acid methyl ester (30 mg, 0.16 mmol) obtained in Preparation Example 4 were used to react sequentially in the same manner as in Steps A and B of Example 1 to obtain the title compound (29 mg, 56%).

$^1$H NMR (CDCl$_3$) 7.54 (1H, m), 7.13 (1H, m), 6.87 (3H, m), 4.97 (2H, s), 4.19 (1H, m), 2.91 (2H, t), 2.66 (2H, t), 2.50 (3H, s), 1.41 (6H, d)

Experimental Example 1

Measurement of activity of GPR120 agonist (cell-based assay)

CHO-K1 cells expressing Ga16 and hGPR120 were dispensed into each well of a 96-well plate (3×10$^4$ cells/100 μl/well) and then incubated in 5% CO$_2$, 37° C. incubator for 18 hours. Each well was treated with 100 μl of Calcium 5 dye (Molecular Devices) solution including 2% DMSO and then incubated in 5% CO$_2$, 37° C. incubator for 1 hour. Serially diluted GPR120 agonists were prepared to a final concentration of 0.5% DMSO in a 96-well plate. Each well was treated with 50 μl of the agonist compounds using Plexstation II, and then fluorescence was measured at Ex 485 nm, Em 525 nm.

Fluorescence increased by the serially diluted GPR120 agonists is calculated as a relative percent (%) value based on the fluorescence represented by the treatment of 0.1% DMSO only. EC$_{50}$ refers to the concentration of agonist which shows 50% of maximum fluorescence increased by the treatment of agonist. The calculation of measurement was carried out by using statistical software (Prizm).

The agonistic effects of the Example compounds obtained by the above experiment are shown in the following Table 1 with EC$_{50}$ unit (μM). Activity is denoted based on the following criteria:

A=>20 μM, B=20μ2 μM, C=2~0.2 μM, D=<0.2 μM

As shown in the table, most of the novel compounds according to the present invention have superior GPR120 agonistic effects (EC$_{50}$), lower than 0.2 μM.

Table 1

TABLE 1

| Example | EC$_{50}$ | Example | EC$_{50}$ | Example | EC$_{50}$ | Example | EC$_{50}$ |
|---|---|---|---|---|---|---|---|
| 1 | D | 2 | D | 3 | C | 4 | C |
| 5 | D | 6 | D | 7 | D | 8 | D |
| 9 | D | 10 | D | 11 | D | 12 | 0.058 |
| 13 | D | 14 | D | 15 | C | 16 | D |
| 17 | D | 18 | C | 19 | D | 20 | C |
| 21 | 0.068 | 22 | C | 23 | D | 24 | C |
| 25 | D | 26 | D | 27 | C | 28 | C |
| 29 | D | 30 | D | 31 | D | 32 | C |
| 33 | D | 34 | D | 35 | D | 36 | D |
| 37 | D | 38 | D | 39 | D | 40 | D |
| 41 | D | 42 | C | 43 | D | 44 | D |
| 45 | D | 46 | D | 47 | D | 48 | C |
| 49 | D | 50 | D | 51 | D | 52 | D |
| 53 | C | 54 | D | 55 | D | 56 | D |
| 57 | 0.454 | 58 | D | 59 | C | 60 | D |
| 61 | D | 62 | D | 63 | D | 64 | 0.108 |
| 65 | D | 66 | D | 67 | C | 68 | C |
| 69 | C | 70 | 1.884 | 71 | C | 72 | D |
| 73 | C | 74 | D | 75 | D | 76 | C |
| 77 | D | 78 | D | 79 | 0.033 | 80 | D |
| 81 | D | 82 | D | 83 | 0.110 | 84 | D |

TABLE 1-continued

| Example | EC$_{50}$ | Example | EC$_{50}$ | Example | EC$_{50}$ | Example | EC$_{50}$ |
|---|---|---|---|---|---|---|---|
| 85 | D | 86 | D | 87 | 64 | 88 | 57 |
| 89 | C | 90 | D | 91 | D | 92 | D |
| 93 | D | 94 | D | 95 | 0.088 | 96 | D |
| 97 | D | 98 | D | 99 | D | 100 | D |
| 101 | D | 102 | D | 103 | D | 104 | C |
| 105 | B | 106 | A | 107 | D | 108 | D |
| 109 | C | 110 | C | 111 | D | 112 | A |
| 113 | A | 114 | B | 115 | D | 116 | C |
| 117 | 0.108 | 118 | 0.135 | 119 | D | 120 | C |
| 121 | D | 122 | D | 123 | D | 124 | C |
| 125 | D | 126 | 0.091 | 127 | D | 128 | 0.042 |
| 129 | C | 130 | C | 131 | C | 132 | D |
| 133 | C | 134 | D | 135 | 0.027 | 136 | C |
| 137 | D | 138 | 0.056 | 139 | D | 140 | D |
| 141 | D | 142 | 0.011 | 143 | D | 144 | D |
| 145 | D | 146 | D | 147 | 0.054 | 148 | D |
| 149 | D | 150 | D | 151 | D | 152 | D |
| 153 | D | 154 | D | 155 | D | 156 | D |
| 157 | D | 158 | D | 159 | D | 160 | 0.202 |
| 161 | C | 162 | D | 163 | D | 164 | D |
| 165 | D | 166 | D | 167 | 0.006 | 168 | D |
| 169 | D | 170 | D | 171 | C | 172 | B |
| 173 | D | 174 | C | 175 | C | 176 | 0.176 |
| 177 | C | 178 | C | 179 | C | 180 | C |
| 181 | D | 182 | D | 183 | C | 184 | C |
| 185 | 0.441 | | | | | | |

The invention claimed is:

1. A compound of the following Formula 1, or a pharmaceutically acceptable salt or R or S isomer thereof:

[Formula 1]

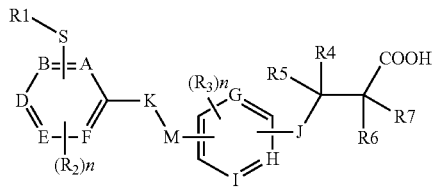

wherein,

A, B, D, E, F, G, H and I represent independently carbon or nitrogen,

R1 represents optionally substituted alkyl, cycloalkyl, heterocycloalkyl, alkylcycloalkyl, alkylaryl, heteroaryl or alkylheteroaryl, R2 and R3 represent independently hydrogen, halogen, or optionally substituted alkyl, cycloalkyl, heterocycloalkyl, alkoxy, cycloalkoxy, aryloxy, heteroaryloxy, aminoalkyl, aminocycloalkyl, aminoaryl, alkylamine, cycloalkylamine, aminoheteroaryl, thioalkyl, thioaryl or thioheteroaryl, R4, R5, R6 and R7 represent independently hydrogen, fluoro, alkyl or cycloalkyl;

alternatively, R4 and R6 are connected together to form cycloalkyl, R5 and R7 are connected together to form cycloalkyl, or one of R4 and R5 is connected with J to form cycloalkyl, heteroaryl or heterocycloalkyl, J does not exist, or represents CH$_2$, CH, NH or O, K represents CH$_2$, M represents CH$_2$, NH, N-alkyl, O or S, and n represents an integer of 0 to 4.

2. The compound, or a pharmaceutically acceptable salt or R or S isomer thereof according to claim 1, selected from the following compounds of Formulas 1-1 and 1-2:

[Formula 1-1]

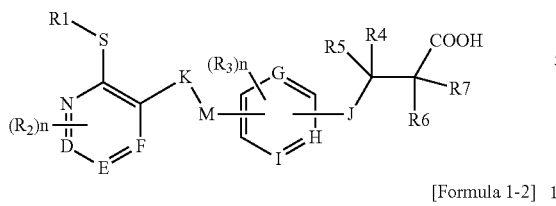

[Formula 1-2]

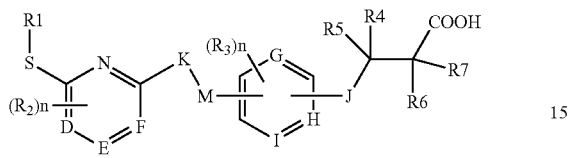

wherein,

R1 represents $C_1$-$C_6$-alkyl, $C_3$-$C_{10}$-cycloalkyl, $C_1$-$C_6$-alkyl-$C_3$-$C_{10}$-cycloalkyl, $C_1$-$C_6$-alkyl-$C_3$-$C_{10}$-heterocycloalkyl, $C_1$-$C_6$-alkylaryl or $C_1$-$C_6$-alkyl-$C_5$-$C_6$-heteroaryl, each of R2 represents independently hydrogen, halogen or optionally substituted $C_1$-$C_6$-alkyl, $C_3$-$C_{10}$-cyclo-$C_1$-$C_6$-alkyl, heterocycloalkyl, $C_1$-$C_6$-alkoxy, $C_3$-$C_{10}$-cycloalkoxy, aryloxy, heteroaryloxy, amino-$C_1$-$C_6$-alkyl, amino-$C_3$-$C_{10}$-cycloalkyl, aminoaryl, di($C_1$-$C_6$-alkyl)amine, $C_3$-$C_{10}$-cycloalkylamine, aminoheteroaryl, thio-$C_1$-$C_6$-alkyl, thioaryl or thioheteroaryl, n represents an integer of 0 to 3, and D, E, F, G, H, I, J, K, M, R3, R4, R5, R6 and R7 are as defined in claim 1.

3. The compound, or a pharmaceutically acceptable salt or R or S isomer thereof according to claim 1, selected from the following compounds of Formulas 1-3 to 1-7:

[Formula 1-3]

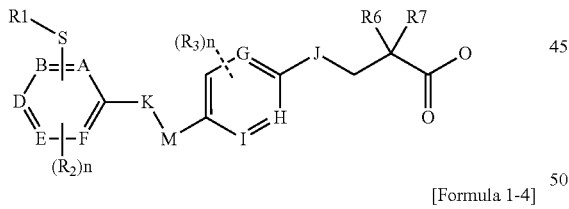

[Formula 1-4]

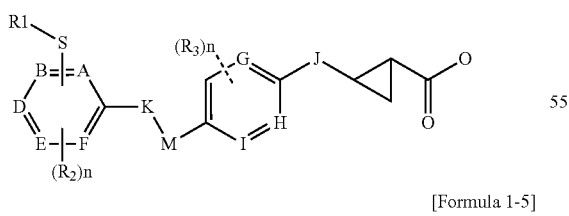

[Formula 1-5]

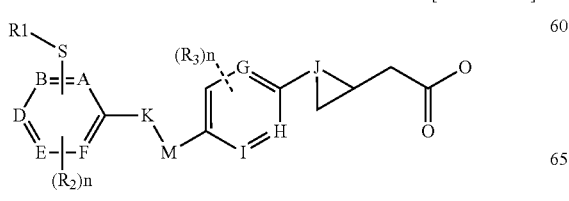

[Formula 1-6]

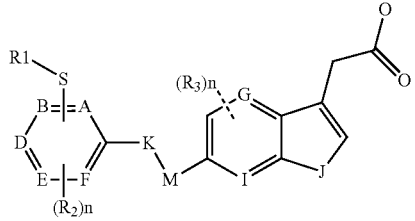

[Formula 1-7]

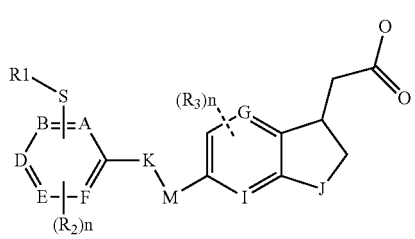

wherein, each of R3 represents independently hydrogen, halogen or optionally substituted $C_1$-$C_6$-alkyl, $C_3$-$C_{10}$-cyclo-$C_1$-$C_6$-alkyl, heterocycloalkyl, $C_1$-$C_6$-alkoxy, $C_3$-$C_{10}$1-cycloalkoxy, aryloxy, heteroaryloxy, amino-$C_1$-$C_6$-alkyl, amino-$C_3$-$C_{10}$-cycloalkyl, aminoaryl, di($C_1$-$C_6$-alkyl)amine, $C_3$-$C_{10}$-cycloalkylamine, aminoheteroaryl, thio-$C_1$-$C_6$-alkyl, thioaryl or thioheteroaryl, R6 and R7 represent independently hydrogen, fluoro or $C_1$-$C_6$alkyl, and n, A, B, D, E, F, G, H, I, J, K, M, R1 and R2 are as defined in claim 1.

4. The compound, or a pharmaceutically acceptable salt or R or S isomer thereof according to claim 1, selected from the following compounds:

3-[3,5-difluoro-4-(2-isopropylsulfanyl-pyridin-3-ylmethoxy)-phenyl]-propionic acid;

3-[4-(2-isopropylsulfanyl-pyridin-3-ylmethoxy)-phenyl]-propionic acid;

3-[4-(2-isopropylsulfanyl-5-methyl-pyridin-3-ylmethoxy)-phenyl]-2-methyl-propionic acid;

3-[4-(2-isopropylsulfanyl-pyridin-3-ylmethoxy)-phenyl]-2-methyl-propionic acid;

3-[4-(2-isopropylsulfanyl-5-methyl-pyridin-3-ylmethoxy)-phenyl]-propionic acid;

3-[3-fluoro-4-(2-isopropylsulfanyl-pyridin-3-ylmethoxy)-phenyl]-propionic acid;

3-[2-fluoro-4-(2-isopropylsulfanyl-pyridin-3-ylmethoxy)-phenyl]-propionic acid;

3-[4-(2-cyclopentylsulfanyl-pyridin-3-ylmethoxy)-phenyl]-2-methyl-propionic acid;

3-[3,5-difluoro-4-(2-isopropylsulfanyl-6-methyl-pyridin-3-ylmethoxy)-phenyl]-propionic acid;

3-[4-(2-ethylsulfanyl-pyridin-3-ylmethoxy)-3,5-difluorophenyl]-propionic acid;

3-[3,5-difluoro-4-(2-isobutylsulfanyl-pyridin-3-ylmethoxy)-phenyl]-propionic acid;

3-[4-(2-cyclopentylsulfanyl-pyridin-3-ylmethoxy)-3,5-difluoro-phenyl]-propionic acid;

4-[4-(2-isopropylsulfanyl-pyridin-3-ylmethoxy)-phenyl]-butyric acid;

3-[3,5-difluoro-4-(2-propylsulfanyl-pyridin-3-ylmethoxy)-phenyl]-propionic acid;

3-[4-(2-t-butylsulfanyl-pyridin-3-ylmethoxy)-3,5-difluoro-phenyl]-propionic acid;

3-[4-(2-cyclopropylmethylsulfanyl-pyridin-3-yl-methoxy)-3,5-difluoro-phenyl]-propionic acid;
3-{3,5-difluoro-4-[2-(2,2,2-trifluoro-ethylsulfanyl)-pyridin-3-ylmethoxy]-phenyl}-propionic acid;
3-[4-(2-sec-butylsulfanyl-pyridin-3-ylmethoxy)-3,5-difluoro-phenyl]-propionic acid;
3-[3,5-difluoro-4-(3-isopropylsulfanyl-pyrazin-2-yl-methoxy)-phenyl]-propionic acid;
4-[4-(2-cyclopentylsulfanyl-pyridin-3-ylmethoxy)-phenyl]-butyric acid;
3-[4-(2-cyclohexylsulfanyl-pyridin-3-ylmethoxy)-3,5-difluoro-phenyl]-propionic acid;
3-[4-(2-cyclobutylsulfanyl-pyridin-3-ylmethoxy)-3,5-difluoro-phenyl]-propionic acid;
3-[3,5-difluoro-4-(2-isopropylsulfanyl-pyrimidin-4-yl-methoxy)-phenyl]-propionic acid;
3-[4-(2-cyclopentylsulfanyl-pyridin-3-ylmethoxy)-phenyl]-2-methyl-propionic acid;
3-[4-(2-butylsulfanyl-pyridin-3-ylmethoxy)-3,5-difluoro-phenyl]-propionic acid;
3-{3,5-difluoro-4-[243,3,3-trifluoro-propylsulfanyl)-pyridin-3-ylmethoxy]-phenyl}-propionic acid;
3-14-[2-(2,2-dimethyl-propylsulfanyl)-pyridin-3-yl-methoxy]-3,5-difluoro-phenyll-propionic acid;
3-[4-(6-cyclopentylsulfanyl)-pyridin-2-ylmethoxy]-phenyl]-propionic acid;
3-[4-(6-cyclopentylsulfanyl)-pyridin-2-ylmethoxy]-3,5-difluoro-phenyll-propionic acid;
3-[4-(6-cyclohexylsulfanyl)-pyridin-2-ylmethoxy]-3,5-difluoro-phenyll-propionic acid;
3-[4-(6-ethyl-2-isopropylsulfanyl)-pyridin-3-ylmethoxy]-3,5-difluoro-phenyl]-propionic acid;
3-[3,5-difluoro-4-(6-isopropylsulfanyl-pyridin-2-yl-methoxy)-phenyl]-propionic acid;
3-[4-(6-sec-butylsulfanyl-pyridin-2-ylmethoxy)-3,5-difluoro-phenyl]-propionic acid;
2-[4-(6-cyclopentylsulfanyl-pyridin-2-ylmethoxy)-3,5-difluoro-phenyl]-cyclopropane carboxylic acid;
2-[4-(2-cyclobutylsulfanyl-pyridin-3-ylmethoxy)-3,5-difluoro-phenyl]-cyclopropane carboxylic acid;
3-[4-(2-cyclobutylsulfanyl-pyridin-3-ylmethoxy)-3-fluoro-phenyl]-2-methyl-propionic acid;
3-[4-(2-sec-butylsulfanyl-pyridin-3-ylmethoxy)-3-fluoro-phenyl]-2-methyl-propionic acid;
3-[4-(2-cyclopropylmethylsulfanyl-pyridin-3-yl-methoxy)-3-fluoro-phenyl]-2-methyl-propionic acid;
3-[3,5-difluoro-4-(2-isopropylsulfanyl-pyridin-3-yl-methoxy)-phenyl]-2-methyl-propionic acid;
3-[4-(2-sec-butylsulfanyl-pyridin-3-ylmethoxy)-3,5-difluoro-phenyl]-2-methyl-propionic acid;
3-[3,5-difluoro-4-(2-isopropylsulfanyl-6-methoxy-pyridin-3-ylmethoxy)-phenyl]-propionic acid;
3-[4-(6-cyclopentylsulfanyl-pyridin-2-ylmethoxy)-3,5-difluoro-phenyl]-2-methyl-propionic acid;
3-[4-(2-cyclopentylsulfanyl-6-methyl-pyridin-3-yl-methoxy)-3,5-difluoro-phenyfl-propionic acid;
3-[4-(6-cyclobutylsulfanyl-pyridin-2-ylmethoxy)-3,5-difluoro-phenyl]-2-methyl-propionic acid;
3-[4-(2-cyclopentylsulfanyl-pyridin-3-ylmethoxy)-3,5-difluoro-phenyl]-2-methyl-propionic acid;
3-[4-(6-sec-butylsulfanyl-pyridin-2-ylmethoxy)-3,5-difluoro-phenyl]-2-methyl-propionic acid;
3-[3,5-difluoro-4-(6-isopropylsulfanyl-pyridin-2-yl-methoxy)-phenyl]-2-methyl-propionic acid;
3-[4-(2-cyclopropylmethylsulfanyl-pyridin-3-yl-methoxy)-3,5-difluoro-phenyl]-2-methyl-propionic acid;
3-[3,5-difluoro-4-(2-propylsulfanyl-pyridin-3-yl-methoxy)-phenyl]-2-methyl-propionic acid;
3-[3-fluoro-4-(6-isopropylsulfanyl-pyridin-2-yl-methoxy)-phenyl]-2-methyl-propionic acid;
3-[4-(6-sec-butylsulfanyl-pyridin-2-ylmethoxy)-3-fluoro-phenyl]-2-methyl-propionic acid;
3-[4-(6-cyclopentylsulfanyl-pyridin-2-ylmethoxy)-3-fluoro-phenyl]-2-methyl-propionic acid;
3-[4-(6-cyclobutylsulfanyl-pyridin-2-ylmethoxy)-3-fluoro-phenyl]-2-methyl-propionic acid;
3-[4-(2-cyclobutylsulfanyl-pyridin-3-ylmethoxy)-3,5-difluoro-phenyl]-2-methyl-propionic acid;
3-[4-(2-isopropylsulfanyl-pyridin-3-ylmethoxy)-3-methoxy-phenyl]-propionic acid;
3-[4-(2-cyclopentylsulfanyl-pyridin-3-ylmethoxy)-3-methoxy-phenyl]-propionic acid;
[6-(2-isopropylsulfanyl-pyridin-3-ylmethoxy)-2,3-dihydro-benzofuran-3-A-acetic acid;
3-[3-fluoro-4-(2-isopropylsulfanyl-pyridin-3-yl-methoxy)-phenyl]-2-methyl-propionic acid;
3-[4-(2-butylsulfanyl-pyridin-3-ylmethoxy)-3-fluoro-phenyl]-2-methyl-propionic acid;
2-[4-(2-cyclopentylsulfanyl-pyridin-3-ylmethoxy)-3,5-difluoro-phenyl]-cyclopropane carboxylic acid;
2-[4-(2-cyclopropylmethylsulfanyl-pyridin-3-yl-methoxy)-3,5-difluoro-phenyl]-cyclopropane carboxylic acid;
2-[3,5-difluoro-4-(6-isopropylsulfanyl-pyridin-2-yl-methoxy)-phenyl]-cyclopropane carboxylic acid;
2-[3,5-difluoro-4-(2-isopropylsulfanyl-pyridin-3-yl-methoxy)-phenyl]-cycloprppane carboxylic acid;
2-[4-(2-butylsulfanyl-pyridin-3-ylmethoxy)-3,5-difluoro-phenyl]-cyclopropane carboxylic acid;
[6-(6-isopropylsulfanyl-pyridin-2-ylmethoxy)-2,3-dihydro-benzofuran-3-yl]-acetic acid;
[6-(6-cyclopentylsulfanyl-pyridin-2-ylmethoxy)-2,3-dihydro-benzofuran-3-yl]-acetic acid;
3-[4-(2-isopropylsulfanyl-pyridin-3-ylmethoxy)-phenyl]-2,2-dimethyl-propionic acid;
3-[4-(6-isopropylsulfanyl-pyridin-2-ylmethoxy)-phenyl]-2,2-dimethyl-propionic acid;
3-[3,5-difluoro-4-(4-isopropylsulfanyl-2-methyl-pyrimidin-5-ylmethoxy)-phenyl]-propionic acid;
3-[4-(6-isopropylsulfanyl-pyridin-2-ylmethoxy)-3-methoxy-phenyl]-propionic acid;
3-[4-(6-cyclopentylsulfanyl-pyridin-2-ylmethoxy)-3-methoxy-phenyl]-propionic acid;
[6-(2-cyclopentylsulfanyl-pyridin-3-ylmethoxy)-2,3-dihydro-benzofuran-3-yl]-acetic acid;
2-[4-(6-cyclobutylsulfanyl-pyridin-2-ylmethoxy)-3,5-difluoro-phenyl]-cyclopropane carboxylic acid;
3-[4-(2-cyclopentylsulfanyl-6-methoxy-pyridin-3-yl-methoxy)-3,5-difluoro-phenyTh propionic acid;
3-[3-chloro-4-(2-isopropylsulfanyl-pyridin-3-yl-methoxy)-phenyl]-propionic acid;
343-chloro-4-(2-cyclopentylsulfanyl-pyridin-3-yl-methoxy)-phenyl]-propionic acid;
3-[4-(2-isopropylsulfanyl-pyridin-3-ylmethoxy)-2,3-dimethyl-phenyl]-propionic acid;
3-[4-(2-cyclopentylsulfanyl-pyridin-3-ylmethoxy)-2,3-dimethyl-phenyThpropionic acid;
[(S)-6-(2-cyclopentylsulfanyl-pyridin-3-ylmethoxy)-2,3-dihydro-benzofuran-3-yl]-acetic acid;

[(R)-6-(2-cyclopentylsulfanyl-pyridin-3-ylmethoxy)-2,3-dihydro-benzofuran-3-yl]-acetic acid;
2-[3-fluoro-4-(2-isopropylsulfanyl-pyridin-3-yl-methoxy)-phenyl]-cyclopropane carboxylic acid;
2-[4-(2-cyclopropylmethylsulfanyl-pyridin-3-yl-methoxy)-3-fluoro-phenyl]-cyclopropane carboxylic acid;
2-[4-(6-cyclopentylsulfanyl-pyridin-2-ylmethoxy)-3-fluoro-phenyl]-cyclopropane carboxylic acid;
2-[4-(6-cyclobutyl sulfanyl-pyridin-2-ylmethoxy)-3-fluoro-phenyl]-cyclopropane carboxylic acid;
2-[4-(2-cyclopentylsulfanyl-pyridin-3-ylmethoxy)-3-fluoro-phenyl]-cyclopropane carboxylic acid;
2-[4-(2-cyclobutylsulfanyl-pyridin-3-ylmethoxy)-3-fluoro-phenyl]-cyclopropane carboxylic acid;
2-[2-chloro-4-(2-isopropyl sulfanyl-pyridin-3-yl-methoxy)-phenyl]-cyclopropane carboxylic acid;
2-[2-chloro-4-(6-chlorobutylsulfanyl-pyridin-2-yl-methoxy)-phenyl]-cyclopropane carboxylic acid;
3-[3-chloro-4-(2-cyclopropylmethylsulfanyl-pyridin-3-ylmethoxy)-phenyl]-2-methyl-propionic acid;
343-chloro-4-(2-propylsulfanyl-pyridin-3-ylmethoxy)-phenyl]-2-methyl-propionic acid;
3-[3-chloro-4-(6-isopropylsulfanyl-pyridin-2-yl-methoxy)-phenyl]-2-methyl-propionic acid;
3-[3-chloro-4-(6-cyclopentylsulfanyl-pyridin-2-yl-methoxy)-phenyl]-2-methyl-propionic acid;
3-[3-chloro-4-(2-cyclobutylsulfanyl-pyridin-3-yl-methoxy)-phenyl]-2-methyl-propionic acid;
3-[3-chloro-4-(6-cyclobutylsulfanyl-pyridin-2-yl-methoxy)-phenyl]-2-methyl-propionic acid;
2-[3-chloro-4-(2-isopropylsulfanyl-pyridin-3-yl-methoxy)-phenyl]-cyclopropane carboxylic acid;
2-[3-chloro-4-(6-cyclopropylmethylsulfanyl-pyridin-2-ylmethoxy)-phenyl]-cyclopropane carboxylic acid;
2-[3-chloro-4-(6-isopropylsulfanyl-pyridin-2-yl-methoxy)-phenyl]-cyclopropane carboxylic acid;
2-[3-chloro-4-(6-cyclopentylsulfanyl-pyridin-2-yl-methoxy)-phenyl]-cyclopropane carboxylic acid;
2-[3-chloro-4-(2-cyclop entylsulfanyl-pyridin-3-yl-methoxy) -phenyl]-cyclopropane carboxylic acid;
2-[3-chloro-4-(2-cyclobutylsulfanyl-pyridin-3-yl-methoxy)-phenyl]-cyclopropane carboxylic acid;
2-[3-chloro-4-(6-cyclobutylsulfanyl-pyridin-2-yl-methoxy)-phenyl]-cyclopropane carboxylic acid;
2-[2-chloro-4-(6-chloropentylsulfanyl-pyridin-2-yl-methoxy)-phenyl]-cyclopropane carboxylic acid;
2-[4-(2-isopropylsulfanyl-pyridin-3-ylmethoxy)-2,3-dimethyl-phenyl]-cyclopropane carboxylic acid;
2-[4-(2-cyclopropylmethylsulfanyl-pyridin-3-yl-methoxy)-2,3-dimethyl-phenyl]-cyclopropane carboxylic acid;
2-[3-chloro-4-(2-cyclopropylmethylsulfanyl-pyridin-3-ylmethoxy)-phenyl]-cyclopropane carboxylic acid;
2-[3-chloro-4-(2-propylsulfanyl-pyridin-3-ylmethoxy)-phenyl]-cyclopropane carboxylic acid;
2-[3-chloro-4-(2-isopropylsulfanyl-6-methoxy-pyridin-3-ylmethoxy)-phenyl]-cyclopropane carboxylic acid;
2-[4-(6-cyclopentylsulfanyl-pyridin-2-ylmethoxy)-3,5-difluoro-benzyl]-cyclopropane carboxylic acid;
[6-(2-cyclobutylsulfanyl-pyridin-3-ylmethoxy)-5,7-difluoro-2,3-dihydro-benzofuran-3-yl]-acetic acid;
2-[2,3-dimethyl-4-(2-propylsulfanyl-pyridin-3-ylmethoxy)-phenyl]-cyclopropane carboxylic acid;
2-[4-(cyclobutylsulfanyl-pyridin-3-ylmethoxy)-2,3-dimethyl-phenyl]-cyclopropane carboxylic acid;
2-[4-(6-isopropylsulfanyl-pyridin-2-ylmethoxy)-2,3-dimethyl-phenyl]-cyclopropane carboxylic acid;
2-[4-(6-cyclobutylsulfanyl-pyridin-2-ylmethoxy)-3,5-difluoro-benzyl]-cyclopropane carboxylic acid;
2-[3,5-difluoro-4-(2-isopropylsulfanyl-pyridin-3-yl-methoxy)-benzyl]-cyclopropane carboxylic acid;
2-[3,5-difluoro-4-(2-propylsulfanyl-pyridin-3-yl-methoxy)-benzyl]-cyclopropane carboxylic acid;
[6-(2-cyclopentylsulfanyl-pyridin-3-ylmethoxy)-7-methyl-benzofuran-3-yl]-acetic acid;
2-[3-fluoro-4-(2-propylsulfanyl-pyridin-3-ylmethoxy)-phenyl]-cyclopropane carboxylic acid (less polar);
{2-[4-(6-cyclopentylsulfanyl-pyridin-2-ylmethoxy)-3-fluoro-phenyl]-cyclopropyl -acetic acid;
{2-[3-fluoro-4-(2-propylsulfanyl-pyridin-3-ylmethoxy)-phenyl]-cyclopropyll-acetic acid;
[6-(2-cyclopentylsulfanyl-pyridin-3-ylmethoxy)-5,7-difluoro-benzofuran-3-yl]-acetic acid;
[6-(2-cyclopentylsulfanyl-pyridin-3-ylmethoxy)-5,7-difluoro-2,3-dihydro-benzofuran-3-yl]-acetic acid;
2-[3-chloro-4-(2-cyclobutylsulfanyl-pyridin-3-yl-methoxy)-phenyl]-cyclopropane carboxylic acid (less polar);
2-[3-chloro-4-(2-cyclobutylsulfanyl-pyridin-3-yl-methoxy)-phenyThcyclopropane carboxylic acid (more polar);
2-[3-chloro-4-(2-isopropylsulfanyl-pyridin-3-yl-methoxy)-phenyll-cyclopropane carboxylic acid (more polar);
2-[3-chloro-4-(2-cyclopropylmethylsulfanyl-pyridin-3-ylmethoxy)-phenyl]-cyclopropane carboxylic acid (more polar);
2-[3-chloro-4-(6-cyclopropylmethyl sulfanyl-pyridin-2-ylmethoxy) -phenyl]-cyclopropane carboxylic acid (more polar);
2-[4-(2-cyclopropylmethylsulfanyl-pyridin-3-yl-methoxy)-3-fluoro-phenyl]-cyclopropane carboxylic acid (less polar);
2-[4-(2-cyclopentylsulfanyl-pyridin-3-ylmethoxy)-3-fluoro-phenyl]-cyclopropane carboxylic acid (less polar);
2-[3-fluoro-4-(6-isopropylsulfanyl-pyridin-2-yl-methoxy)-phenyl]-cyclopropane carboxylic acid (less polar);
2-[3-chloro-4-(6-cyclobutylsulfanyl-pyridin-2-yl-methoxy)-phenyl]-cyclopropane carboxylic acid (more polar);
2-[4-(2-cyclobutylsulfanyl-pyridin-3-ylmethoxy)-3-fluoro-phenyl]-cyclopropane carboxylic acid (less polar);
2-[4-(6-cyclopentyl sulfanyl-pyridin-2-ylmethoxy)-3-fluoro-phenyl]-cyclopropane carboxylic acid (less polar);
2-[4-(6-cyclobutylsulfanyl-pyridin-2-ylmethoxy)-3-fluoro-phenyl]-cyclopropane carboxylic acid (less polar);
2-[4-(2-cyclopropylmethylsulfanyl-pyridin-3-yl-methoxy)-3,5-difluoro-phenyl]-cyclopropane carboxylic acid (less polar);
2-[4-(2-cyclopropylmethylsulfanyl-pyridin-3-yl-methoxy)-3,5-difluoro-phenyl]-cyclopropane carboxylic acid (more polar);
2-[3,5-difluoro-4-(2-isopropylsulfanyl-pyridin-3-yl-methoxy)-phenyThcyclopropane carboxylic acid (more polar);

2-[3,5-difluoro-4-(2-propylsulfanyl-pyridin-3-yl-methoxy)-phenyl]-cyclopropane carboxylic acid (more polar);
2-[4-(2-cyclopentylsulfanyl-pyridin-3-ylmethoxy)-3,5-difluoro-phenyl]-cyclopropane carboxylic acid (more polar);
3-[3-chloro-4-(6-isopropylsulfanyl-pyridin-2-yl-methoxy)-phenyl]-propionic acid;
3-[3-chloro-4-(6-cyclopropylmethylsulfanyl-pyridin-2-ylmethoxy)-phenyl]-propionic acid;
3-[3-chloro-4-(6-cyclopentylsulfanyl-pyridin-2-yl-methoxy)-phenyl]-propionic acid;
3-[3-fluoro-4-(2-propylsulfanyl-pyridin-3-ylmethoxy)-phenyl]-propionic acid;
3-[4-(2-cyclobutylsulfanyl-pyridin-3-ylmethoxy)-3-fluoro-phenyl]-propionic acid;
3-[4-(2-cyclopentylsulfanyl-pyridin-3-ylmethoxy)-3-fluoro-phenyl]-propionic acid;
3-[4-(2-cyclopropylmethylsulfanyl-pyridin-3-yl-methoxy)-3-fluoro-phenyl]-propionic acid;
3-[4-(6-cyclobutylsulfanyl-pyridin-2-ylmethoxy)-3-fluoro-phenyl]-propionic acid;
3-[3-fluoro-4-(6-isopropylsulfanyl-pyridin-2-yl-methoxy)-phenyl]-propionic acid;
3-[4-(6-cyclopentylsulfanyl-pyridin-2-ylmethoxy)-3-fluoro-phenyl]-propionic acid;
3-[4-(6-cyclopropylmethylsulfanyl-pyridin-2-yl-methoxy)-3-fluoro-phenyThpropionic acid;
2-[3,5-difluoro-4-(6-isopropylsulfanyl-pyridin-2-yl-methoxy)-phenyl]-cyclopropane carboxylic acid (more polar);
2-[4-(6-cyclopropylmethylsulfanyl-pyridin-2-yl-methoxy)-3,5-difluoro-phenyl]-cyclopropane carboxylic acid (more polar);
2-[4-(6-cyclopentylsulfanyl-pyridin-2-ylmethoxy)-3,5-difluoro-phenyl]-cyclopropane carboxylic acid (more polar);
2-[4-(6-cyclobutylsulfanyl-pyridin-2-ylmethoxy)-3,5-difluoro-phenyl]-cyclopropane carboxylic acid (more polar);
2-[4-(2-cyclobutylsulfanyl-pyridin-3-ylmethoxy)-3,5-difluoro-phenyl]-cyclopropane carboxylic acid (more polar);
3-[3-chloro-4-(2-cyclopropylmethylsulfanyl-pyridin-3-ylmethoxy)-phenyl]-propionic acid;
3-[3-chloro-4-(2-cyclobutylsulfanyl-pyridin-3-yl-methoxy)-phenyl]-propionic acid;
3-[3-chloro-4-(6-cyclobutylsulfanyl-pyridin-2-yl-methoxy)-phenylj -propionic acid;
3-[3-chloro-4-(2-isopropylsulfanyl-6-methyl-pyridin-3-ylmethoxy)-phenyl]-propionic acid;
3-[3-chloro-4-(2-cyclopentylsulfanyl-6-methyl-pyridin-3-ylmethoxy)-phenyl]-propionic acid;
2-[3-fluoro-4-(2-isopropylsulfanyl-pyridin-3-yl-methoxy)-phenyl]-cyclopropane carboxylic acid (more polar);
2-[3-fluoro-4-(2-propylsulfanyl-pyridin-3-ylmethoxy)-phenyl]-cyclopropane carboxylic acid (more polar);
2-[4-(2-cyclopentylsulfanyl-pyridin-3-ylmethoxy)-3-fluoro-phenyl]-cyclopropane carboxylic acid (more polar);
2-[4-(2-cyclopropylmethylsulfanyl-pyridin-3-yl-methoxy)-3-fluoro-phenyl]-cyclopropane carboxylic acid (more polar);
2-[3-fluoro-4-(6-isopropylsulfanyl-pyridin-2-yl-methoxy)-phenyl]-cyclopropane carboxylic acid (more polar);
2-[4-(6-cyclobutylsulfanyl-pyridin-2-ylmethoxy)-3-fluoro-phenyl]-cyclopropane carboxylic acid (more polar);
2-[4-(6-cyclopentylsulfanyl-pyridin-2-ylmethoxy)-3-fluoro-phenyl]-cyclopropane carboxylic acid (more polar);
2-[4-(2-cyclobutylsulfanyl-pyridin-3-ylmethoxy)-3-fluoro-phenyl]-cyclopropane carboxylic acid (more polar);
2-[4-(6-cyclopropylmethyl sulfanyl-pyridin-2-yl-methoxy)-3-fluoro-phenyl]-cyclopropane carboxylic acid (more polar);
3-{4-[(2-cyclopentylsulfanyl-pyridin-3-ylmethyl)-amino]-phenyl}-propionic acid;
3-{4-[(6-cyclopentylsulfanyl-pyridin-2-ylmethyl)-amino]-phenyl}-propionic acid;
3-[4-[(2-cyclopentylsulfanyl-pyridin-3-ylmethoxy)-2-fluoro-phenyl]-propionic acid;
2-[4-[(2-cyclopentylsulfanyl-pyridin-3-ylmethoxy)-2-fluoro-phenyl]-cyclopropane carboxylic acid;
3-[4-[(2-cyclobutylsulfanyl-pyridin-3-ylmethoxy)-2-fluoro-phenyl]-propionic acid;
3-[4(6-cyclobutylsulfanyl-pyridin-2-ylmethoxy)-2-fluoro-phenyl]-propionic acid;
3-[4(6-cyclopentylsulfanyl-pyridin-2-ylmethoxy)-2-fluoro-phenyl]-propionic acid;
3-[4-[(2-cyclopropylmethylsulfanyl-pyridin-3-yl-methoxy)-2-fluoro-phenyl]-propionic acid;
3-[4-[(6-cyclopropylmethylsulfanyl-pyridin-2-yl-methoxy)-2-fluoro-phenyl]-propionic acid;
3-[4-[(2-cyclobutylsulfanyl-pyridin-3-ylmethoxy)-phenyl]-propionic acid;
3-[4-[(6-cyclobutylsulfanyl-pyridin-2-ylmethoxy)-phenyl]-propionic acid;
3-[4-[(2-cyclopropylmethylsulfanyl-pyridin-3-yl-methoxy)-phenyl]-propionic acid;
3-[4-[(6-cyclopropylmethylsulfanyl-pyridin-2-yl-methoxy)-phenyl]-propionic acid;
3-[4-[(2-cyclopentylsulfanyl-6-methyl-pyridin-3-yl-methoxy)-phenyl]-propionic acid; and
3-[4-[(2-isopropylsulfanyl-6-methyl-pyridin-3-yl-methoxy)-phenyl]-propionic acid.

5. A pharmaceutical composition as GPR120 agonists, comprising the compound, a pharmaceutically acceptable salt or R or S isomer thereof according to claim 1 and a pharmaceutically acceptable carrier.

6. A pharmaceutical composition which is suitable for use in treating diabetes, complications of diabetes, inflammation, obesity, non-alcoholic fatty liver, steatohepatitis or osteoporosis, comprising the compound, a pharmaceutically acceptable salt or R or S isomer thereof according to claim 1 and a pharmaceutically acceptable carrier.

7. A composition which is suitable for use in lowering blood glucose level, comprising the compound, a pharmaceutically acceptable salt or R or S isomer thereof according to claim 1 and a pharmaceutically acceptable carrier.

8. A method for preparing a composition for treating diabetes, complications of diabetes, inflammation, obesity, non-alcoholic fatty liver, steatohepatitis or osteoporosis, which comprises the step of mixing the compound, a pharmaceutically acceptable salt or R or S isomer thereof according to claim 1 with a pharmaceutically acceptable carrier.

9. A method for treating a disease selected from the group consisting of diabetes, complications of diabetes, inflammation, obesity, non-alcoholic fatty liver, steatohepatitis or osteoporosis, comprising:

administering the compound, a pharmaceutically acceptable salt or R or S isomer thereof according to claim 1 and a pharmaceutically acceptable carrier to a subject suffering from the disease.

10. A method for lowering blood glucose level, comprising:
administering the compound, a pharmaceutically acceptable salt or R or S isomer thereof according to claim 1 and a pharmaceutically acceptable carrier to a subject in need of lowering blood glucose level.

* * * * *